(12) United States Patent
Olhava

(10) Patent No.: US 9,175,032 B2
(45) Date of Patent: Nov. 3, 2015

(54) METHODS OF SYNTHESIZING SUBSTITUTED PURINE COMPOUNDS

(71) Applicant: Epizyme, Inc., Cambridge, MA (US)

(72) Inventor: Edward James Olhava, Newton, MA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

(21) Appl. No.: 14/210,888

(22) Filed: Mar. 14, 2014

(65) Prior Publication Data

US 2015/0011495 A1    Jan. 8, 2015

Related U.S. Application Data

(60) Provisional application No. 61/799,147, filed on Mar. 15, 2013.

(51) Int. Cl.
| | | |
|---|---|---|
| A01N 43/04 | (2006.01) | |
| A61K 31/70 | (2006.01) | |
| C07H 19/16 | (2006.01) | |
| A61K 31/7076 | (2006.01) | |
| A61K 31/4184 | (2006.01) | |
| C07D 235/12 | (2006.01) | |

(52) U.S. Cl.
CPC ............ *C07H 19/16* (2013.01); *A61K 31/4184* (2013.01); *A61K 31/7076* (2013.01); *C07D 235/12* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 7,576,069 B2 * | 8/2009 | Rieger et al. ................ 514/46 | |
| 8,580,762 B2 | 11/2013 | Olhava et al. | |
| 2004/0147464 A1 | 7/2004 | Roberts et al. | |
| 2006/0040889 A1 | 2/2006 | Rieger et al. | |
| 2006/0189636 A1 | 8/2006 | Critchley et al. | |
| 2006/0235037 A1 | 10/2006 | Purandare et al. | |
| 2007/0191293 A1 | 8/2007 | Langston et al. | |
| 2008/0064653 A1 | 3/2008 | Li et al. | |
| 2008/0132525 A1 | 6/2008 | Wahhab et al. | |
| 2009/0105476 A1 | 4/2009 | Fairhurst et al. | |
| 2010/0144655 A1 | 6/2010 | Chen et al. | |
| 2012/0122895 A1 | 5/2012 | Jiang et al. | |
| 2014/0051654 A1 | 2/2014 | Olhava et al. | |

FOREIGN PATENT DOCUMENTS

| | | |
|---|---|---|
| CN | 1678619 A | 10/2005 |
| CN | 102066372 A | 5/2011 |
| EP | 1138688 A1 | 10/2001 |
| EP | 2208721 A1 | 7/2010 |
| WO | WO 01/72764 A1 | 10/2001 |
| WO | WO 01/77075 A2 | 10/2001 |
| WO | WO 02/100152 A2 | 12/2002 |
| WO | WO 03/074083 A1 | 9/2003 |
| WO | WO 2004/007512 A2 | 1/2004 |
| WO | WO 2004/022572 A1 | 3/2004 |
| WO | WO 2006/015357 A2 | 2/2006 |
| WO | WO 2006/028618 A1 | 3/2006 |
| WO | WO 2006/078752 A2 | 7/2006 |
| WO | WO 2006/113615 A2 | 10/2006 |
| WO | WO 2007/100304 A1 | 9/2007 |
| WO | WO 2008/124150 A1 | 10/2008 |
| WO | WO 2009/089425 A1 | 7/2009 |
| WO | WO 2010/027005 A1 | 3/2010 |
| WO | WO 2010/048149 A2 | 4/2010 |
| WO | WO 2012/075492 A2 | 6/2012 |
| WO | WO 2012/075500 A2 | 6/2012 |
| WO | WO 2012/082436 A2 | 6/2012 |

OTHER PUBLICATIONS

Daigle, S.R. et al. "Selective Killing of Mixed Lineage Leukemia Cells by a Potent Small-Molecule DOT1L Inhibitor", *Cancer Cell*, 20:53-65 (2011).

Gao and Liu, "DOT1: A distinct class of histone lysine methyltransferase", *Hereditas*, 29(12):1449-1454 (2007).

* cited by examiner

*Primary Examiner* — Patrick Lewis
(74) *Attorney, Agent, or Firm* — Cooley LLP; Heidi A. Elacher; Lian Ouyang

(57) ABSTRACT

The present invention provides an efficient process for the synthesis of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol and hydrates thereof and methods for treating disorders in which DOT1-mediated protein methylation plays a part, such as cancer and neurological disorders, by administering these compounds and pharmaceutical compositions to subjects in need thereof. The present invention also provides novel crystalline forms of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol and hydrates thereof (Form A, Form B, and Form C), characterized by a unique X-ray diffraction pattern and Differential Scanning Calorimetry profile, as well as a unique crystalline structure.

20 Claims, 158 Drawing Sheets

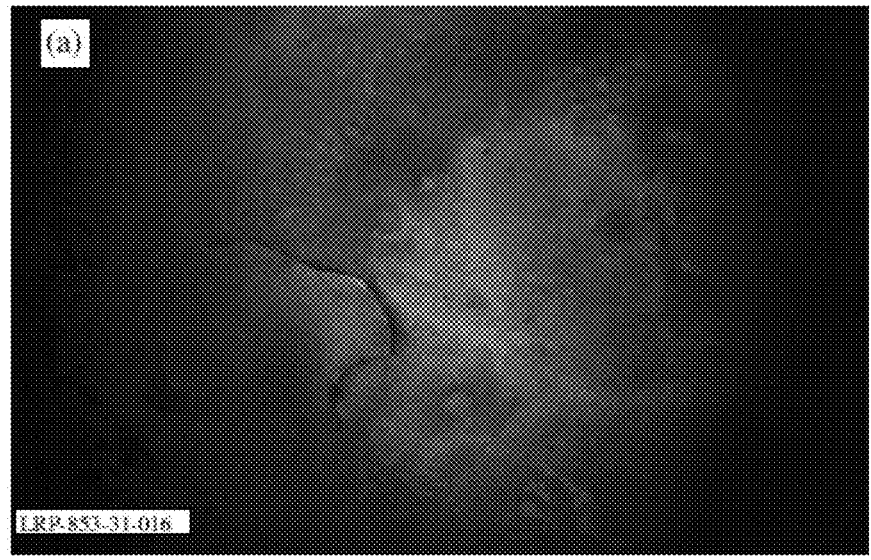
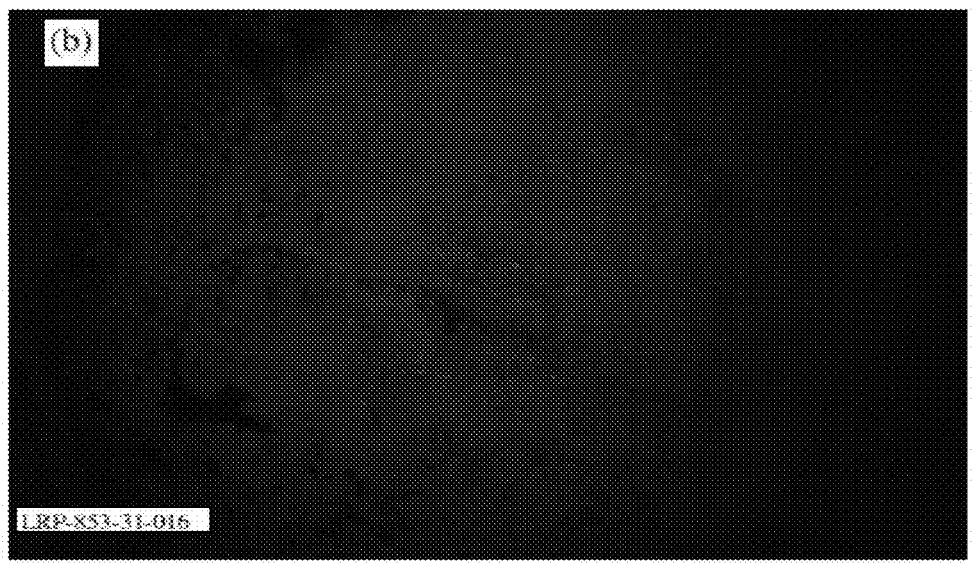
FIG. 146

(a) under normal light and (b) under polarised light
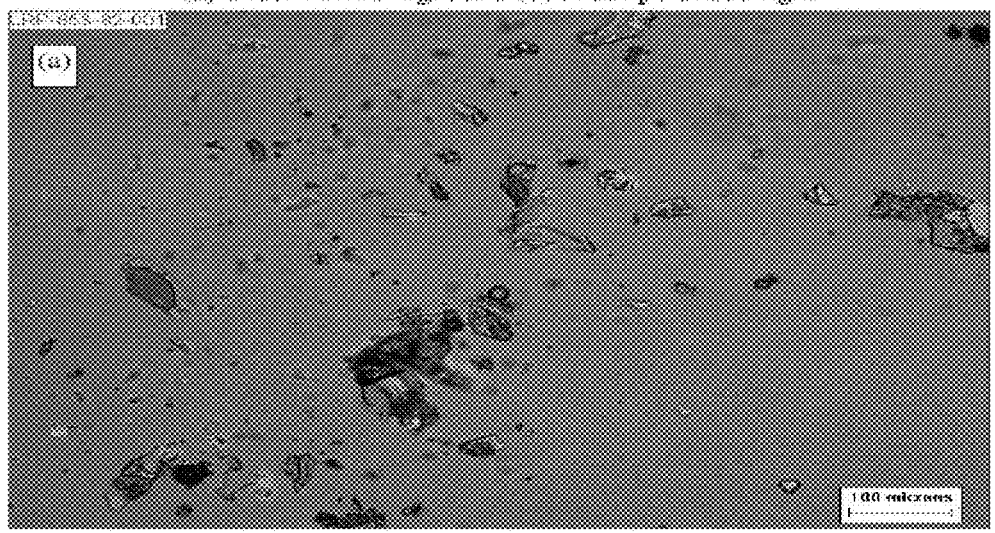
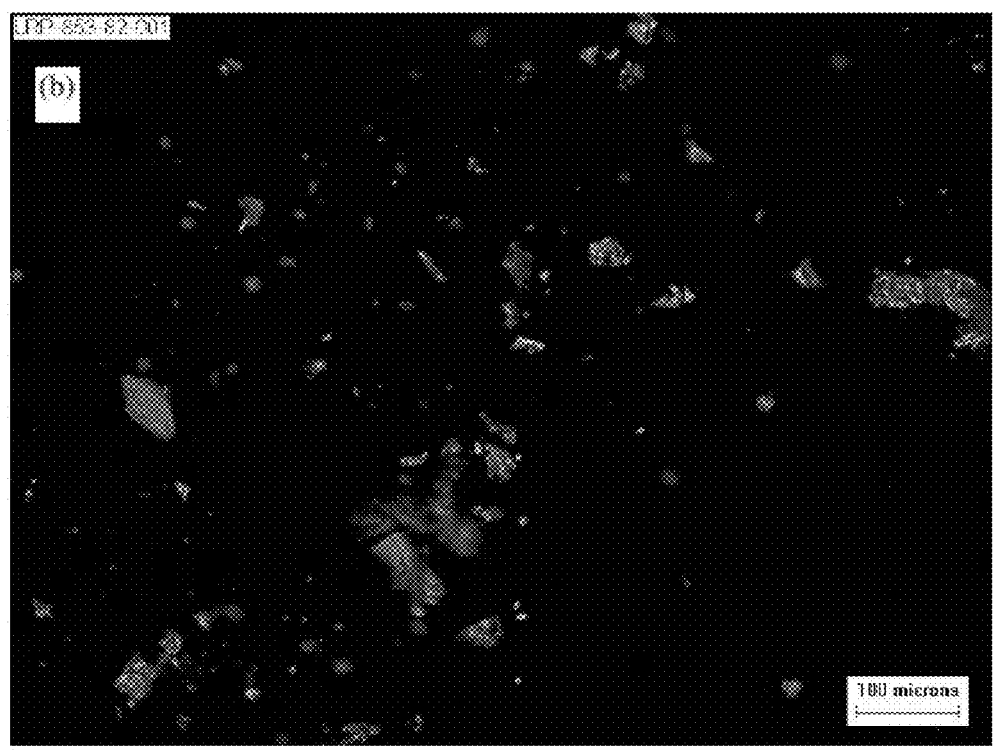
FIG. 189

METHODS OF SYNTHESIZING SUBSTITUTED PURINE COMPOUNDS

RELATED APPLICATIONS

This application claims priority to, and the benefit of, U.S. provisional application No. 61/799,147, filed Mar. 15, 2013, the entire content of which is incorporated herein by reference in its entirety.

BACKGROUND OF THE INVENTION

In eukaryotic cells, DNA is packaged with histones to form chromatin. Approximately 150 base pairs of DNA are wrapped twice around an octamer of histones (two each of histones 2A, 2B, 3, and 4) to form a nucleosome, the basic unit of chromatin. Changes in the ordered structure of chromatin can lead to alterations in transcription of associated genes. This process is highly controlled because changes in gene expression patterns can profoundly affect fundamental cellular processes such as differentiation, proliferation, and apoptosis. Control of changes in chromatin structure (and hence of transcription) is mediated by covalent modifications to histones, most notably of their N-terminal tails. These modifications are often referred to as epigenetic because they can lead to heritable changes in gene expression, but do not affect the sequence of the DNA itself. Covalent modifications (for example, methylation, acetylation, phosphorylation, and ubiquitination) of the side chains of amino acids are enzymatically mediated.

The selective addition of methyl groups to specific amino acid sites on histones is controlled by the action of a unique family of enzymes known as histone methyltransferases (HMTs). The level of expression of a particular gene is influenced by the presence or absence of a methyl group at a relevant histone site. The specific effect of a methyl group at a particular histone site persists until the methyl group is removed by a histone demethylase, or until the modified histone is replaced through nucleosome turnover. In a like manner, other enzyme classes can decorate DNA and histones with other chemical species and still other enzymes can remove these species to provide temporal control of gene expression.

The orchestrated collection of biochemical systems behind transcriptional regulation must be tightly controlled in order for cell growth and differentiation to proceed optimally. Disease states result when these controls are disrupted by aberrant expression and/or activity of the enzymes responsible for DNA and histone modification. In human cancers, for example, there is a growing body of evidence to suggest that dysregulated epigenetic enzyme activity contributes to the uncontrolled cell proliferation associated with cancer as well as other cancer-relevant phenotypes such as enhanced cell migration and invasion. Beyond cancer, there is growing evidence for a role of epigenetic enzymes in a number of other human diseases, including metabolic diseases (such as diabetes), inflammatory diseases (such as Crohn's disease), neurodegenerative diseases (such as Alzheimer's disease) and cardiovascular diseases. Therefore, selectively modulating the aberrant action of epigenetic enzymes holds great promise for the treatment of a range of diseases.

There is an ongoing need for new agents which modulate the aberrant action of epigenetic enzymes. The present invention provides compounds that meet this need.

SUMMARY OF THE INVENTION

The present invention is directed to 2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol:

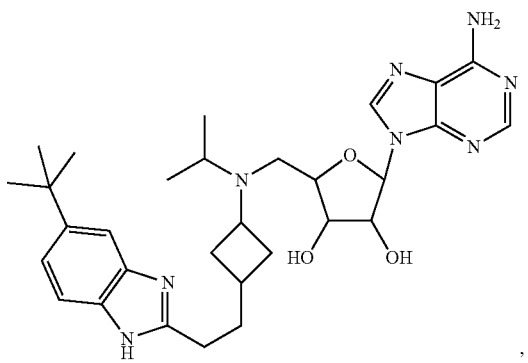 [SMILES: CC(C)N(CC1OC(n2cnc3c(N)ncnc32)C(O)C1O)C1CC(CCc2nc3cc(C(C)(C)C)ccc3[nH]2)C1]

or a hydrate, salt, or crystalline form thereof.

The present invention is also directed to (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl) (isopropyl)amino)methyl)tetrahydrofuran-3,4-diol:

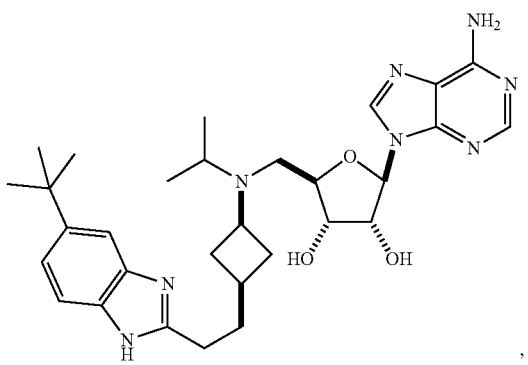

or a hydrate, salt, or crystalline form thereof.

The present invention relates to a crystalline form of (2R, 3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol hydrate. The present invention relates to a crystalline form of (2R,3R, 4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol trihydrate.

The present invention relates to a crystalline form of (2R, 3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol hydrate (Form A) characterized by an X-ray powder diffraction (XRPD) pattern comprising peaks at about 5.5, 16.9, and 16.6° 2θ using Cu Kα radiation. In one embodiment, the crystalline form (Form A) is characterized by an XRPD pattern comprising peaks at about 5.5, 16.9, 16.6, and 18.8° 2θ using Cu Kα radiation. In one embodiment, the crystalline form (Form A) is characterized by an XRPD pattern comprising peaks at about 5.5, 16.9, 16.6, 18.8, 14.3, and 12.7° 2θ using Cu Kα radiation. In one embodiment, the crystalline form (Form A) is characterized by an XRPD pattern comprising peaks at about 5.5, 16.9, 16.6, 18.8, 14.3, 12.7, 21.8, 20.0, 10.0, and 11.0° 2θ using Cu Kα radiation. In one embodiment, the crystalline form (Form A) is characterized by an XRPD pattern substantially similar to that set forth in FIG. 1.

The present invention relates to a crystalline form of (2R, 3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol hydrate (Form A) characterized by a Differential Scanning Calorimetry (DSC) thermogram having a single maximum value at about 80.4° C.

The present invention relates to a crystalline form of (2R, 3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol hydrate (Form A) characterized by an XRPD pattern comprising peaks at about 5.5, 16.9, and 16.6° 2θ using Cu Kα radiation and by a DSC thermogram having a single maximum value at about 80.4° C. In one embodiment, the crystalline form (Form A) is characterized by an XRPD pattern comprising peaks at about 5.5, 16.9, 16.6, and 18.8° 2θ using Cu Kα radiation and by a DSC thermogram having a single maximum value at about 80.4° C. In one embodiment, the crystalline form (Form A) is characterized by an XRPD pattern comprising peaks at about 5.5, 16.9, 16.6, 18.8, 14.3, and 12.7° 2θ using Cu Kα radiation and by a DSC thermogram having a single maximum value at about 80.4° C. In one embodiment, the crystalline form (Form A) is characterized by an XRPD pattern comprising peaks at about 5.5, 16.9, 16.6, 18.8, 14.3, 12.7, 21.8, 20.0, 10.0, and 11.0° 2θ using Cu Kα radiation and by a DSC thermogram having a single maximum value at about 80.4° C. In one embodiment, the crystalline form (Form A) is characterized by an XRPD pattern substantially similar to that set forth in FIG. 1 and by a DSC thermogram having a single maximum value at about 80.4° C.

The present invention relates to a crystalline form of (2R, 3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol hydrate (Form A) characterized by a DSC thermogram having two endotherms with onsets of about 39.3° C. and about 127.2° C.

The invention relates to a crystalline form of (2R,3R,4S, 5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol hydrate (Form A) characterized by an XRPD pattern comprising peaks at about 5.5, 16.9, and 16.6° 2θ using Cu Kα radiation and by a DSC thermogram having two endotherms with onsets of about 39.3° C. and about 127.2° C. In one embodiment, the crystalline form (Form A) is characterized by an XRPD pattern comprising peaks at about 5.5, 16.9, 16.6, and 18.8° 2θ using Cu Kα radiation and by a DSC thermogram having two endotherms with onsets of about 39.3° C. and about 127.2° C. In one embodiment, the crystalline form (Form A) is characterized by an XRPD pattern comprising peaks at about 5.5, 16.9, 16.6, 18.8, 14.3, and 12.7° 2θ using Cu Kα radiation and by a DSC thermogram having two endotherms with onsets of about 39.3° C. and about 127.2° C. In one embodiment, the crystalline form (Form A) is characterized by an XRPD pattern comprising peaks at about 5.5, 16.9, 16.6, 18.8, 14.3, 12.7, 21.8, 20.0, 10.0, and 11.0° 2θ using Cu Kα radiation and by a DSC thermogram having two endotherms with onsets of about 39.3° C. and about 127.2° C. In one embodiment, the crystalline form (Form A) is characterized by an XRPD pattern substantially similar to that set forth in FIG. 1 and by a DSC thermogram having two endotherms with onsets of about 39.3° C. and about 127.2° C.

The present invention relates to a crystalline form of (2R, 3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol trihydrate (Form B) characterized by an XRPD pattern comprising peaks at about 16.5, 20.5, and 5.2° 2θ using Cu Kα radiation. In one embodiment, the crystalline form (Form B) is characterized by an XRPD pattern comprising peaks at about 16.5, 20.5, 5.2, and 14.2° 2θ using Cu Kα radiation. In one embodiment, the crystalline form (Form B) is characterized by an XRPD pattern comprising peaks at about 16.5, 20.5, 5.2, 14.2, 18.0, and 10.4° 2θ using Cu Kα radiation. In one embodiment, the crystalline form (Form B) is characterized by an XRPD pattern comprising peaks at about 16.5, 20.5, 5.2, 14.2, 18.0, 10.4, 12.3, 10.0, 22.7, and 20.9° 2θ using Cu Kα radiation. In one embodiment, the crystalline form (Form B) is characterized by an XRPD pattern substantially similar to that set forth in FIG. 6.

The present invention relates to a crystalline form of (2R, 3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol trihydrate (Form B) characterized by a DSC thermogram having a single maximum value at about 132.3° C.

The present invention relates to a crystalline form of (2R, 3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol trihydrate (Form B) characterized by an XRPD pattern comprising peaks at about 16.5, 20.5, and 5.2° 2θ using Cu Kα radiation and by a DSC thermogram having a single maximum value at about 132.3° C. In one embodiment, the crystalline form (Form B) is characterized by an XRPD pattern comprising peaks at about 16.5, 20.5, 5.2, and 14.2° 2θ using Cu Kα radiation and by a DSC thermogram having a single maximum value at about 132.3° C. In one embodiment, the crystalline form (Form B) is characterized by an XRPD pattern comprising peaks at about 16.5, 20.5, 5.2, 14.2, 18.0, and 10.4° 2θ using Cu Kα radiation and by a DSC thermogram having a single maximum value at about 132.3° C. In one embodiment, the crystalline form (Form B) is characterized by an XRPD pattern comprising peaks at about 16.5, 20.5, 5.2, 14.2, 18.0, 10.4, 12.3, 10.0, 22.7, and 20.9° 2θ using Cu Kα radiation and by DSC thermogram having a single maximum value at about 132.3° C. In one embodiment, the crystalline form (Form B) is characterized by an XRPD pattern substantially similar to that set forth in FIG. 6 and further characterized by a DSC thermogram having a single maximum value at about 132.3° C.

The present invention relates to a crystalline form of (2R, 3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol trihydrate (Form B) characterized by a DSC thermogram having an endotherm with an onset of about 102.6° C.

The invention relates to a crystalline form of (2R,3R,4S, 5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl) amino)methyl)tetrahydrofuran-3,4-diol trihydrate (Form B) characterized by an XRPD pattern comprising peaks at about 16.5, 20.5, and 5.2° 2θ using Cu Kα radiation and by a DSC thermogram having an endotherm with an onset of about 102.6° C. In one embodiment, the crystalline form (Form B) is characterized by an XRPD pattern comprising peaks at about 16.5, 20.5, 5.2, and 14.2° 2θ using Cu Kα radiation and by a DSC thermogram having an endotherm with an onset of about 102.6° C. In one embodiment, the crystalline form (Form B) is characterized by an XRPD pattern comprising peaks at about 16.5, 20.5, 5.2, 14.2, 18.0, and 10.4° 2θ using Cu Kα radiation and by a DSC thermogram having an endotherm with an onset of about 102.6° C. In one embodiment, the crystalline form (Form B) is characterized by an XRPD pattern comprising peaks at about 16.5, 20.5, 5.2, 14.2, 18.0, 10.4, 12.3, 10.0, 22.7, and 20.9° 2θ using Cu Kα radiation and by a DSC thermogram having an endotherm with an onset of about 102.6° C. In one embodiment, the crystalline form (Form B) is characterized by an XRPD pattern substantially similar to that set forth in FIG. 6 and by a DSC thermogram having an endotherm with an onset of about 102.6° C.

The present invention relates to a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol anhydrate (Form C) characterized by an XRPD pattern comprising peaks at about 16.9, 5.7, and 14.5° 2θ using Cu Kα radiation. In one embodiment, the crystalline form (Form C) is characterized by an XRPD pattern comprising peaks at about 16.9, 5.7, 14.5, and 22.2° 2θ using Cu Kα radiation. In one embodiment, the crystalline form (Form C) is characterized by an XRPD pattern comprising peaks at about 16.9, 5.7, 14.5, 22.2, 19.1, and 20.0° 2θ using Cu Kα radiation. In one embodiment, the crystalline form (Form C) is characterized by an X-ray diffraction pattern comprising peaks at about 16.9, 5.7, 14.5, 22.2, 19.1, 20.0, 11.3, 12.9, 10.0, and 23.7° 2θ using Cu Kα radiation. In one embodiment, the crystalline form (Form C) is characterized by an XRPD pattern substantially similar to that set forth in FIG. 11.

The present invention relates to a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol anhydrate (Form C) characterized by a DSC thermogram having a single maximum value at about 148.0° C.

The present invention relates to a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol anhydrate (Form C) characterized by an XRPD pattern comprising peaks at about 16.9, 5.7, and 14.5° 2θ using Cu Kα radiation and by a DSC thermogram having a single maximum value at about 148.0° C. In one embodiment, the crystalline form (Form C) is characterized by an XRPD pattern comprising peaks at about 16.9, 5.7, 14.5, and 22.2° 2θ using Cu Kα radiation and by a DSC thermogram having a single maximum value at about 148.0° C. In one embodiment, the crystalline form (Form C) is characterized by an XRPD pattern comprising peaks at about 16.9, 5.7, 14.5, 22.2, 19.1, and 20.0° 2θ using Cu Kα radiation and by a DSC thermogram having a single maximum value at about 148.0° C. In one embodiment, the crystalline form (Form C) is characterized by an XRPD pattern comprising peaks at about 16.9, 5.7, 14.5, 22.2, 19.1, 20.0, 11.3, 12.9, 10.0, and 23.7° 2θ using Cu Kα radiation and by a DSC thermogram having a single maximum value at about 148.0° C.

In one embodiment, the crystalline form (Form C) is characterized by an XRPD pattern substantially similar to that set forth in FIG. 11 and by a DSC thermogram having a single maximum value at about 148.0° C.

The present invention relates to a pharmaceutical composition comprising a crystalline form of 2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol and a pharmaceutically acceptable excipient or carrier. The present invention relates to a pharmaceutical composition comprising a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol and a pharmaceutically acceptable excipient or carrier. The present invention relates to a pharmaceutical composition comprising a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol hydrate and a pharmaceutically acceptable excipient or carrier. The present invention relates to a pharmaceutical composition comprising a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol trihydrate and a pharmaceutically acceptable excipient or carrier. The present invention relates to a pharmaceutical composition comprising crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol hydrate (Form A) and a pharmaceutically acceptable excipient or carrier. The present invention relates to a pharmaceutical composition comprising a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol trihydrate (Form B) and a pharmaceutically acceptable excipient or carrier. The present invention relates to a pharmaceutical composition comprising a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol anhydrate (Form C) and a pharmaceutically acceptable excipient or carrier.

The present invention relates to a process for preparing a crystalline form of 2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol (e.g., (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl) amino)methyl)tetrahydrofuran-3,4-diol) or a hydrate thereof, comprising the step of recrystallizing (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol in a solvent.

The present invention relates to a process for preparing a crystalline form of 2-(6-amino-9H-purin-9-yl)-5-(((3-(2-(5-(tert-butyl)-1H-benzo[d]imidazol-2-yl)ethyl)cyclobutyl)(isopropyl) amino)methyl)tetrahydrofuran-3,4-diol (e.g., (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol) or a hydrate thereof, by slow evaporation, solvent-mediated phase transition, anti-solvent addition, solvent sweeping, or vapor diffusion. In one embodiment, the crystalline form of the present invention is prepared by slow evaporation, solvent-mediated phase transition, or anti-solvent addition In one embodiment, the process comprises recrystallizing 2-(6-amino-9H-purin-9-yl)-5-(((3-(2-(5-(tert-butyl)-1H-benzo[d]imidazol-2-yl)ethyl)cyclobutyl)(isopropyl) amino) methyl)tetrahydrofuran-3,4-diol in a mixture of acetonitrile and water. In one embodiment, the crystalline form is Form A, Form B, or Form C.

The present invention relates to a compound of formula I:

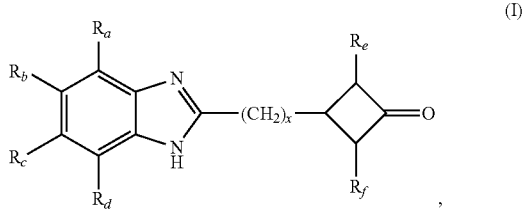

or a salt or solvate thereof, wherein:
$R_a$, $R_b$, $R_c$, and $R_d$ are each independently -$M_2$-$T_2$;
$M_2$ is a bond, $S(O)_2$, $S(O)$, S, C(O), C(O)O, O, O—$C_1$-$C_4$ alkyl linker, $C_1$-$C_4$ alkyl linker, NH, or $NR_t$;
$R_t$ is $C_1$-$C_6$ alkyl;
$T_2$ is H, halogen, or $R_{S4}$;
$R_{S4}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl;
$R_e$ and $R_f$ are each independently H or $C_1$-$C_6$ alkyl; and
x is 1, 2, 3, 4, 5, or 6,
wherein each of O—$C_1$-$C_4$ alkyl linker, $C_1$-$C_4$ alkyl linker, $R_t$, and $R_{S4}$ is optionally substituted with one or more substituents selected from the group consisting of halogen, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl.

The present invention relates to a process for preparing (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol or a salt or hydrate thereof, comprising the steps of:

(1) reacting 9-((3aR,4R,6R,6aR)-6-(aminomethyl)-2,2-dimethyltetrahydrofuro[3,4-d][1,3]dioxol-4-yl)-9H-purin-6-amine with acetone to yield 9-((3aR,4R,6R,6aR)-6-((isopropylamino)methyl)-2,2-dimethyltetrahydrofuro[3,4-d][1,3]dioxol-4-yl)-9H-purin-6-amine;

(2) reacting 9-((3aR,4R,6R,6aR)-6-((isopropylamino)methyl)-2,2-dimethyltetrahydrofuro[3,4-d][1,3]dioxol-4-yl)-9H-purin-6-amine with 3-(2-(5-(tert-butyl)-1H-benzo[d]imidazol-2-yl)ethyl)cyclobutanone to yield 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine; and (3) converting 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine to (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol.

The process of the present invention may further comprise step (4): recrystallizing (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol to yield (2R,3R,4S,5R)-2-(6-amino-9H-purin-9-yl)-5-((((1r,3S)-3-(2-(5-(tert-butyl)-1H-benzo[d]imidazol-2-yl)ethyl) cyclobutyl)(isopropyl)amino)methyl) tetrahydrofuran-3,4-diol or a salt of hydrate thereof.

The present invention relates to a process for preparing 3-(2-(5-(tert-butyl)-1H-benzo[d]imidazol-2-yl)ethyl)cyclobutanoneor a salt thereof, comprising the steps of:

(1) converting pent-4-enoic acid to benzyl pent-4-enoate;
(2) converting benzyl pent-4-enoate to benzyl 3-(2,2-dichloro-3-oxo-cyclobutyl)propanoate;
(3) converting benzyl 3-(2,2-dichloro-3-oxo-cyclobutyl) propanoate to benzyl 3-(3-oxo-cyclobutyl)propanoate;
(4) converting benzyl 3-(3-oxo-cyclobutyl)propanoate to 3-(3-oxo-cyclobutyl)propanoic acid;
(5) reacting 3-(3-oxocyclobutyl)propanoic acid with 4-tert-butyl-2-nitroaniline to yield N-(4-tert-butyl-2-nitrophenyl)-3-(3-oxo-cyclobutyl)propanamide; and
(6) converting N-(4-tert-butyl-2-nitrophenyl)-3-(3-oxo-cyclobutyl)propanamide to 3-(2-(5-(tert-butyl)-1H-benzo[d]imidazol-2-yl)ethyl)cyclobutanone. In one embodiment, 3-(2-(5-(tert-butyl)-1H-benzo[d]imidazol-2-yl)ethyl)cyclobutanone salt is a hydrochloride salt.

The present invention relates to methods of treating or preventing cancer. The present invention provides methods of treating cancer. The present invention also provides methods of preventing cancer. The method includes administering to a subject in need thereof a therapeutically effective amount of 2-(6-amino-9H-purin-9-yl)-5-(((3-(2-(5-(tert-butyl)-1H-benzo[d]imidazol-2-yl)ethyl)cyclobutyl)(isopropyl)amino) methyl)tetrahydrofuran-3,4-diol (e.g., (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino) methyl)tetrahydrofuran-3,4-diol) or a pharmaceutically acceptable salt or solvate thereof. The cancer can be a hematological cancer. In one embodiment, the cancer is leukemia. In a further embodiment, the cancer is acute myeloid leukemia, acute lymphocytic leukemia, or mixed lineage leukemia.

BRIEF DESCRIPTION OF THE DRAWINGS

FIG. 116 is a $^1$H NMR spectrum of EP-1 trihydrate (x is 3) 1,5-naphthalene disulfonic hemi-salt.

FIG. 117 is a $^1$H NMR spectrum of EP-1 trihydrate (x is 3) maleic hemi-salt.

FIG. 118 is a $^1$H NMR spectrum of EP-1 trihydrate (x is 3) $H_3PO_4$ hemi-salt.

FIG. 119 is a $^1$H NMR spectrum of EP-1 trihydrate (x is 3) HCl bis-salt.

FIG. 120 is a $^1$H NMR spectrum of EP-1 trihydrate (x is 3) 1,5-naphthalene disulfonic bis-salt.

FIG. 121 is a TGA/DSC plot of EP-1 trihydrate (x is 3) 1,5-naphthalene disulfonic bis-salt.

FIG. 122 is a $^1$H NMR spectrum of EP-1 trihydrate (x is 3) $H_2SO_4$ bis-salt.

FIG. 123 is a TGA/DSC plot of EP-1 trihydrate (x is 3) $H_2SO_4$ bis-salt.

FIG. 124 is a $^1$H NMR spectrum of EP-1 trihydrate (x is 3) p-toluene sulfonic bis-salt.

FIG. 125 is a $^1$H NMR spectrum of EP-1 trihydrate (x is 3) methane sulfonic bis-salt.

FIG. 126 is a $^1$H NMR spectrum of EP-1 trihydrate (x is 3) benzene sulfonic bis-salt.

FIG. 127 is a $^1$H NMR spectrum of EP-1 trihydrate (x is 3) aspartic bis-salt.

Figure 128:
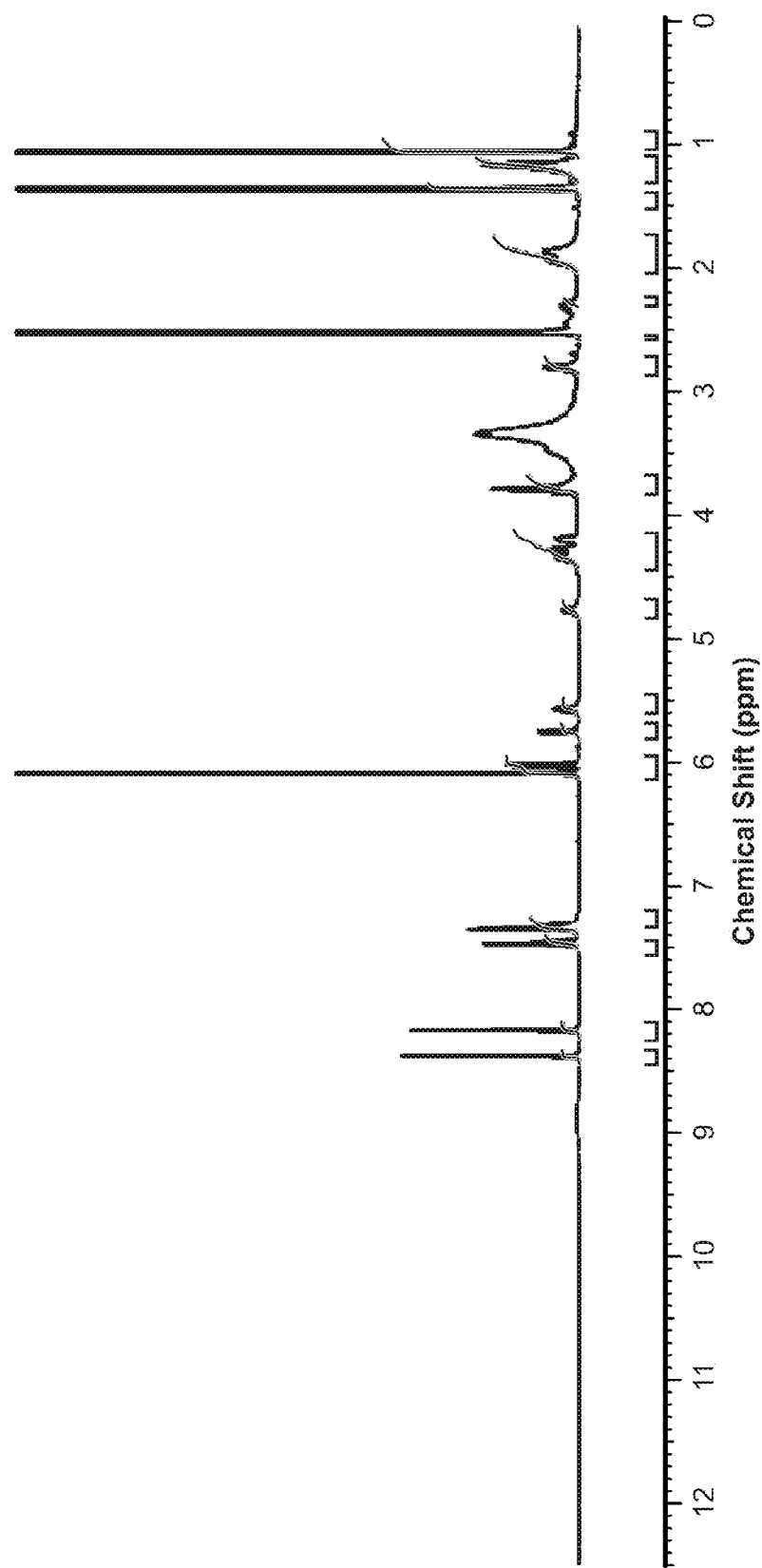

FIG. 128 is a $^1$H NMR spectrum of EP-1 trihydrate (x is 3) maleic bis-salt.

Figure 129:
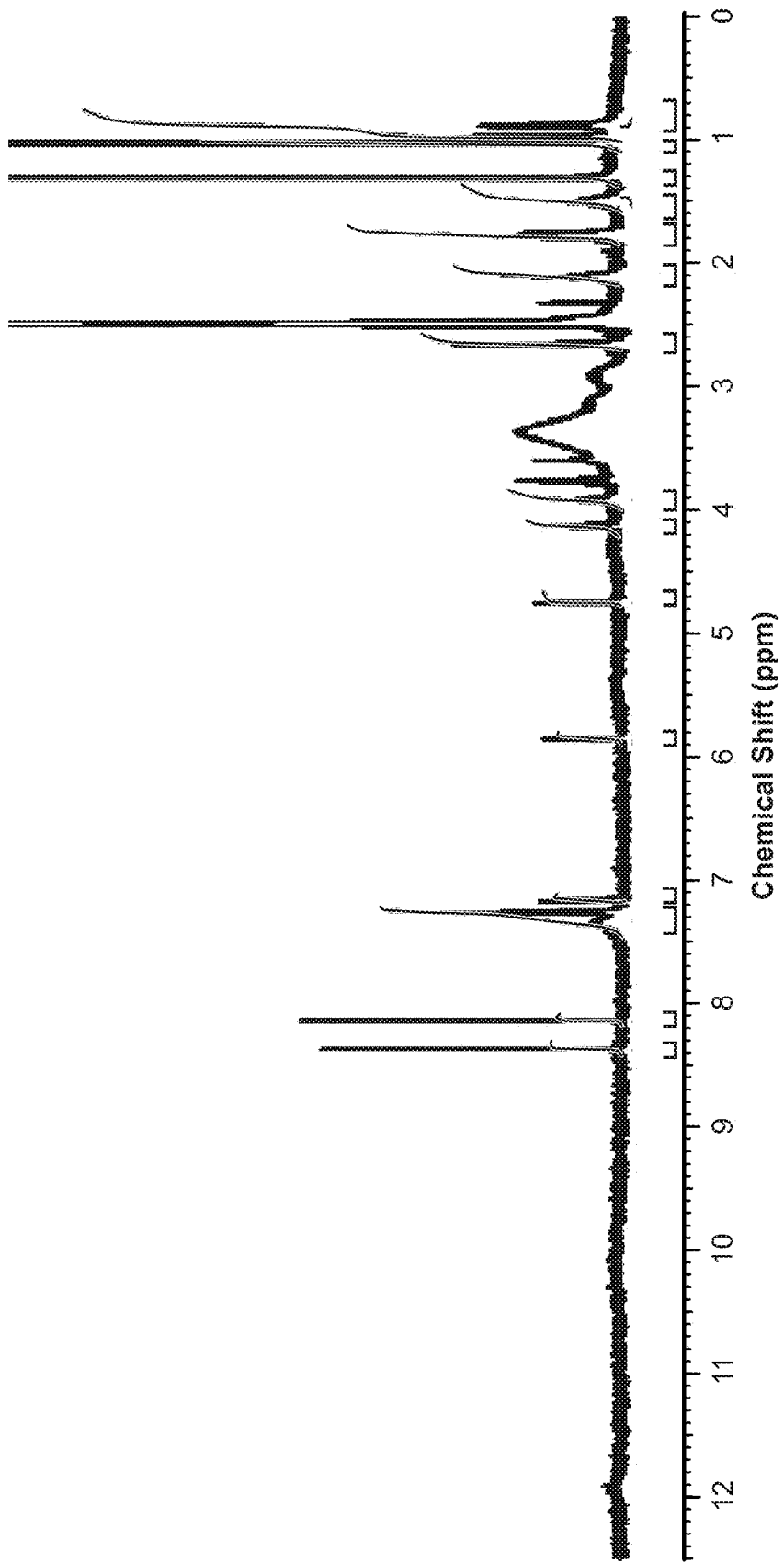

FIG. 129 is a $^1$H NMR spectrum of EP-1 trihydrate (x is 3) $H_3PO_4$ bis-salt.

Figure 130:
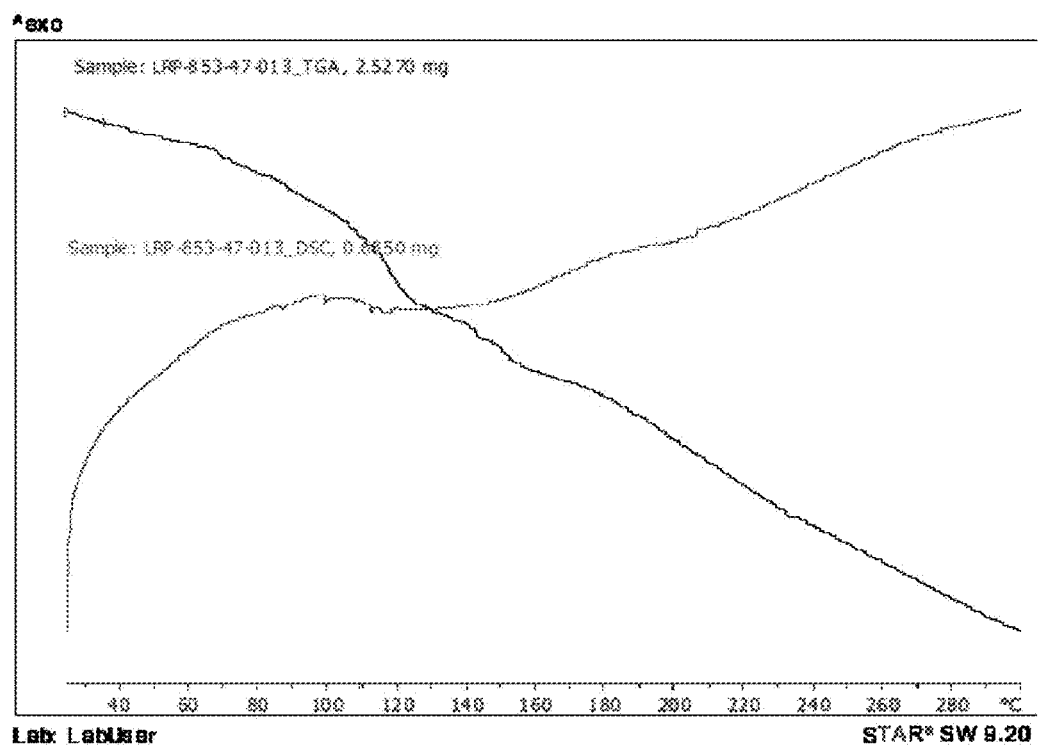

FIG. 130 is a TGA/DSC plot of EP-1 trihydrate (x is 3) $H_3PO_4$ bis-salt.

Figure 131:
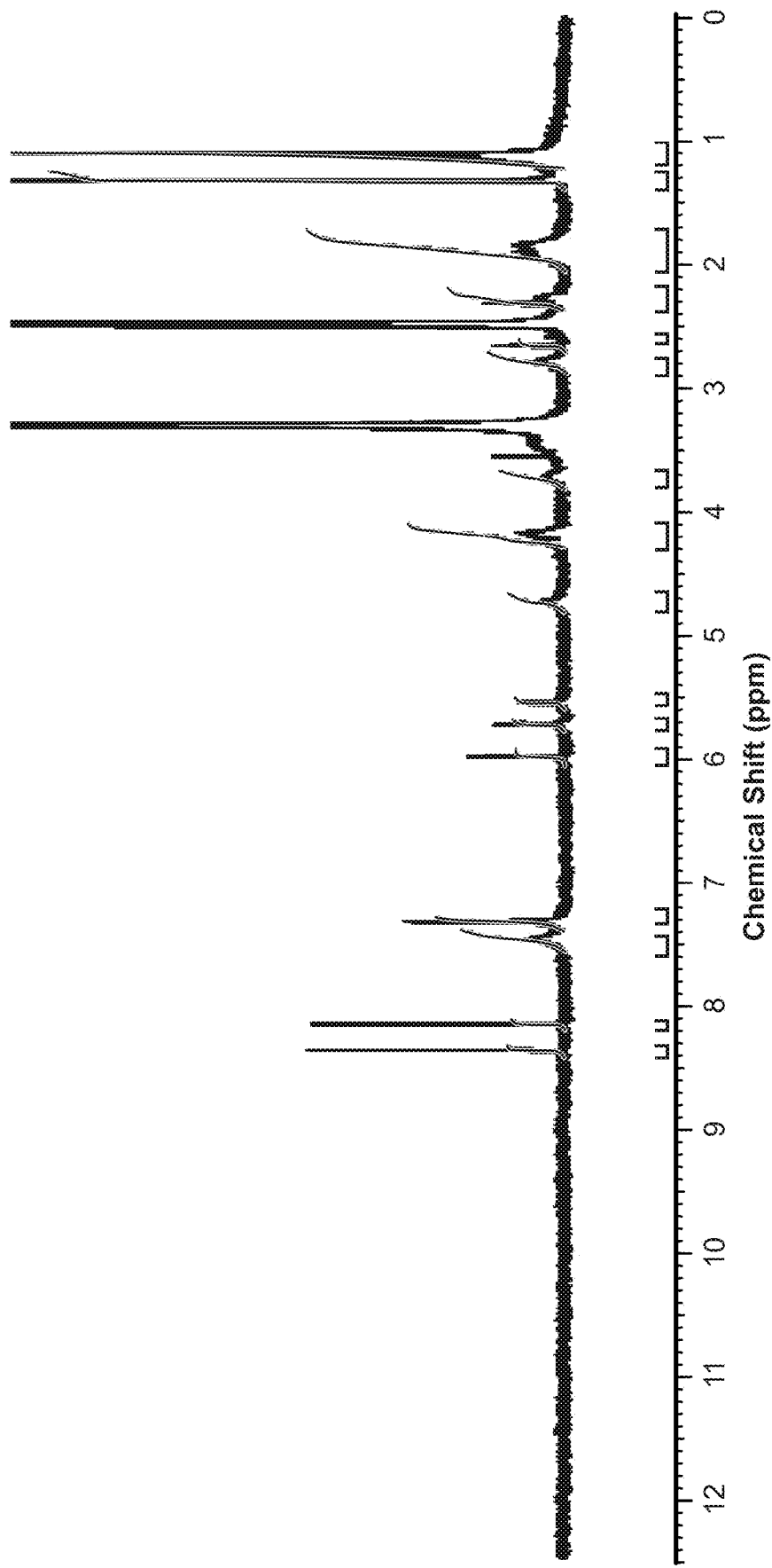

FIG. 131 is a $^1$H NMR spectrum of EP-1 trihydrate (x is 3) salt obtained by lyophilization from HCl.

Figure 132:
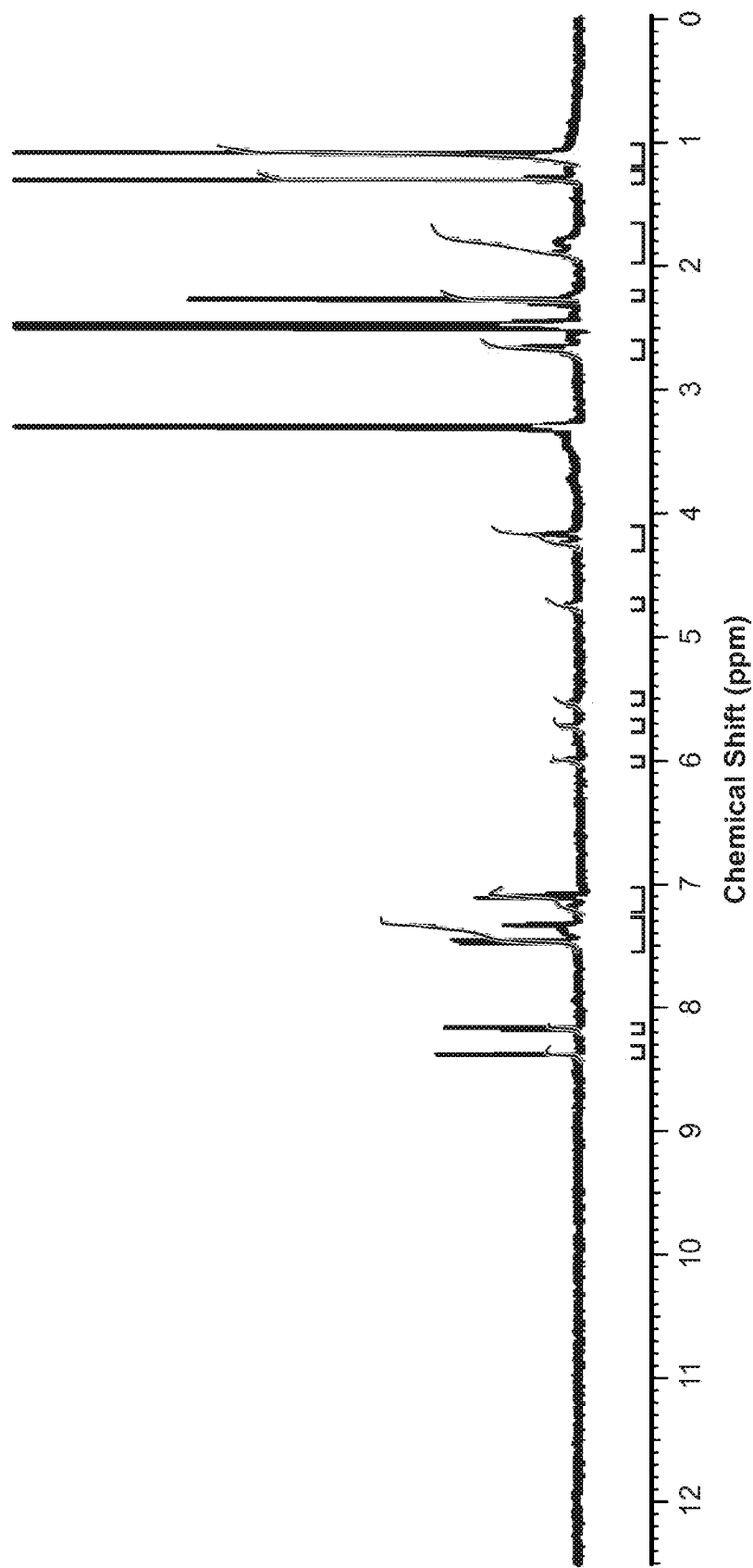

FIG. 132 is a $^1$H NMR spectrum of EP-1 trihydrate (x is 3) salt obtained by lyophilization from p-toluene sulfonic acid.

Figure 133:
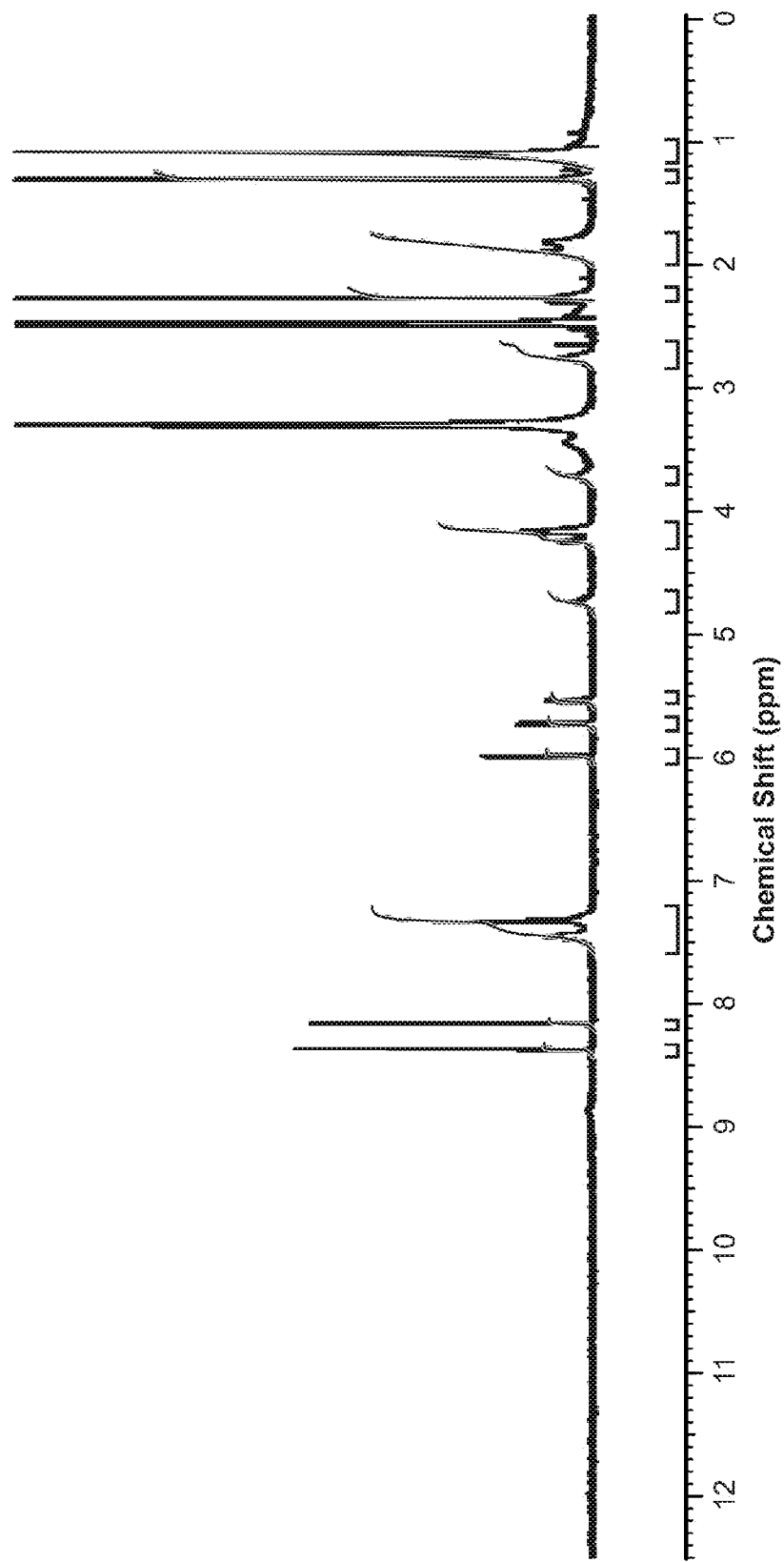

FIG. 133 is a $^1$H NMR spectrum of EP-1 trihydrate (x is 3) salt obtained by lyophilization from methane sulfonic acid.

Figure 134:
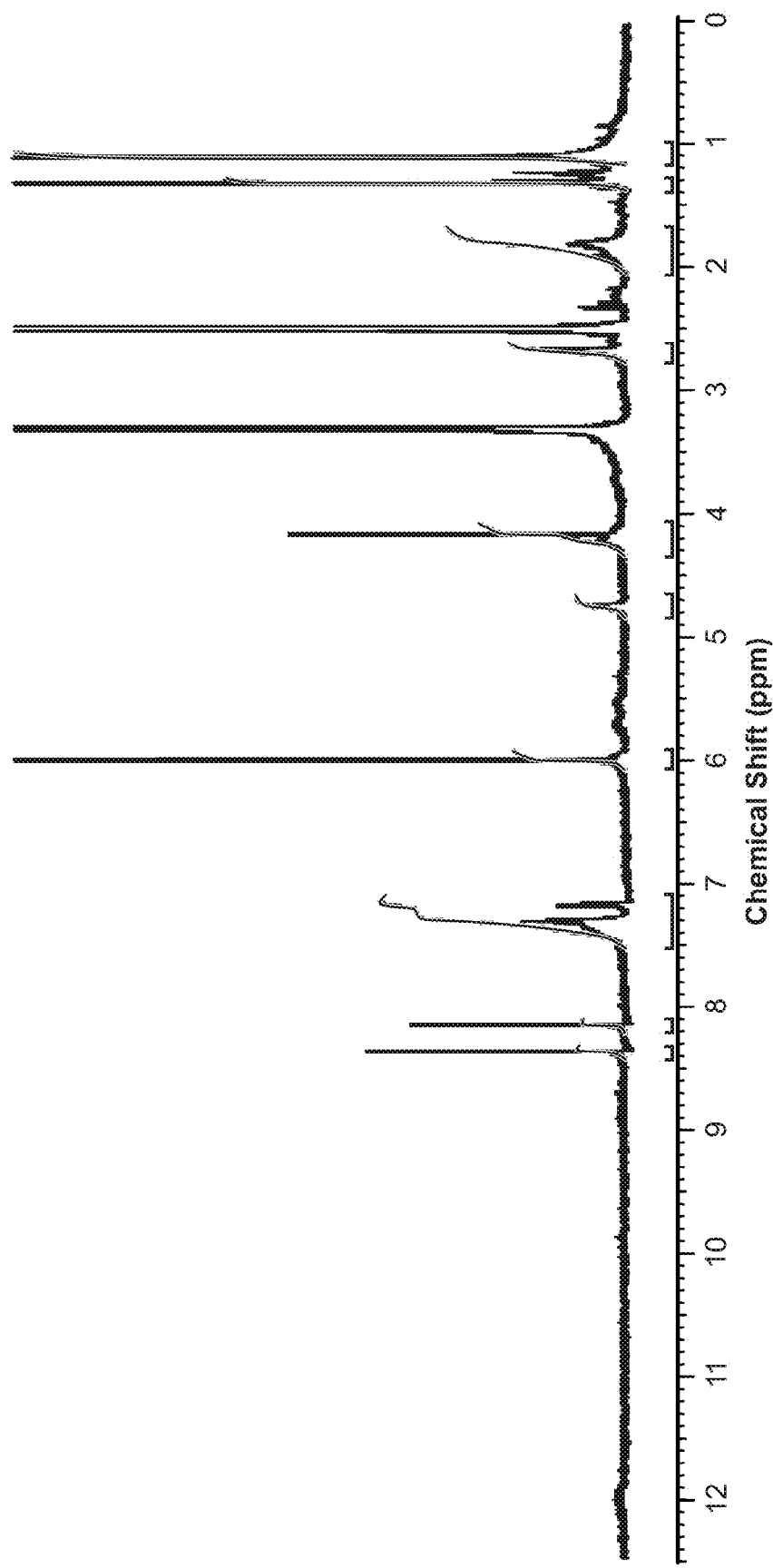

FIG. 134 is a $^1$H NMR spectrum of EP-1 trihydrate (x is 3) salt obtained by lyophilization from maleic acid.

Figure 135:
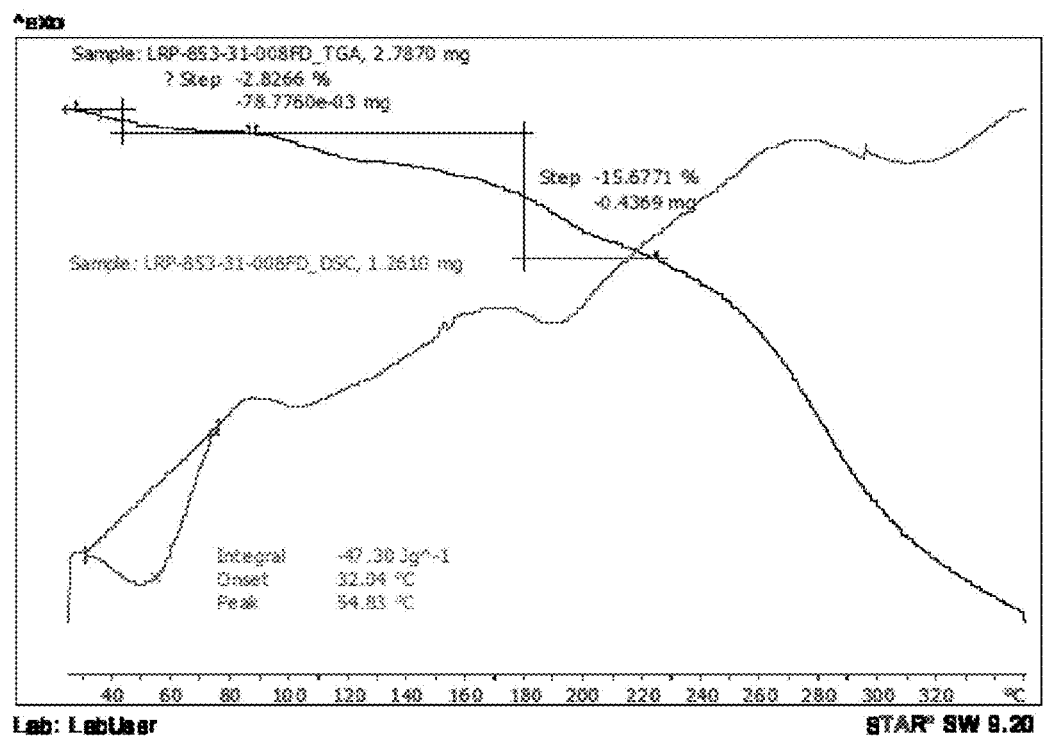

FIG. 135 is a TGA/DSC plot of EP-1 trihydrate (x is 3) salt obtained by lyophilization from maleic acid.

Figure 136:
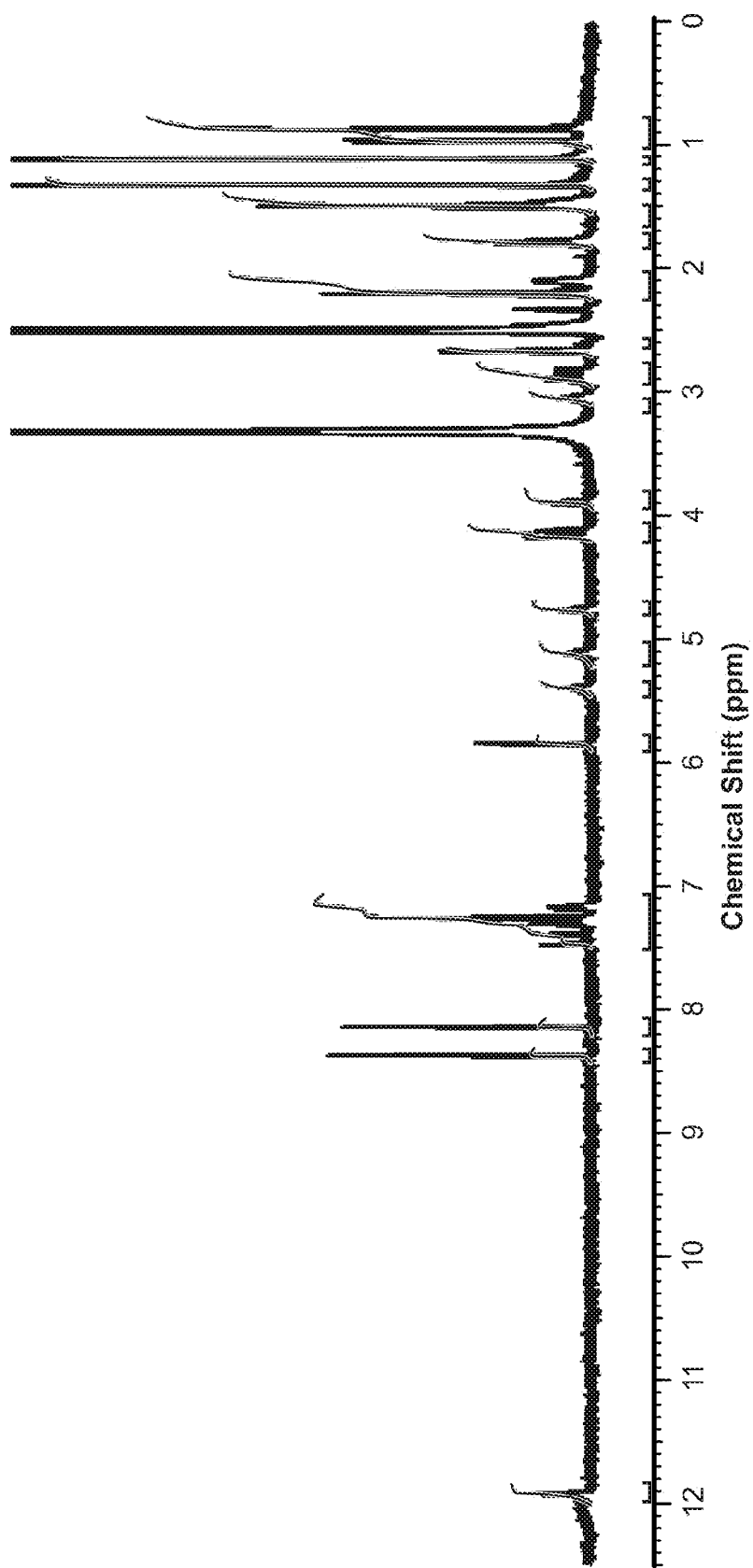

FIG. 136 is a $^1$H NMR spectrum of EP-1 trihydrate (x is 3) salt obtained by lyophilization from adipic acid.

Figure 137:
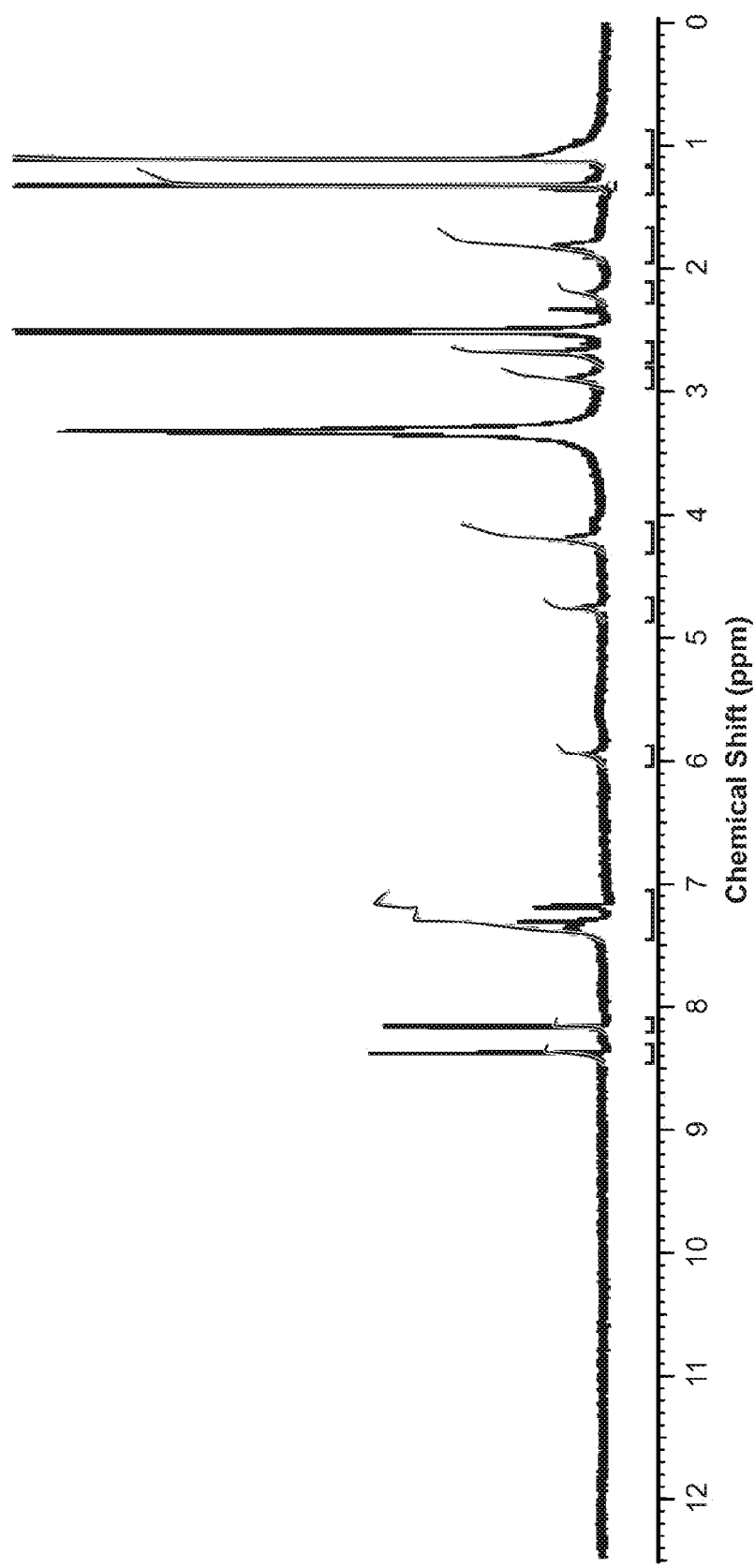

FIG. 137 is a $^1$H NMR spectrum of EP-1 trihydrate (x is 3) salt obtained by lyophilization from malonic acid.

Figure 138:
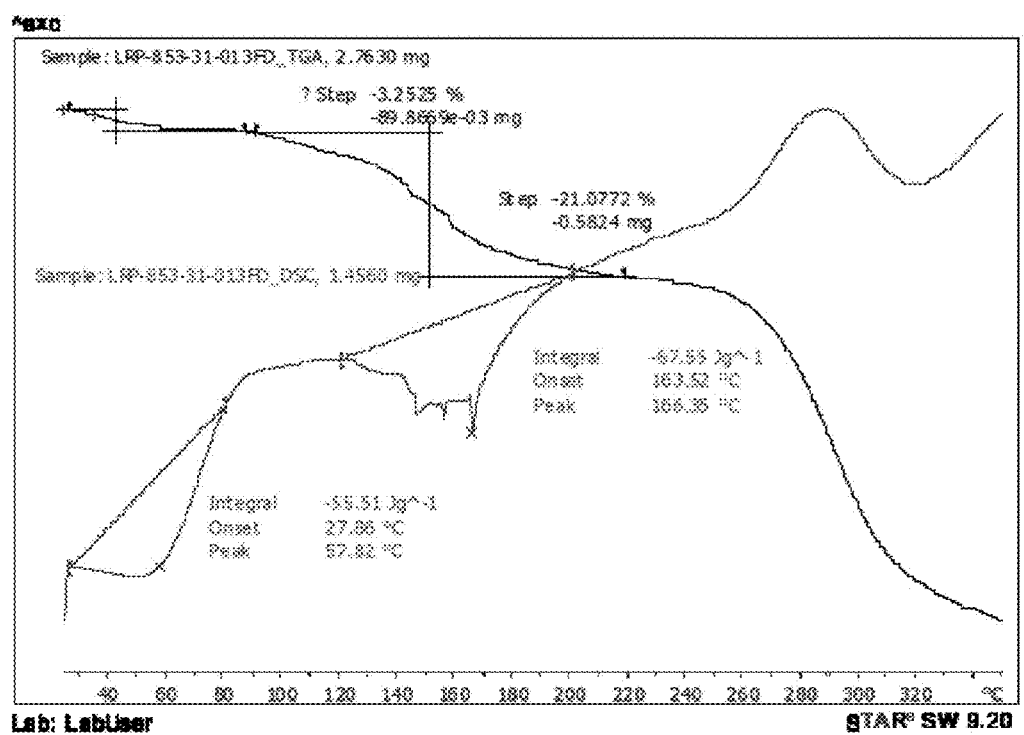

FIG. 138 is a TGA/DSC plot of EP-1 trihydrate (x is 3) salt obtained by lyophilization from malonic acid.

Figure 139:
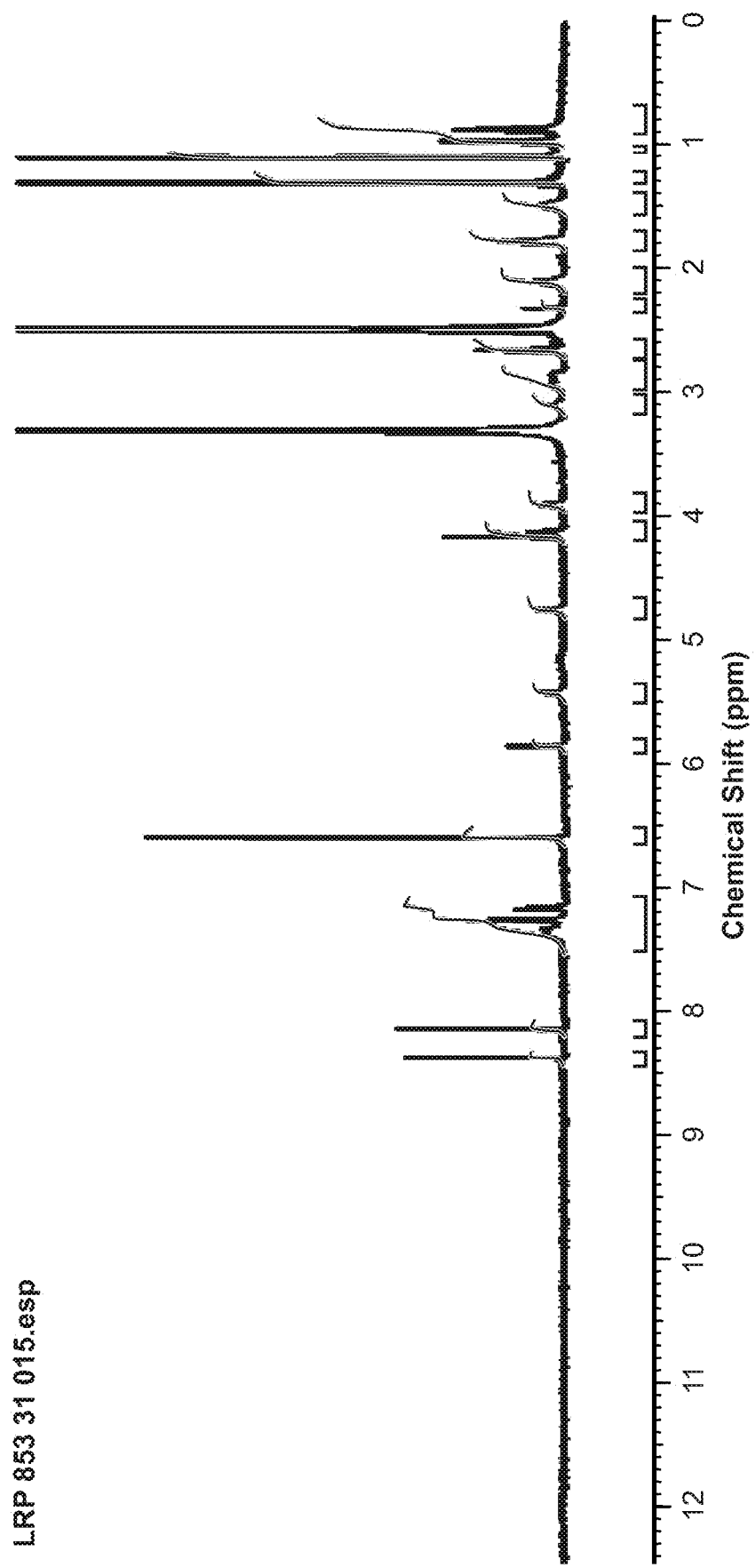

FIG. 139 is a $^1$H NMR spectrum of EP-1 trihydrate (x is 3) salt obtained by lyophilization from fumaric acid.

Figure 140:
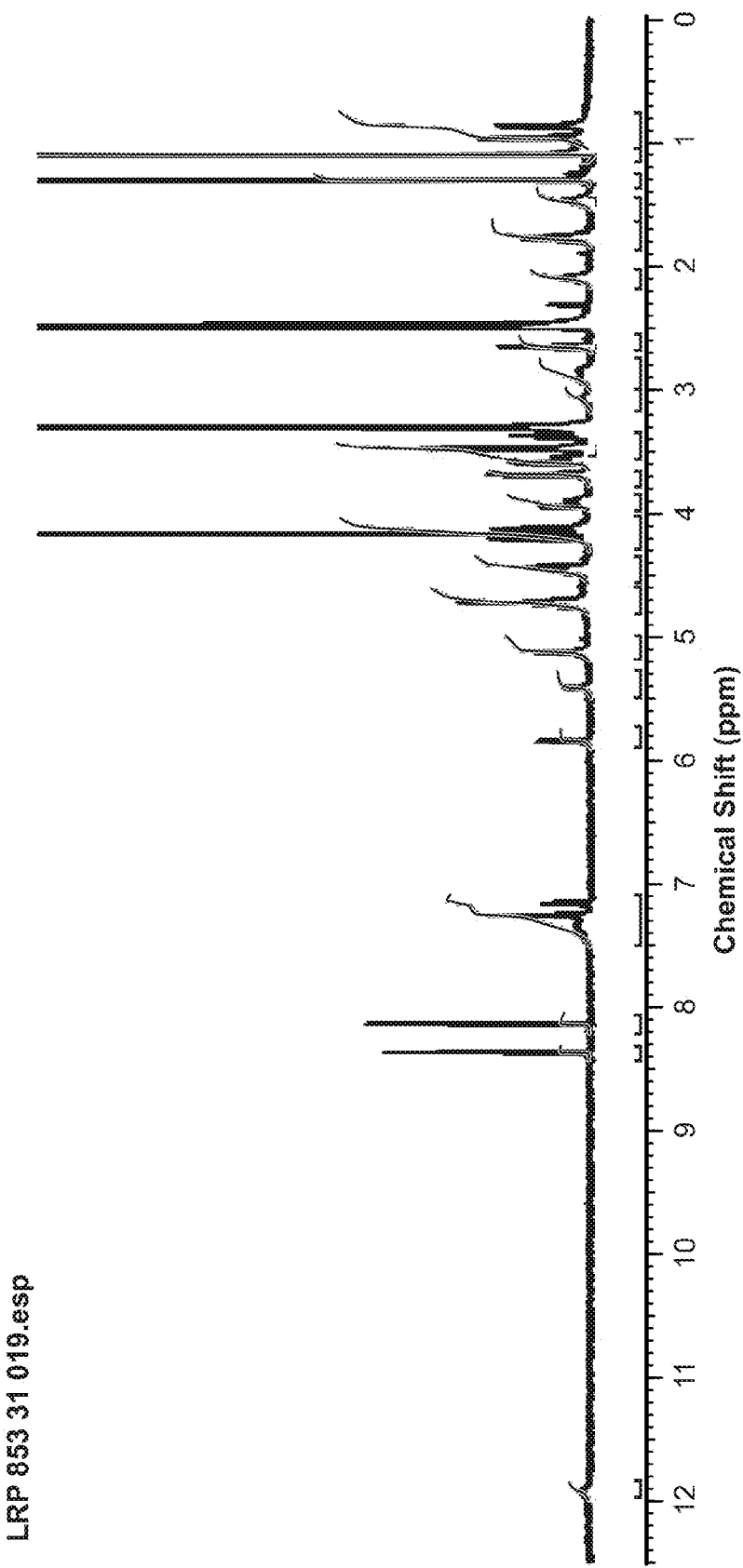

FIG. 140 is a $^1$H NMR spectrum of EP-1 trihydrate (x is 3) salt obtained by lyophilization from lactobionic acid.

Figure 141:
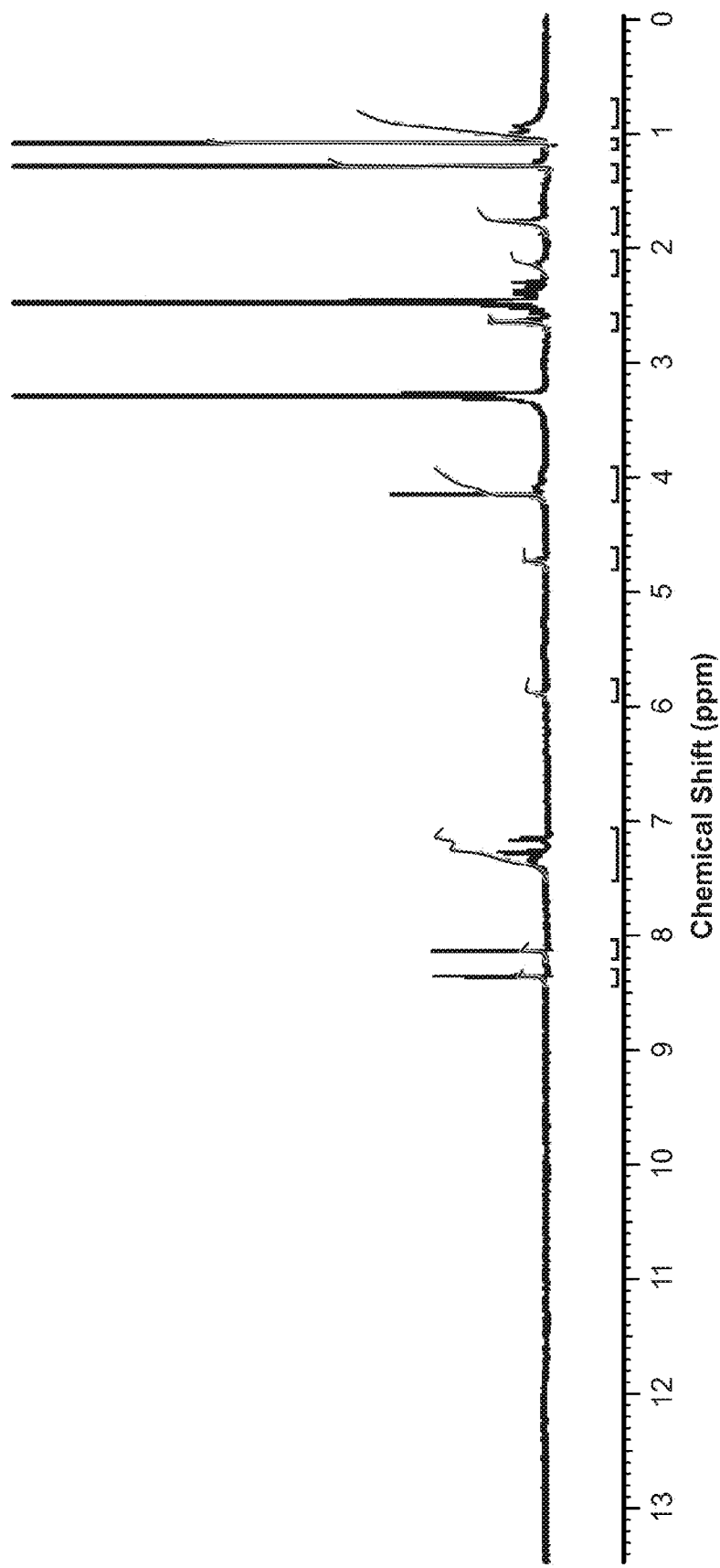

FIG. 141 is a $^1$H NMR spectrum of EP-1 trihydrate (x is 3) salt obtained by lyophilization from L-malic acid.

Figure 142:
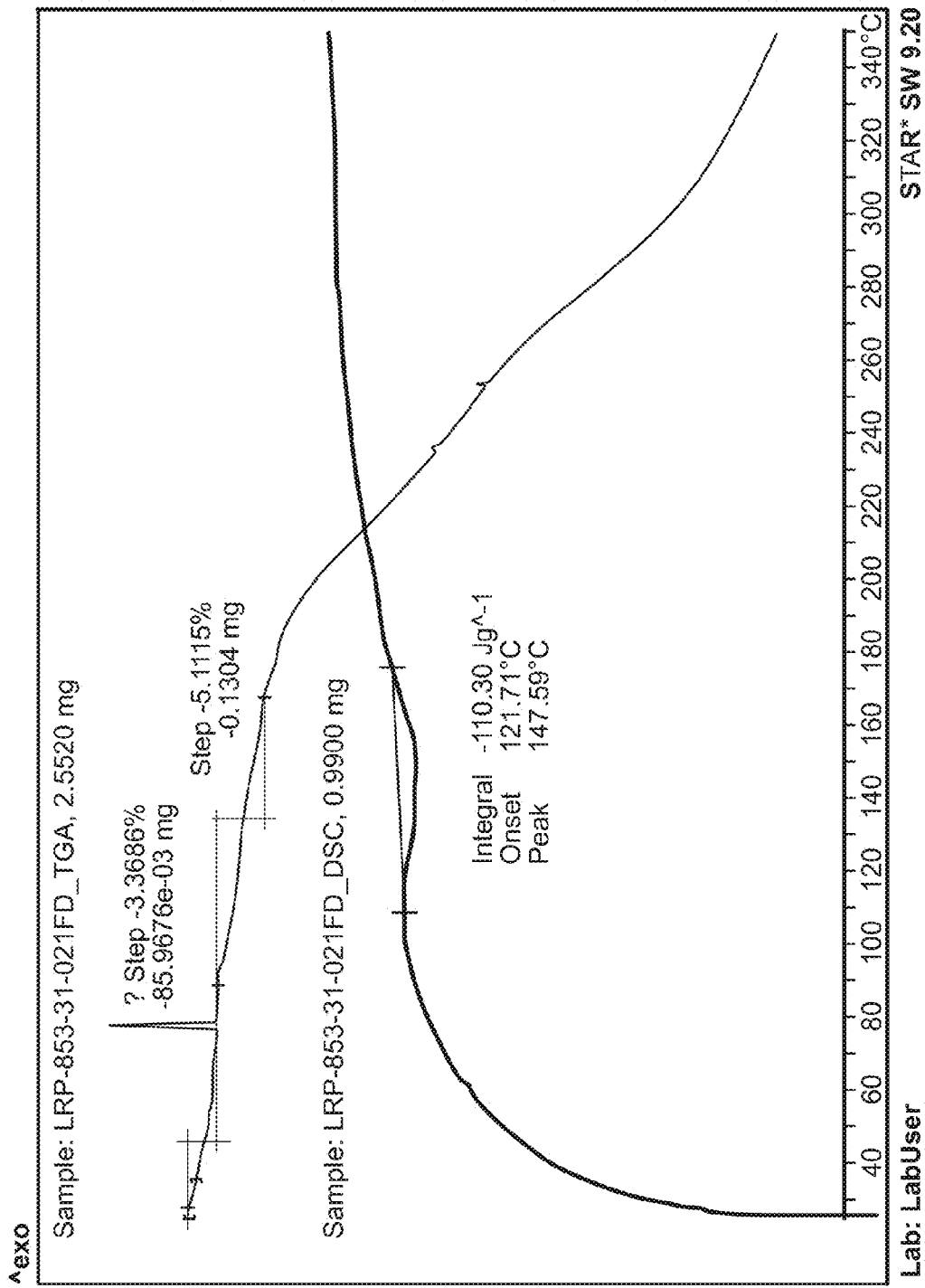

FIG. 142 is a TGA/DSC plot of EP-1 trihydrate (x is 3) salt obtained by lyophilization from L-malic acid.

Figure 143:
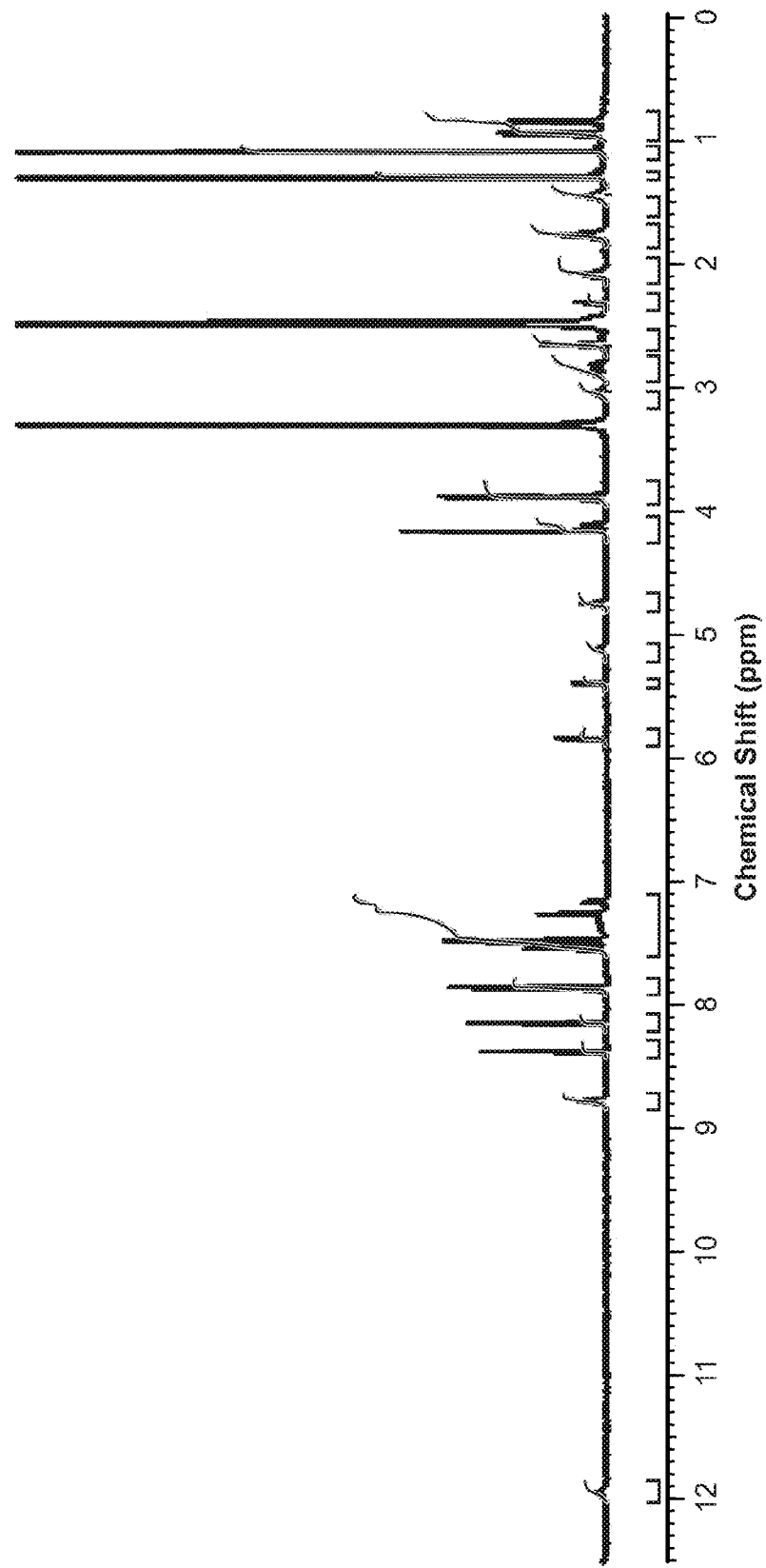

FIG. 143 is a $^1$H NMR spectrum of EP-1 trihydrate (x is 3) salt obtained by lyophilization from hippuric acid.

Figure 144:
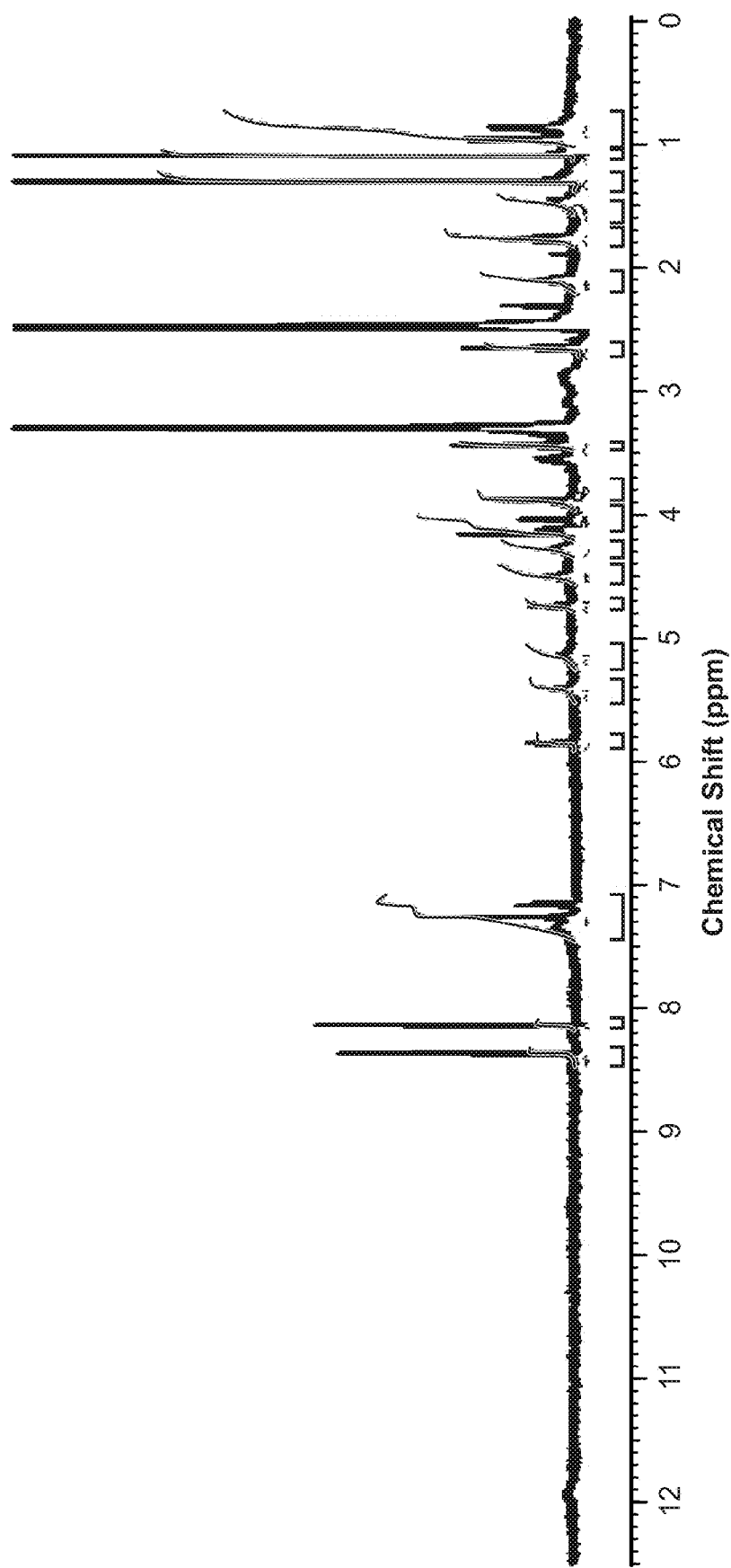

FIG. 144 is a $^1$H NMR spectrum of EP-1 trihydrate (x is 3) salt obtained by lyophilization from D-gluconic acid.

Figure 145:
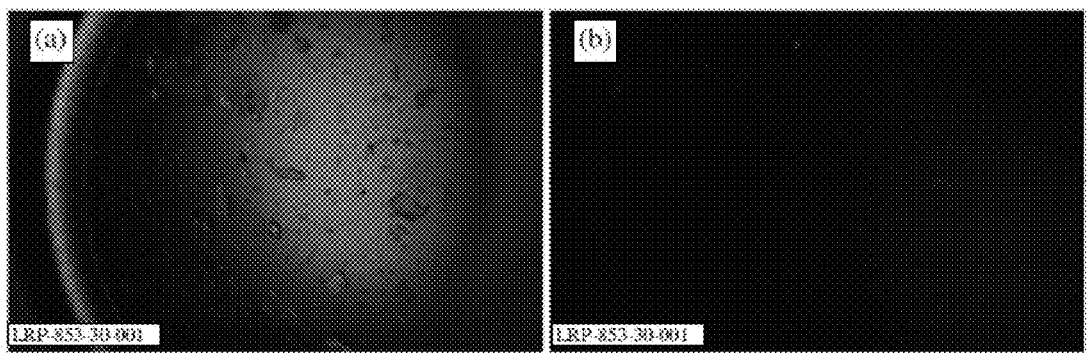

FIG. 145A is an image of glass materials of EP-1 trihydrate (x is 3) observed under normal light.

FIG. 145B is an image of glass materials of EP-1 trihydrate (x is 3) observed under polarized light.

FIG. 146A is an image showing birefringence in a powder sample under normal light.

FIG. 146B is an image showing birefringence in a powder sample under polarized light.

Figure 147:
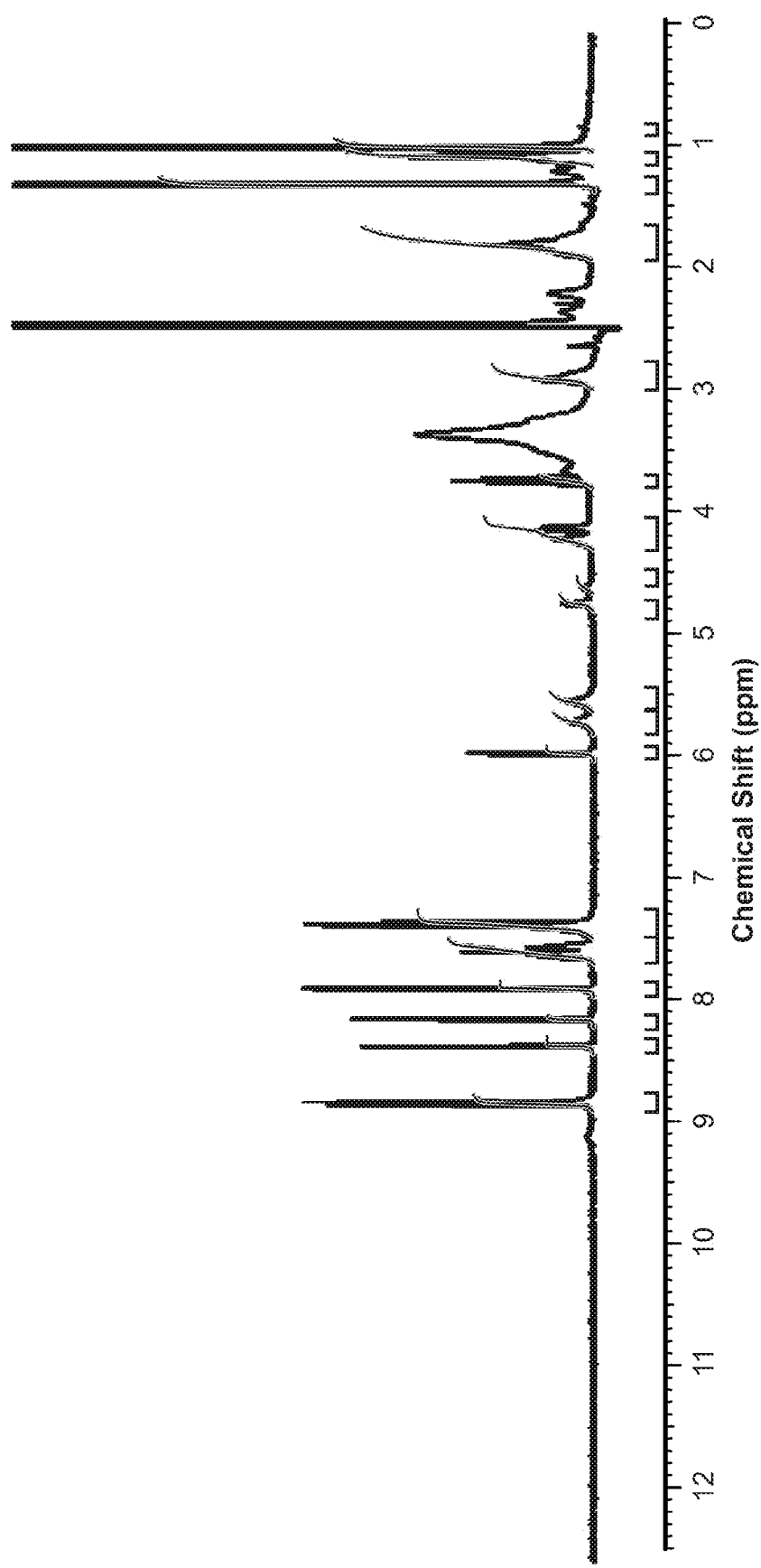

FIG. 147 is a $^1$H NMR spectrum of EP-1 trihydrate (x is 3) 1,5-naphthalene disulfonic salt.

Figure 148:
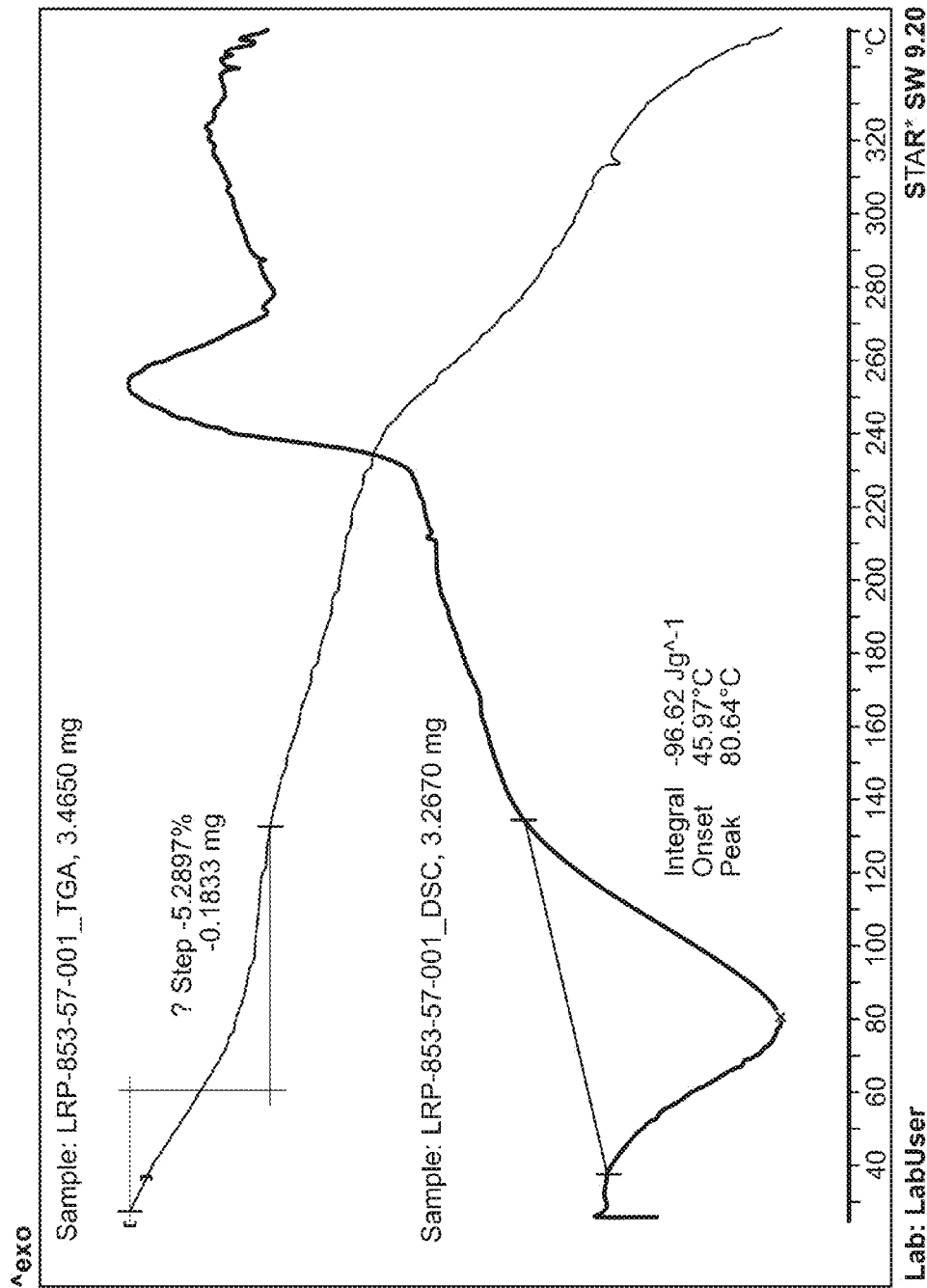

FIG. 148 is a TGA/DSC plot of EP-1 trihydrate (x is 3) 1,5-naphthalene disulfonic salt.

Figure 149:
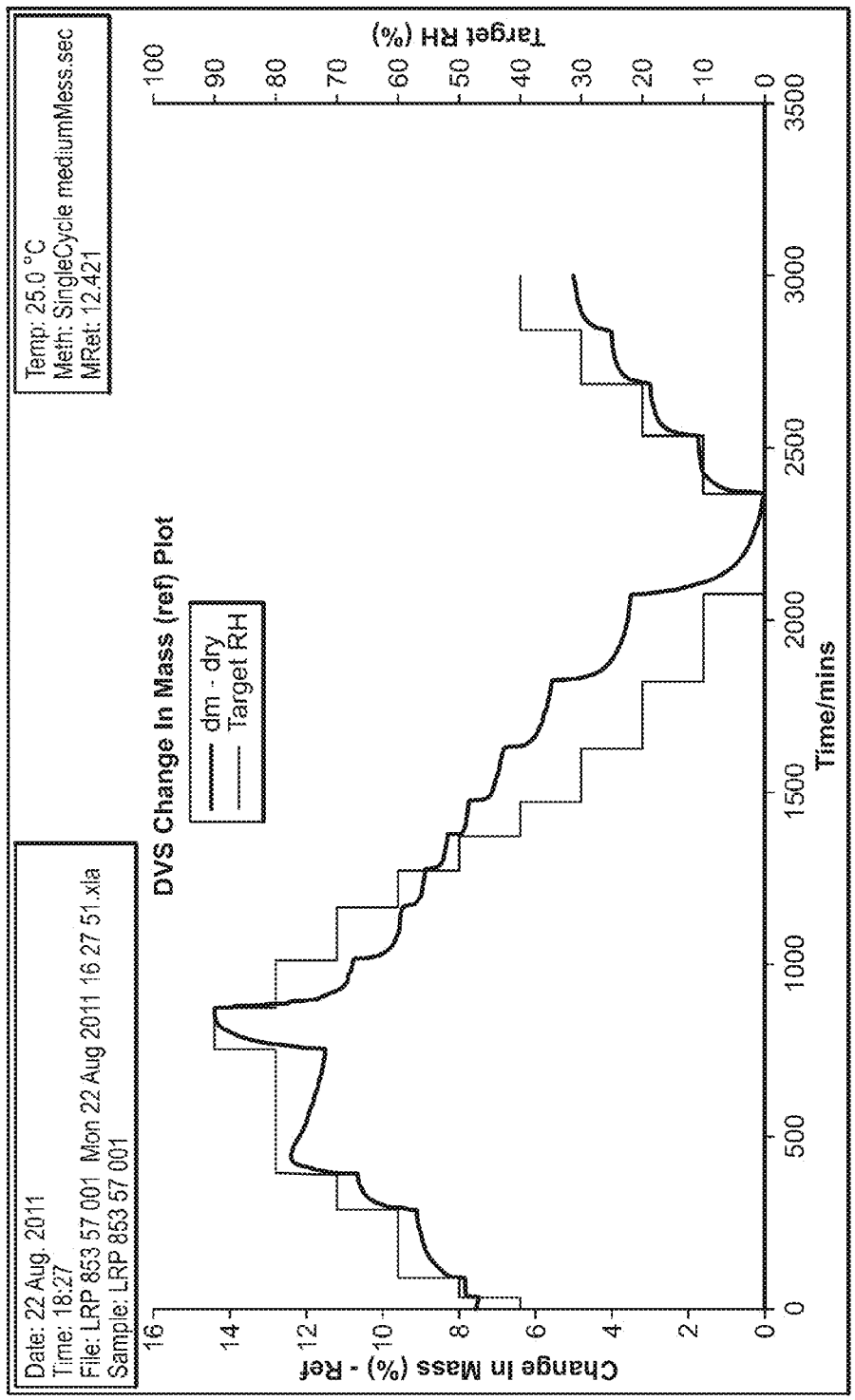

FIG. 149 is a GVS kinetic plot of EP-1 trihydrate (x is 3) 1,5-naphthalene disulfonic salt.

Figure 150:
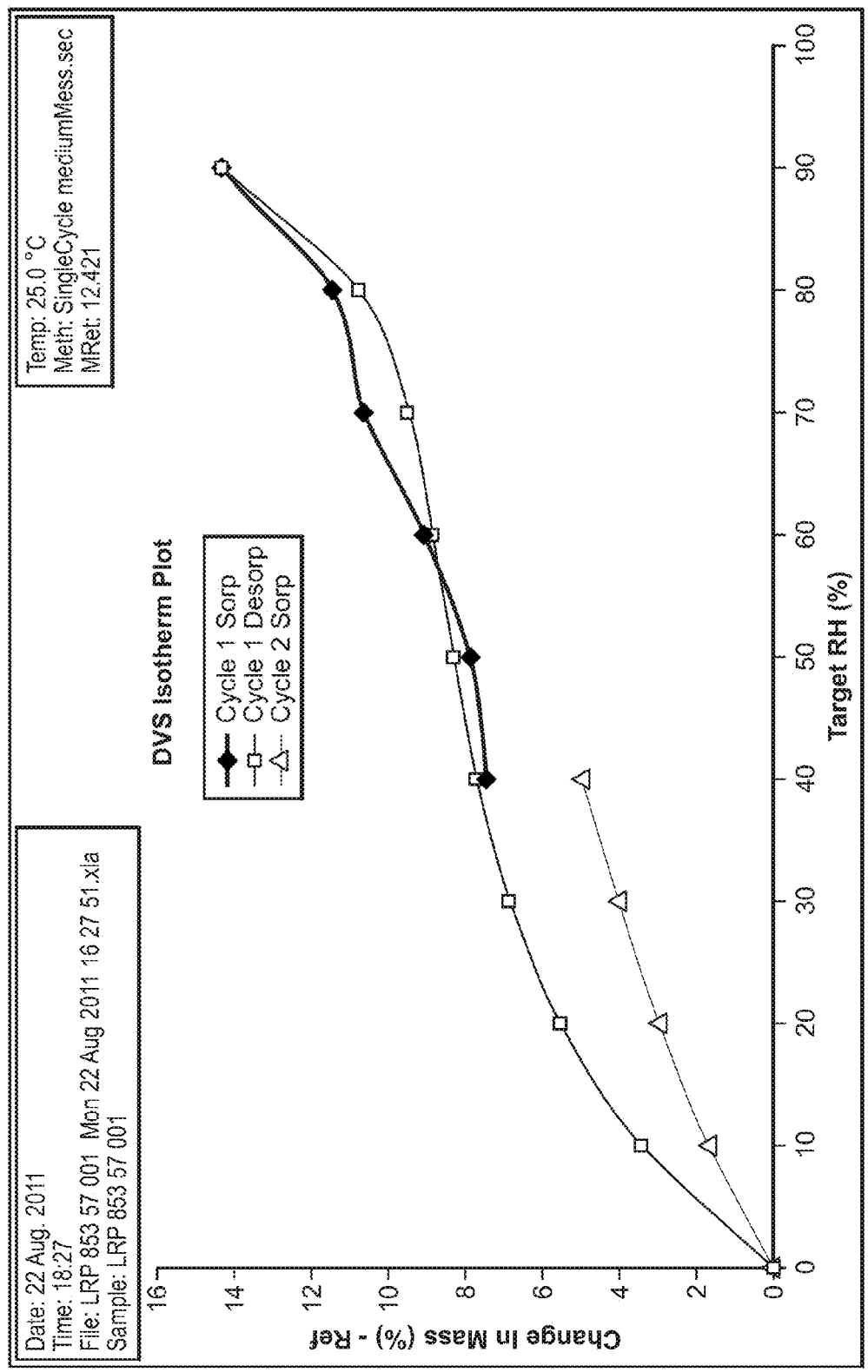

FIG. 150 is a GVS isotherm of EP-1 trihydrate (x is 3) 1,5-naphthalene disulfonic salt.

Figure 151:
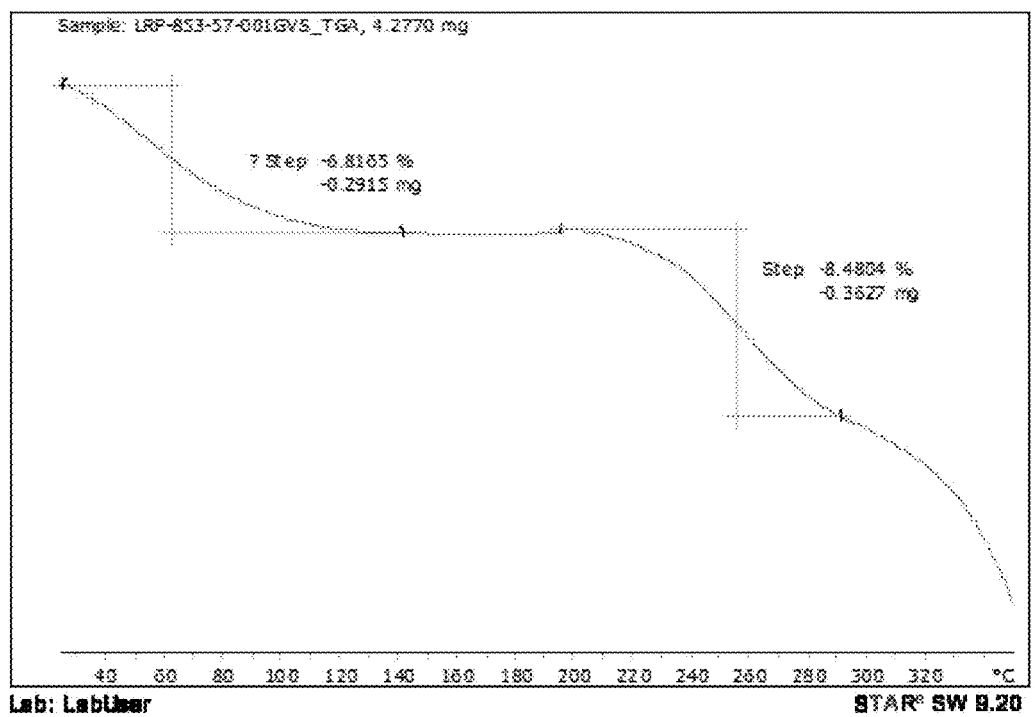

FIG. 151 is a TGA plot after GVS of EP-1 trihydrate (x is 3) 1,5-naphthalene disulfonic salt.

Figure 152:
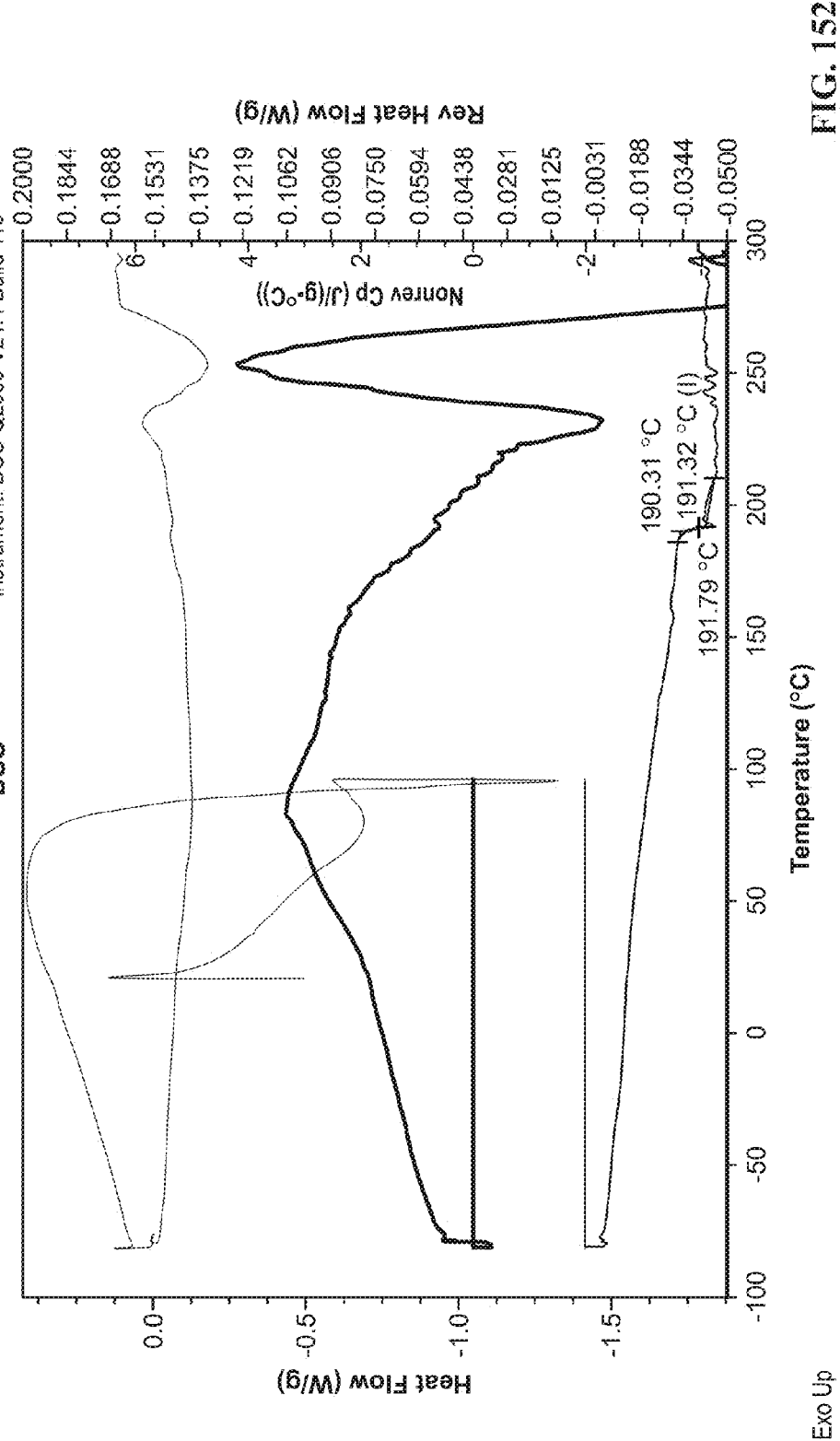

FIG. 152 is a mDSC plot of EP-1 trihydrate (x is 3) 1,5-naphthalene disulfonic salt.

Figure 153:
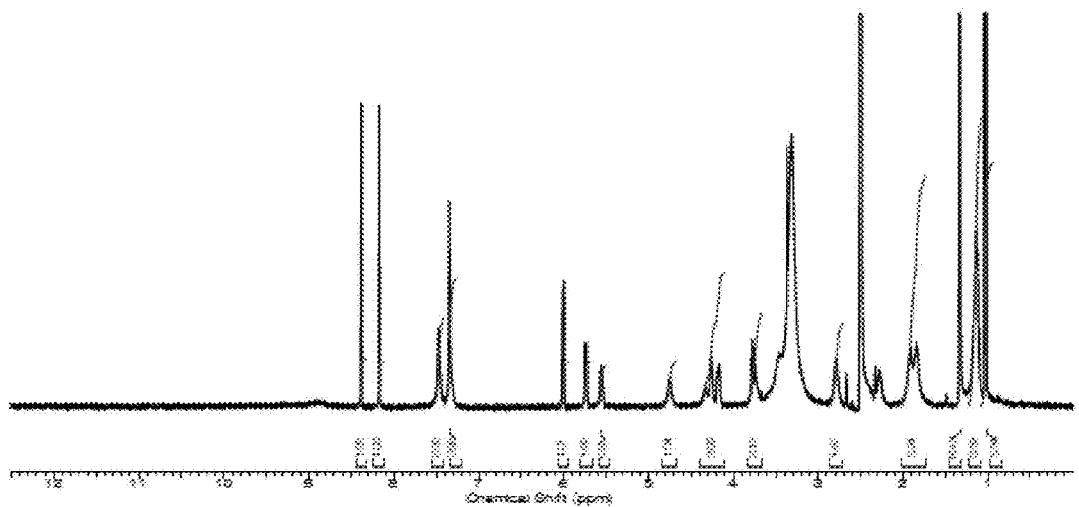

FIG. 153 is a $^1$H NMR spectrum of EP-1 trihydrate (x is 3) $H_2SO_4$ salt.

Figure 154:
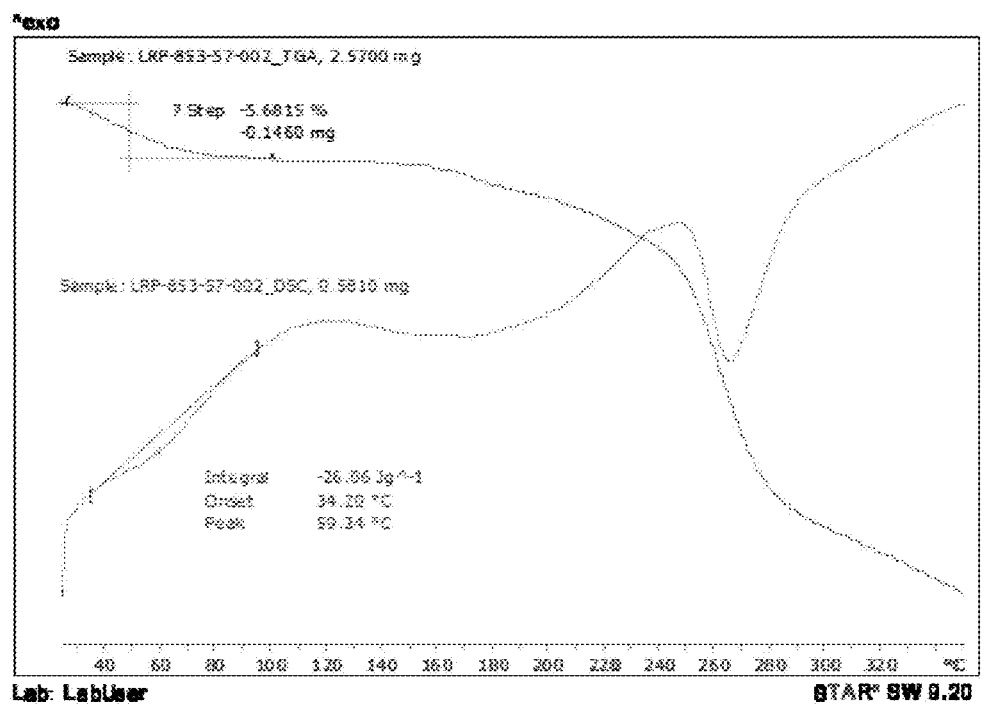

FIG. 154 is a TGA/DSC plot of EP-1 trihydrate (x is 3) $H_2SO_4$ salt.

Figure 155:
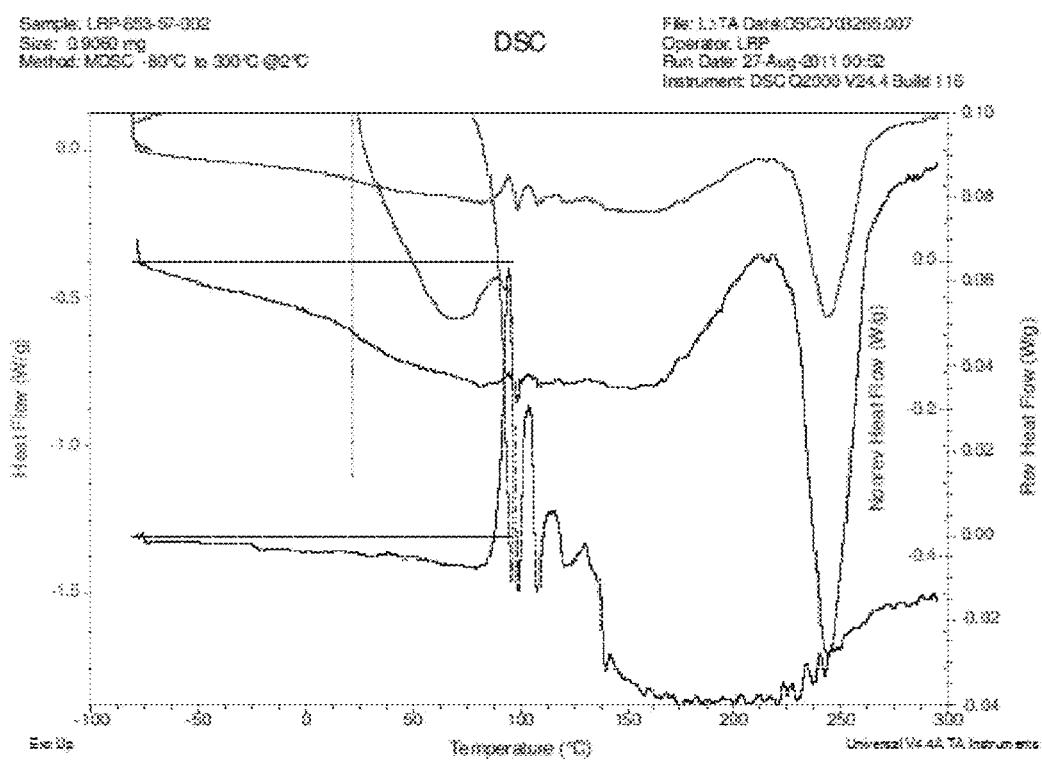

FIG. 155 is a mDSC plot of EP-1 trihydrate (x is 3) $H_2SO_4$ salt.

Figure 156:
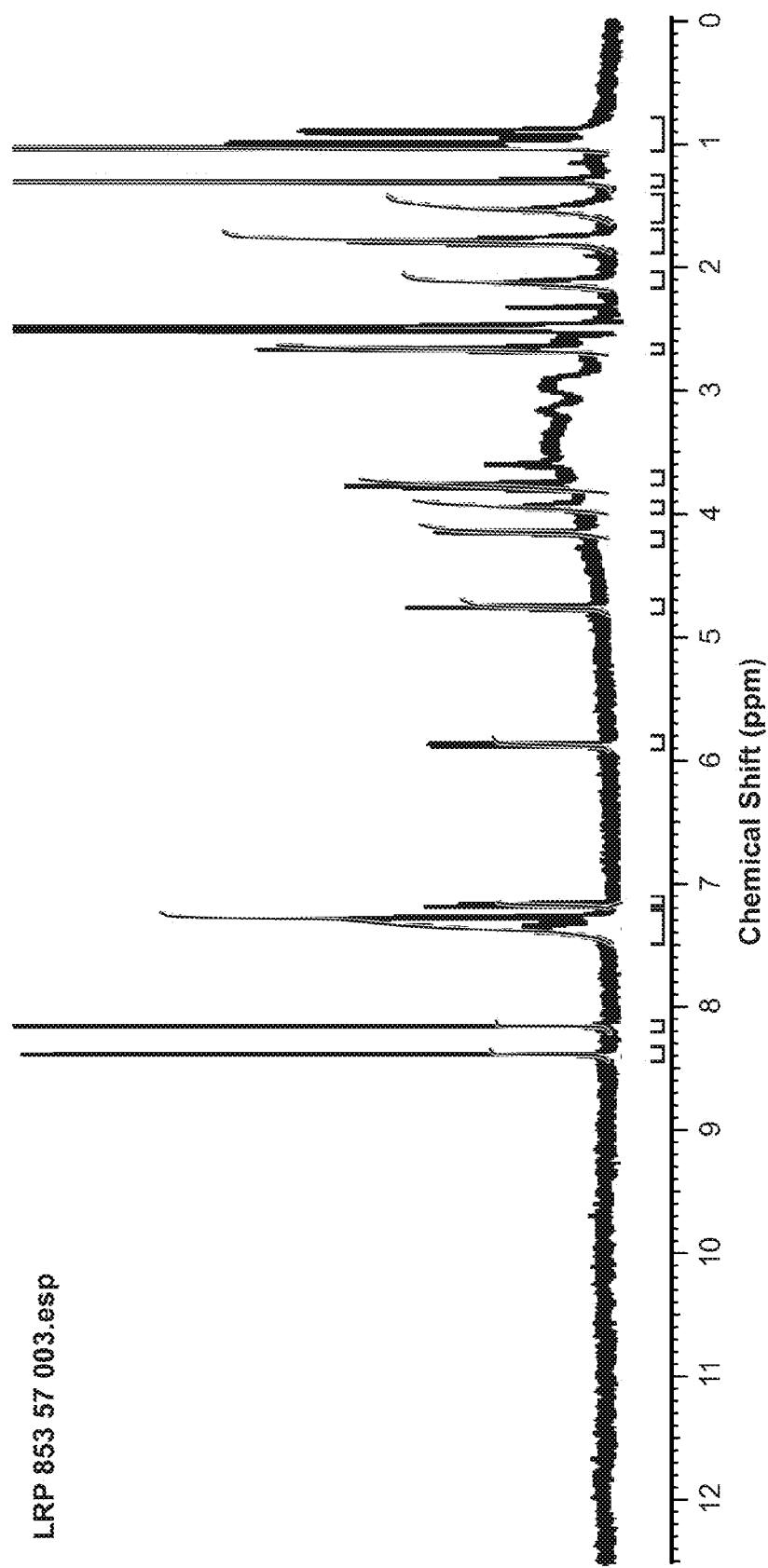

FIG. 156 is a $^1$H NMR spectrum of EP-1 trihydrate (x is 3) $H_3PO_4$ salt.

Figure 157:
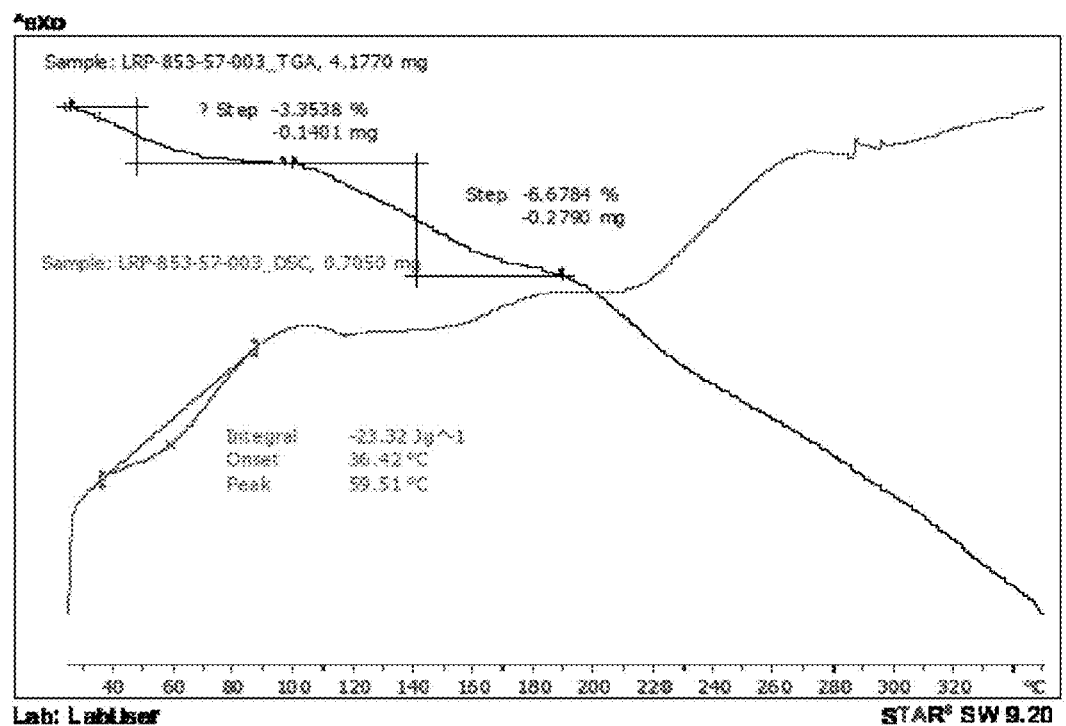

FIG. 157 is a TGA/DSC plot of EP-1 trihydrate (x is 3) $H_3PO_4$ salt.

Figure 158:
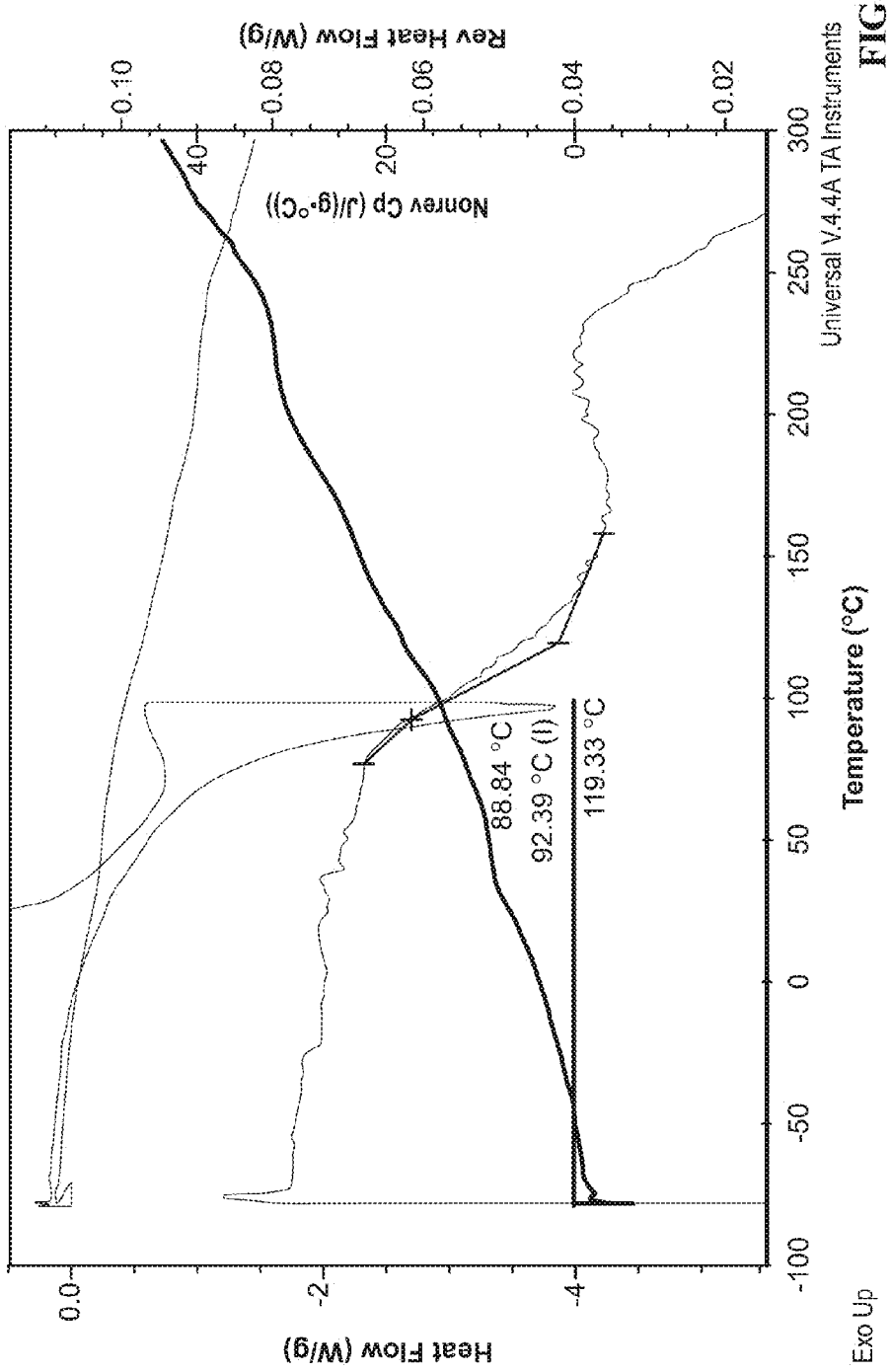

FIG. 158 is a mDSC plot of EP-1 trihydrate (x is 3) $H_3PO_4$ salt.

Figure 159:
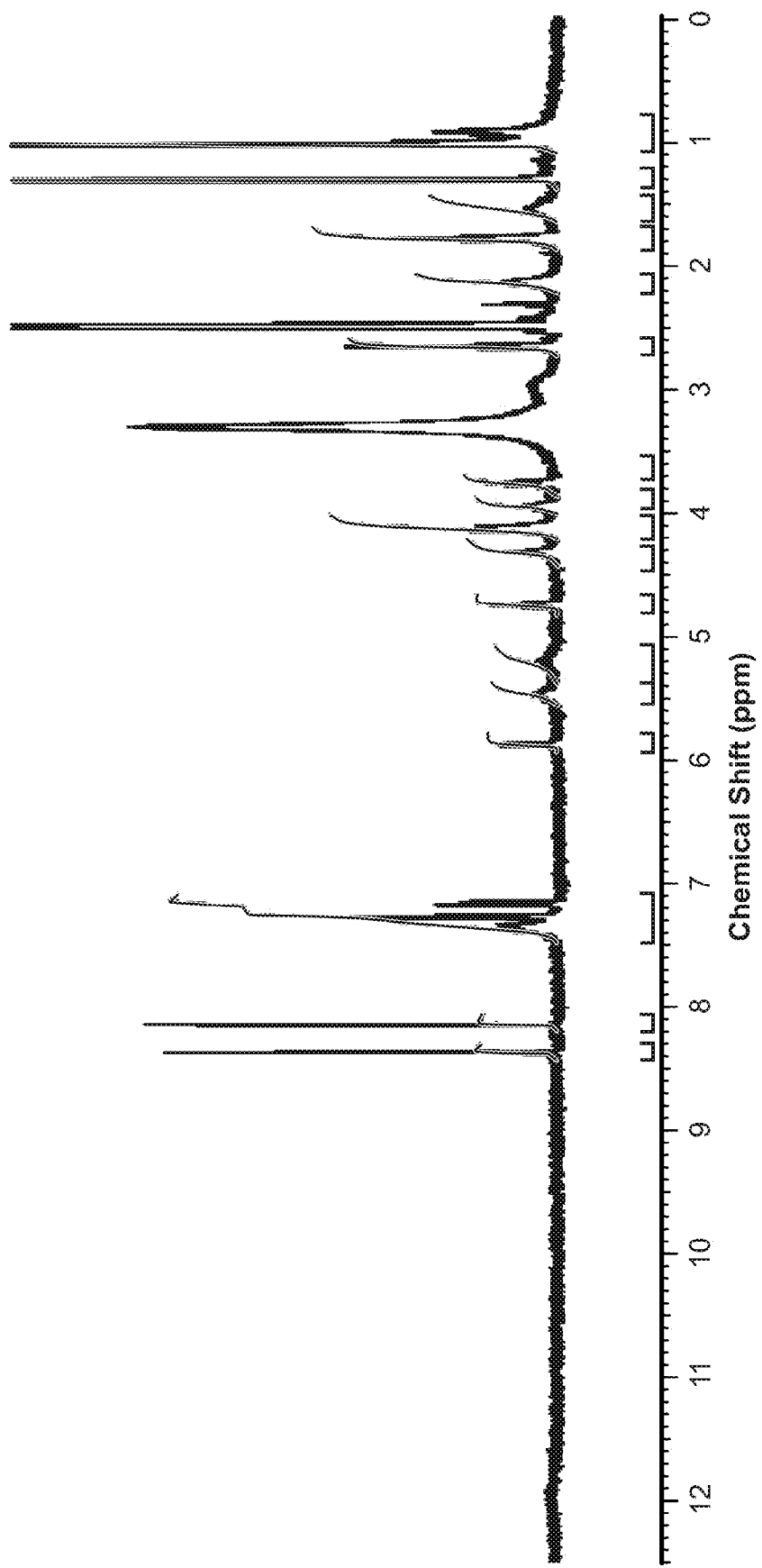

FIG. 159 is a $^1$H NMR spectrum of EP-1 trihydrate (x is 3) $H_3PO_4$ salt.

Figure 160:
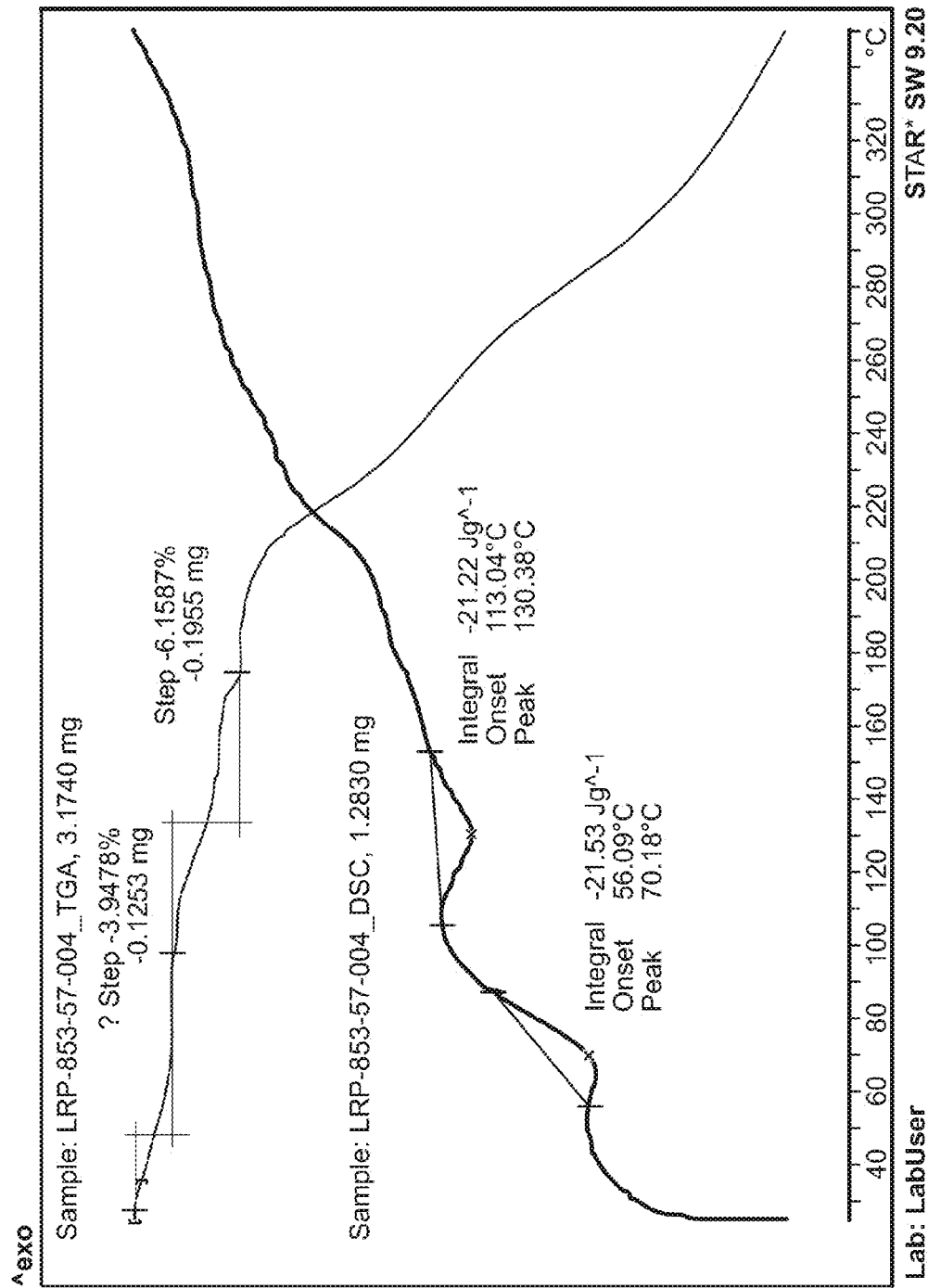

FIG. 160 is a TGA/DSC plot of EP-1 trihydrate (x is 3) L-tartrate salt.

Figure 161:
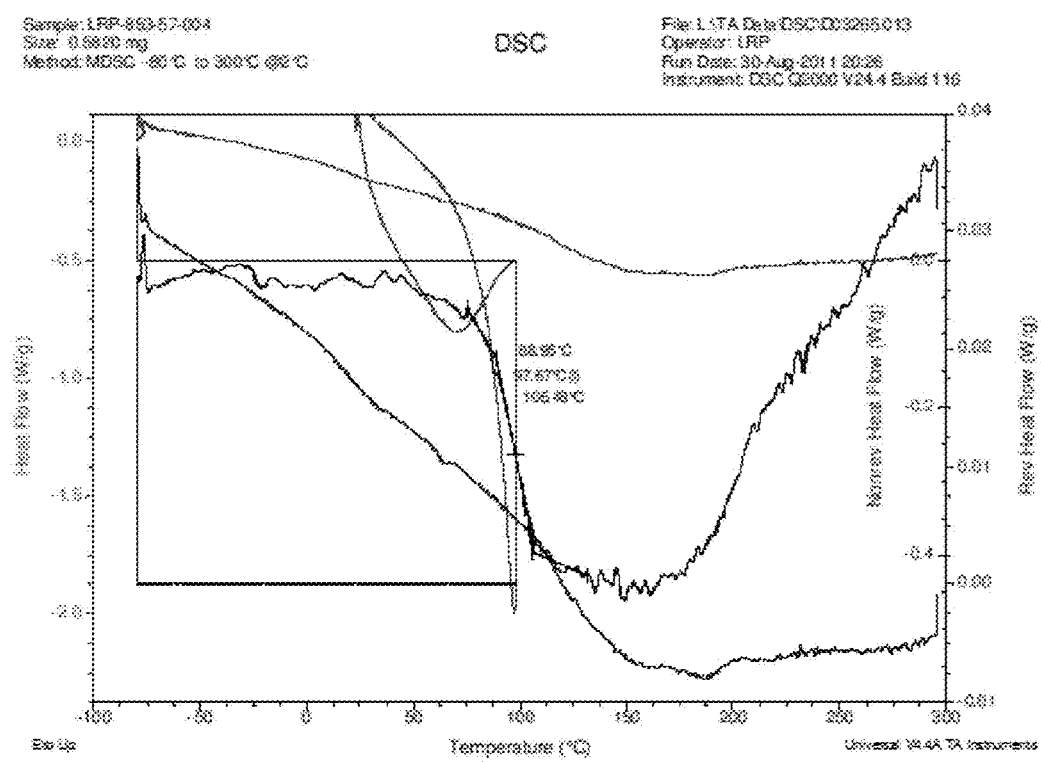

FIG. 161 is a mDSC plot of EP-1 trihydrate (x is 3) L-tartrate salt.

Figure 162:
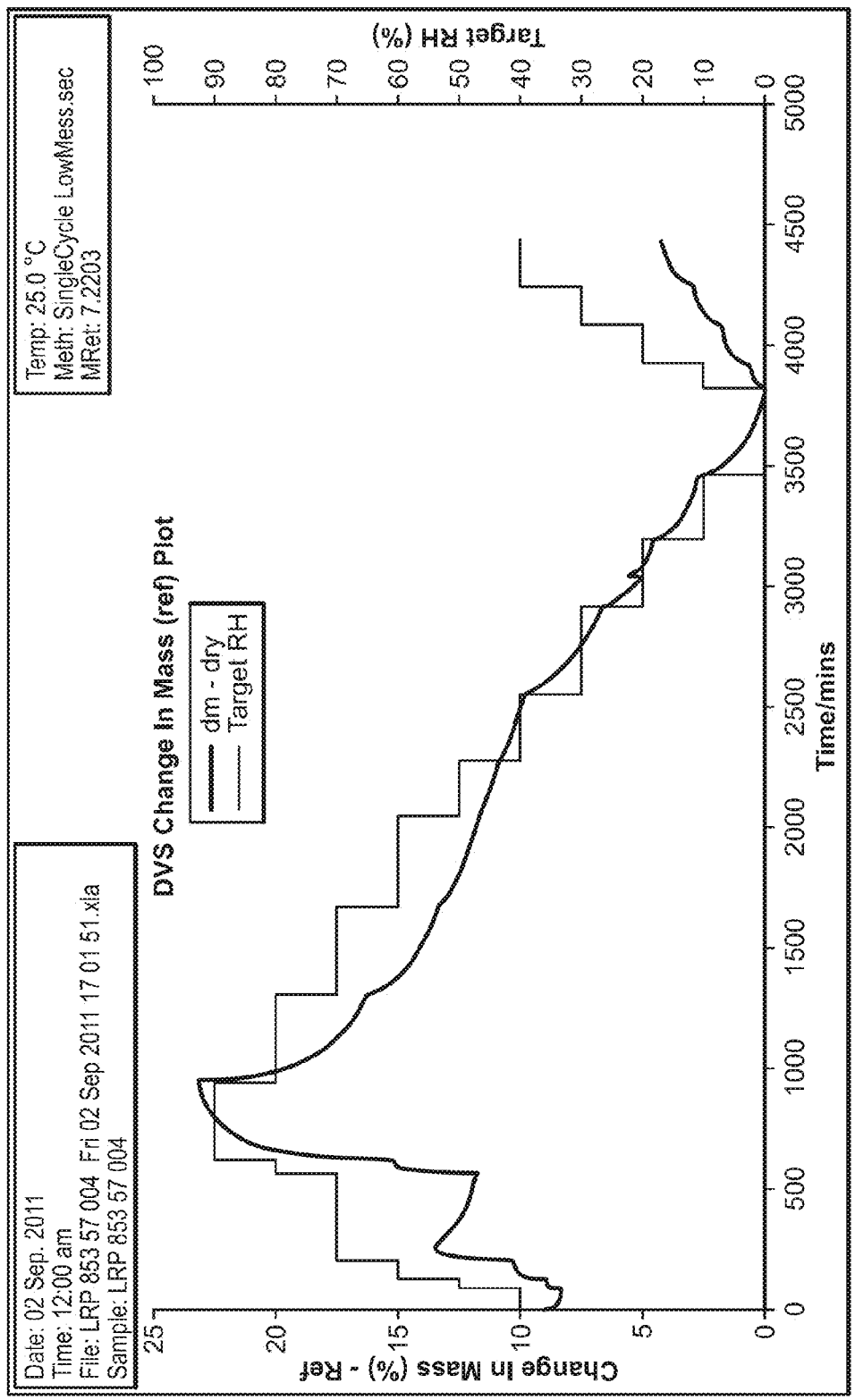

FIG. 162 is a GVS kinetic plot of EP-1 trihydrate (x is 3) L-tartrate salt.

Figure 163:
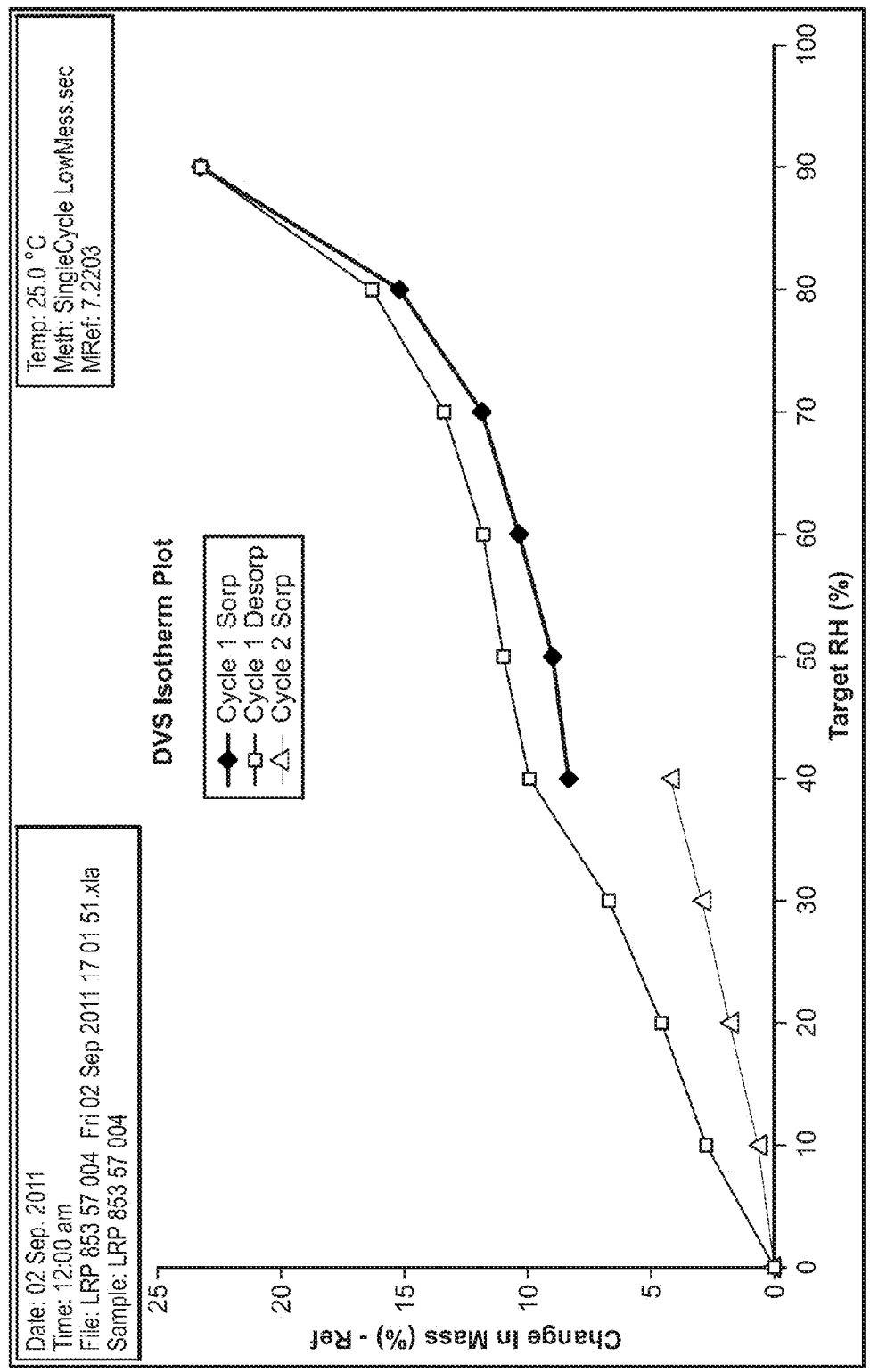

FIG. 163 is a GVS isotherm of EP-1 trihydrate (x is 3) L-tartrate salt.

Figure 164:
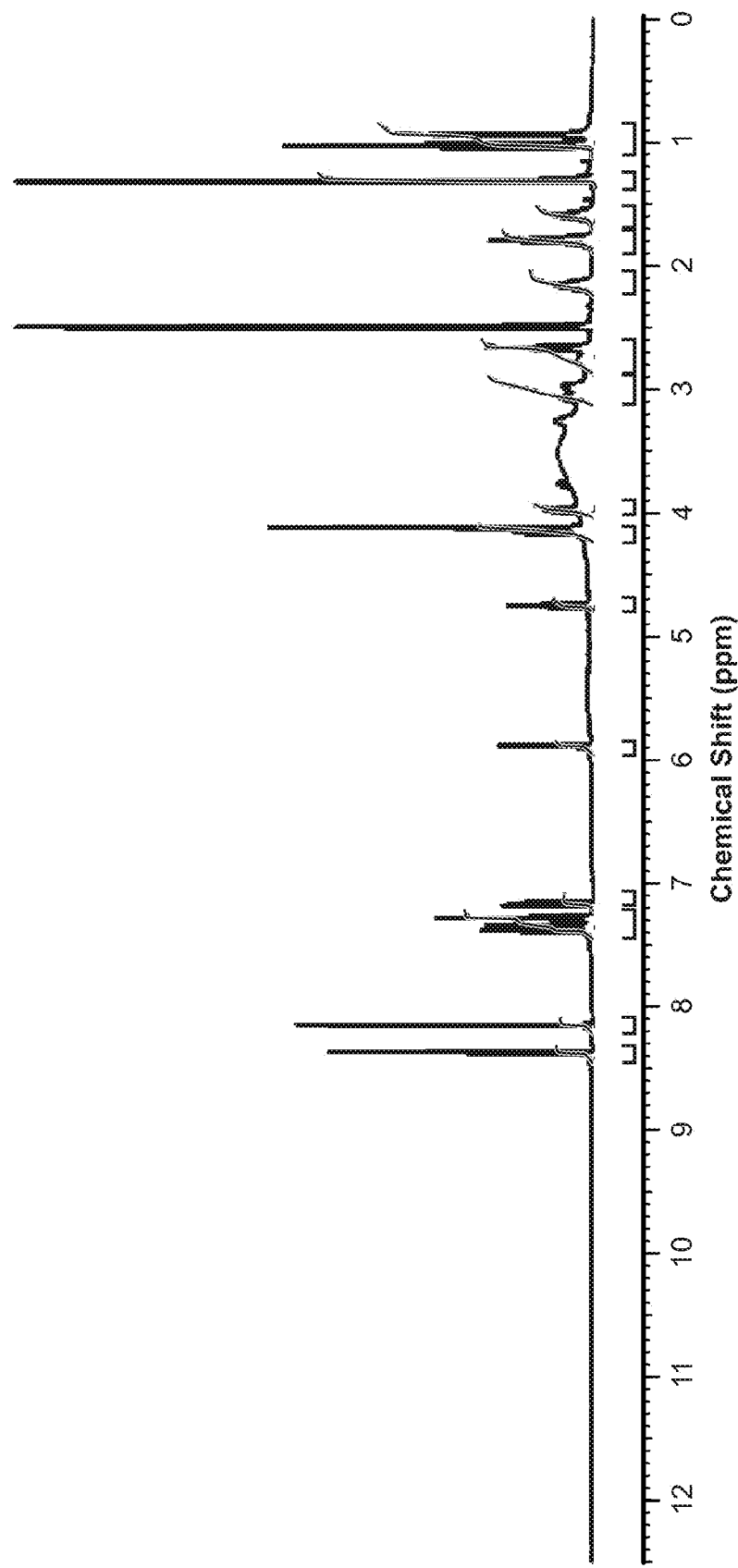

FIG. 164 is a $^1$H NMR spectrum post-GVS of EP-1 trihydrate (x is 3) L-tartrate salt.

Figure 165:
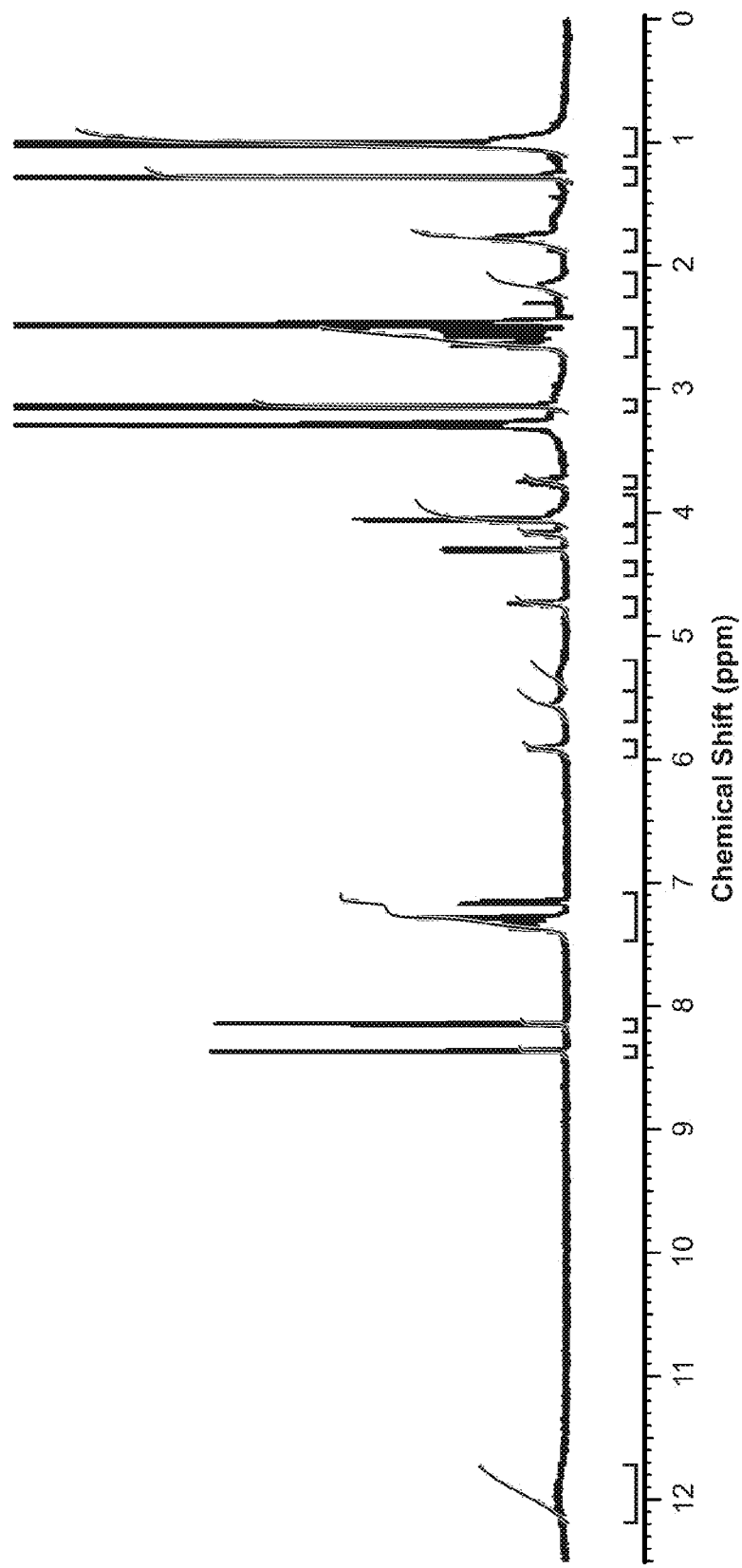

FIG. 165 is a $^1$H NMR spectrum of EP-1 trihydrate (x is 3) citrate salt.

Figure 166:
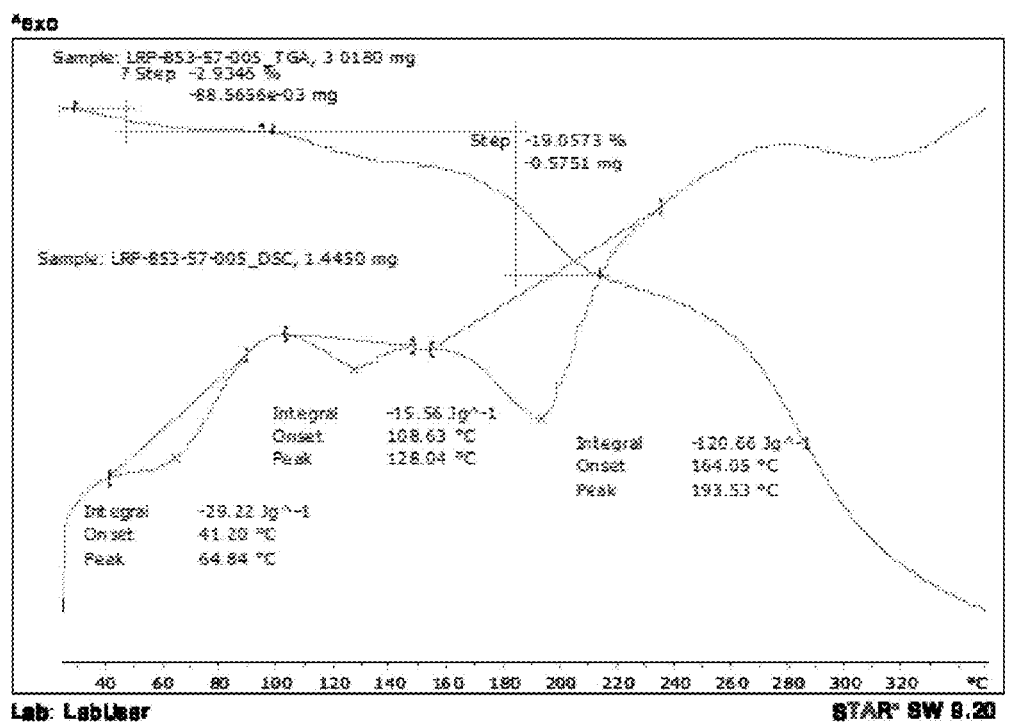

FIG. 166 is a TGA/DSC plot of EP-1 trihydrate (x is 3) citrate salt.

Figure 167:
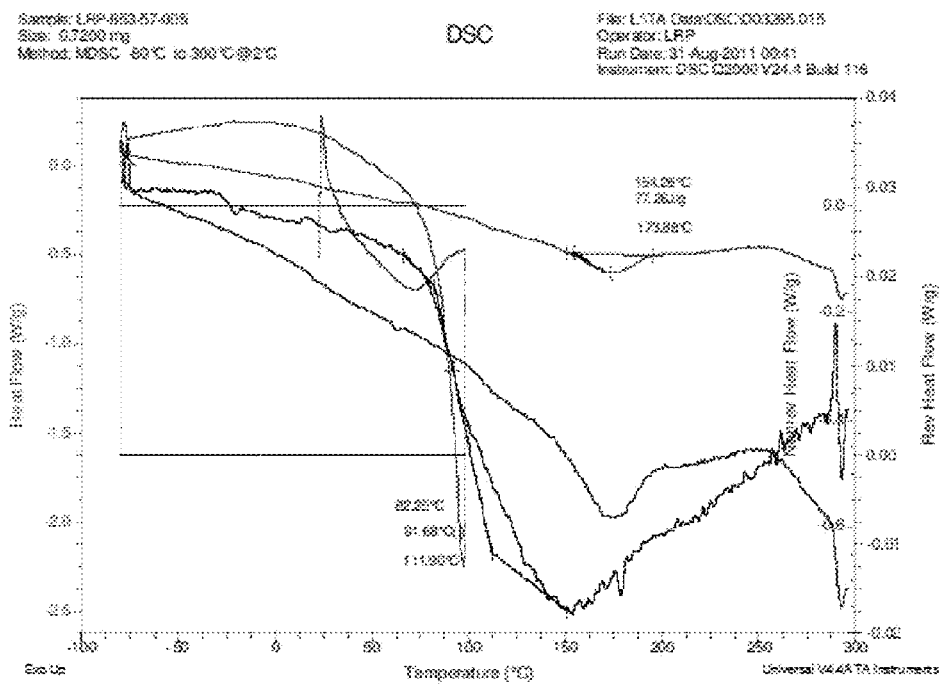

FIG. 167 is a mDSC plot of EP-1 trihydrate (x is 3) citrate salt.

Figure 168:
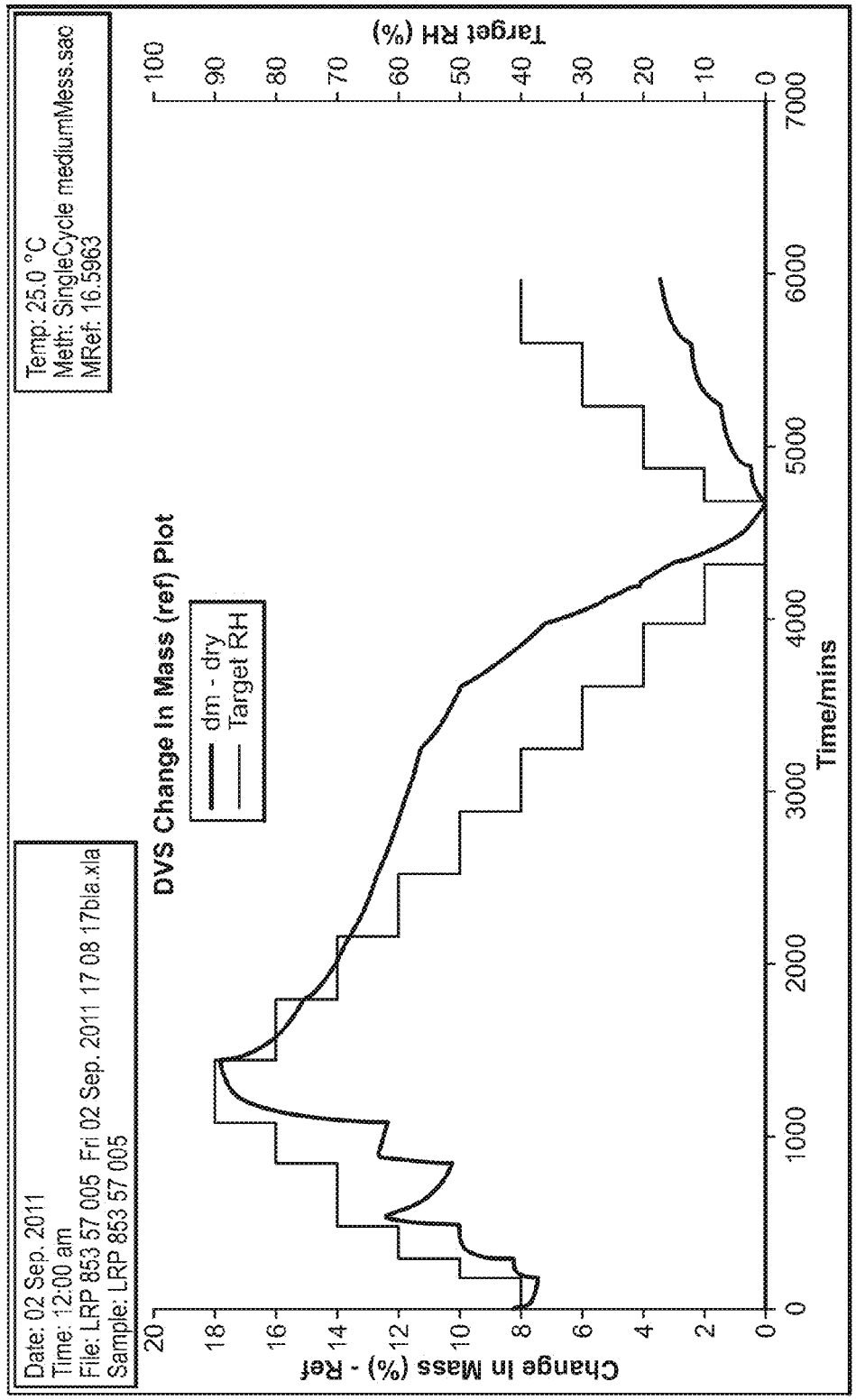

FIG. 168 is a GVS kinetic plot of EP-1 trihydrate (x is 3) citrate salt.

Figure 169:
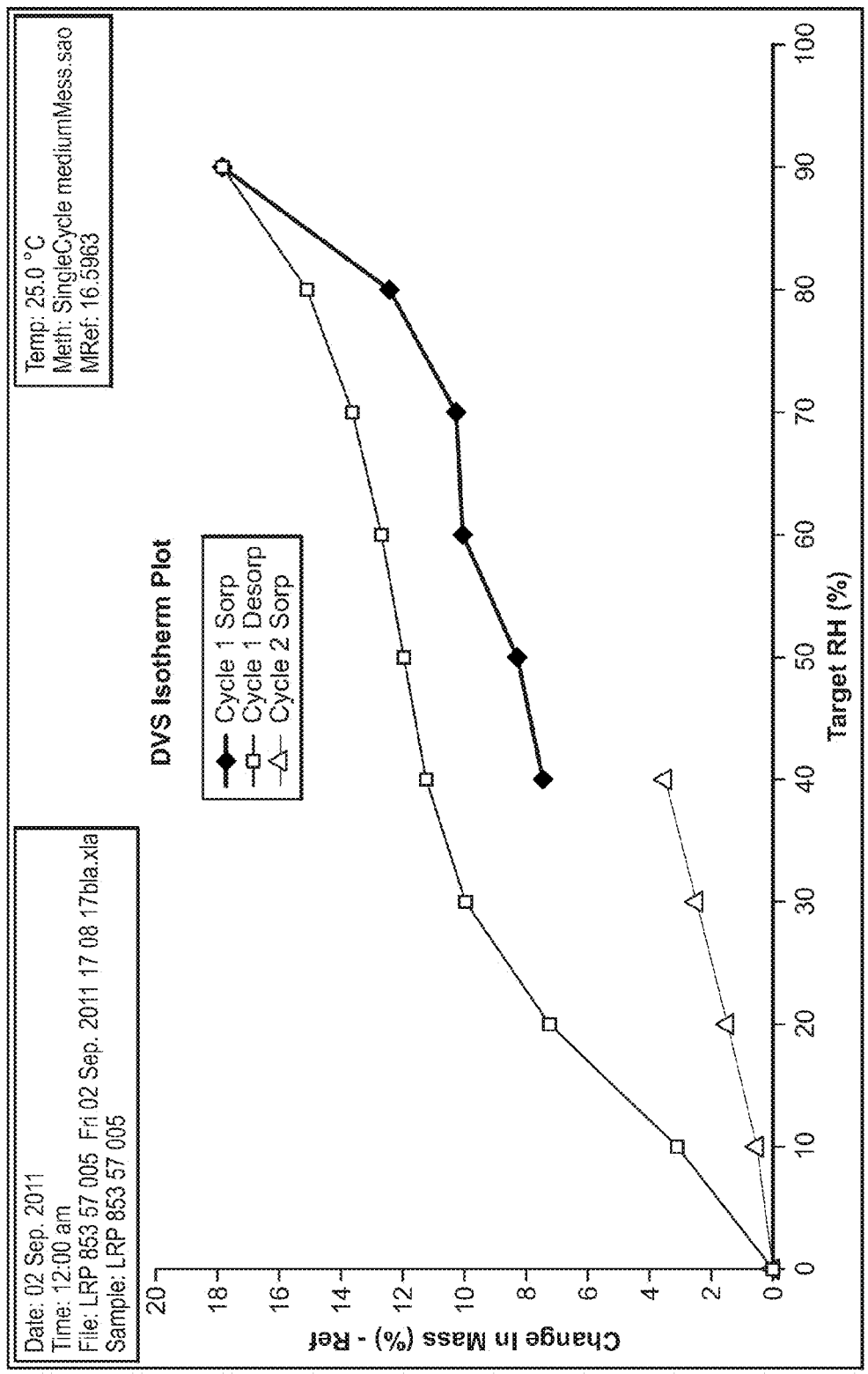

FIG. 169 is a GVS isotherm of EP-1 trihydrate (x is 3) citrate salt.

Figure 170:
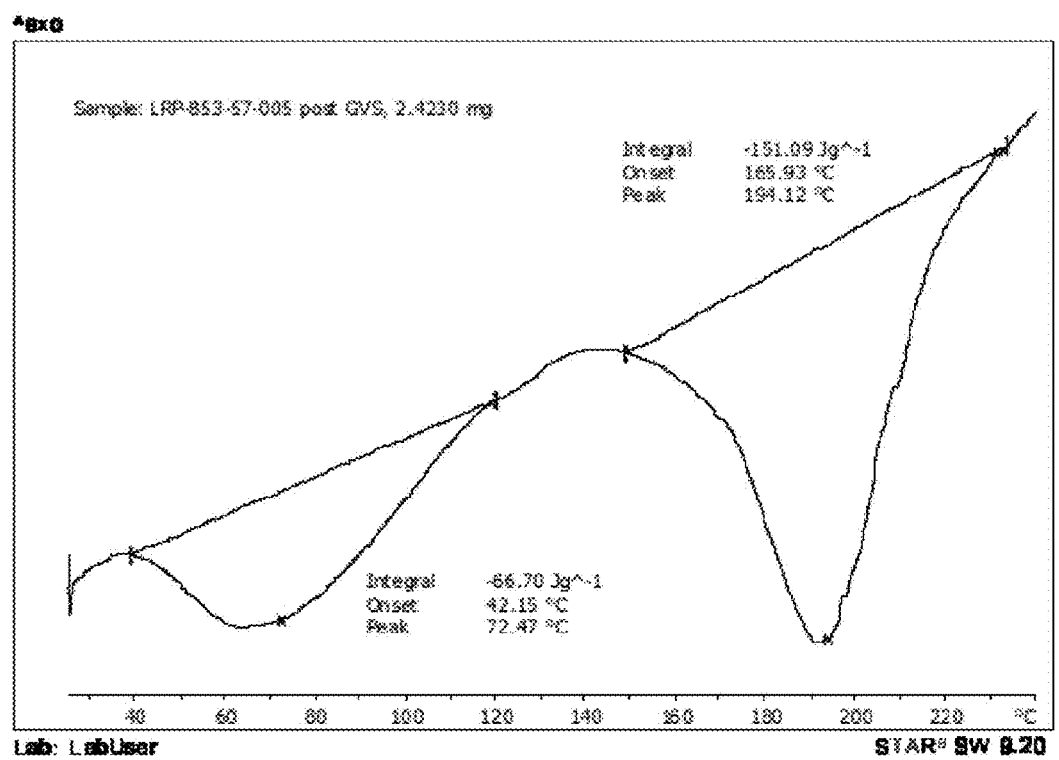

FIG. 170 is a DSC plot post-GVS of EP-1 trihydrate (x is 3) citrate salt.

Figure 171:
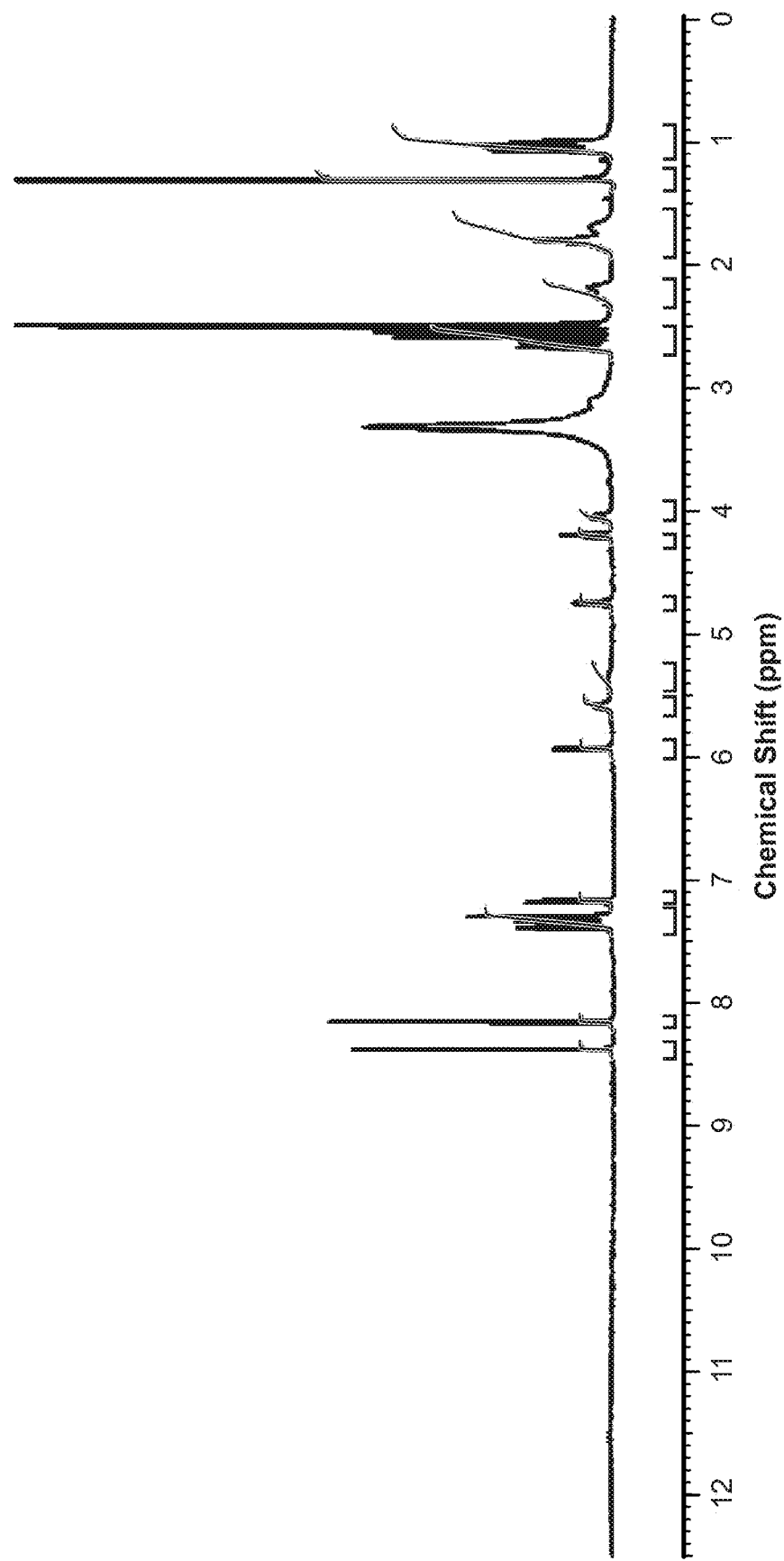

FIG. 171 is a $^1$H NMR spectrum post-GVS of EP-1 trihydrate (x is 3) citrate salt.

Figure 172:
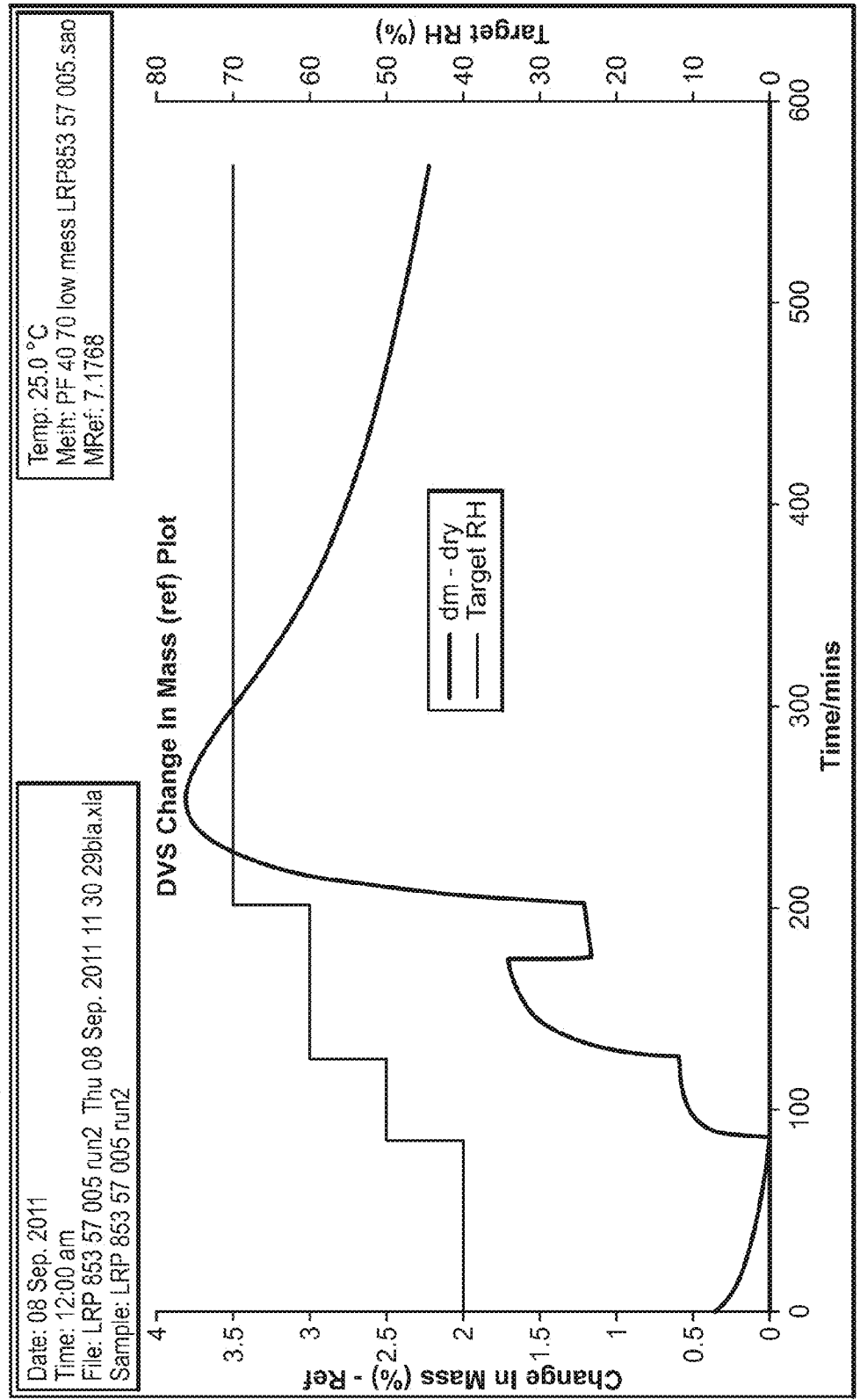

FIG. 172 is a GVS kinetic plot at 70% RH of EP-1 trihydrate (x is 3) citrate salt.

Figure 173:
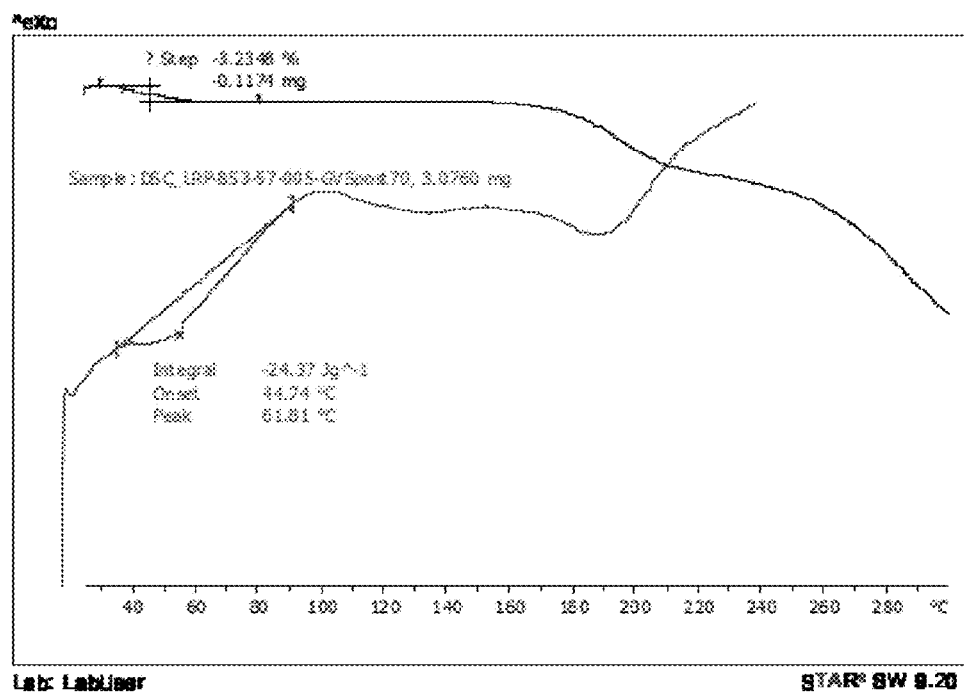

FIG. 173 is a TGA/DSC post-GVS at 70% RH of EP-1 trihydrate (x is 3) citrate salt.

Figure 174:
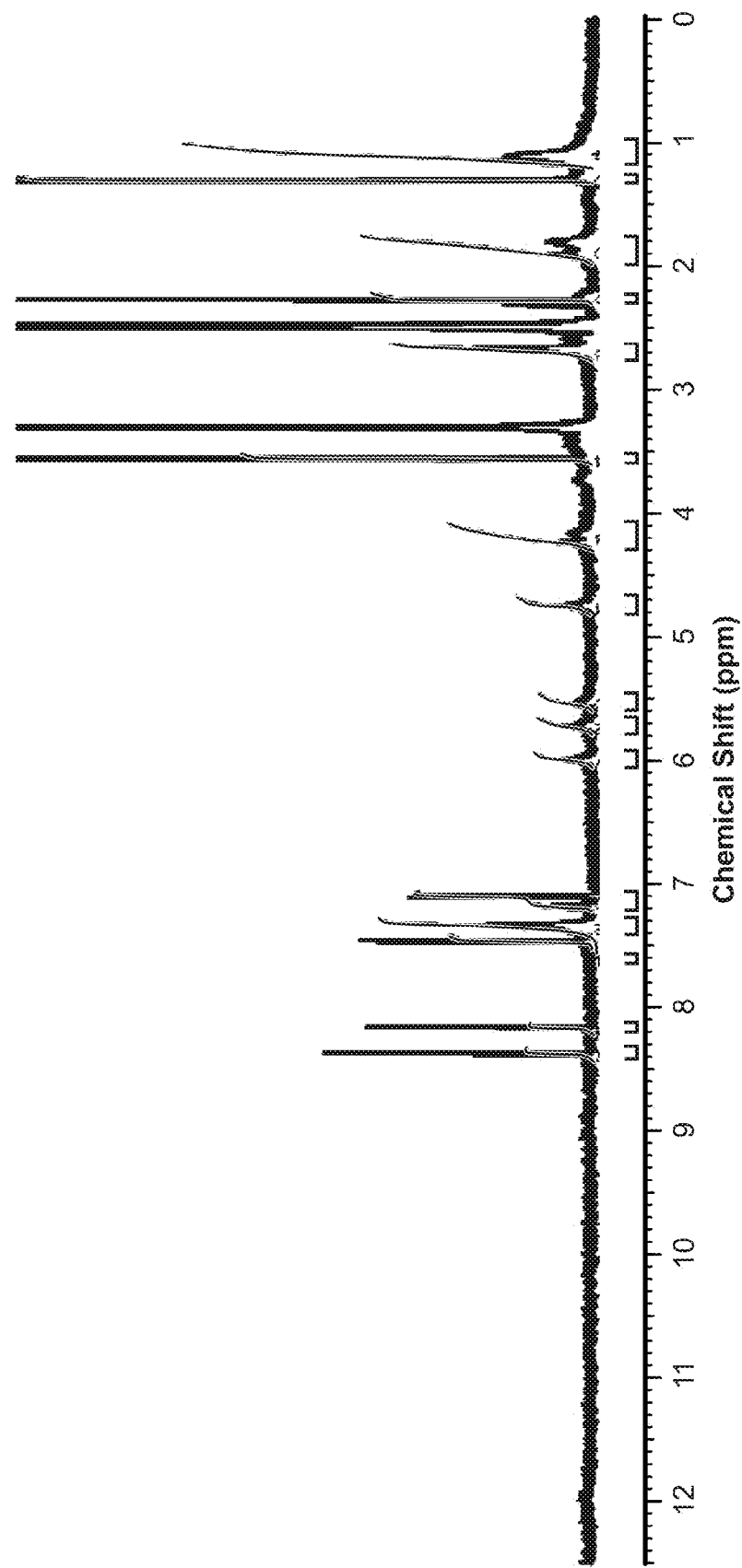

FIG. 174 is a $^1$H NMR spectrum of EP-1 trihydrate (x is 3) p-toluene sulfonate salt.

Figure 175:
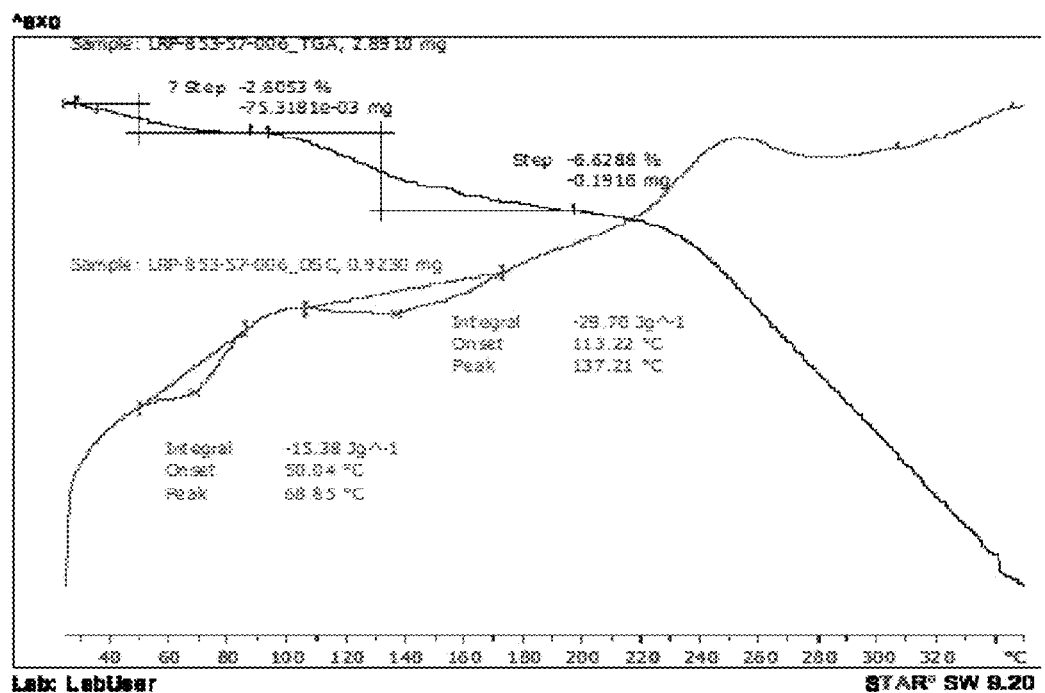

FIG. 175 is a TGA/DSC plot of EP-1 trihydrate (x is 3) p-toluene sulfonate salt.

Figure 176:
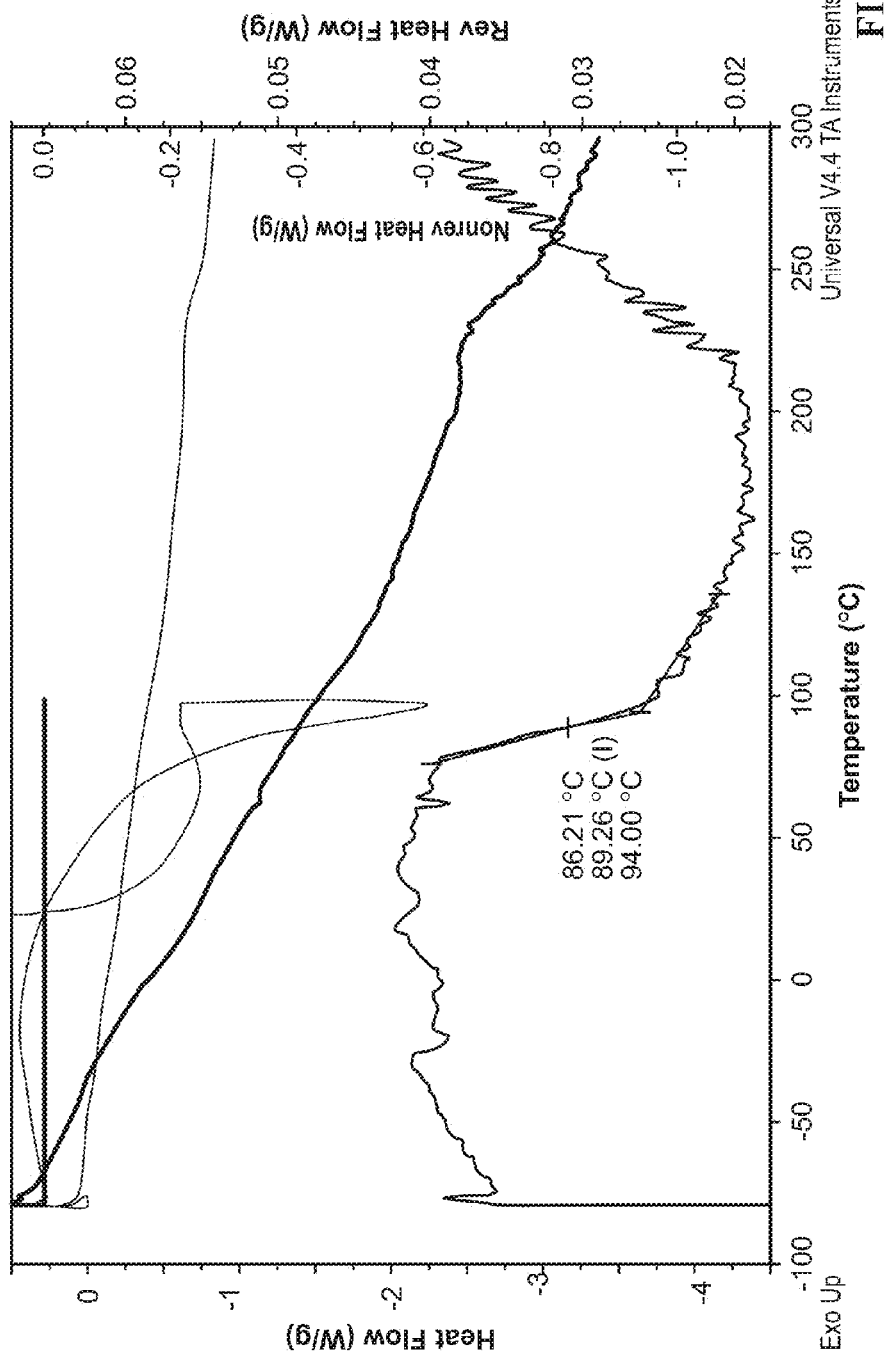

FIG. 176 is a mDSC plot of EP-1 trihydrate (x is 3) p-toluene sulfonate salt.

Figure 177:
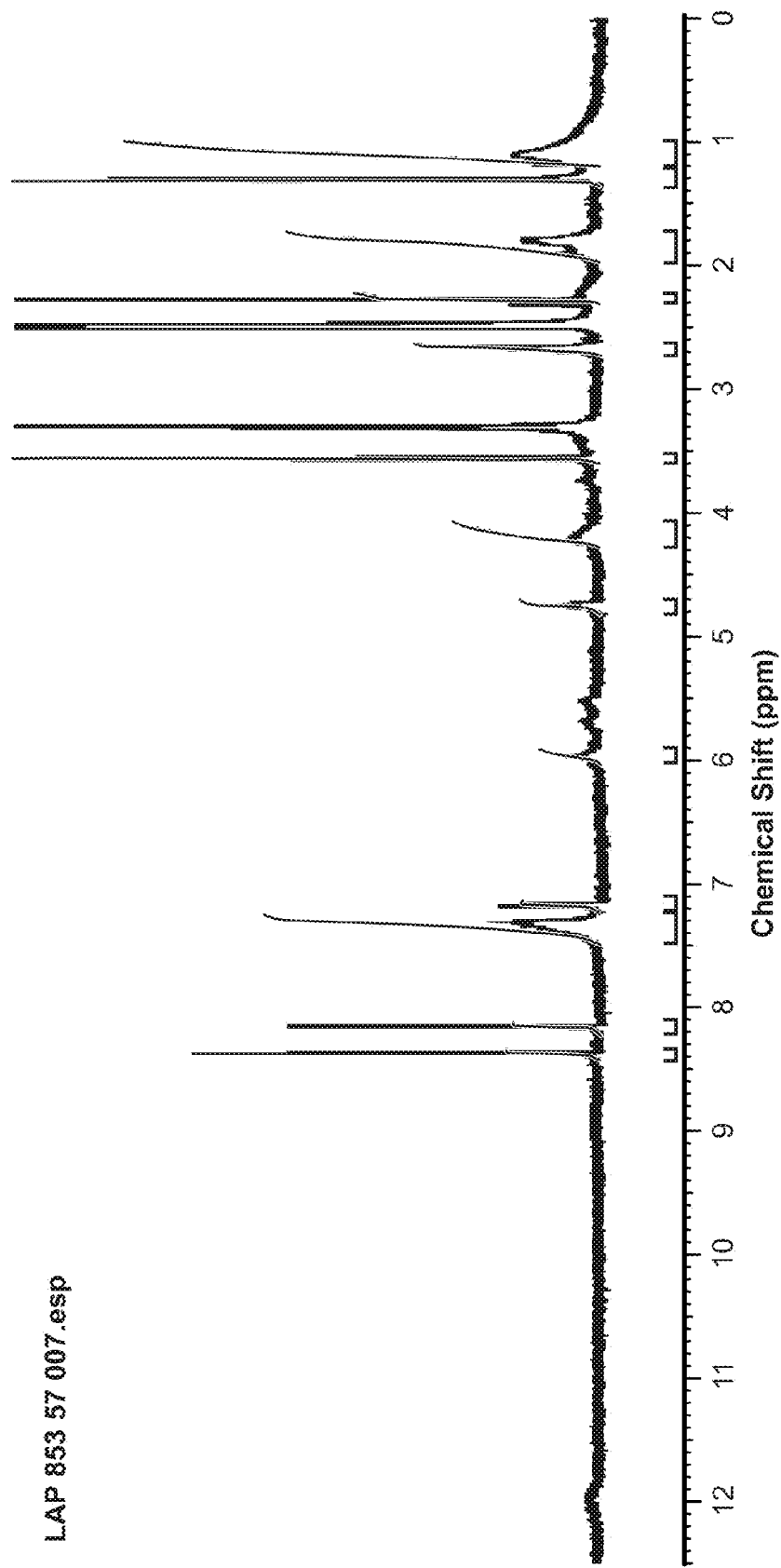

FIG. 177 is a $^1$H NMR spectrum of EP-1 trihydrate (x is 3) methane sulfonate salt.

Figure 178:
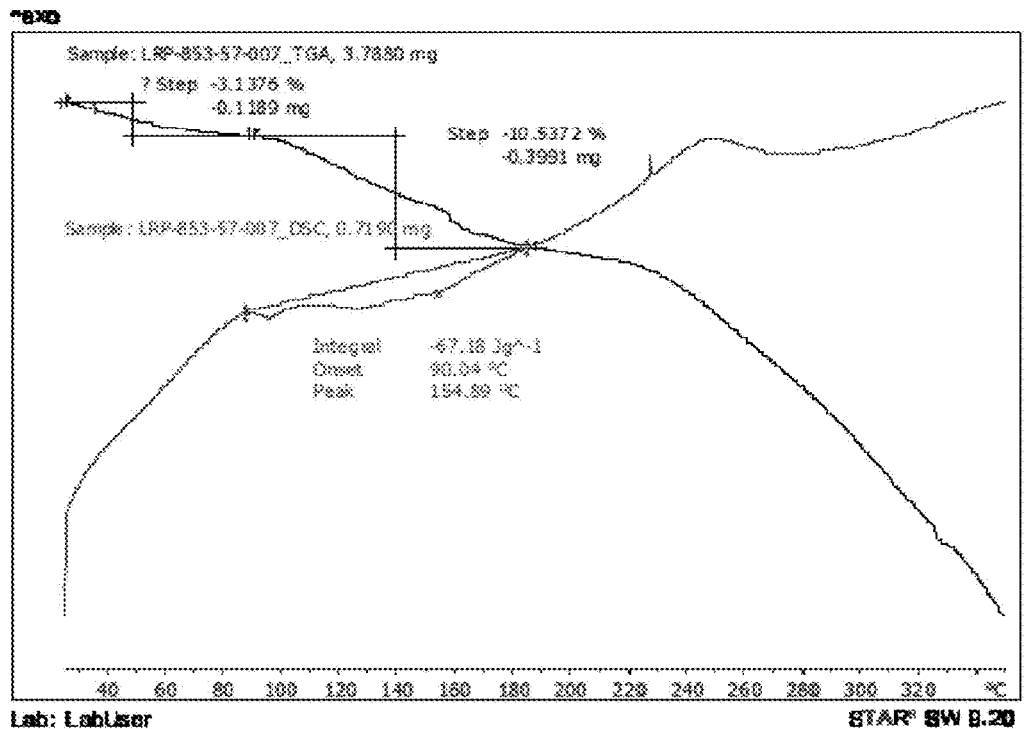

FIG. 178 is a TGA/DSC plot of EP-1 trihydrate (x is 3) methane sulfonate salt.

Figure 179:
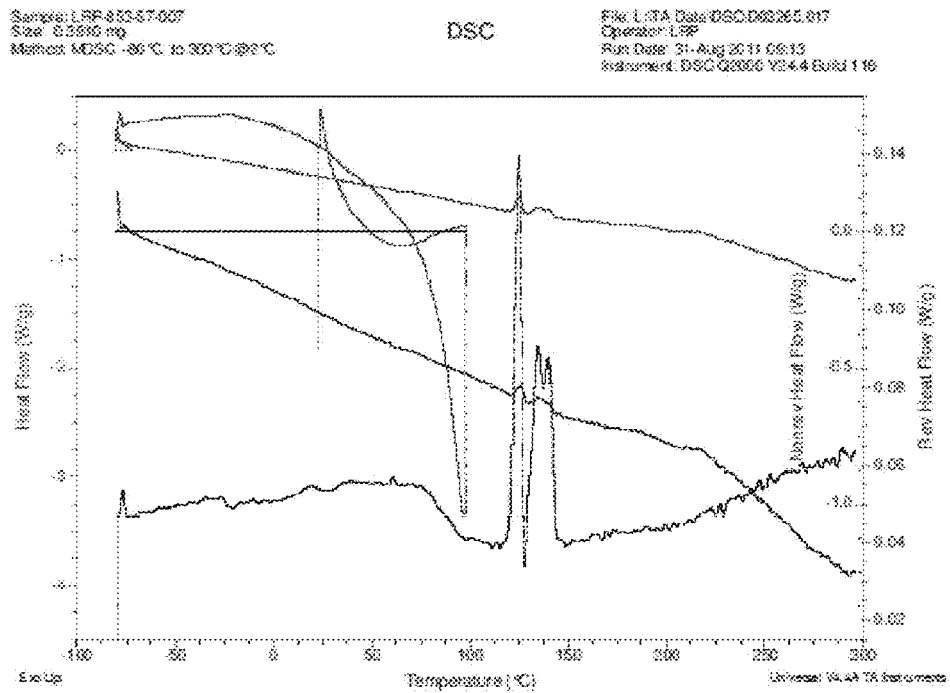

FIG. 179 is a mDSC plot of EP-1 trihydrate (x is 3) methane sulfonate salt.

Figure 180:
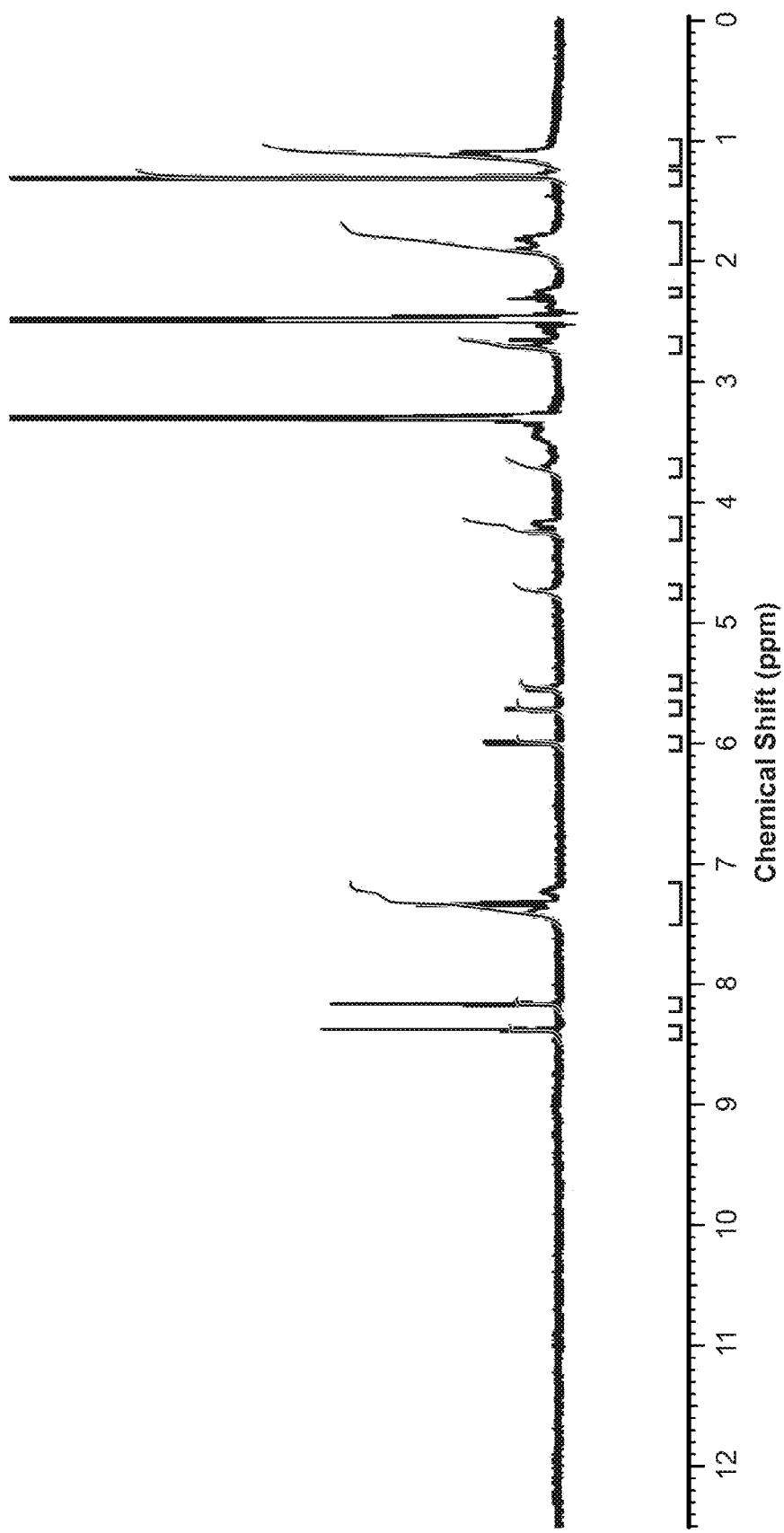

FIG. 180 is a $^1$H NMR spectrum of EP-1 trihydrate (x is 3) HCl salt.

Figure 181:
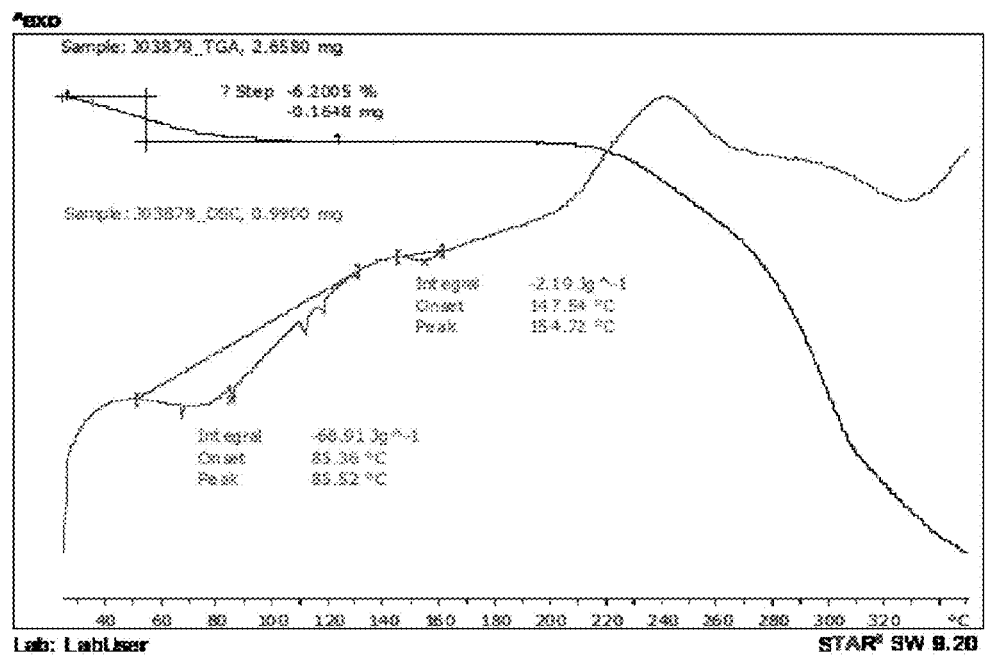

FIG. 181 is a TGA/DSC plot of EP-1 trihydrate (x is 3) HCl salt.

Figure 182:
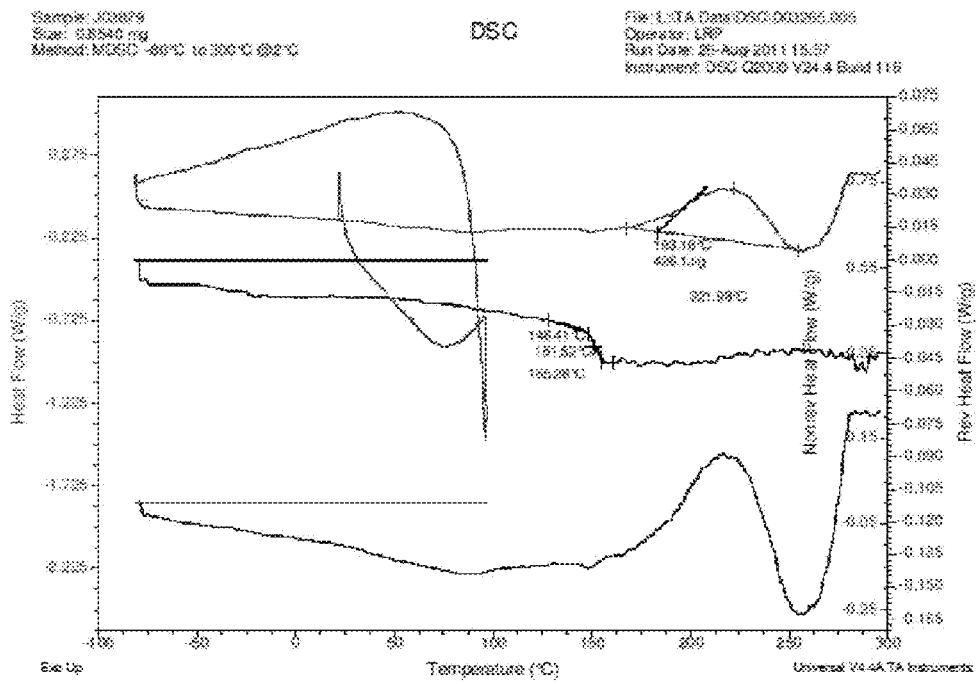

FIG. 182 is a mDSC plot of EP-1 trihydrate (x is 3) HCl salt.

Figure 183:
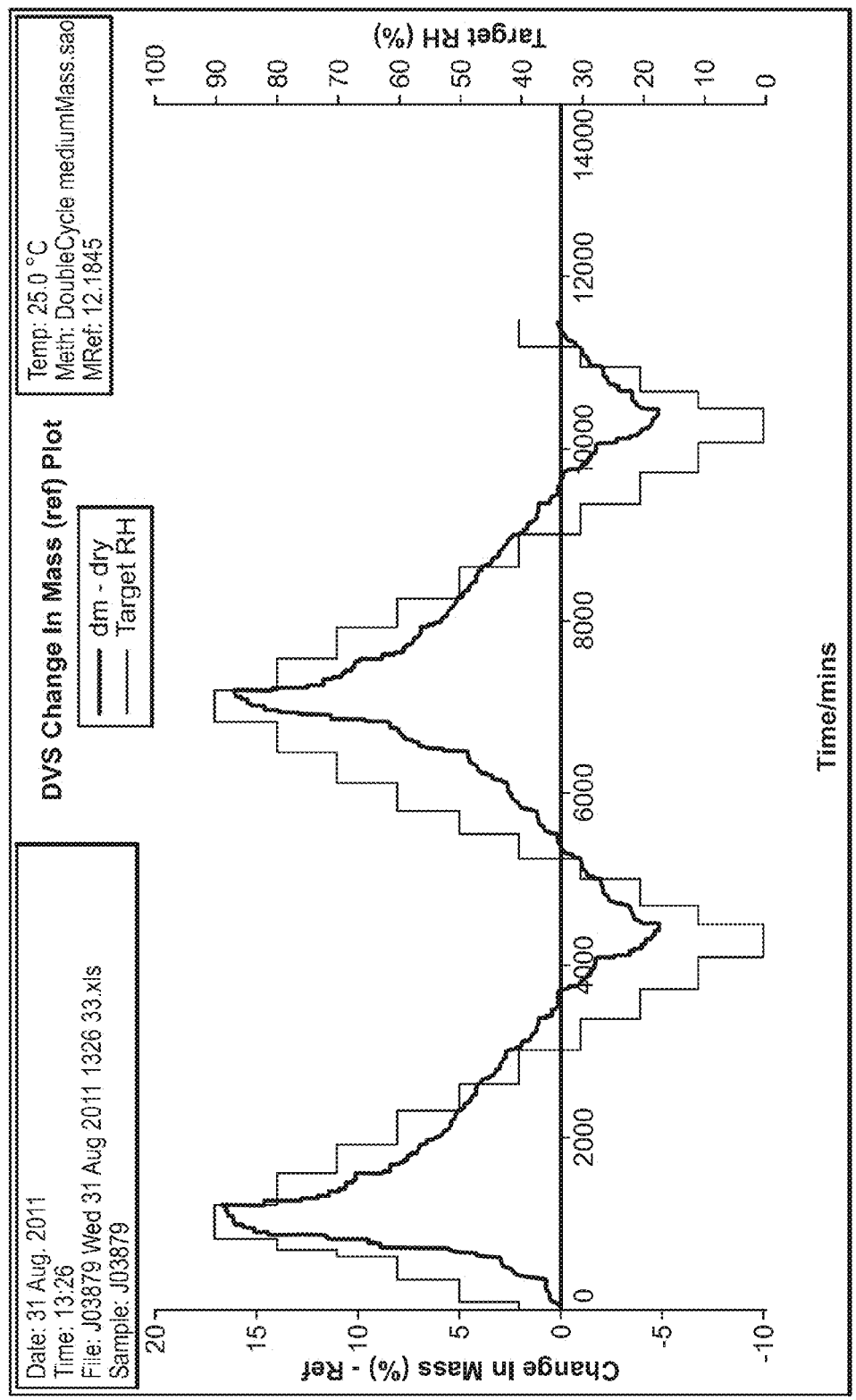

FIG. 183 is a GVS kinetic plot of EP-1 trihydrate (x is 3) HCl salt.

Figure 184:
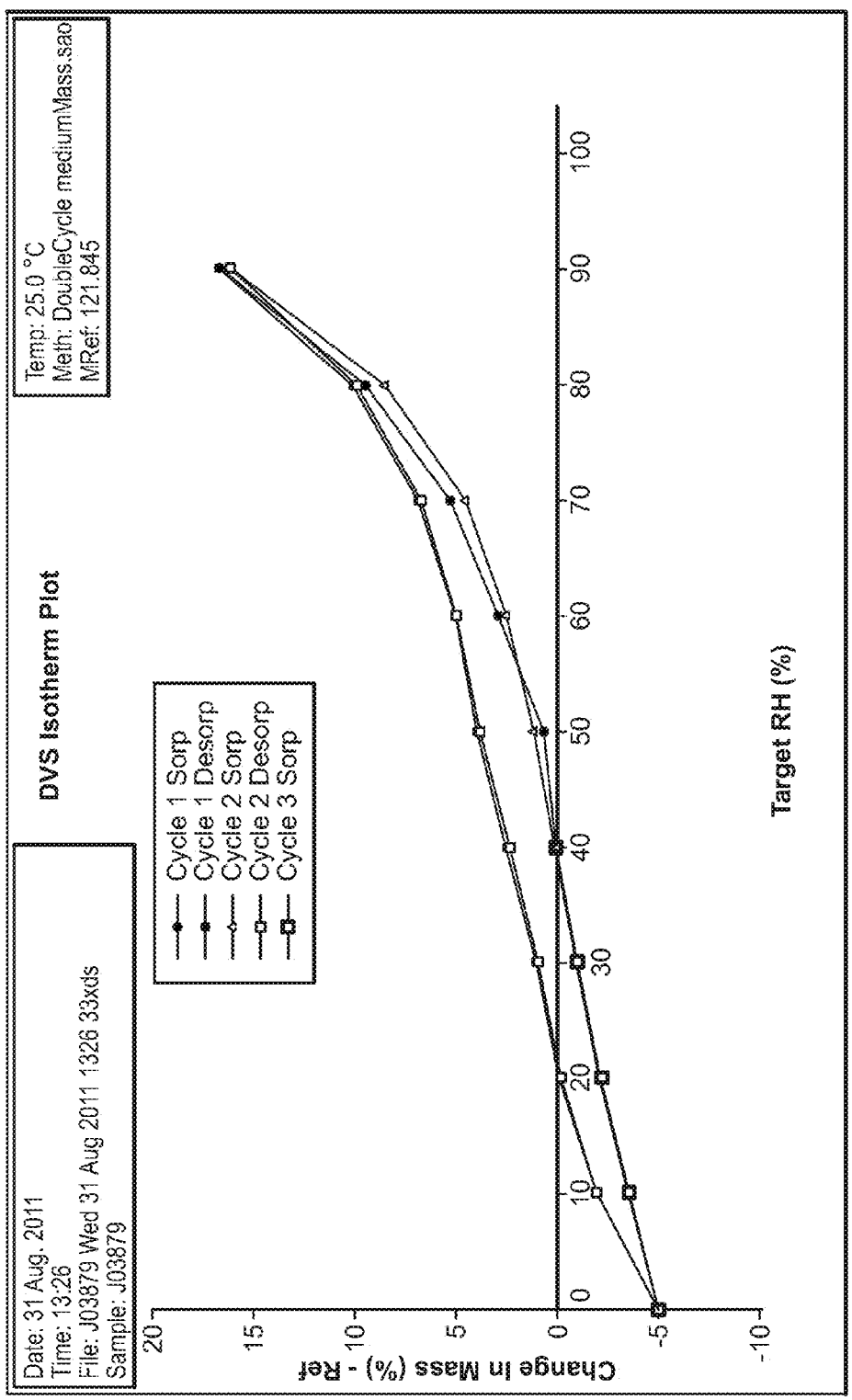

FIG. 184 is a GVS isotherm of EP-1 trihydrate (x is 3) HCl salt.

Figure 185:
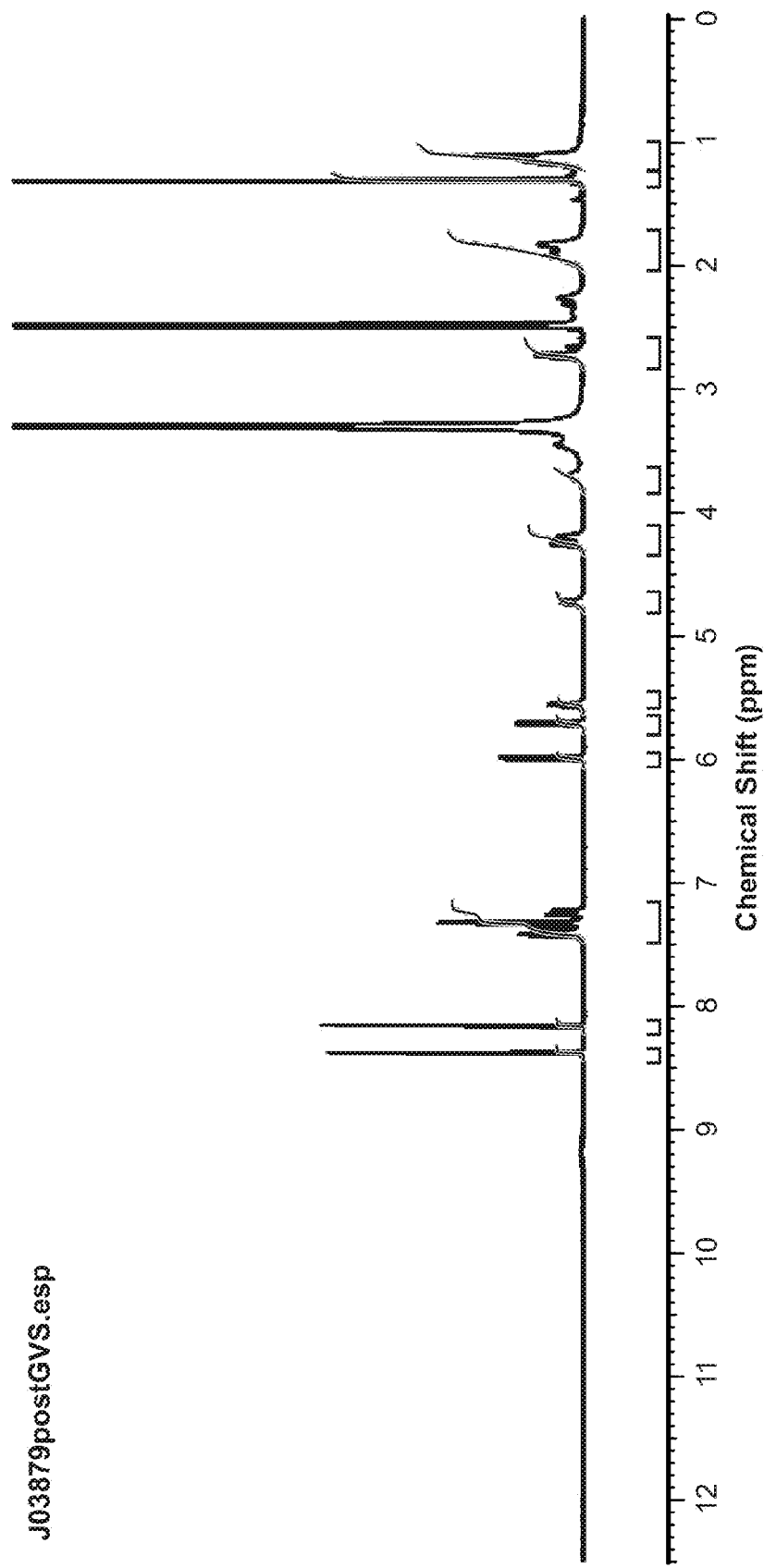

FIG. 185 is a $^1$H NMR spectrum post-GVS of EP-1 trihydrate (x is 3) HCl salt.

Figure 186:
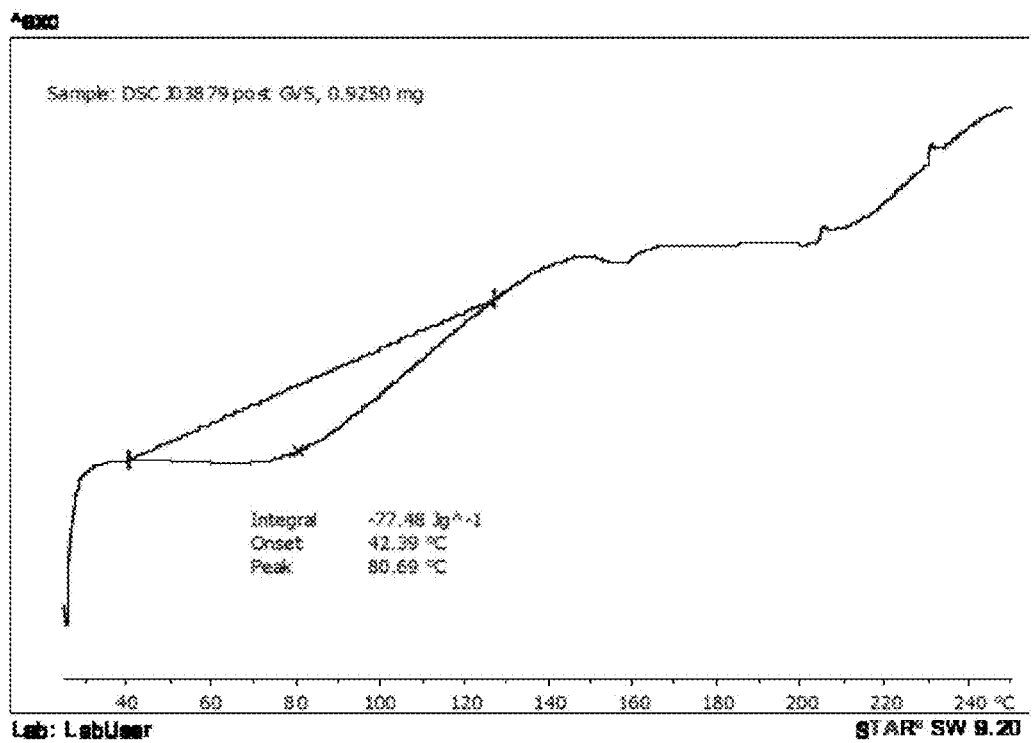

FIG. 186 is a DSC plot post-GVS of EP-1 trihydrate (x is 3) HCl salt.

Figure 187:
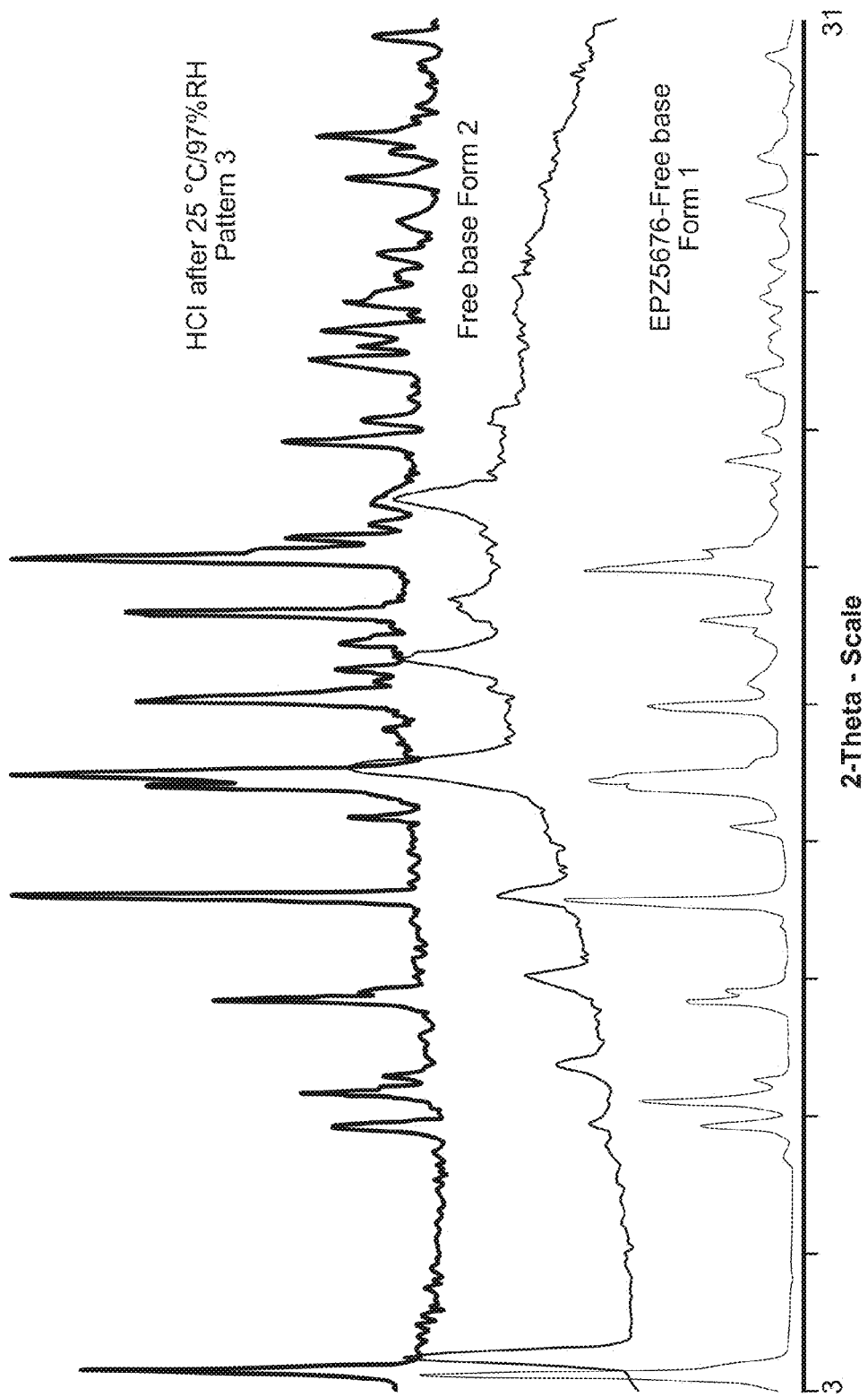

FIG. 187 is an overlap of XRPD diffractograms for EP-1 trihydrate (x is 3) free base (Form 1 &2) and HCl salt after 3 weeks at 25° C./75% RH 121.

Figure 188:
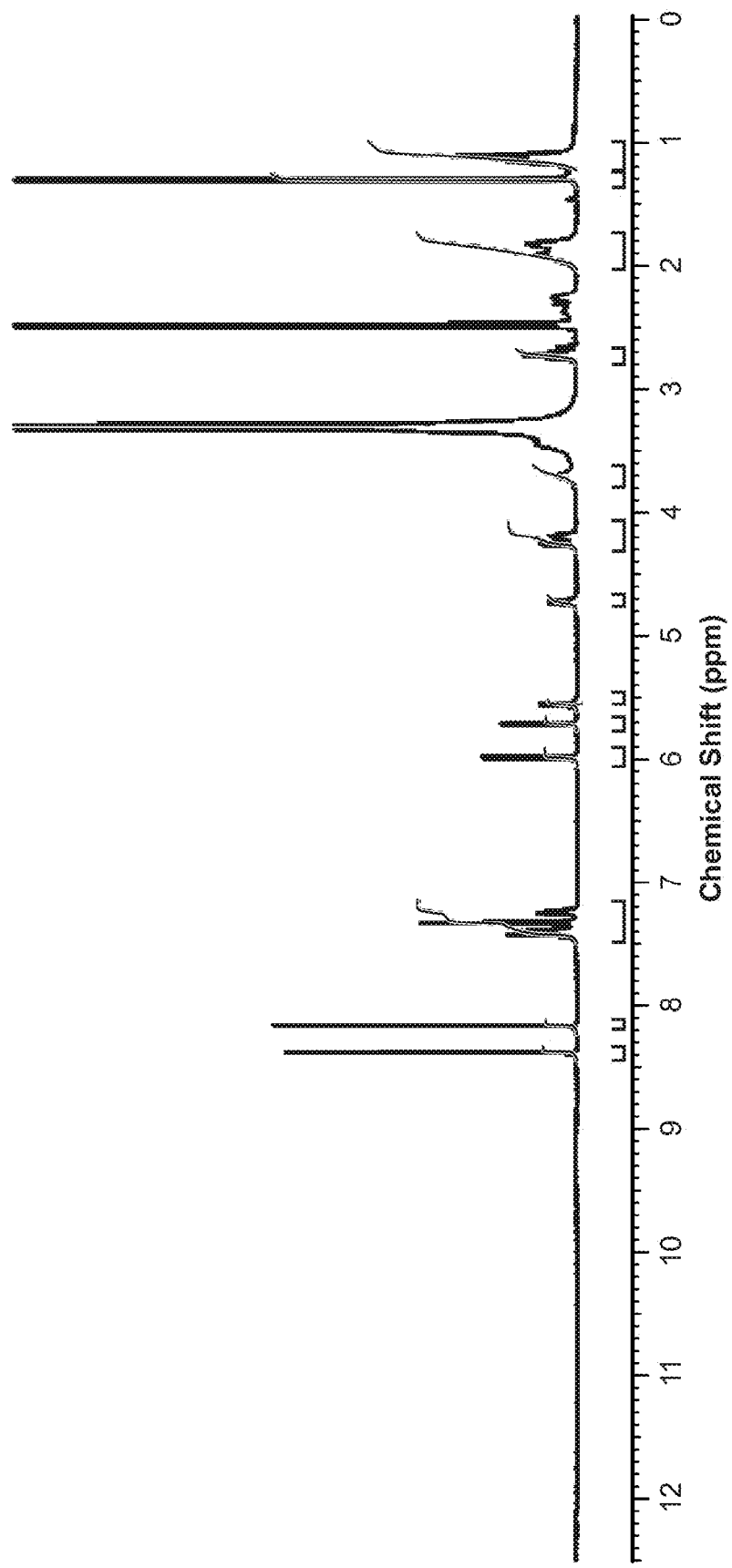

FIG. 188 is a $^1$H NMR spectrum of EP-1 trihydrate (x is 3) HCl salt after 3 weeks at 25° C./75% RH.

FIG. 189A is an image of EP-1 trihydrate (x is 3) HCl salt after 3 weeks at 25° C./75% RH under normal light.

FIG. 189B is an image of EP-1 trihydrate (x is 3) HCl salt after 3 weeks at 25° C./75% RH under polarized light.

Figure 190:
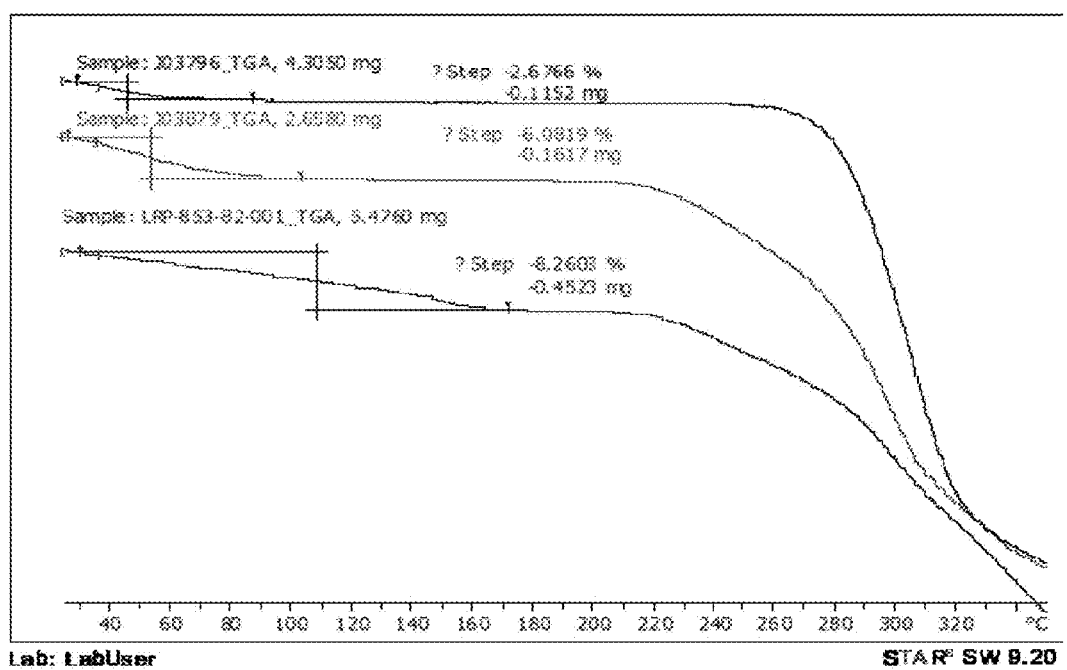

FIG. 190 is a TGA overlay of EP-1 trihydrate (x is 3) free base, EP-1 trihydrate (x is 3) HCl salt, and EP-1 trihydrate (x is 3) HCl salt after 3 weeks at 25° C./75% RH.

Figure 191:
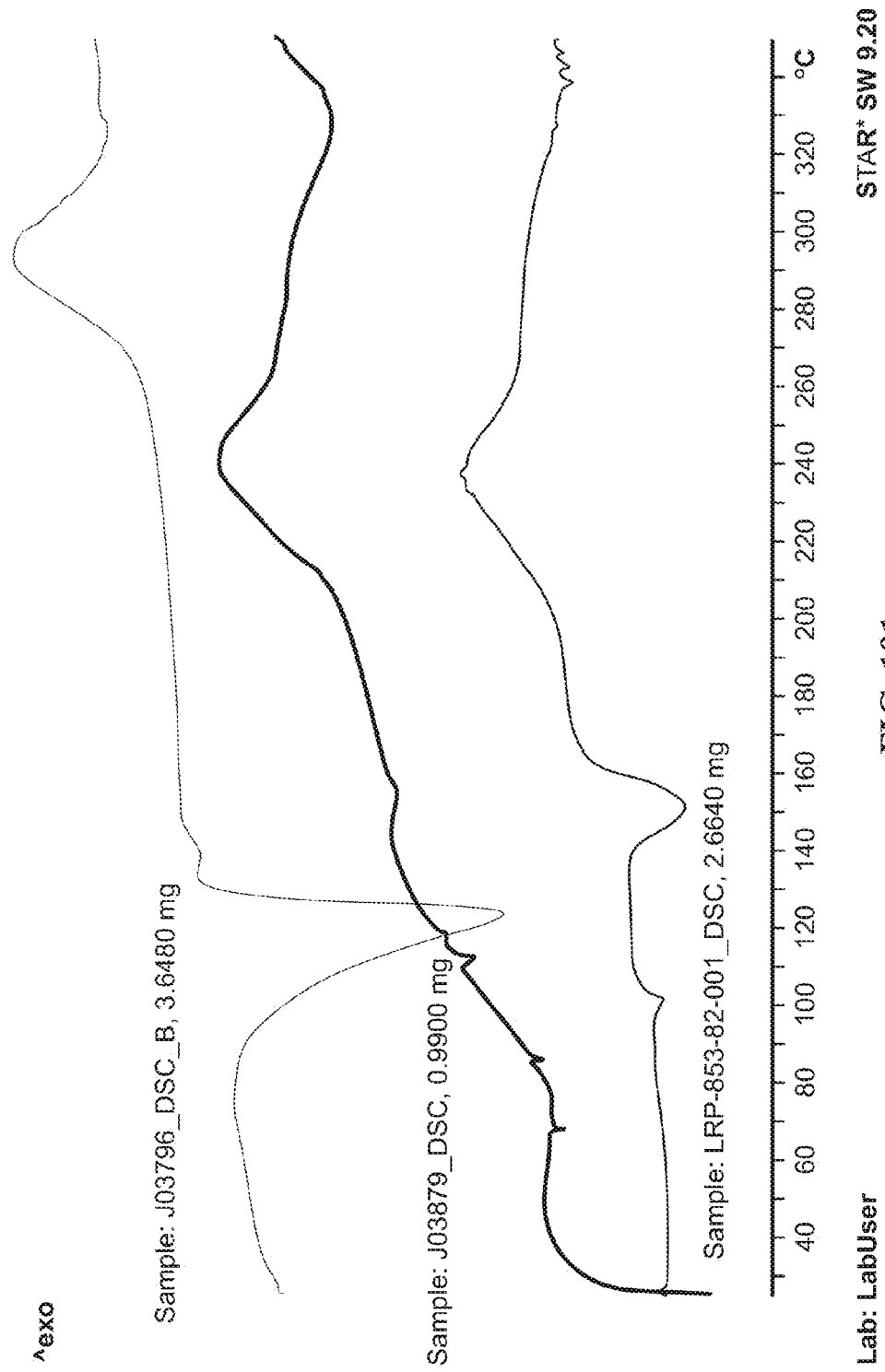

FIG. 191 is a DSC overlay of EP-1 trihydrate (x is 3) free base, EP-1 trihydrate (x is 3) HCl salt, and EP-1 trihydrate (x is 3) HCl salt after 3 weeks at 25° C./75% RH.

DETAILED DESCRIPTION OF THE INVENTION

The present invention is directed to 2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol:

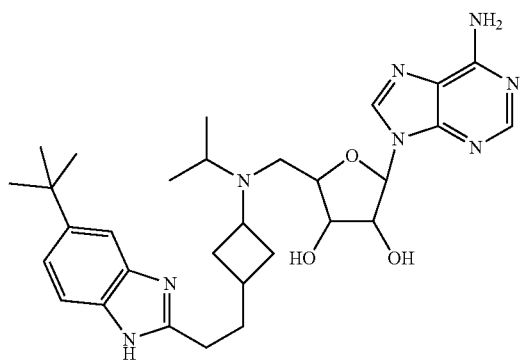

or a hydrate, salt, or crystalline form thereof.

The present invention is also directed to (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol:

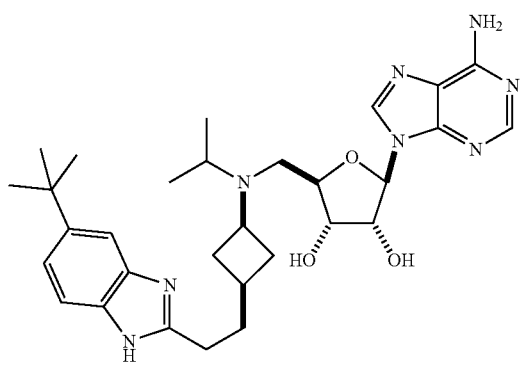

or a hydrate, salt, or crystalline form thereof.

The present invention is also directed to a crystalline form of 2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol or a hydrate or salt thereof. The present invention is also directed to a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl) amino)methyl)tetrahydrofuran-3,4-diol or a hydrate or salt thereof.

In one embodiment, the crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl) amino)methyl)tetrahydrofuran-3,4-diol is Form A, characterized by an XRPD pattern comprising peaks at about 5.5, 16.9, and 16.6° 2θ using Cu Kα radiation. In one embodiment, Form A is characterized by an XRPD pattern comprising peaks at about 5.5, 16.9, 16.6, and 18.8° 2θ using Cu Kα radiation. In one embodiment, Form A is characterized by an XRPD pattern comprising peaks at about 5.5, 16.9, 16.6, 18.8, 14.3, and 12.7° 2θ using Cu Kα radiation. In one embodiment, Form A is characterized by an XRPD pattern comprising peaks at about 5.5, 16.9, 16.6, 18.8, 14.3, 12.7, 21.8, 20.0, 10.0, and 11.0° 2θ using Cu Kα radiation. In one embodiment, Form A is characterized by an XRPD pattern substantially similar to that set forth in FIG. 1.

In one embodiment, Form A is characterized by a DSC thermogram having a single maximum value at about 80.4° C.

In one embodiment, Form A is characterized by a DSC thermogram having two endotherms with onsets of about 39.3° C. and about 127.2° C.

In one embodiment, Form A is characterized by an XRPD pattern comprising peaks at about 5.5, 16.9, and 16.6° 2θ using Cu Kα radiation and by a DSC thermogram having a single maximum value at about 80.4° C. or by a DSC thermogram having two endotherms with onsets of about 39.3° C. and about 127.2° C. In one embodiment, Form A is characterized by an XRPD pattern comprising peaks at about 5.5, 16.9, 16.6, and 18.8° 2θ using Cu Kα radiation and by a DSC thermogram having a single maximum value at about 80.4° C. or by a DSC thermogram having two endotherms with onsets of about 39.3° C. and about 127.2° C. In one embodiment, Form A is characterized by an XRPD pattern comprising peaks at about 5.5, 16.9, 16.6, 18.8, 14.3, and 12.7° 2θ using Cu Kα radiation and by a DSC thermogram having a single maximum value at about 80.4° C. or by a DSC thermogram having two endotherms with onsets of about 39.3° C. and about 127.2° C. In one embodiment, Form A is characterized by an XRPD pattern comprising peaks at about 5.5, 16.9, 16.6, 18.8, 14.3, 12.7, 21.8, 20.0, 10.0, and 11.0° 2θ using Cu Kα radiation and by a DSC thermogram having a single maximum value at about 80.4° C. or by a DSC thermogram having two endotherms with onsets of about 39.3° C. and about 127.2° C.

Figure 1:
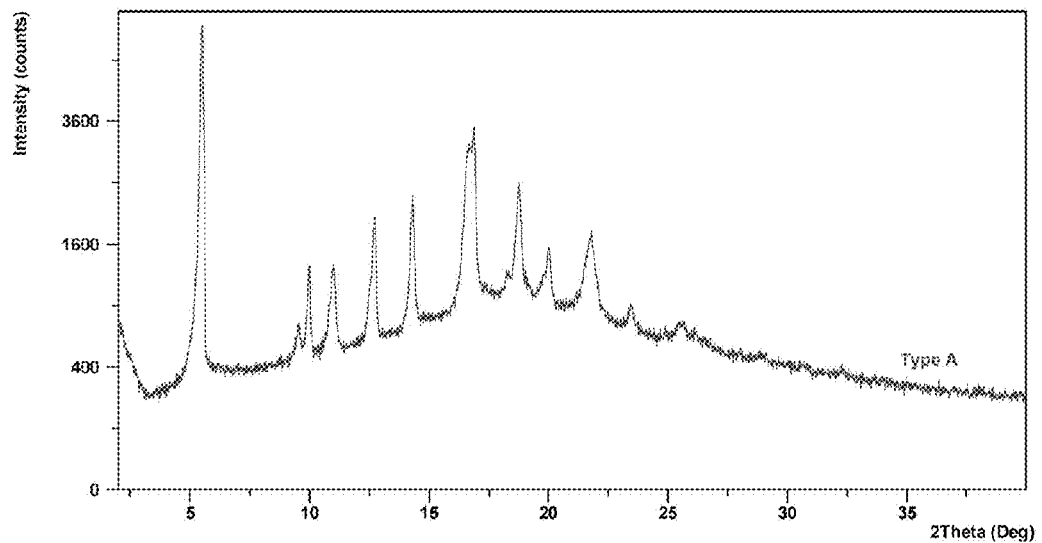
FIG. 1 is a graph indicating the XRPD of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl) amino)methyl)tetrahydrofuran-3,4-diol hydrate (Form A).

In one embodiment, Form A is characterized by an XRPD pattern substantially similar to that set forth in FIG. 1 and by a DSC thermogram having a single maximum value at about 80.4° C. or by a DSC thermogram having two endotherms with onsets of about 39.3° C. and about 127.2° C.

In one embodiment, the crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl) amino)methyl)tetrahydrofuran-3,4-diol is characterized by an XRPD pattern comprising at least three peaks selected from the group consisting of about 5.5, 16.9, 16.6, 18.8, 14.3, 12.7, 21.8, 20.0, 10.0, and 11.0° 2θ using Cu Kα radiation, by an XRPD pattern comprising at least four peaks selected from the group consisting of about 5.5, 16.9, 16.6, 18.8, 14.3, 12.7, 21.8, 20.0, 10.0, and 11.0° 2θ using Cu Kα radiation, by an XRPD pattern comprising at least five peaks selected from the group consisting of about 5.5, 16.9, 16.6, 18.8, 14.3, 12.7, 21.8, 20.0, 10.0, and 11.0° 2θ using Cu Kα radiation, by an XRPD pattern comprising at least six peaks selected from the group consisting of about 5.5, 16.9, 16.6, 18.8, 14.3, 12.7, 21.8, 20.0, 10.0, and 11.0° 2θ using Cu Kα radiation, by an XRPD pattern comprising at least seven peaks selected from the group consisting of about 5.5, 16.9, 16.6, 18.8, 14.3, 12.7, 21.8, 20.0, 10.0, and 11.0° 2θ using Cu Kα radiation, or by an XRPD pattern comprising at least eight peaks selected from the group consisting of about 5.5, 16.9, 16.6, 18.8, 14.3, 12.7, 21.8, 20.0, 10.0, and 11.0° 2θ using Cu Kα radiation.

In one embodiment, the crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl) amino)methyl)tetrahydrofuran-3,4-diol is Form A, characterized as shown in Table A below.

TABLE A

| Selected XRPD diffraction peaks of Form A | | |
|---|---|---|
| Angle 2-Theta (2θ) | d-spacing (Å) | Intensity % |
| 5.5 | 15.9835 | 100 |
| 16.9 | 5.2468 | 59.49 |
| 16.6 | 5.3558 | 45.67 |
| 18.8 | 4.7245 | 38.23 |

TABLE A-continued

| Selected XRPD diffraction peaks of Form A | | |
|---|---|---|
| Angle 2-Theta (2θ) | d-spacing (Å) | Intensity % |
| 14.3 | 6.1836 | 34.91 |
| 12.7 | 6.9600 | 30.34 |
| 21.8 | 4.0756 | 24.26 |
| 20.0 | 4.4336 | 21.36 |
| 10.0 | 8.8499 | 17.84 |
| 11.0 | 8.0267 | 17.29 |

In one embodiment, the crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol is Form B, characterized by an XRPD pattern comprising peaks at about 16.5, 20.5, and 5.2° 2θ using Cu Kα radiation. In one embodiment, the crystalline form (Form B) is characterized by an XRPD pattern comprising peaks at about 16.5, 20.5, 5.2, and 14.2° 2θ using Cu Kα radiation. In one embodiment, the crystalline form (Form B) is characterized by an XRPD pattern comprising peaks at about 16.5, 20.5, 5.2, 14.2, 18.0, and 10.4° 2θ using Cu Kα radiation. In one embodiment, the crystalline form (Form B) is characterized by an XRPD pattern comprising peaks at about 16.5, 20.5, 5.2, 14.2, 18.0, 10.4, 12.3, 10.0, 22.7, and 20.9° 2θ using Cu Kα radiation. In one embodiment, the crystalline form (Form B) is characterized by an XRPD pattern substantially similar to that set forth in FIG. 6.

In one embodiment, Form B is characterized by a DSC thermogram having a single maximum value at about 132.3° C. In one embodiment, Form B is characterized by a DSC thermogram having an endotherm with an onset of about 102.6° C.

In one embodiment, Form B is characterized by an XRPD pattern comprising peaks at about 16.5, 20.5, and 5.2° 2θ using Cu Kα radiation and by a DSC thermogram having a single maximum value at about 132.3° C. or by a DSC thermogram having an endotherm with an onset of about 102.6° C. In one embodiment, the crystalline form (Form B) is characterized by an XRPD pattern comprising peaks at about 16.5, 20.5, 5.2, and 14.2° 2θ using Cu Kα radiation and by a DSC thermogram having a single maximum value at about 132.3° C. or by a DSC thermogram having an endotherm with an onset of about 102.6° C. In one embodiment, the crystalline form (Form B) is characterized by an XRPD pattern comprising peaks at about 16.5, 20.5, 5.2, 14.2, 18.0, and 10.4° 2θ using Cu Kα radiation and by a DSC thermogram having a single maximum value at about 132.3° C. or by a DSC thermogram having an endotherm with an onset of about 102.6° C. In one embodiment, the crystalline form (Form B) is characterized by an XRPD pattern comprising peaks at about 16.5, 20.5, 5.2, 14.2, 18.0, 10.4, 12.3, 10.0, 22.7, and 20.9° 2θ using Cu Kα radiation and by a DSC thermogram having a single maximum value at about 132.3° C. or by a DSC thermogram having an endotherm with an onset of about 102.6° C. In one embodiment, the crystalline form (Form B) is characterized by an XRPD pattern substantially similar to that set forth in FIG. 6 and by a DSC thermogram having a single maximum value at about 132.3° C. or by a DSC thermogram having an endotherm with an onset of about 102.6° C.

In one embodiment, the crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl) amino)methyl)tetrahydrofuran-3,4-diol is characterized by an XRPD pattern comprising at least three peaks selected from the group consisting of about 16.5, 20.5, 5.2, 14.2, 18.0, 10.4, 12.3, 10.0, 22.7, and 20.9° 2θ using Cu Kα radiation, by an XRPD pattern comprising at least four peaks selected from the group consisting of about 16.5, 20.5, 5.2, 14.2, 18.0, 10.4, 12.3, 10.0, 22.7, and 20.9° 2θ using Cu Kα radiation, by an XRPD pattern comprising at least five peaks selected from the group consisting of about 16.5, 20.5, 5.2, 14.2, 18.0, 10.4, 12.3, 10.0, 22.7, and 20.9° 2θ using Cu Kα radiation, by an XRPD pattern comprising at least six peaks selected from the group consisting of about 16.5, 20.5, 5.2, 14.2, 18.0, 10.4, 12.3, 10.0, 22.7, and 20.9° 2θ using Cu Kα radiation, by an XRPD pattern comprising at least seven peaks selected from the group consisting of about 16.5, 20.5, 5.2, 14.2, 18.0, 10.4, 12.3, 10.0, 22.7, and 20.9° 2θ using Cu Kα radiation, or by an XRPD pattern comprising at least eight peaks selected from the group consisting of about 16.5, 20.5, 5.2, 14.2, 18.0, 10.4, 12.3, 10.0, 22.7, and 20.9° 2θ using Cu Kα radiation.

In one embodiment, the crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl) amino)methyl)tetrahydrofuran-3,4-diol is Form B, characterized as shown in Table B below.

TABLE B

Selected XRPD diffraction peaks of Form B

| Angle 2-Theta (2θ) | d-spacing (Å) | Intensity % |
|---|---|---|
| 16.5 | 5.3655 | 100 |
| 20.5 | 4.3247 | 99.11 |
| 5.2 | 16.9764 | 89.5 |
| 14.2 | 6.2371 | 86.31 |
| 18.0 | 4.9360 | 79.87 |
| 10.4 | 8.5065 | 56.50 |
| 12.3 | 7.1799 | 52.56 |
| 10.0 | 8.8652 | 40.06 |
| 22.7 | 3.9245 | 38.12 |
| 20.9 | 4.2505 | 34.10 |

In one embodiment, the crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol is Form C, characterized by an XRPD pattern comprising peaks at about 16.9, 5.7, and 14.5° 2θ using Cu Kα radiation. In one embodiment, the crystalline form (Form C) is characterized by an XRPD pattern comprising peaks at about 16.9, 5.7, 14.5, and 22.2° 2θ using Cu Kα radiation. In one embodiment, the crystalline form (Form C) is characterized by an XRPD pattern comprising peaks at about 16.9, 5.7, 14.5, 22.2, 19.1, and 20.0° 2θ using Cu Kα radiation. In one embodiment, the crystalline form (Form C) is characterized by an X-ray diffraction pattern comprising peaks at about 16.9, 5.7, 14.5, 22.2, 19.1, 20.0, 11.3, 12.9, 10.0, and 23.7° 2θ using Cu Kα radiation. In one embodiment, the crystalline form (Form C) is characterized by an XRPD pattern substantially similar to that set forth in FIG. 11.

In one embodiment, Form C is characterized by a DSC thermogram having a single maximum value at about 148.0° C.

In one embodiment, Form C is characterized by an XRPD pattern comprising peaks at about 16.9, 5.7, and 14.5° 2θ using Cu Kα radiation and by a DSC thermogram having a single maximum value at about 148.0° C. In one embodiment, the crystalline form (Form C) is characterized by an XRPD pattern comprising peaks at about 16.9, 5.7, 14.5, and 22.2° 2θ using Cu Kα radiation and by a DSC thermogram having a single maximum value at about 148.0° C. In one embodiment, the crystalline form (Form C) is characterized by an XRPD pattern comprising peaks at about 16.9, 5.7, 14.5, 22.2, 19.1, and 20.0° 2θ using Cu Kα radiation and by a DSC thermogram having a single maximum value at about 148.0° C. In one embodiment, the crystalline form (Form C) is characterized by an X-ray diffraction pattern comprising peaks at about 16.9, 5.7, 14.5, 22.2, 19.1, 20.0, 11.3, 12.9, 10.0, and 23.7° 2θ using Cu K radiation and by a DSC thermogram having a single maximum value at about 148.0° C. In one embodiment, the crystalline form (Form C) is characterized by an XRPD pattern substantially similar to that set forth in FIG. 11 and by a DSC thermogram having a single maximum value at about 148.0° C.

In one embodiment, the crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl) amino)methyl)tetrahydrofuran-3,4-diol is characterized by an XRPD pattern comprising at least three peaks selected from the group consisting of about 16.9, 5.7, 14.5, 22.2, 19.1, 20.0, 11.3, 12.9, 10.0, and 23.7° 2θ using Cu Kα radiation, by an XRPD pattern comprising at least four peaks selected from the group consisting of about 16.9, 5.7, 14.5, 22.2, 19.1, 20.0, 11.3, 12.9, 10.0, and 23.7° 2θ using Cu Kα radiation, by an XRPD pattern comprising at least five peaks selected from the group consisting of about 16.9, 5.7, 14.5, 22.2, 19.1, 20.0, 11.3, 12.9, 10.0, and 23.7° 2θ using Cu Kα radiation, by an XRPD pattern comprising at least six peaks selected from the group consisting of about 16.9, 5.7, 14.5, 22.2, 19.1, 20.0, 11.3, 12.9, 10.0, and 23.7° 2θ using Cu Kα radiation, by an XRPD pattern comprising at least seven peaks selected from the group consisting of about 16.9, 5.7, 14.5, 22.2, 19.1, 20.0, 11.3, 12.9, 10.0, and 23.7° 2θ using Cu Kα radiation, or by an XRPD pattern comprising at least eight peaks selected from the group consisting of about 16.9, 5.7, 14.5, 22.2, 19.1, 20.0, 11.3, 12.9, 10.0, and 23.7° 2θ using Cu Kα radiation.

In one embodiment, the crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl) amino)methyl)tetrahydrofuran-3,4-diol is Form C, characterized as shown in Table C below.

TABLE C

Selected XRPD diffraction peaks of Form C

| Angle 2-Theta (2θ) | d-spacing (Å) | Intensity % |
|---|---|---|
| 16.9 | 5.2410 | 100 |
| 5.7 | 15.6364 | 88.18 |
| 14.5 | 6.1144 | 44.82 |
| 22.2 | 3.9984 | 39.09 |
| 19.1 | 4.6404 | 31.18 |
| 20.0 | 4.4421 | 30.79 |
| 11.3 | 7.8204 | 25.55 |
| 12.9 | 6.8744 | 22.74 |
| 10.0 | 8.8715 | 17.84 |
| 23.7 | 3.7529 | 10.23 |

When it is stated that the present invention relates to a crystalline form of Form A, Form B, or Form C, the degree of crystallinity is conveniently greater than about 60%, more conveniently greater than about 80%, preferably greater than about 90% and more preferably greater than about 95%. Most preferably the degree of crystallinity is greater than about 98%.

It will be understood that the 2-theta values of the XRPD pattern may vary slightly from one machine to another or from one sample to another, and so the values quoted are not to be construed as absolute.

It is known that an XRPD pattern may be obtained which has one or more measurement errors depending on measurement conditions (such as equipment or machine used). In particular, it is generally known that intensities in an XRPD pattern may fluctuate depending on measurement conditions. Therefore it should be understood that the Form A, Form B, and Form C of the present invention are not limited to the crystals that provide XRPD patterns identical to the XRPD pattern shown in Figures of the present invention and any crystals providing XRPD patterns substantially the same as those shown in Figures of the present invention fall within the scope of the present invention. A person skilled in the art of XRPD is able to judge the substantial identity of XRPD patterns.

Persons skilled in the art of XRPD will realize that the relative intensity of peaks can be affected by, for example, grains above 30 microns in size and non-unitary aspect ratios, which may affect analysis of samples. The skilled person will also realize that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is approximately plus or minus 0.2° 2-theta, and such degree of a measurement error should be taken into account when considering the XRPD patterns presented in the Figures and Tables of the present invention. Furthermore, it should be understood that intensities might fluctuate depending on experimental conditions and sample preparation (preferred orientation). Any crystal form that provides a XRPD diffractogram, Raman/IR spectrum, SSNMR spectrum or DSC thermogram substantially identical to those disclosed herein, fall within the scope of the present disclosures. One skilled in the art will have the ability to determine substantial identities of diffractograms, spectra and thermograms.

Preparation of Crystalline Forms of the Present Invention

The present invention is directed to a process for preparing a crystalline form of 2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol (e.g., (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl) amino)methyl)tetrahydrofuran-3,4-diol) or a hydrate thereof. In one embodiment, the crystalline forms of the present invention can be prepared by slow evaporation, solvent-mediated phase transition, anti-solvent addition, solvent sweeping, or vapor diffusion. In one embodiment, the crystalline form of the present invention can be prepared by slow evaporation, solvent-mediated phase transition, or anti-solvent addition.

In one embodiment, the crystalline form of the present invention is prepared by slow evaporation. In one embodiment, 2-(6-amino-9H-purin-9-yl)-5-(((3-(2-(5-(tert-butyl)-1H-benzo[d]imidazol-2-yl)ethyl)cyclobutyl)(isopropyl) amino)methyl)tetrahydrofuran-3,4-diol is dissolved in a solvent. In one embodiment, the solvent is water, an alkane, a haloalkane, a nitrile, an alcohol, a carboxylic acid, an ester, an ether, toluene, tetrahydrofuran (THF), an acetone, a glycol, or a combination thereof. In one embodiment, the solvent is benzonitrile, acetonitrile, THF, ethyl acetate, dichloroethane, toluene, isopropyl acetate, isopropyl alcohol, cylcohexanol, ethyl alcohol, methyl t-butyl ether (MTBE), water, acetone, glycol, hexane, or a combination thereof.

In one embodiment, after 2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol is dissolved in the solvent, the solvent is evaporated slowly to precipitate 2-(6-amino-9H-purin-9-yl)-5-(((3-(2-(5-(tert-butyl)-1H-benzo[d]imidazol-2-yl)ethyl)cyclobutyl)(isopropyl) amino)methyl)tetrahydrofuran-3,4-diol. In one embodiment, the solvent is evaporated over a period of 6 hours, 12 hours, 18 hours, 24 hours, 48 hours, 72 hours, 96 hours, or 120 hours, or more. In one embodiment, the solvent is evaporated over a period sufficient to allow 2-(6-amino-9H-purin-9-yl)-5-(((3-(2-(5-(tert-butyl)-1H-benzo[d]imidazol-2-yl)ethyl)cyclobutyl)(isopropyl) amino)methyl)tetrahydrofuran-3,4-diol to precipitate from the solvent. In one embodiment, the solvent is evaporated over a period until the solvent completely disappears.

In one embodiment, the slow evaporation is conducted under ambient temperature (e.g., room temperature). In one embodiment, the slow evaporation is conducted at an elevated temperature (e.g., 20° C., 25° C., 30° C., 35° C., 40° C., 45° C., 50° C., 55° C., or 60° C., or higher). In one embodiment, the slow evaporation is conducted at normal pressure (e.g., atmospheric pressure). In one embodiment, the slow evaporation is conducted at a reduced pressure (e.g., 0.9, 0.8, 0.7, 06, 0.5, 0.4, 0.3, 0.2, or 0.1 of the atmospheric pressure, or lower).

In one embodiment, the crystalline form of the present invention is prepared by solvent-mediated phase transition. In one embodiment, 2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol is dissolved or suspended in a solvent. In one embodiment, the solvent is water, an alkane, a haloalkane, an oxane, a nitrile, an alcohol, an ester, an ether, toluene, THF, an acetone, or a combination thereof. In one embodiment, the solvent is acetonitrile, THF, methyl THF, trifluoromethane, dioxane, heptane, toluene, isopropyl acetate, isopropyl alcohol, ethyl alcohol, methanol, MTBE, water, acetone, or a combination thereof.

In one embodiment, the solvent-mediated phase transition is conducted over a period of 6 hours, 12 hours, 18 hours, 24 hours, 48 hours, 72 hours, 96 hours, or 120 hours or more.

In one embodiment, the solvent-mediated phase transition is conducted under ambient temperature (e.g., room temperature). In one embodiment, the solvent-mediated phase transition is conducted at an elevated temperature (e.g., 20° C., 25° C., 30° C., 35° C., 40° C., 45° C., 50° C., 55° C., or 60° C., or higher). In one embodiment, the solvent-mediated phase transition is conducted at normal pressure (e.g., atmospheric pressure). In one embodiment, the solvent-mediated phase transition is conducted at a reduced pressure (e.g., 0.9, 0.8, 0.7, 06, 0.5, 0.4, 0.3, 0.2, or 0.1 of the atmospheric pressure, or lower). In one embodiment, the solution or suspension is stirred.

In one embodiment, the crystalline form of the present invention is prepared by anti-solvent addition. In one embodiment, 2-(6-amino-9H-purin-9-yl)-5-(((3-(2-(5-(tert-butyl)-1H-benzo[d]imidazol-2-yl)ethyl)cyclobutyl)(isopropyl) amino)methyl)tetrahydrofuran-3,4-diol is dissolved in a solvent. In one embodiment, the solvent is an oxane, a nitrile, an alcohol, THF, an acetone, a carboxylic acid, or a combination thereof. In one embodiment, the solvent is acetonitrile, THF, dioxane, isopropyl alcohol, ethyl alcohol, methanol, acetone, acetic acid, or a combination thereof. In one embodiment, 2-(6-amino-9H-purin-9-yl)-5-(((3-(2-(5-(tert-butyl)-1H-benzo[d]imidazol-2-yl)ethyl)cyclobutyl)(isopropyl) amino)methyl)tetrahydrofuran-3,4-diol is saturated in the solvent.

In one embodiment, an anti-solvent is added to the solution of 2-(6-amino-9H-purin-9-yl)-5-(((3-(2-(5-(tert-butyl)-1H-benzo[d]imidazol-2-yl)ethyl)cyclobutyl)(isopropyl)amino) methyl)tetrahydrofuran-3,4-diol. In one embodiment, the anti-solvent is an alkane, water, or a combination thereof. In one embodiment, the anti-solvent is hexane or water.

In one embodiment, the anti-solvent addition is conducted over a period of 6 hours, 12 hours, 18 hours, 24 hours, 48 hours, 72 hours, 96 hours, or 120 hours or 6 days, 7 days, 10 days, 14 days, or more. In one embodiment, the anti-solvent addition is conducted over a period sufficient to allow 2-(6-amino-9H-purin-9-yl)-5-(((3-(2-(5-(tert-butyl)-1H-benzo[d] imidazol-2-yl)ethyl)cyclobutyl)(isopropyl)amino)methyl) tetrahydrofuran-3,4-diol to precipitate from the solvent.

In one embodiment, the anti-solvent addition is conducted under ambient temperature (e.g., room temperature). In one embodiment, the anti-solvent addition is conducted at an elevated temperature (e.g., 20° C., 25° C., 30° C., 35° C., 40° C., 45° C., 50° C., 55° C., or 60° C., or higher).

In one embodiment, the anti-solvent addition is conducted at normal pressure (e.g., atmospheric pressure). In one embodiment, the anti-solvent addition is conducted at a reduced pressure (e.g., 0.9, 0.8, 0.7, 06, 0.5, 0.4, 0.3, 0.2, or 0.1 of the atmospheric pressure, or lower).

In one embodiment, the crystalline form of the present invention is prepared by vapor sweeping. In one embodiment, 2-(6-amino-9H-purin-9-yl)-5-(((3-(2-(5-(tert-butyl)-1H-benzo[d]imidazol-2-yl)ethyl)cyclobutyl)(isopropyl)amino) methyl)tetrahydrofuran-3,4-diol is added to a container (e.g., a vial). In one embodiment, the container is placed inside a larger container. In one embodiment, a solvent is added to the larger container and the larger container is sealed.

In one embodiment, the solvent is volatile and forms a vapor in the larger container. In one embodiment, the solvent is a nitrile, an alcohol, THF, methyl THF, an ester or a combination thereof. In one embodiment, the solvent is acetonitrile, THF, methyl THF, acetonitrile, ethyl acetate, methanol, or a combination thereof.

In one embodiment, the vapor sweeping is conducted over a period of 6 hours, 12 hours, 18 hours, 24 hours, 48 hours, 72 hours, 96 hours, or 120 hours or 6 days, 7 days, 10 days, 14 days, or more. In one embodiment, the vapor sweeping is conducted over a period sufficient to allow the solvent vapor to interact with 2-(6-amino-9H-purin-9-yl)-5-(((3-(2-(5-(tert-butyl)-1H-benzo[d]imidazol-2-yl)ethyl)cyclobutyl) (isopropyl)amino)methyl)tetrahydrofuran-3,4-diol.

In one embodiment, the vapor sweeping is conducted under ambient temperature (e.g., room temperature). In one embodiment, the vapor sweeping is conducted at an elevated temperature (e.g., 20° C., 25° C., 30° C., 35° C., 40° C., 45° C., 50° C., 55° C., or 60° C., or higher). In one embodiment, the vapor sweeping is conducted at normal pressure (e.g., atmospheric pressure). In one embodiment, the vapor sweeping is conducted at a reduced pressure (e.g., 0.9, 0.8, 0.7, 06, 0.5, 0.4, 0.3, 0.2, or 0.1 of the atmospheric pressure, or lower).

In one embodiment, the crystalline form of the present invention is prepared by vapor diffusion. In one embodiment, 2-(6-amino-9H-purin-9-yl)-5-(((3-(2-(5-(tert-butyl)-1H-benzo[d]imidazol-2-yl)ethyl)cyclobutyl)(isopropyl)amino) methyl)tetrahydrofuran-3,4-diol is dissolved in a solvent in a container (e.g., a vial). In one embodiment, the container is placed inside a larger container. In one embodiment, an anti-solvent is added to the larger container and the larger container is sealed. In one embodiment, the anti-solvent is volatile.

In one embodiment, the vapor diffusion is conducted over a period of 6 hours, 12 hours, 18 hours, 24 hours, 48 hours, 72 hours, 96 hours, or 120 hours or 6 days, 7 days, 10 days, 14 days, or more. In one embodiment, the vapor diffusion is conducted over a period sufficient to allow the anti-solvent vapor to interact with 2-(6-amino-9H-purin-9-yl)-5-(((3-(2-(5-(tert-butyl)-1H-benzo[d]imidazol-2-yl)ethyl)cyclobutyl) (isopropyl) amino)methyl)tetrahydrofuran-3,4-diol.

In one embodiment, the vapor diffusion is conducted under ambient temperature (e.g., room temperature). In one embodiment, the vapor diffusion is conducted at an elevated temperature (e.g., 20° C., 25° C., 30° C., 35° C., 40° C., 45° C., 50° C., 55° C., or 60° C., or higher). In one embodiment, the vapor diffusion is conducted at normal pressure (e.g., atmospheric pressure). In one embodiment, the vapor diffusion is conducted at a reduced pressure (e.g., 0.9, 0.8, 0.7, 06, 0.5, 0.4, 0.3, 0.2, or 0.1 of the atmospheric pressure, or lower).

Compounds of Formula I

The present invention relates to a compound of formula I:

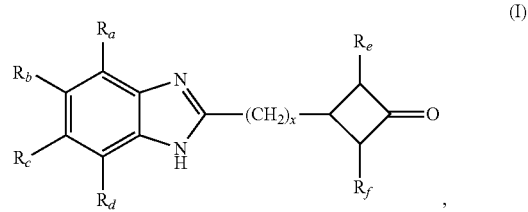

or a salt or solvate thereof, wherein:

$R_a$, $R_b$, R, and $R_d$ are each independently -$M_2$-$T_2$;

$M_2$ is a bond, $S(O)_2$, S(O), S, C(O), C(O)O, O, O—$C_1$-$C_4$ alkyl linker, $C_1$-$C_4$ alkyl linker, NH, or $NR_t$;

$R_t$ is $C_1$-$C_6$ alkyl;

$T_2$ is H, halogen, or $R_{S4}$;

$R_{S4}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 8-membered heterocycloalkyl, or 5 to 10-membered heteroaryl;

$R_e$ and $R_f$ are each independently H or $C_1$-$C_6$ alkyl; and x is 1, 2, 3, 4, 5, or 6, wherein each of O—$C_1$-$C_4$ alkyl linker, $C_1$-$C_4$ alkyl linker, $R_t$, and $R_{S4}$ is optionally substituted with one or more substituents selected from the group consisting of halogen, hydroxyl, carboxyl, cyano, $C_1$-$C_6$ alkyl, $C_2$-$C_6$ alkenyl, $C_2$-$C_6$ alkynyl, $C_1$-$C_6$ alkoxyl, amino, mono-$C_1$-$C_6$alkylamino, di-$C_1$-$C_6$ alkylamino, $C_3$-$C_8$ cycloalkyl, $C_6$-$C_{10}$ aryl, 4 to 6-membered heterocycloalkyl, and 5 to 6-membered heteroaryl.

In one embodiment, $R_a$, $R_b$, $R_c$, and $R_d$ are each -$M_2$-$T_2$, wherein $M_2$ is a bond; and $T_2$ is H.

In one embodiment, one of $R_a$, $R_b$, $R_c$, and $R_d$ is -$M_2$-$T_2$, wherein $M_2$ is a bond and $T_2$ is H; and the rest of $R_a$, $R_b$, $R_c$, and $R_d$ are each independently -$M_2$-$T_2$; wherein $M_2$ is a bond, $S(O)_2$, S(O), S, C(O), C(O)O, O, O—$C_1$-$C_4$ alkyl linker, $C_1$-$C_4$ alkyl linker, NH, or $NR_t$; and $T_2$ is H, halogen, or $R_{S4}$.

In one embodiment, two of $R_a$, $R_b$, $R_c$, and $R_d$ is -$M_2$-$T_2$, wherein $M_2$ is a bond and $T_2$ is H; and the rest of $R_a$, $R_b$, $R_c$, and $R_d$ are each independently -$M_2$-$T_2$; wherein $M_2$ is a bond, $S(O)_2$, S(O), S, C(O), C(O)O, O, O—$C_1$-$C_4$ alkyl linker, $C_1$-$C_4$ alkyl linker, NH, or $NR_t$; and $T_2$ is H, halogen, or $R_{S4}$.

In one embodiment, three of $R_a$, $R_b$, $R_c$, and $R_d$ is -$M_2$-$T_2$, wherein $M_2$ is a bond and $T_2$ is H; and the rest of Ra, $R_b$, R, and $R_d$ is -$M_2$-$T_2$; wherein $M_2$ is a bond, S(O)$_2$, S(O), S, C(O), C(O)O, O, O—$C_1$-$C_4$ alkyl linker, $C_1$-$C_4$ alkyl linker, NH, or $NR_i$; and $T_2$ is H, halogen, or $R_{S4}$.

In one embodiment, $R_a$, $R_c$, and $R_d$ are each -$M_2$-$T_2$, wherein $M_2$ is a bond and $T_2$ is H; and $R_b$ is -$M_2$-$T_2$; wherein $M_2$ is a bond; $T_2$ is $R_{S4}$; and $R_{S4}$ is $C_1$-$C_6$ alkyl. In one embodiment, $R_{S4}$ is t-butyl.

In one embodiment, x is 2.

In one embodiment, $R_e$ and $R_f$ are each H.

In one embodiment, the present invention relates to a compound having the following structure:

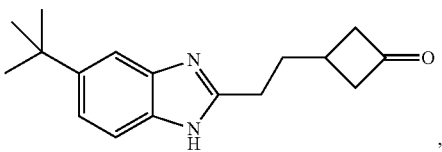 [SMILES: CC(C)(C)c1ccc2[nH]c(CCC3CC(=O)C3)nc2c1]

, or a salt or solvate thereof.

Salts of the Present Invention

The present invention relates to pharmaceutically acceptable salts of (2R,3R,4S,5R)-2-(6-amino-9H-purin-9-yl)-5-((((1r,3S)-3-(2-(5-(tert-butyl)-1H-benzo[d]imidazol-2-yl) ethyl) cyclobutyl)(isopropyl)amino)methyl)tetrahydrofuran-3,4-diol or a hydrate thereof. In one embodiment, the present invention relates to mono-salts from (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino) methyl)tetrahydrofuran-3,4-diol or a hydrate thereof and 1,5-naphthalene disulfonic acid, $H_2SO_4$, $H_3PO_4$, L-tartaric acid and citric acid which may be obtained from direct salt formation. In one embodiment, the present invention relates to mono-salts from (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof and p-toluene sulfonic acid, methane sulfonic acid, HCl, maleic acid and L-malic acid salt which may be obtained from freeze-drying. In one embodiment, the salts are obtained as amorphous solids. In one embodiment, the present invention relates to mono-salts from (2R,3R,4S,5R)-2-(6-amino-9H-purin-9-yl)-5-((((1r,3S)-3-(2-(5-(tert-butyl)-1H-benzo[d]imidazol-2-yl)ethyl) cyclobutyl)(isopropyl)amino)methyl)tetrahydrofuran-3,4-diol or a hydrate thereof and malonic acid, fumaric acid, galactaric acid and lactobionic acid. In one embodiment, the salts are formed in gums.

In one embodiment, the present invention relates to hemi-salts from (2R,3R,4S,5R)-2-(6-amino-9H-purin-9-yl)-5-((((1r,3S)-3-(2-(5-(tert-butyl)-1H-benzo[d]imidazol-2-yl) ethyl)cyclobutyl)(isopropyl)amino)methyl)tetrahydrofuran-3,4-diol or a hydrate thereof and maleic acid. In one embodiment, the salt is isolated as a gum. In one embodiment, the present invention relates to bis-salts from (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl) amino)methyl)tetrahydrofuran-3,4-diol or a hydrate thereof and p-toluene sulfonic acid, methane sulfonic acid, and maleic acid. In one embodiment, the salt is isolated as a gum.

Methods of Preparing the Compounds of the Present Invention

The present invention relates to a process for preparing (2R,3R,4S,5R)-2-(6-amino-9H-purin-9-yl)-5-((((1r,3 S)-3-(2-(5-(tert-butyl)-1H-benzo[d]imidazol-2-yl)ethyl)cyclobutyl)(isopropyl)amino)methyl)tetrahydrofuran-3,4-diol:

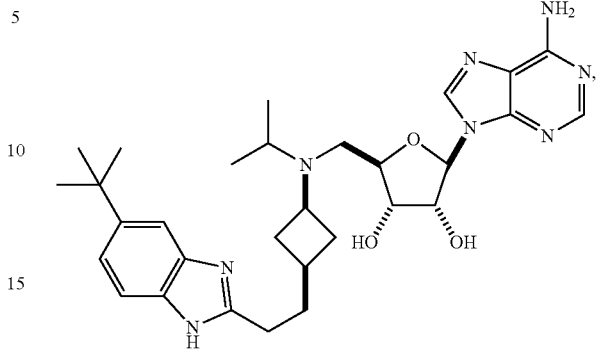

or a salt or hydrate thereof, comprising at least one step, or at least two steps selected from the group consisting of:

(1) reacting 9-((3aR,4R,6R,6aR)-6-(aminomethyl)-2,2-dimethyltetrahydrofuro[3,4-d][1,3]dioxol-4-yl)-9H-purin-6-amine with acetone to yield 9-((3aR,4R,6R,6aR)-6-((isopropylamino)methyl)-2,2-dimethyltetrahydrofuro[3,4-d][1,3]dioxol-4-yl)-9H-purin-6-amine;

(2) reacting 9-((3aR,4R,6R,6aR)-6-((isopropylamino)methyl)-2,2-dimethyltetrahydrofuro[3,4-d][1,3]dioxol-4-yl)-9H-purin-6-amine with 3-(2-(5-(tert-butyl)-1H-benzo[d]imidazol-2-yl)ethyl)cyclobutanone to yield 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine; and (3) converting 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine to (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol.

The present invention relates to a process for preparing (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol:

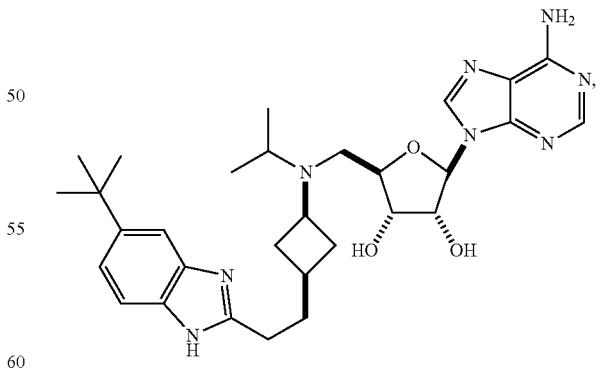

or a salt or hydrate thereof, comprising the steps of:

(1) reacting 9-((3aR,4R,6R,6aR)-6-(aminomethyl)-2,2-dimethyltetrahydrofuro[3,4-d][1,3]dioxol-4-yl)-9H-purin-6-amine with acetone to yield 9-((3aR,4R,6R,6aR)-6-((isopropylamino)methyl)-2,2-dimethyltetrahydrofuro[3,4-d][1,3] dioxol-4-yl)-9H-purin-6-amine;

(2) reacting 9-((3aR,4R,6R,6aR)-6-((isopropylamino)methyl)-2,2-dimethyltetrahydrofuro[3,4-d][1,3]dioxol-4-yl)-9H-purin-6-amine with 3-(2-(5-(tert-butyl)-1H-benzo[d]imidazol-2-yl)ethyl)cyclobutanone to yield 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine; and (3) converting 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine to (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol.

In one embodiment, step (1) comprises a solvent. In one embodiment, the solvent comprises an alcohol. In one embodiment, the solvent comprises methanol. In one embodiment, 9-((3aR,4R,6R,6aR)-6-(aminomethyl)-2,2-dimethyltetrahydrofuro[3,4-d][1,3]dioxol-4-yl)-9H-purin-6-amine is dissolved in the solvent. In one embodiment, acetone is mixed in the solvent. In one embodiment, stirring is performed to facilitate the dissolvation of 9-((3aR,4R,6R,6aR)-6-(aminomethyl)-2,2-dimethyltetrahydrofuro[3,4-d][1,3]dioxol-4-yl)-9H-purin-6-amine. In one embodiment, the dissolvation is conducted under ambient temperature (e.g., room temperature).

In one embodiment, step (1) further comprises a carboxylic acid. In one embodiment, the carboxylic acid is acetic acid.

In one embodiment, step (1) further comprises a reducing agent. In one embodiment, the reducing agent is a borohydride. In one embodiment, the borohydride is sodium triacetoxy borohydride (STAB). In one embodiment, the reducing agent is added to the reaction after 9-((3aR,4R,6R,6aR)-6-(aminomethyl)-2,2-dimethyltetrahydrofuro[3,4-d][1,3]dioxol-4-yl)-9H-purin-6-amine and/or acetone is dissolved in the solvent. In one embodiment, the reducing agent is added to the reaction in multiple portions. In one embodiment, the solution comprising 9-((3aR,4R,6R,6aR)-6-(aminomethyl)-2,2-dimethyltetrahydrofuro[3,4-d][1,3]dioxol-4-yl)-9H-purin-6-amine and/or acetone is cooled before the reducing agent is added. In one embodiment, the solution is cooled to a temperature below the ambient temperature (e.g., room temperature).

In one embodiment, the solution is cooled to a temperature below 30° C., 25° C., or 20° C. In one embodiment, the solution is cooled to 16-18° C.

In one embodiment, the reaction in step (1) is conducted under ambient temperature (e.g., room temperature). In one embodiment, the reaction is conducted at a temperature below 50° C., 40° C., 35° C., 30° C., 25° C., or 20° C. In one embodiment, the reaction is conducted at 20-25° C.

In one embodiment, step (1) may further comprise concentrating the resulting 9-((3aR,4R,6R,6aR)-6-((isopropylamino)methyl)-2,2-dimethyltetrahydrofuro[3,4-d][1,3]dioxol-4-yl)-9H-purin-6-amine before step (2). In one embodiment, the concentration is achieved through vacuum evaporation of acetone and the solvent. In one embodiment, 9-((3aR,4R,6R,6aR)-6-((isopropylamino)methyl)-2,2-dimethyltetrahydrofuro[3,4-d][1,3]dioxol-4-yl)-9H-purin-6-amine is filtered before step (2).

In one embodiment, the yield of 9-((3aR,4R,6R,6aR)-6-((isopropylamino)methyl)-2,2-dimethyltetrahydrofuro[3,4-d][1,3]dioxol-4-yl)-9H-purin-6-amine through step (1) is at least 50%, 60%, 70%, 80%, 90%, 95%, or 99%. In one embodiment, the yield is at least 90%. In one embodiment, the yield is at least 95%.

In one embodiment, acetonitrile is added to 9-((3aR,4R,6R,6aR)-6-((isopropylamino)methyl)-2,2-dimethyltetrahydrofuro[3,4-d][1,3]dioxol-4-yl)-9H-purin-6-amine from step (1), and the mixture is used in step (2) for further reaction.

In one embodiment, step (2) further comprises a carboxylic acid. In one embodiment, the carboxylic acid is acetic acid.

In one embodiment, step (2) is conducted under an inert gas. In one embodiment, the inert gas is nitrogen.

In one embodiment, step (2) further comprises a reducing agent. In one embodiment, the reducing agent is a borohydride. In one embodiment, the borohydride is STAB. In one embodiment, the reducing agent is added to the mixture of 3-(2-(5-(tert-butyl)-1H-benzo[d]imidazol-2-yl)ethyl)cyclobutanone and 9-((3aR,4R,6R,6aR)-6-((isopropylamino)methyl)-2,2-dimethyltetrahydrofuro[3,4-d][1,3]dioxol-4-yl)-9H-purin-6-amine. In one embodiment, the reducing agent is added to the reaction in multiple portions. In one embodiment, the mixture of 3-(2-(5-(tert-butyl)-1H-benzo[d]imidazol-2-yl)ethyl)cyclobutanone and 9-((3aR,4R,6R,6aR)-6-((isopropylamino)methyl)-2,2-dimethyltetrahydrofuro[3,4-d][1,3]dioxol-4-yl)-9H-purin-6-amine forms a slurry. In one embodiment, the slurry is heated before STAB is added to the slurry. In one embodiment, the slurry is heated to 40° C., 45° C., 50° C., 55° C., or 60° C., or higher. In one embodiment, the slurry is heated to 55° C.

In one embodiment, the reaction is stirred for a period of at least 2 hours, 4 hours, 8 hours, 12 hours, 18 hours, 24 hours, or 48 hours. In one embodiment, the reaction is stirred for 14-16 hours.

In one embodiment, the reaction is conducted at a temperature up to 40° C., 45° C., 50° C., 55° C., or 60° C., or higher. In one embodiment, the reaction is conducted at a temperature of 55° C. In one embodiment, the reaction mixture is cooled. In one embodiment, the reaction mixture is cooled to room temperature.

In one embodiment, water is added to the reaction mixture after the mixture is cooled.

In one embodiment, step (2) may further comprise concentrating the resulting 9-((3aR,4R,6R,6aR)-6-(((3-((2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine before step (3). In one embodiment, the concentration removes acetonitrile.

In one embodiment, the pH of the reaction mixture comprising 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine is adjusted with a base (e.g., a hydroxide, such as sodium hydroxide). In one embodiment, the pH is adjusted to about 10. In one embodiment, the aqueous layer is removed after the pH adjustment and the organic layer is concentrated before step (3).

In one embodiment, the yield of 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine through step (2) is at least 50%, 60%, 70%, 80%, 90%, 95%, or 99%. In one embodiment, the yield is at least 80%.

In one embodiment, step (3) is conducted under an inert gas. In one embodiment, the inert gas is nitrogen.

In one embodiment, step (3) comprises a solvent. In one embodiment, the solvent comprises an alcohol. In one embodiment, the solvent comprises methanol. In one embodiment, step (3) comprises hydrochloric acid. In one embodiment, 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine is mixed with hydrochloric acid and methanol to form a solution. In one embodiment, the reaction solution is heated to 40° C., 45° C., 50° C., 55° C., or 60° C., or higher. In one embodiment, the reaction solution is heated to 45° C. In one embodiment, the reaction solution is kept at ambient temperature (e.g., room temperature) after the heating.

In one embodiment, 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine is converted to (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol after the heating. In one embodiment, at least 50%, 60%, 70%, 80%, 90%, 95%, or 99% of 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine is converted. In one embodiment, at least 90% of 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine is converted.

In one embodiment, step (3) further comprises adjusting the pH of the reaction solution with a base (e.g., a hydroxide, such as sodium hydroxide, and a bicarbonate, such as sodium bicarbonate). In one embodiment, after the pH adjustment the organic layer is concentrated.

The process of the present invention may further comprise step (4): recrystallizing (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol to yield (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl) tetrahydrofuran-3,4-diol or a salt of hydrate thereof.

In one embodiment, step (4) further comprises stirring. In one embodiment, a slurry is formed in step (4). In one embodiment, a seed crystal is added to the slurry.

In one embodiment, the slurry is heated to 50° C., 55° C., 60° C., 65° C., 70° C., or 75° C., or higher. In one embodiment, the slurry is heated to 75° C. In one embodiment, the slurry is cooled to 25-30° C. after the heating and stirred for 8 hours, 12 hours, 18 hours, or 24 hours.

In one embodiment, the heating, cooling, and stirring of the slurry are repeated.

In one embodiment, the process of the present invention is advantageous as compared to other processes in that the process of the present invention produces (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol at a large commercial scale. In one embodiment, the process of the present invention is able to process at least 100 g, 200 g, 500 g, 1 kg, 2 kg, 5 kg, 10 kg, 20 kg, 50 kg, 100 kg, 200 kg, 500 kg, or 1000 kg, or more (2R,3R,4S,5R)-2-(6-amino-9H-purin-9-yl)-5-((((1r,3 S)-3-(2-(5-(tert-butyl)-1H-benzo[d]imidazol-2-yl)ethyl)cyclobutyl) (isopropyl)amino)methyl)tetrahydrofuran-3,4-diol, without the need to scale up. In one embodiment, the process of the present invention is advantageous as compared to other processes in that the process of the present invention produces (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol at a high purity such that cumbersome purification (e.g., column chromatography, filtration, extraction, phase separation, and solvent evaporation) is not needed. In one embodiment, the process of the present invention is able to process (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol at a purity of at least 75%, 80%, 85%, 90%, 95%, 96%, 97%, 98%, 99%, or 99.5%, or higher. In one embodiment, the process of the present invention is advantageous as compared to other processes in that the process of the present invention produces (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol with little or none impurity (e.g., toxic impurity). In one embodiment, the impurity produced in the process of the present invention, even if produced, is easy to be separated from (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol without any cumbersome purification (e.g., column chromatography, filtration, extraction, phase separation, and solvent evaporation). In one embodiment, the process of the present invention is advantageous as compared to other processes in that the process of the present invention uses less or none catalyst (e.g., metal catalyst, such as transition metal catalyst) such that minimum or none separation is needed to remove the catalyst. In one embodiment, the process of the present invention is advantageous as compared to other processes in that the process of the present invention produces (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol at a significantly reduced cost, due to its high yield, high purity, little or no impurity, reduced amount of or no catalyst, or a combination thereof.

The present invention relates to a process for preparing 3-(2-(5-(tert-butyl)-1H-benzo[d]imidazol-2-yl)ethyl)cyclobutanone:

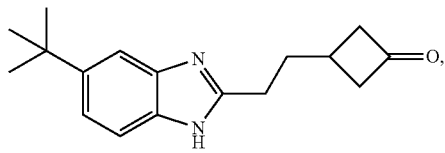

or a salt thereof, comprising at least one step, at least two steps, at least three steps, at least four steps, or at least five steps, selected from the group consisting of:

(1) converting pent-4-enoic acid to benzyl pent-4-enoate;

(2) converting benzyl pent-4-enoate to benzyl 3-(2,2-dichloro-3-oxo-cyclobutyl)propanoate;

(3) converting benzyl 3-(2,2-dichloro-3-oxo-cyclobutyl) propanoate to benzyl 3-(3-oxo-cyclobutyl)propanoate;

(4) converting benzyl 3-(3-oxo-cyclobutyl)propanoate to 3-(3-oxo-cyclobutyl)propanoic acid;

(5) reacting 3-(3-oxocyclobutyl)propanoic acid with 4-tert-butyl-2-nitroaniline to yield N-(4-tert-butyl-2-nitrophenyl)-3-(3-oxo-cyclobutyl)propanamide; and (6) converting N-(4-tert-butyl-2-nitrophenyl)-3-(3-oxocyclobutyl)propanamide to 3-(2-(5-(tert-butyl)-1H-benzo[d] imidazol-2-yl)ethyl)cyclobutanone.

The present invention relates to a process for preparing 3-(2-(5-(tert-butyl)-1H-benzo[d]imidazol-2-yl)ethyl)cyclobutanone:

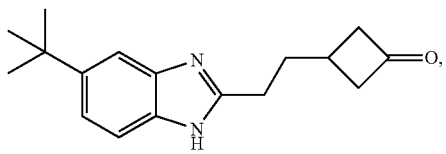 [SMILES: CC(C)(C)c1ccc2[nH]c(CCC3CC(=O)C3)nc2c1]

or a salt thereof, comprising the steps of:

(1) converting pent-4-enoic acid to benzyl pent-4-enoate;

(2) converting benzyl pent-4-enoate to benzyl 3-(2,2-dichloro-3-oxo-cyclobutyl)propanoate;

(3) converting benzyl 3-(2,2-dichloro-3-oxo-cyclobutyl) propanoate to benzyl 3-(3-oxo-cyclobutyl)propanoate;

(4) converting benzyl 3-(3-oxo-cyclobutyl)propanoate to 3-(3-oxo-cyclobutyl)propanoic acid;

(5) reacting 3-(3-oxocyclobutyl)propanoic acid with 4-tert-butyl-2-nitroaniline to yield N-(4-tert-butyl-2-nitrophenyl)-3-(3-oxo-cyclobutyl)propanamide; and (6) converting N-(4-tert-butyl-2-nitrophenyl)-3-(3-oxo-cyclobutyl)propanamide to 3-(2-(5-(tert-butyl)-1H-benzo[d]imidazol-2-yl)ethyl)cyclobutanone. In one embodiment, 3-(2-(5-(tert-butyl)-1H-benzo[d]imidazol-2-yl)ethyl)cyclobutanone salt is a hydrochloride salt.

In one embodiment, step (1) is conducted under an inert gas. In one embodiment, the inert gas is nitrogen. In one embodiment, step (1) comprises a carbonate (e.g., potassium carbonate). In one embodiment, step (1) further comprises tetrabutylammonium iodide. In one embodiment, the yield of benzyl pent-4-enoate through step (1) is at least 90%.

In one embodiment, step (2) comprises a mixture of benzyl pent-4-enoate and zinc-copper in diethyl ether and 1,2-dimethoxyethane. In one embodiment, trichloroacetyl chloride is added to the mixture. In one embodiment, the mixture is stirred at about 50° C. In one embodiment, the mixture is cooled after the stirring. In one embodiment, step (2) further comprises washing and concentrating the organic layer comprising benzyl 3-(2,2-dichloro-3-oxo-cyclobutyl)propanoate.

In one embodiment, step (3) comprises treating benzyl 3-(2,2-dichloro-3-oxo-cyclobutyl)propanoate with zinc powder a solvent. In one embodiment, the mixture of benzyl 3-(2,2-dichloro-3-oxo-cyclobutyl)propanoate and zinc powder is heated to 65° C., 70° C., 75° C., 80° C., or 85° C. In one embodiment, the mixture of benzyl 3-(2,2-dichloro-3-oxo-cyclobutyl)propanoate and zinc powder is heated to 80° C. In one embodiment, the mixture is cooled after the heating. In one embodiment, step (3) further comprises washing and concentrating the organic layer comprising benzyl 3-(3-oxo-cyclobutyl)propanoate.

In one embodiment, step (4) comprises an inert gas. In one embodiment, the inert gas is nitrogen. In one embodiment, step (4) comprises a catalyst. In one embodiment, the catalyst is a palladium catalyst (e.g., Pd/C). In one embodiment, step (4) comprises hydrogen gas. In one embodiment, step (4) further comprises washing and concentrating the organic layer comprising 3-(3-oxo-cyclobutyl)propanoic acid.

In one embodiment, step (5) comprises a solvent. In one embodiment, the solvent comprises dioxane (e.g., 1,4-dioxane). In one embodiment, 3-(3-oxo-cyclobutyl)propanoic acid and 4-tert-butyl-2-nitroaniline are mixed with pyridine and propylphosphonic anhydride. In one embodiment, the mixture is heated to 80° C., 85° C., 90° C., 95° C., 100° C., 105° C., or 110° C. In one embodiment, the mixture of is heated to 100° C. In one embodiment, the mixture is cooled after the heating. In one embodiment, step (5) further comprises washing and concentrating the organic layer comprising N-(4-tert-butyl-2-nitrophenyl)-3-(3-oxo-cyclobutyl)propanamide.

In one embodiment, step (6) comprises mixing N-(4-tert-butyl-2-nitrophenyl)-3-(3-oxo-cyclobutyl)propanamide with iron powder in a solvent. In one embodiment, the mixture is heated to 65° C., 70° C., 75° C., 80° C., or 85° C. In one embodiment, the mixture of is heated to 80° C.

In one embodiment, the mixture is cooled after the heating. In one embodiment, step (6) further comprises washing and concentrating the organic layer comprising 3-(2-(5-(tert-butyl)-1H-benzo[d]imidazol-2-yl)ethyl)cyclobutanone.

In one embodiment, the process of the present invention is shown in Scheme 1. The process is a 4-step synthesis including a purification step to produce pure (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof.

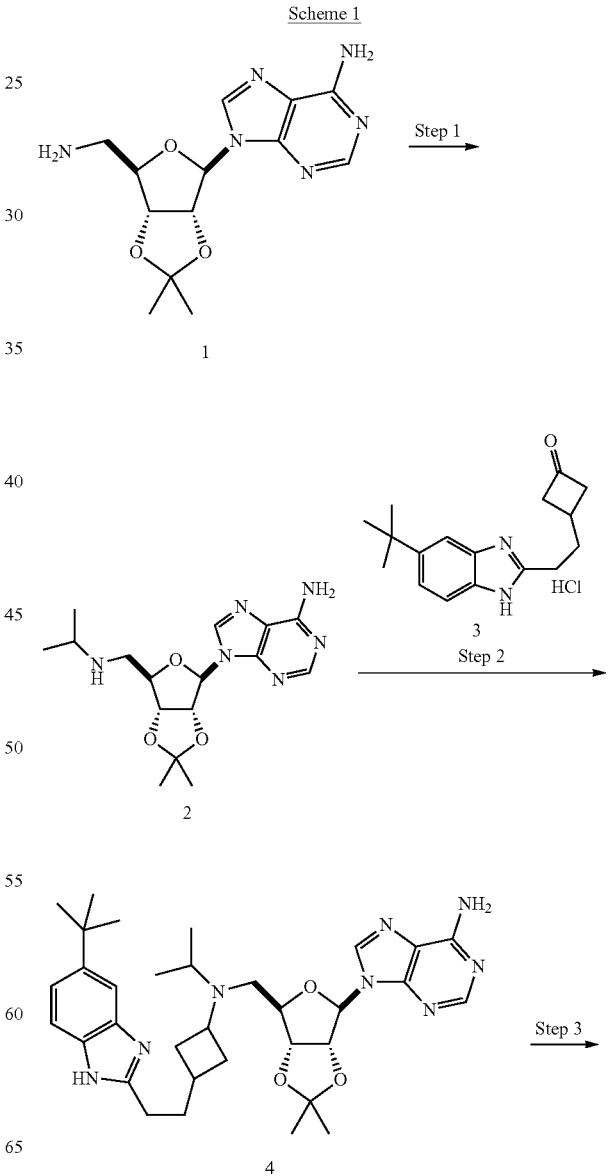

Scheme 1

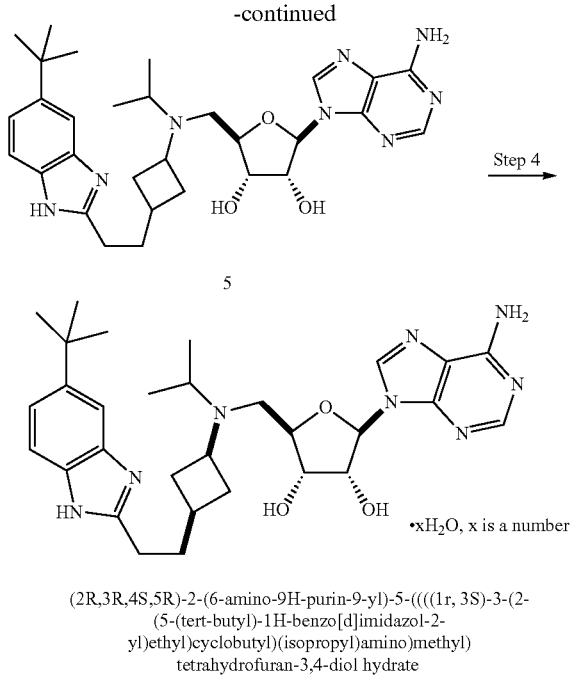

5

(2R,3R,4S,5R)-2-(6-amino-9H-purin-9-yl)-5-((((1r, 3S)-3-(2-
(5-(tert-butyl)-1H-benzo[d]imidazol-2-
yl)ethyl)cyclobutyl)(isopropyl)amino)methyl)
tetrahydrofuran-3,4-diol hydrate The process of the present invention has never been reported in the art. The process is a 4-step synthesis including one purification step. Step 1 is the coupling of compound 1 and acetone in the presence of methanol, acetic acid, and sodium triacetoxyborohydride to produce compound 2. Compound 1 may be prepared from commercially available starting material as described in Journal of Medicinal Chemistry, 1969, 12 (4), 658-662. Step 2 is the coupling of compound 2 and compound 3 (for the preparation of compound 3, see below) in the presence of acetonitrile, acetic acid, and sodium triacetoxyborohydride to produce compound 4. Step 3 is the conversion of compound 4 into compound 5 in the presence of methanol and 6N HCl. Step 4 is the recrystallization of compound 5 using a mixture of acetonitrile and water to afford a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof.

The process of the present invention relates to a process for preparing a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof comprising a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof as a synthetic intermediate.

Step 1

Compound 1 and acetone are coupled in the presence of a solvent, an organic acid, and a reducing agent to produce compound 2. In one embodiment, the solvent is methanol. In one embodiment, the organic acid is acetic acid. In one embodiment, the reducing agent is sodium triacetoxyborohydride. Compound 1 may be prepared from commercially available starting material as described in Journal of Medicinal Chemistry, 1969, 12 (4), 658-662.

Compound 1, acetone, acetic acid, and methanol are added to a reaction vessel at room temperature, the reaction mixture being stirred for 5-10 min until all solids are dissolved. In one embodiment, the reaction mixture comprising compound 1, acetone, acetic acid, and methanol is cooled to 16-18° C., and sodium acetoxyborohydride is added over 1-2 min. In one embodiment, sodium acetoxyborohydride is added to the reaction mixture comprising compound 1, acetone, acetic acid, and methanol in 4 equal portions over 2 h, maintaining the batch temperature between 20-25° C. The batch as a solution is stirred at the same temperature for an additional 1-2h. In one embodiment, the reaction mixture is concentrated on a rotary evaporator under vacuum to remove all acetone and methanol, and flushed with acetonitrile (4.4 L×2). Some inorganic solids were precipitated out during the concentration.

In one embodiment, solid is removed by filtration, the wet cake is washed with acetonitrile. The combined filtrate is concentrated and flushed with acetonitrile to give a concentrated oil. In one embodiment, acetonitrile is added to the concentrated oil, the resulting solution is analyzed by HPLC assay. In one embodiment, the resulting solution is passed through an in-line filter (10 micron) to the reaction vessel (50 L size) to be used in Step 2. The line is rinsed with acetonitrile to maintain an appropriate volume of solvent.

Step 2

Compound 2 and compound 3 are coupled in the presence of a solvent, an organic acid, and a reducing agent to produce compound 4. In one embodiment, the solvent is acetonitrile. In one embodiment, the organic acid is acetic acid. In one embodiment, the reducing agent is sodium triacetoxyborohydride.

Compound 2 and acetonitrile are added to a reaction vessel at room temperature. In one embodiment, acetic acid and compound 3 are added to the reaction vessel at room temperature under nitrogen. In one embodiment, the reaction mixture comprising compound 2, acetonitrile, acetic acid, and compound 3 is heated to 55° C. In one embodiment, sodium triacteoxyborohydride is added to the reaction mixture over 1-2 minutes. In one embodiment, additional compound 3 is added to the reaction mixture in 3 portions over 4 hours and additional sodium triacteoxyborohydride in 9 portions over 5 hours. In one embodiment, the reaction mixture is stirred at 55° C. for 14-16h. In one embodiment, the reaction mixture is cooled to room temperature and water is added over 1-2 min with stirring. In one embodiment the reaction mixture (batch) is warmed to room temperature and the bottom aqueous layer is removed. In one embodiment, the organic layer was concentrated to remove most of the acetonitrile. Methyl tert-butyl ether (MTBE) and methanol are added. The resulting solution is cooled to 5-10° C. In one embodiment, 3N NaOH is added slowly with stirring to adjust aqueous layer pH from 6 to 10, while the mixture temperature was maintained at 25-30° C. When the aqueous layer reached to pH 10, the stirring was stopped and the layers were separated. In one embodiment, the aqueous layer is removed, and the organic layer is washed with 5% $NaHCO_3$. The aqueous layer was removed again, the used aqueous layer pH should be 9. In one embodiment, the organic layer is concentrated and flushed with methanol to remove all MTBE. The resulting thick oil is diluted with MeOH to afford a clear light brown solution. The solution was ready for Step 3 without further purification.

Step 3

Compound 4 is converted into compound 5 in the presence of a solvent and an acid. In one embodiment, the solvent is methanol. In one embodiment, the acid is hydrochloric acid (HCl). In one embodiment, the acid is 6N hydrochloric acid.

Compound 4, methanol, and 6N HCl are added to a reaction vessel. In one embodiment, the reaction mixture comprising compound 4, methanol, and 6N HCl are heated at 45° C. for 7-9h. In one embodiment, the reaction mixture is maintained at ambient temperature for 12-16h. In one embodiment, the reaction mixture is cooled to 5-10° C., and 3N NaOH is added slowly keeping the temperature at the range of 25-30° C. The aqueous layer pH should be at the range of 3-4. In one embodiment, MTBE is added with stirring. 3N NaOH is added slowly with stirring keeping the temperature at the same range of 25-30° C. The target pH should be 10. In one embodiment, saturated aqueous NaHCO$_3$ is added with stirring. The aqueous layer pH should be around 9. In one embodiment, the layers are separated; the aqueous layer is extracted with MTBE and MeOH once. The combined organic layers are concentrated and the concentrated residue is flushed with acetonitrile to remove all MTBE and methanol to afford a sticky residue. In one embodiment, the sticky residue is mixed with 3:1 MeCN/water and warmed to 45° C., to obtain a clear solution. In one embodiment, the solution is transferred to a reaction vessel via an inline filter (Polycap 36 TC, 1.0 micron) to remove all fibers and dust. In one embodiment, the line is rinsed with 3:1 MeCN/water. The solution in the vessel was ready for Step 4 without further purification.

Step 4

Compound 5 is recrystallized using a solvent to afford a crystalline form of (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(isopropyl)amino)methyl)tetrahydrofuran-3,4-diol hydrate. In one embodiment, the solvent is a mixture of acetonitrile and water. In one embodiment, the solvent is a 3:1 mixture of acetonitrile and water Compound 5 and 3:1 MeCN/water are added to a reaction vessel. In one embodiment, the reaction mixture (batch) comprising compound 5 and 3:1 MeCN/water is maintained at 30° C. In one embodiment, the reaction mixture is heated to 45° C. to dissolve any precipitate and cooled back to 30° C. In one embodiment, solid seeds of (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(isopropyl)amino)methyl)tetrahydrofuran-3,4-diol hydrate are added at 30° C. with stirring. In one embodiment, a white, thin slurry is generated within 30 min, and the mixture is stirred at 25-30° C. for 1h. In one embodiment, the slurry is heated to 75° C. and stirred at the same temperature for 1-2h. In one embodiment, the slurry is cooled slowly back to 30° C. over 4-5h and stirred at the same temperature for an additional 12-16h. In one embodiment, the slurry is cooled to room temperature. After being stirred at the same temperature for 2-3h, the slurry is filtered through coarse porosity sintered glass funnel to afford a wet cake. In one embodiment, the wet cake is washed with 3:1 MeCN/water to afford a solid. In one embodiment, the solid is dried in air at room temperature with a vacuum suction for 2-3h to remove most of solvent to afford a partially dried solid.

In one embodiment, the partially dried solid and 3:1 MeCN/water is added to a reaction vessel to afford a mixture as a slurry. In one embodiment, the slurry is heated to 75° C. and stirred at the same temperature for 1-2h. In one embodiment, the mixture is cooled slowly to 30° C. over 6h, and stirred at the same temperature for an additional 12-16h. In one embodiment, the mixture is cooled to room temperature. After being stirred at the same temperature for 2-3h, the slurry is filtered through coarse porosity sintered glass funnel to afford a wet cake. In one embodiment, the wet cake is washed with 3:1 MeCN/water to afford a solid. In one embodiment, the solid is dried in air at room temperature with a vacuum suction for 20-30h to remove solvent. In one embodiment, the solids are occasionally turned over to speed up the drying process. When the weight of batch remained as constant it was considered to be dry.

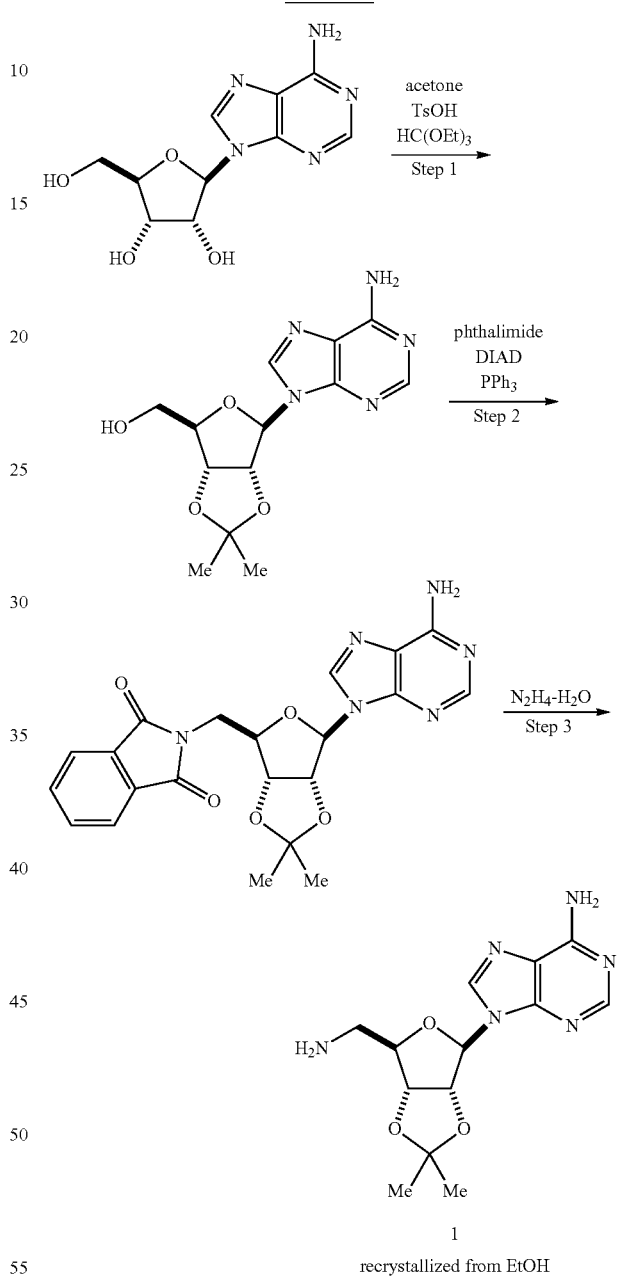

Scheme 1-1 recrystallized from EtOH

The process of the present invention relates to a process for preparing a crystalline form of (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof comprising a crystalline form of (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof as a synthetic intermediate.

In one embodiment, the present invention relates to a process for preparing a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof, comprising the step of recrystallizing (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol in a first solvent to yield (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof.

In one embodiment, the present invention relates to a process for preparing a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof, comprising the steps of recrystallizing (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol in a first solvent to yield (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol or a hydrate thereof, and converting 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine in the presence of a second solvent and an acid to (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol.

In one embodiment, the present invention relates to a process for preparing a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof, comprising the steps of recrystallizing (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol in a first solvent to yield (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof, converting 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine in the presence of a second solvent and an acid to (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol, and coupling 9-((3aR,4R,6R,6aR)-6-(((isopropylamino)methyl)-2,2-dimethyltetrahydrofuro[3,4-d][1,3]dioxol-4-yl)-9H-purin-6-amine with 3-(2-(5-(tert-butyl)-1H-benzo[d]imidazol-2-yl)ethyl)cyclobutanone or a salt thereof in the presence of a third solvent, a first organic acid, and a first reducing agent to yield 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine.

In one embodiment, the present invention relates to a process for preparing a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof, comprising the steps of recrystallizing (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol in a first solvent to yield (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof, converting 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine in the presence of a second solvent and an acid to (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol, and coupling 9-((3aR,4R,6R,6aR)-6-(((isopropylamino)methyl)-2,2-dimethyltetrahydrofuro[3,4-d][1,3]dioxol-4-yl)-9H-purin-6-amine with 3-(2-(5-(tert-butyl)-1H-benzo[d]imidazol-2-yl)ethyl)cyclobutanone or a salt thereof in the presence of a third solvent, a first organic acid, and a first reducing agent to yield 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine.

coupling 9-((3aR,4R,6R,6aR)-6-(aminomethyl)-2,2-dimethyltetrahydrofuro[3,4-d][1,3]dioxol-4-yl)-9H-purin-6-amine with acetone in the presence of a fourth solvent, a second organic acid, and a second reducing agent to yield 9-((3aR,4R,6R,6aR)-6-((isopropylamino)methyl)-2,2-dimethyltetrahydrofuro[3,4-d][1,3]dioxol-4-yl)-9H-purin-6-amine.

In one embodiment, the present invention relates to a process for preparing a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof, where the crystalline form is the free base of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol trihydrate.

In one embodiment, the present invention relates to a process for preparing a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof, further comprising one or more additional steps of recrystallizing (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol in a first solvent to yield (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol or a hydrate thereof.

In one embodiment, the present invention relates to a process for preparing a crystalline form of Form A of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol hydrate.

In one embodiment, the present invention relates to a process for preparing a crystalline form of Form B of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol trihydrate.

In one embodiment, the present invention relates to a process for preparing a crystalline form of Form C of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol anhydrate.

In one embodiment, the present invention relates to a process for preparing a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof having a purity greater than 98.0%

In one embodiment, the present invention relates to a process for preparing a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof having a purity greater than 98.5%

In one embodiment, the present invention relates to a process for preparing a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof having a purity greater than 99.0%

In one embodiment, the present invention relates to a process for preparing a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof containing a total of less than 2.0% of one or more impurities.

In one embodiment, the present invention relates to a process for preparing a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof containing a total of less than 1.5% of one or more impurities.

In one embodiment, the present invention relates to a process for preparing a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof containing a total of less than 1% of one or more impurities.

In one embodiment, the present invention relates to a process for preparing a crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof containing (2R,3R,4S,5R)-2-(6-amino-9H-purin-9-yl)-5-((((1s,3R)-3-(2-(5-(tert-butyl)-1H-benzo[d]imidazol-2-yl)ethyl)cyclobutyl)(isopropyl)amino)methyl)tetrahydrofuran-3,4-diol or a hydrate thereof as an impurity.

The present invention is directed to a process for preparing 3-(2-(5-(tert-butyl)-1H-benzo[d]imidazol-2-yl)ethyl)cyclobutanone or a salt thereof, having the chemical structure:

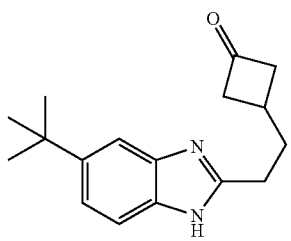 [SMILES: CC(C)(C)c1ccc2[nH]c(CCC3CC(=O)C3)nc2c1]

The present invention is directed to a process for preparing 3-(2-(5-(tert-butyl)-1H-benzo[d]imidazol-2-yl)ethyl)cyclobutanone or a salt thereof. The process of the present invention is a six-step synthesis and is shown in Scheme 2.

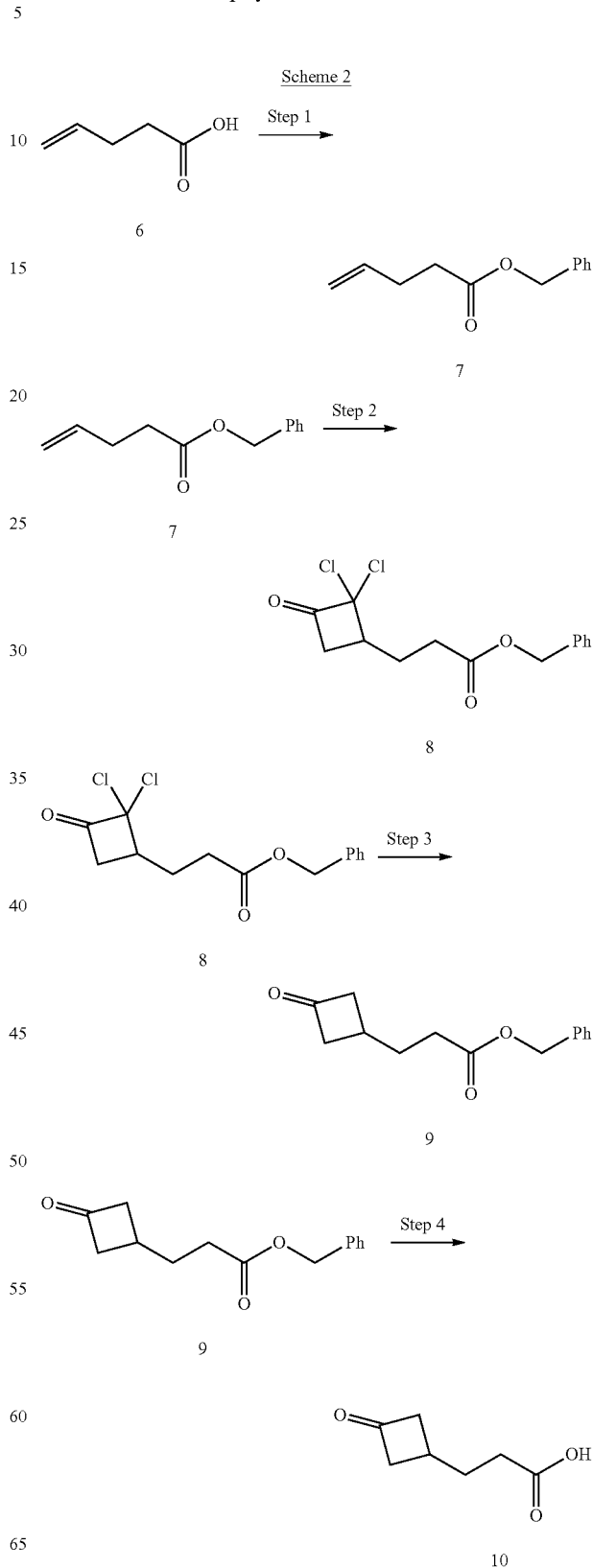

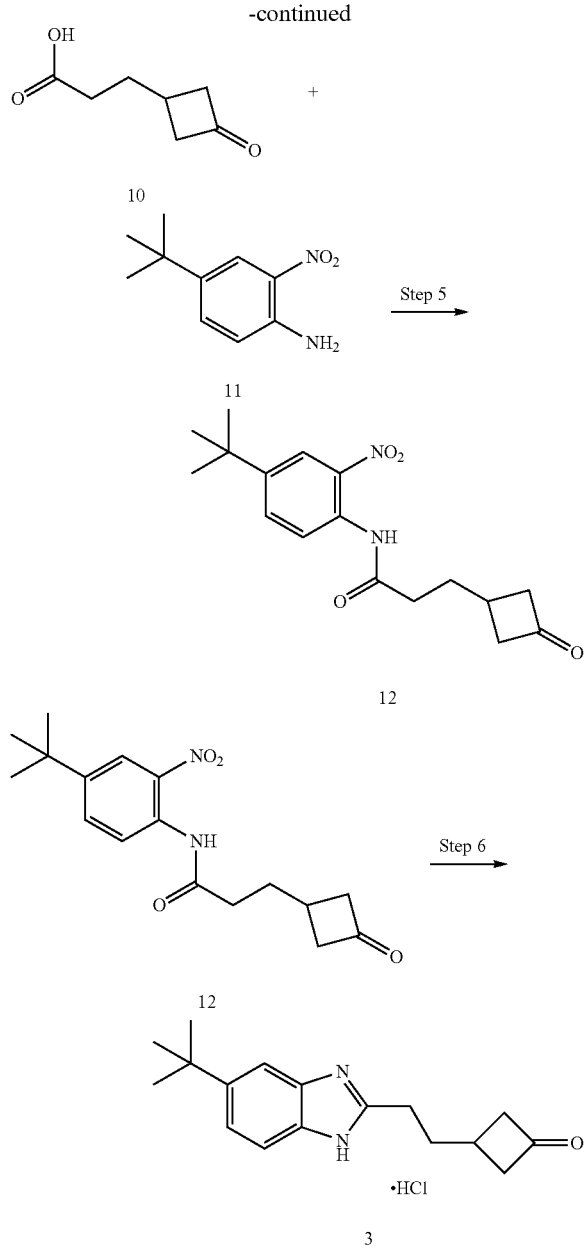

Step 1

Compound 6 is converted into compound 7 in the presence of a solvent, metal carbonate, tetraalkyllammonium salt, and benzyl bromide. In one embodiment, the solvent is acetone. In one embodiment, the metal carbonate is potassium carbonate. In one embodiment, the tetraalkyllammonium salt is tetrabutylammonium iodide.

Compound 6, benzyl bromide, and acetone are added to a reaction vessel. In one embodiment, potassium carbonate tetrabutylammonium iodidine are added to the reaction mixture comprising compound 6, benzyl bromide, and acetone to afford a suspension. In one embodiment, the suspension is stirred at room temperature for two days to afford a solid. In one embodiment, the solid is filtered and washed with acetone. In one embodiment, the organic solvent is evaporated and the resulting residue is dissolved in ethyl acetate, washed with 2M HCl, saturated $NaHCO_3$, brine, dried over $Na_2SO_4$, filtered and concentrated to yield a colorless oil. In one embodiment, no purification is required.

Step 2

Compound 7 is converted into compound 8 in the presence of a solvent, zinc-copper couple, and trichloroacetyl chloride. In one embodiment, the solvent is an ethereal solvent. In one embodiment, the solvent is a mixture of diethyl ether and 1,2-dimethoxyethane.

In Step 2, zinc-copper couple in diethyl ether and 1,2-dimethoxyethane is treated dropwise with trichloroacetyl chloride to form a mixture. In one embodiment, the mixture is stirred at 50° C. for 3 days. In one embodiment, the mixture is cooled to room temperature, celite is added, and the mixture is stirred for ~5 minutes and then filtered through a plug of celite. The resulting solid and celite is washed with TBME. The combined organic washings are washed with water, saturated $NaHCO_3$ solution, brine, dried over $Na_2SO_4$, filtered and concentrated to yield a brown oil. In one embodiment, the brown oil is stirred with 50 ml of heptane for 10-15 min. Next, the stirring is stopped and the heptane layer is removed. This is repeated until the brown oil turns into a solid. In one embodiment, the combined heptane layers are concentrated to a yellow oil.

Step 3

Compound 8 is converted into compound 9 in the presence of a solvent and zinc powder.

In one embodiment, the solvent is acetic acid.

Compound 8 in acetic acid is treated with small portions of zinc powder at room temperature to form a reaction mixture. In one embodiment, the reaction mixture is stirred at 80° C. for 2 hours. In one embodiment, the reaction mixture is cooled to room temperature, diluted with TBME, filtered, and concentrated in vacuo. For example, heptane is added to remove most of the acetic acid azeotropically to give a viscous liquid. In one embodiment, water is added to the viscous liquid and the mixture is extracted with ethyl acetate. In one embodiment, the combined organic phase is washed with saturated $NaHCO_3$, brine, dried over $Na_2SO_4$, filtered, and concentrated to yield a clear yellow oil.

Step 4

Compound 9 is converted into compound 10 in the presence of a solvent, Pd/C, and hydrogen gas. In one embodiment, the solvent is ethyl acetate.

A solution of compound 9 in ethyl acetate is purged 3 times with $N_2$ before 10% Pd/C is added. The reaction mixture is purged again 3 times with $N_2$ then twice with $H_2$ before leaving the reaction under an atmosphere of $H_2$. In one embodiment, the reaction is monitored by LCMS until no more sign of starting material is observed. In one embodiment, the reaction is purged 3 times with $N_2$, filtered through The process of the present invention has never been reported in the art. The process is a 6-step synthesis. Step 1 is the conversion of compound 6 into compound 7 in the presence of acetone, potassium carbonate, tetrabutylammonium iodide, and benzyl bromide. Step 2 is the conversion of compound 7 into compound 8 in the presence of diethyl ether, 1,2-dimethoxyethane, zinc-copper couple, and trichloroacetyl chloride. Step 3 is the conversion of compound 8 into compound 9 in the presence of acetic acid and zinc powder. Step 4 is the conversion of compound 9 into compound 10 in the presence of ethyl acetate, Pd/C, and hydrogen gas. Step 5 is the coupling of compound 10 and compound 11 in the presence of 1,4-dioxane, pyridine, and propylphosphonic anhydride. Step 6 is the conversion of compound 12 into compound 3 in the presence of acetic acid and iron powder.

The present invention is directed to a process for preparing 3-(2-(5-(tert-butyl)-1H-benzo[d]imidazol-2-yl)ethyl)cyclobutanone or a salt thereof, as a synthetic intermediate.

celite, and Pd/C is washed 3 times with ethyl acetate. In one embodiment, the combined organic washes are concentrated to yield a light yellow oil. In one embodiment, NMR analysis shows clean product and no further purification is required.

Step 5

Compound 10 is coupled to compound 11 in the presence of a solvent, a base, and a coupling reagent to form compound 12. In one embodiment, the solvent is 1,4-dioxane. In one embodiment, the base is an amine base. In one embodiment, the amine base is pyridine. In one embodiment, the coupling reagent is propylphosphonic anhydride. In one embodiment, the propylphosphonic anhydride is a 50% solution in ethyl acetate.

Compound 10 and compound 11 is dissolved in 1,4-dioxane and pyridine and propylphosphonic anhydride is added in the form of a 50% solution in ethyl acetate at room temperature to form a reaction mixture. In one embodiment, the reaction mixture is heated to 100° C. and left for 7 hrs. In one embodiment, the reaction mixture is cooled to room temperature, diluted with ethyl acetate, and washed with 2M NaOH, 2M HCl, and brine and dried over MgSO$_4$ and concentrated in vacuo to give the crude product. In one embodiment, the crude product is purified by silica flash column chromatography using between 100% heptanes to 40% ethyl acetate: 60% heptanes as eluent to give the product as a yellow oil.

Step 6

Compound 12 is converted to compound 3 in the presence of a solvent and iron powder. In one embodiment, the solvent is acetic acid.

Compound 12 is dissolved in acetic acid and iron powder is added at room temperature to form a reaction mixture. In one embodiment, the reaction mixture is heated to 80° C. and left for 1 hr. In one embodiment, the reaction mixture is cooled to room temperature and filtered through GF (glass fibre) filter paper under suction to give a solid. In one embodiment, the solid is washed with ethyl acetate. In one embodiment, the solvents are removed in vacuo and the resultant residue is dissolved in dichloromethane. Saturated Na$_2$CO$_3$ solution is added until the mixture is no longer acidic. In one embodiment, the mixture is filtered through Celite under suction and the plug washed with dichloromethane. In one embodiment, the layers are separated and the aqueous layer is extracted with dichloromethane. The combined organic layers are dried over MgSO$_4$, filtered and concentrated in vacuo to give the crude product as a residue. In one embodiment, the product is salted by dissolving the residue in dichloromethane and adding 2M HCl in ether. For example, after about 30 seconds of swirling the solvent a white precipitate is formed. In one embodiment, the precipitate is filtered under suction, washed with ether and dried under vacuum at 50° C. for 2 hours to give the pure product, which was pure enough for use without subsequent purification, as a white powder.

The process of the present invention is an improvement over the processes disclosed in the prior art. The preparation of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol is disclosed in WO 2012/075381 (referred to herein as the "'381 application").

The process to prepare (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol as described in the '381 application is depicted in Scheme 3.

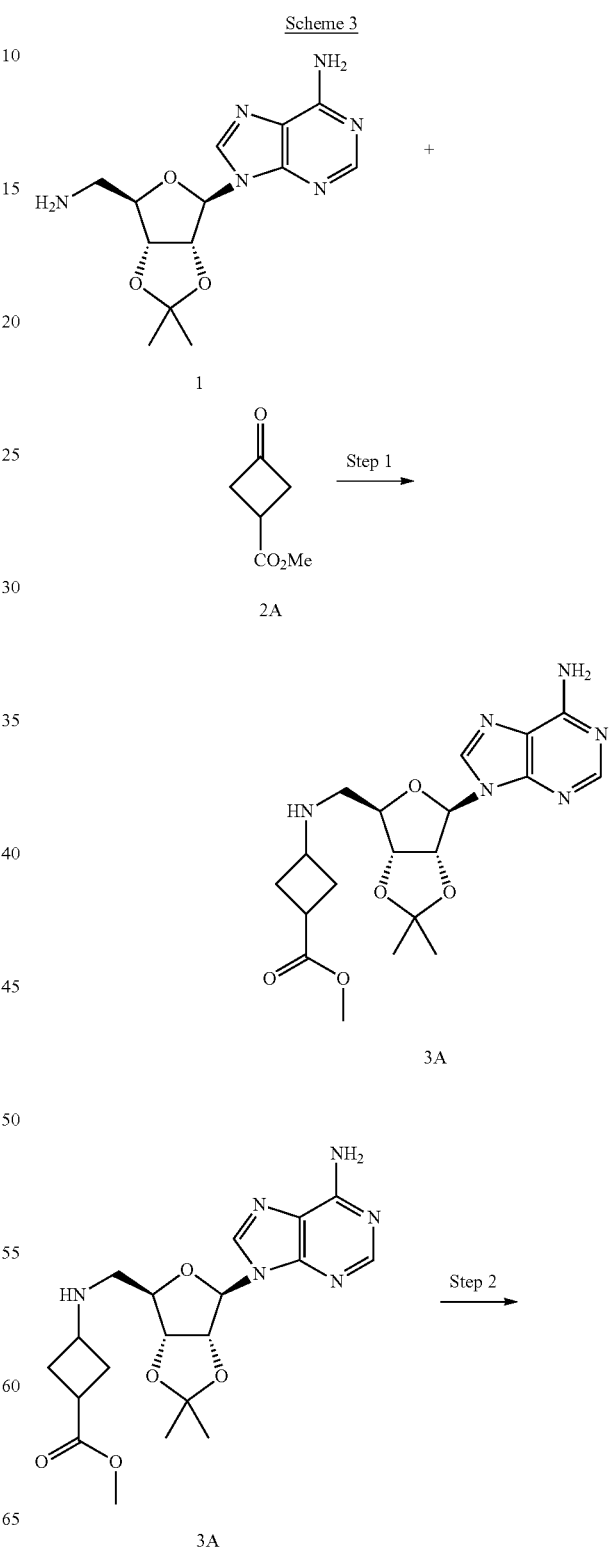

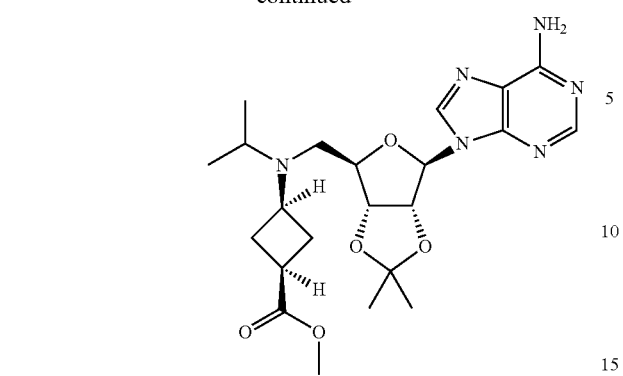
4A
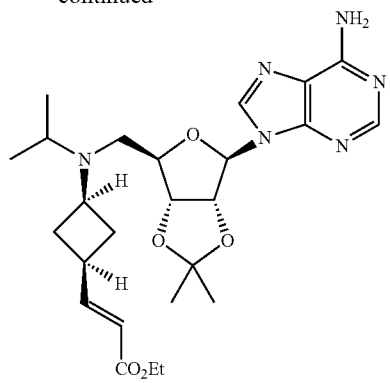
6A
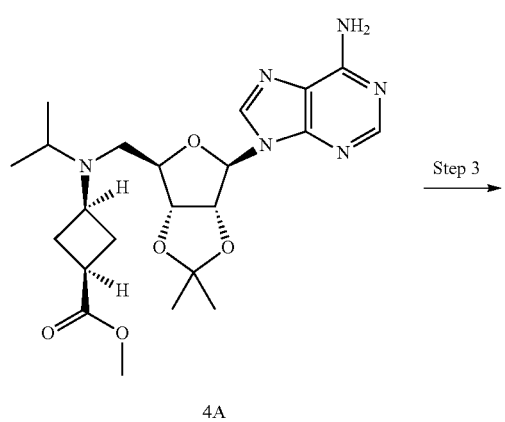
4A → Step 3
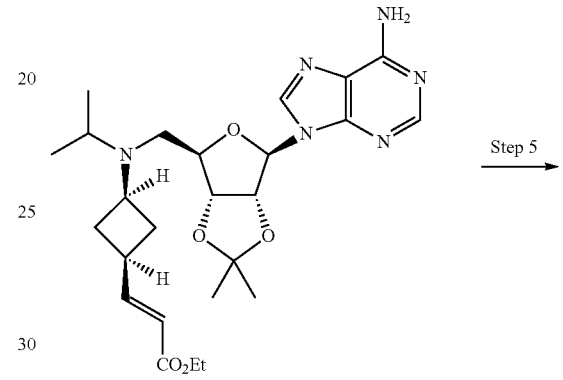
6A → Step 5
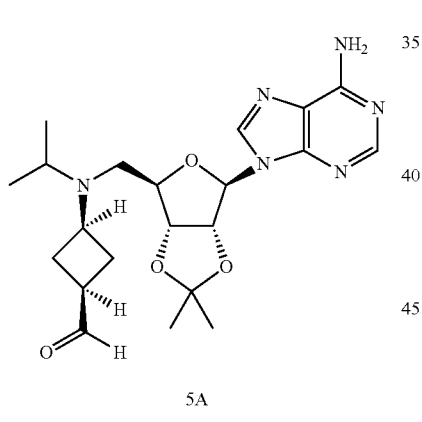
5A
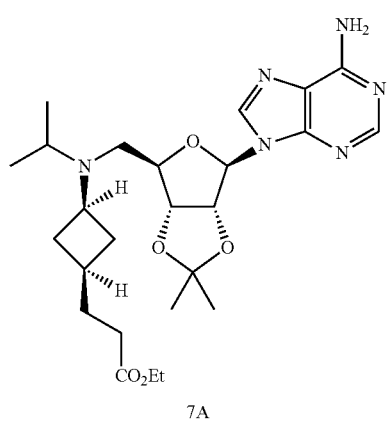
7A
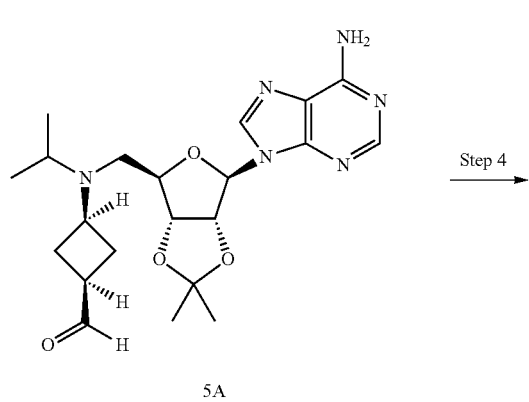
5A → Step 4
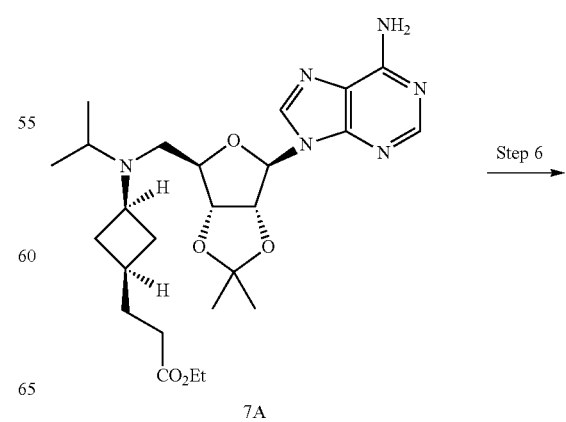
7A → Step 6

47
-continued

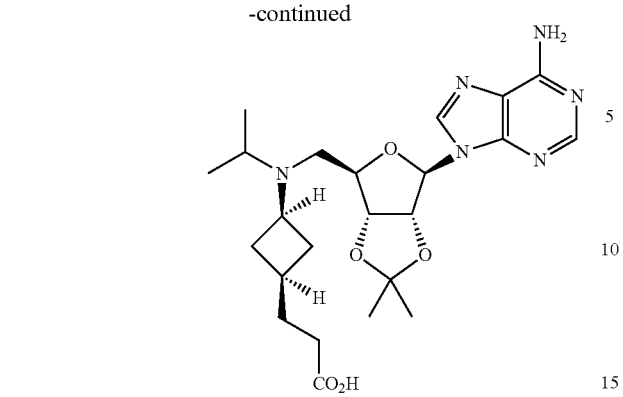

8A

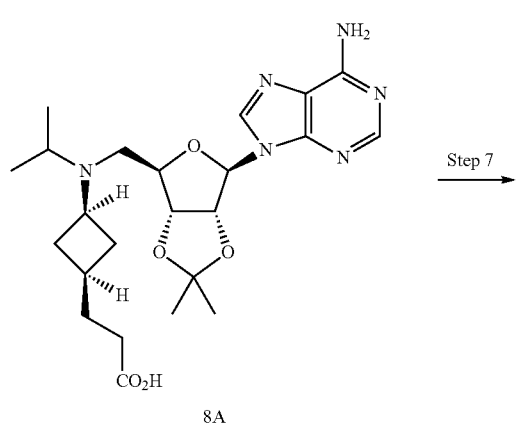

8A

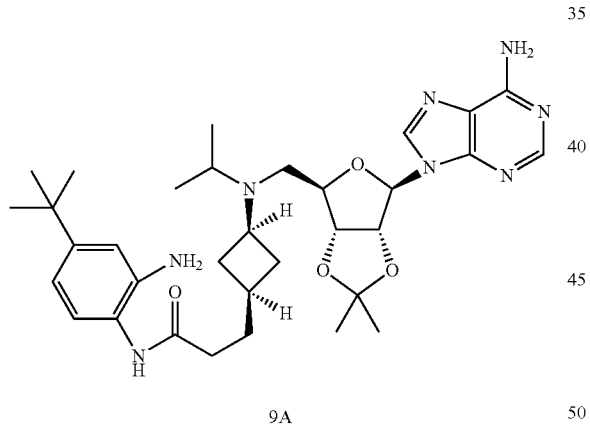

9A

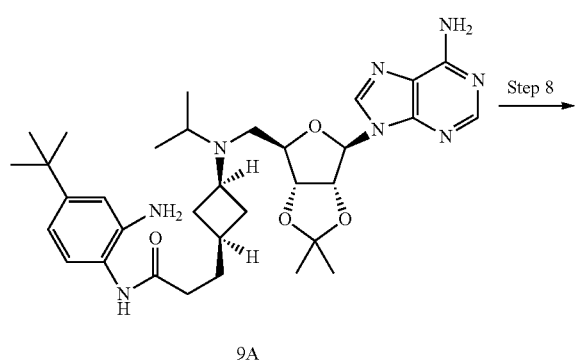

9A

48
-continued

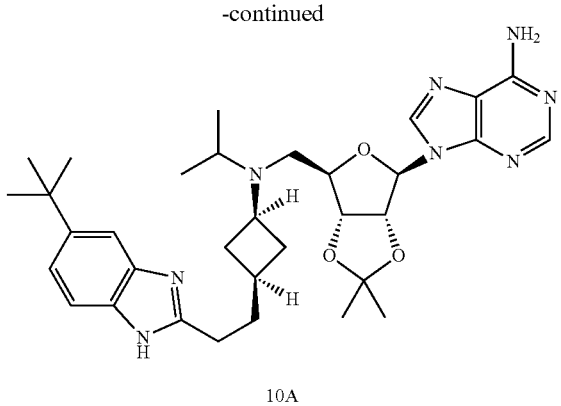

10A

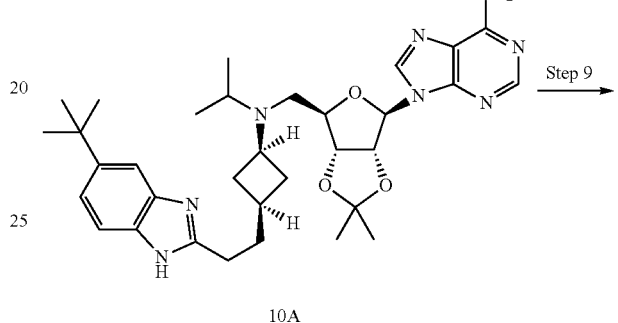

10A

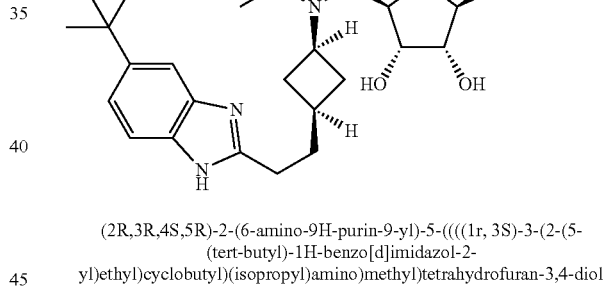

(2R,3R,4S,5R)-2-(6-amino-9H-purin-9-yl)-5-((((1r, 3S)-3-(2-(5-(tert-butyl)-1H-benzo[d]imidazol-2-yl)ethyl)cyclobutyl)(isopropyl)amino)methyl)tetrahydrofuran-3,4-diol The process of the '381 application as outlined in Scheme 3 is a linear 9-step synthetic process which includes 6 purification steps. The process of the present application is a convergent synthetic process consisting of the 4 steps as outlined in Scheme 1 and the 6 steps needed to synthesize compound 3 as outlined in Scheme 2.

The process of the '381 application is significantly different than the process of the present invention. The synthetic sequence of the '381 application is significantly different than the synthetic sequence of the present invention. The structures of the intermediates in the synthetic sequence of the '381 application are significantly different than the structures of the intermediates in the synthetic sequence of the present invention. The purification step of the final compound, (2R, 3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol of the '381 application is significantly different than the purification step performed in the present invention. For example, the '381 application uses preparative-HPLC to purify the final compound, (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(isopropyl)amino)methyl)tetrahydrofuran-3,4-diol. The present invention uses recrystallization to purify the final compound, (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(isopropyl)amino)methyl)tetrahydrofuran-3,4-diol.

The process of the '381 application as outlined in Scheme 3 includes the following synthetic steps: In Step 1, compound 1A is coupled to compound 2A in a reductive amination reaction to afford compound 3A. In Step 2, compound 3A is coupled to acetone in a reductive amination reaction to afford compound 4A. In Step 3, the methyl ester of compound 4A is reduced to an aldehyde to afford compound 5A. In Step 4, compound 5A is converted into compound 6A in a Wittig-type reaction. In Step 5, the alkene of compound 6A is reduced to afford compound 7A. In Step 6, the ethyl ester of compound 7A is hydrolyzed to afford compound 8A. In Step 7, the carboxylic acid of compound 8A is coupled to an aromatic amine to afford compound 9A. In Step 8, a cyclization reaction converts compound 9A into compound 10A. In Step 9, deprotection of compound 10A affords (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(isopropyl)amino)methyl)tetrahydrofuran-3,4-diol.

Definitions

As used herein, "compound of the invention" or "compounds of the invention" may refer to any compounds, or crystalline forms of the present invention.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, dioxanyl, morpholinyl, and tetrahydrofuranyl.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—CH$_2$—), ethyl (—CH$_2$CH$_2$—), n-propyl (—CH$_2$CH$_2$CH$_2$—), i-propyl (—CHCH$_3$CH$_2$—), n-butyl (—CH$_2$CH$_2$CH$_2$CH$_2$—), s-butyl (—CHCH$_3$CH$_2$CH$_2$—), i-butyl (—C(CH$_3$)$_2$CH$_2$—), n-pentyl (—CH$_2$CH$_2$CH$_2$CH$_2$CH$_2$—), s-pentyl (—CHCH$_3$CH$_2$CH$_2$CH$_2$—) or n-hexyl (—CH$_2$CH$_2$CH$_2$CH$_2$CH$_2$CH$_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5- or 6-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated) which contains at least one ring heteroatom (e.g., N, O or S). Examples of heterocycles include, but are not limited to, morpholine, pyrrolidine, tetrahydrothiophene, piperidine, piperazine and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups.

The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group;

and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted —$NH_2$. "Alkylamino" includes groups of compounds wherein nitrogen of —$NH_2$ is bound to at least one alkyl group. Examples of alkylamino groups include benzylamino, methylamino, ethylamino, phenethylamino, etc. "Dialkylamino" includes groups wherein the nitrogen of —$NH_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

The term "about", "approximately", or "approximate", when used in connection with a numerical value, means that a collection or ranger of values is included. For example, "about X" includes a range of values that are ±10%, ±5%, ±2%, ±1%, ±0.5%, ±0.2%, or ±0.1% of X, where X is a numerical value. In addition, "about X" may also include a range of X±0.5, X±0.4, X±0.3, X±0.2, or X±0.1, where X is a numerical value.

Compounds of the present invention that contain nitrogen atoms can be converted to N-oxides by treatment with an oxidizing agent (e.g., 3-chloroperoxybenzoic acid (mCPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms.

Furthermore, the structures and other compounds discussed in this invention include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. Benzimidazoles also exhibit tautomerism, when the benzimidazole contains one or more substituents in the 4, 5, 6 or 7 positions, the possibility of different isomers arises. For example, 2,5-dimethyl-1H-benzo[d]imidazole can exist in equilibrium with its isomer 2,6-dimethyl-1H-benzo[d]imidazole via tautomerization.

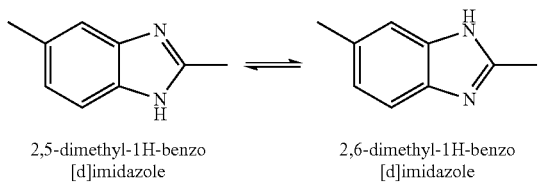

2,5-dimethyl-1H-benzo
[d]imidazole 2,6-dimethyl-1H-benzo
[d]imidazole

Another example of tautomerism is shown below.

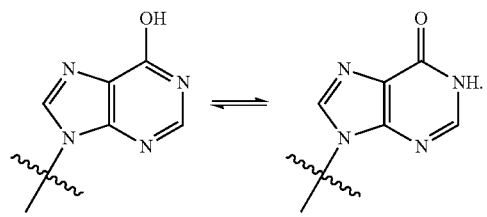 [SMILES: *n1cnc2c(O)ncnc21 ; *n1cnc2c(=O)[nH]cnc21]

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form.

The term "crystal polymorphs", "polymorphs" or "crystalline forms" means crystal structures in which a compound (or a salt or solvate thereof) can crystallize in different crystal packing arrangements, all of which have the same elemental composition. Different crystal forms usually have different XRPD patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Compounds of the invention may be crystalline, semi-crystalline, non-crystalline, amorphous, mesomorphous, etc.

The compounds of Formula (I) and other compounds of the invention include the compounds themselves, as well as their N-oxides, salts, their solvates, and their prodrugs, if applicable. A salt, for example, can be formed between an anion and a positively charged group (e.g., amino) on a substituted purine or 7-deazapurine compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a substituted purine or 7-deazapurine compound. Suitable cations include sodium ion, potassium ion, magnesium ion, calcium ion, and an ammonium cation such as tetramethylammonium ion. The substituted purine or 7-deazapurine compounds also include those salts containing quaternary nitrogen atoms. Examples of prodrugs include esters and other pharmaceutically acceptable derivatives, which, upon administration to a subject, are capable of providing active substituted purine or 7-deazapurine compounds.

Additionally, the compounds or crystalline forms of the present invention, for example, the salts of the compounds or crystalline forms, can exist in either hydrated or unhydrated (the anhydrous) form or as solvates with other solvent molecules. Nonlimiting examples of hydrates include hemihydrates, monohydrates, dihydrates, trihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hemihydrate is formed by the combination of one molecule of water with more than one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are substituted purine compounds or substituted 7-deazapurine compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

Methods of Treatment

The present invention provides methods of treating or preventing cancer. The present invention provides methods of treating cancer. The present invention also provides methods of preventing cancer. The method includes administering to a subject in need thereof a therapeutically effective amount of the compound of the invention. The cancer can be a hematological cancer. Preferably, the cancer is leukemia. More preferably, the cancer is acute myeloid leukemia, acute lymphocytic leukemia or mixed lineage leukemia.

The present invention provides methods of treating or preventing a disease or disorder mediated by translocation of a gene on chromosome 11 q23. The present invention provides methods of treating a disease or disorder mediated by translocation of a gene on chromosome 11q23. The present invention also provides methods of preventing a disease or disorder mediated by translocation of a gene on chromosome 11 q23. The method includes administering to a subject in need thereof a therapeutically effective amount of the compound or crystalline form of the invention.

The present invention provides methods of treating or preventing a disease or disorder in which DOT 1-mediated protein methylation plays a part or a disease or disorder mediated by DOT 1-mediated protein methylation. The present invention provides methods of treating a disease or disorder in which DOT1-mediated protein methylation plays a part or a disease or disorder mediated by DOT 1-mediated protein methylation. The present invention also provides methods of preventing a disease or disorder in which DOT1-mediated protein methylation plays a part or a disease or disorder mediated by DOT1-mediated protein methylation. The method includes administering to a subject in need thereof a therapeutically effective amount of the compound or crystalline form of the invention.

The present invention provides methods of inhibiting DOT1L activity in a cell. The method includes contacting the cell with an effective amount of one or more of the compound or crystalline form of the invention.

Still another aspect of the invention relates to a method of reducing the level of Histone H3 Lysine residue 79 (H3-K79) methylation in a cell. The method includes contacting a cell with a compound of the present invention. Such method can be used to ameliorate any condition which is caused by or potentiated by the activity of DOT1 through H3-K79 methylation.

The present invention relates to use of the compounds disclosed herein in preparation of a medicament for treating or preventing cancer. The use includes a compound or crystalline form of the invention for administration to a subject in need thereof in a therapeutically effective amount. The cancer can be a hematological cancer. Preferably, the cancer is leukemia. More preferably, the cancer is acute myeloid leukemia, acute lymphocytic leukemia or mixed lineage leukemia.

The present invention provides use of the compounds disclosed herein in preparation of a medicament for treating or preventing a disease or disorder mediated by translocation of a gene on chromosome 11q23. The use includes a compound or crystalline form of the invention for administration to a subject in need thereof in a therapeutically effective amount.

The present invention provides use of the compounds disclosed herein in preparation of a medicament for treating or preventing a disease or disorder in which DOT1-mediated protein methylation plays a part or a disease or disorder mediated by DOT1-mediated protein methylation. The use includes a compound or crystalline form of the invention for administration to a subject in need thereof in a therapeutically effective amount.

The present invention provides use of the compounds disclosed herein for inhibiting DOT1L activity in a cell. The use includes contacting the cell with an effective amount of one or more of the compound or crystalline form of the invention.

Still another aspect of the invention relates to a use of the compounds disclosed herein for reducing the level of Histone H3 Lysine residue 79 (H3-K79) methylation in a cell. The use includes contacting a cell with a compound of the present invention. Such use can ameliorate any condition which is caused by or potentiated by the activity of DOT1 through H3-K79 methylation.

In the formula presented herein, the variables can be selected from the respective groups of chemical moieties later defined in the detailed description.

In addition, the invention provides methods of synthesizing the foregoing compounds. Following synthesis, a therapeutically effective amount of one or more of the compounds can be formulated with a pharmaceutically acceptable carrier for administration to a mammal, particularly humans, for use in modulating an epigenetic enzyme. In certain embodiments, the compounds of the present invention are useful for treating, preventing, or reducing the risk of cancer or for the manufacture of a medicament for treating, preventing, or reducing the risk of cancer. Accordingly, the compounds or the formulations can be administered, for example, via oral, parenteral, otic, ophthalmic, nasal, or topical routes, to provide an effective amount of the compound to the mammal.

Mixed lineage leukemia (MLL) is a genetically distinct form of acute leukemia that constitutes over 70% of infant leukemias and approximately 10% of adult acute myeloid leukemias (AML) (Hess, J. L. (2004), Trends Mol Med 10, 500-507; Krivtsov, A. V., and Armstrong, S. A. (2007), Nat Rev Cancer 7, 823-833). MLL represents a particularly aggressive form of leukemia and patients with this disease generally have poor prognoses; these patients often suffer from early relapse after treatment with current chemotherapies. There is thus a great and present need for new treatment modalities for patients suffering with MLL.

A universal hallmark of MLL disease is a chromosomal translocation affecting the MLL gene on chromosome 11q23 (Hess, 2004; Krivtsov and Armstrong, 2007). Normally, the MLL gene encodes for a SET-domain histone methyltransferase that catalyzes the methylation of lysine 4 of histone H3 (H3K4) at specific gene loci (Milne et al. (2002) Mol Cell 10, 1107-1117; Nakamura et al. (2002), Mol Cell 10, 1119-1128). Gene localization is conferred by specific interactions with recognition elements within MLL, external to the SET-domain (Ayton et al. (2004) Mol Cell Biol 24, 10470-10478; Slany et al., (1998) Mol Cell Biol 18, 122-129; Zeleznik-Le et al. (1994) Proc Natl Acad Sci USA 91, 10610-10614). In the disease-linked translocations, the catalytic SET-domain is lost and the remaining MLL protein is fused to a variety of partners, including members of the AF and ENL family of proteins such as AF4, AF9, AF10 and ENL (Hess, 2004; Krivtsov and Armstrong, 2007; Slany (2009) Haematologica 94, 984-993). These fusion partners are capable of interacting directly, or indirectly, with another histone methyltransferase, DOT1L (Bitoun et al. (2007) Hum Mol Genet 16, 92-106; Mohan et al. (2010) Genes Dev. 24, 574-589; Mueller et al. (2007) Blood 110, 4445-4454; Mueller et al. (2009) PLoS Biol 7, e1000249; Okada et al. (2005) Cell 121, 167-178; Park et al. (2010) Protein J 29, 213-223; Yokoyama et al. (2010) Cancer Cell 17, 198-212; Zhang et al. (2006) J Biol Chem 281, 18059-18068). As a result, translocation products retain gene-specific recognition elements within the remainder of the MLL protein, but also gain the ability to recruit DOT1L, to these locations (Monroe et al. (2010) Exp Hematol. 2010 Sep. 18. [Epub ahead of print] Pubmed PMID: 20854876; Mueller et al., 2007; Mueller et al., 2009; Okada et al., 2005). DOT1L catalyzes the methylation of H3K79, a chromatin modification associated with actively transcribed genes (Feng et al. (2002) Curr Biol 12, 1052-1058; Steger et al. (2008) Mol Cell Biol 28, 2825-2839). The ectopic H3K79 methylation that results from MLL fusion protein recruitment of DOT1L leads to enhanced expression of leukemogenic genes, including HOXA9 and MEIS1 (Guenther et al. (2008) Genes & Development 22, 3403-3408; Krivtsov et al. (2008) Nat Rev Cancer 7, 823-833; Milne et al. (2005) Cancer Res 65, 11367-11374; Monroe et al., 2010; Mueller et al., 2009; Okada et al., 2005; Thiel et al. (2010) Cancer Cell 17, 148-159). Hence, while DOT1L is not genetically altered in the disease per se, its mislocated enzymatic activity is a direct consequence of the chromosomal translocation affecting MLL patients; thus, DOT1L has been proposed to be a catalytic driver of leukemogenesis in this disease (Krivtsov et al., 2008; Monroe et al., 2010; Okada et al., 2005; Yokoyama et al. (2010) Cancer Cell 17, 198-212). Further support for a pathogenic role of DOT1L in MLL comes from studies in model systems that demonstrate a requirement for DOT1L in propagating the transforming activity of MLL fusion proteins (Mueller et al., 2007; Okada et al., 2005).

Evidence indicates that the enzymatic activity of DOT1L is critical to pathogenesis in MLL and inhibition of DOT1L may provide a pharmacologic basis for therapeutic intervention in this disease. Compound treatment results in selective, concentration-dependent killing of leukemia cells bearing the MLL-translocation without effect on non-MLL transformed cells. Gene expression analysis of inhibitor treated cells shows downregulation of genes aberrantly over expressed in MLL-rearranged leukemias and similarities with gene expression changes caused by genetic knockout of the Dot1L gene in a mouse model of MLL-AF9 leukemia.

The present invention provides methods for the treatment of a cell proliferative disorder in a subject in need thereof by administering to a subject in need of such treatment, a therapeutically effective amount of a compound of the present invention, or a pharmaceutically acceptable salt, prodrug, metabolite, crystalline form or solvate thereof. The cell proliferative disorder can be cancer or a precancerous condition. The present invention further provides the use of a compound of the present invention, or a pharmaceutically acceptable salt, prodrug, metabolite, crystalline form or solvate thereof, for the preparation of a medicament useful for the treatment of a cell proliferative disorder.

The present invention provides methods for the treatment of hematological cancer or hematologic tumors in a subject in need thereof by administering to a subject in need of such treatment, a therapeutically effective amount of a compound of the present invention, or a pharmaceutically acceptable salt, prodrug, metabolite, crystalline form or solvate thereof. The present invention further provides the use of a compound of the present invention, or a pharmaceutically acceptable salt, prodrug, metabolite, crystalline form or solvate thereof, for the preparation of a medicament useful for the treatment of hematological cancer or hematologic tumors.

The present invention provides methods for the treatment of leukemia in a subject in need thereof by administering to a subject in need of such treatment, a therapeutically effective amount of a compound of the present invention, or a pharmaceutically acceptable salt, prodrug, metabolite, crystalline form or solvate thereof. The leukemia can be acute or chronic leukemia. Preferably, the leukemia is acute myeloid leukemia, acute lymphocytic leukemia or mixed lineage leukemia. The present invention further provides the use of a compound of the present invention, or a pharmaceutically acceptable salt, prodrug, metabolite, crystalline form or solvate thereof, for the preparation of a medicament useful for the treatment of leukemia.

The present invention provides methods for the treatment of a disease or disorder mediated by translocation of a gene on chromosome 11q23 in a subject in need thereof by administering to a subject in need of such treatment, a therapeutically effective amount of a compound of the present invention, or a pharmaceutically acceptable salt, prodrug, metabolite, crystalline form or solvate thereof. The gene can be the MLL gene. The present invention further provides the use of a compound of the present invention, or a pharmaceutically acceptable salt, prodrug, metabolite, crystalline form or solvate thereof, for the preparation of a medicament useful for the treatment of a disease or disorder mediated by translocation of a gene on chromosome 11q23.

The present invention provides methods for the treatment of a disease or disorder mediated by DOT1 (e.g., DOT1L)-mediated protein methylation in a subject in need thereof by administering to a subject in need of such treatment, a therapeutically effective amount of a compound of the present invention, or a pharmaceutically acceptable salt, prodrug, metabolite, crystalline form or solvate thereof. The present invention further provides the use of a compound of the present invention, or a pharmaceutically acceptable salt, prodrug, metabolite, crystalline form or solvate thereof, for the preparation of a medicament useful for the treatment of a disease or disorder mediated by DOT1L-mediated protein methylation.

The present invention provides methods for the treatment of a disorder the course of which is influenced by modulating the methylation status of histones or other proteins, wherein said methylation status is mediated at least in part by the activity of DOT1L. Modulation of the methylation status of histones can in turn influence the level of expression of target genes activated by methylation, and/or target genes suppressed by methylation. The method includes administering to a subject in need of such treatment, a therapeutically effective amount of a compound of the present invention, or a pharmaceutically acceptable salt, prodrug, metabolite, crystalline form, solvate, or stereoisomer or thereof.

The disorder in which DOT1L-mediated protein methylation plays a part can be cancer or a precancerous condition or a neurological disease. The present invention further provides the use of a compound of the present invention, or a pharmaceutically acceptable salt, prodrug, metabolite, crystalline form or solvate thereof, for the preparation of a medicament useful for the treatment of cancer or a neurological disease.

The present invention also provides methods of protecting against a disorder in which DOT1L-mediated protein methylation plays a part in a subject in need thereof by administering a therapeutically effective amount of compound of the present invention, or a pharmaceutically acceptable salt, prodrug, metabolite, crystalline form or solvate thereof, to a subject in need of such treatment. The disorder can be cancer or a neurological disease. The present invention also provides the use of compound of the present invention, or a pharmaceutically acceptable salt, prodrug, metabolite, crystalline form, solvate, or stereoisomeror thereof, for the preparation of a medicament useful for the prevention of a cell proliferative disorder.

The compounds of this invention can be used to modulate protein (e.g., histone) methylation, e.g., to modulate histone methyltransferase or histone demethylase enzyme activity. Histone methylation has been reported to be involved in aberrant expression of certain genes in cancers, and in silencing of neuronal genes in non-neuronal cells. The compounds described herein can be used to treat these diseases, i.e., to decreases methylation or restores methylation to roughly its level in counterpart normal cells.

In general, compounds that are methylation modulators can be used for modulating cell proliferation, generally. For example, in some cases excessive proliferation may be reduced with agents that decrease methylation, whereas insufficient proliferation may be stimulated with agents that increase methylation. Accordingly, diseases that may be treated by the compounds of the invention include hyperproliferative diseases, such as benign cell growth and malignant cell growth.

As used herein, a "subject in need thereof" is a subject having a cell proliferative disorder, or a subject having an increased risk of developing a cell proliferative disorder relative to the population at large. The subject can have cancer or pre-cancer. Preferably, a subject in need thereof has cancer. More preferably, a hematologic cancer or leukemia. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute lymphocytic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present invention may be used to treat a cancer selected from the group consisting of a hematologic cancer of the present invention or a hematologic cell proliferative disorder of the present invention. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Preferably, compositions of the present invention may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma," bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. Preferably, compositions of the present invention may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

The cell proliferative disorder of the breast can be breast cancer. Preferably, compositions of the present invention may be used to treat breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

Preferably, compound of the present invention, or a pharmaceutically acceptable salt, prodrug, metabolite, crystalline form, or solvate thereof, may be used to treat breast cancer. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich, or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the present invention, or a pharmaceutically acceptable salt, prodrug, metabolite, crystalline form or solvate thereof, may be used to treat or prevent a cell proliferative disorder of the breast, or to treat or prevent breast cancer, in a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) ofpNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, prodrug, metabolite, crystalline form or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, prodrug, metabolite, crystalline form or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "monotherapy" refers to the administration of a single active or therapeutic compound to a subject in need thereof. Preferably, monotherapy will involve administration of a therapeutically effective amount of an single active compound. For example, cancer monotherapy with one of the compound of the present invention, or a pharmaceutically acceptable salt, prodrug, metabolite, analog or derivative thereof, to a subject in need of treatment of cancer. In one aspect, the single active compound is a compound of the present invention, or a pharmaceutically acceptable salt, prodrug, metabolite, crystalline form or solvate thereof.

As used herein, "treating" or "treat" describes the management and care of a patient for the purpose of combating a disease, condition, or disorder and includes the administration of a compound of the present invention, or a pharmaceutically acceptable salt, prodrug, metabolite, crystalline form or solvate thereof, to alleviate the symptoms or complications of a disease, condition or disorder, or to eliminate the disease, condition or disorder.

A compound of the present invention, or a pharmaceutically acceptable salt, prodrug, metabolite, crystalline form or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www-.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin (see next section), some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here. However, all art-recognized signs and symptoms of cancer are contemplated and encompassed by the instant invention.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present invention, or a pharmaceutically acceptable salt, prodrug, metabolite, crystalline form or solvate thereof, acts selectively on a cancer or precancerous cell but not on a normal cell. Preferably, a compound of the present invention, or a pharmaceutically acceptable salt, prodrug, metabolite, crystalline form or solvate thereof, acts selectively to modulate one molecular target (e.g., a target protein methyltransferase) but does not significantly modulate another molecular target (e.g., a non-target protein methyltransferase). The invention also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells. A compound of the present invention, or a pharmaceutically acceptable salt, prodrug, metabolite, crystalline form or solvate thereof, can modulate the activity of a molecular target (e.g., a target protein methyltransferase). Modulating refers to stimulating or inhibiting an activity of a molecular target. Preferably, a compound of the present invention, or a pharmaceutically acceptable salt, prodrug, metabolite, crystalline form or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt, prodrug, metabolite, crystalline form or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, prodrug, metabolite, crystalline form or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the present invention, or a pharmaceutically acceptable salt, prodrug, metabolite, crystalline form or solvate thereof, demonstrates a minimum of a fourfold differential, preferably a tenfold differential, more preferably a fifty fold differential, in the dosage required to achieve a biological effect. Preferably, a compound of the present invention, or a pharmaceutically acceptable salt, prodrug, metabolite, crystalline form or solvate thereof, demonstrates this differential across the range of inhibition, and the differential is exemplified at the $IC_{50}$, i.e., a 50% inhibition, for a molecular target of interest.

Administering a compound of the present invention, or a pharmaceutically acceptable salt, prodrug, metabolite, crystalline form or solvate thereof, to a cell or a subject in need thereof can result in modulation (i.e., stimulation or inhibition) of an activity of a protein methyltransferase of interest.

The present invention provides methods to assess biological activity of a compound of the present invention, or a pharmaceutically acceptable salt, prodrug, metabolite, crystalline form or solvate thereof or methods of identifying a test compound as a modulator (e.g., an inhibitor) of DOT1 L. DOT1 L polypeptides and nucleic acids can be used to screen for compounds that bind to and/or modulate (e.g., increase or decrease) one or more biological activities of DOT1 L, including but not limited to H3K79 HMTase activity, SAM binding activity, histone and/or nucleosome binding activity, AF 10 binding activity, AF 10-MLL or other MLL fusion protein binding activity, and/or any other biological activity of interest. A DOT1 L polypeptide can be a functional fragment of a full-length DOT1 L polypeptide or functional equivalent thereof, and may comprise any DOT 1 domain of interest, including but not limited to the catalytic domain, the SAM binding domain and/or the positively charged domain, the AF 10 interaction domain and/or a nuclear export signal.

Methods of assessing DOT1 L binding to histones, nucleosomes, nucleic acids or polypeptides can be carried out using standard techniques that will be apparent to those skilled in the art (see the Exemplification for exemplary methods). Such methods include yeast and mammalian two-hybrid assays and co-immunoprecipitation techniques.

For example, a compound that modulates DOT1 L H3K79 HMTase activity can be verified by: contacting a DOT L polypeptide with a histone or peptide substrate comprising H3 in the presence of a test compound; detecting the level of H3K79 methylation of the histone or peptide substrate under conditions sufficient to provide H3K79 methylation, wherein an elevation or reduction in H3K79 methylation in the presence of the test compound as compared with the level of histone H3K79 methylation in the absence of the test compound indicates that the test compound modulates DOT1 L H3K79 HMTase activity.

The screening methods of the invention can be carried out in a cell-based or cell-free system. As a further alternative, the assay can be performed in a whole animal (including transgenic non-human animals). Further, with respect to cell-based systems, the DOT1 L polypeptide (or any other polypeptide used in the assay) can be added directly to the cell or can be produced from a nucleic acid in the cell. The nucleic acid can be endogenous to the cell or can be foreign (e.g., a genetically modified cell).

In some assays, immunological reagents, e.g., antibodies and antigens, are employed. Fluorescence can be utilized in the measurement of enzymatic activity in some assays. As used herein, "fluorescence" refers to a process through which a molecule emits a photon as a result of absorbing an incoming photon of higher energy by the same molecule. Specific methods for assessing the biological activity of the disclosed compounds are described in the examples.

Administering a compound of the present invention, or a pharmaceutically acceptable salt, prodrug, metabolite, crystalline form or solvate thereof, to a cell or a subject in need thereof results in modulation (i.e., stimulation or inhibition) of an activity of an intracellular target (e.g., substrate). Several intracellular targets can be modulated with the compounds of the present invention, including, but not limited to, protein methyltrasferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

Preferably, an effective amount of a compound of the present invention, or a pharmaceutically acceptable salt, prodrug, metabolite, crystalline form or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, prodrug, metabolite, crystalline form or solvate thereof, can induce or activate cell death selectively in cancer cells. Administering to a subject in need thereof a compound of the present invention, or a pharmaceutically acceptable salt, prodrug, metabolite, crystalline form or solvate thereof, can induce or activate cell death selectively in cancer cells. Contacting a cell with a compound of the present invention, or a pharmaceutically acceptable salt, prodrug, metabolite, crystalline form or solvate thereof, can induce cell death selectively in one or more cells affected by a cell proliferative disorder. Preferably, administering to a subject in need thereof a compound of the present invention, or a pharmaceutically acceptable salt, prodrug, metabolite, crystalline form or solvate thereof, induces cell death selectively in one or more cells affected by a cell proliferative disorder.

The present invention relates to a method of treating or preventing cancer by administering a compound of the present invention, or a pharmaceutically acceptable salt, prodrug, metabolite, crystalline form or solvate thereof, to a subject in need thereof, where administration of the compound of the present invention, or a pharmaceutically acceptable salt, prodrug, metabolite, crystalline form or solvate thereof, results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the invention The compounds of the instant invention can also be utilized to treat or prevent neurologic diseases or disorders. Neurologic diseases or disorders that may be treated with the compounds of this invention include epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's, Amyotrophic Lateral Sclerosis (ALS), and Parkinson's disease. Another class of neurodegenerative diseases includes diseases caused at least in part by aggregation of polyglutamine. Diseases of this class include: Huntington's Diseases, Spinalbulbar Muscular Atrophy (SBMA or Kennedy's Disease) Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCA7), and Spinocerebellar Ataxia 12 (SCA12).

Any other disease in which epigenetic methylation, which is mediated by DOT 1, plays a role may be treatable or preventable using compounds and methods described herein.

Pharmaceutical Compositions

The present invention also provides pharmaceutical compositions comprising a compound of the invention in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug interaction(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystalline forms as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers.

Compounds described herein are assayed for modulation of activity, for example, histone methylation, modulation of cell growth and/or $IC_{50}$, described in the examples below. $IC_{50}$ values are presented as $A=<0.1$ μM; $B=>0.1$ μM and $<1$ μM; $C=>1$ μM and $<10$ μM; and $D=>10$ μM and $<50$ μM.

| Compound | DOT1L $IC_{50}$ (μM) |
|---|---|
| 2 | 0.00074 |
| 3 | 0.00073 |
| 5 | 0.00059 |
| 69 | 0.00251 |
| 75 | 0.00059 |
| 86 | 0.00062 |
| 87 | 0.0008 |
| 91 | 0.00218 |
| 93 | 0.00292 |

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follw.

EXAMPLES

Example 1

Synthesis of (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(isopropyl)amino)methyl)tetrahydrofuran-3,4-diol hydrate (2R,3R,4S,5R)-2-(6-amino-9H-purin-9-yl)-5-(((((1r,3S)-3-(2-(5-(tert-butyl)-1H-benzo[d]imidazol-2-yl)ethyl)cyclobutyl)(isopropyl)amino)methyl)tetrahydrofuran-3,4-diol hydrate was synthesized according to the scheme below.

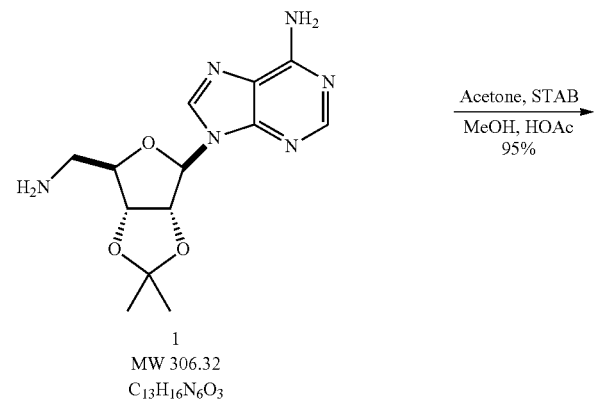

1
MW 306.32
$C_{13}H_{16}N_6O_3$

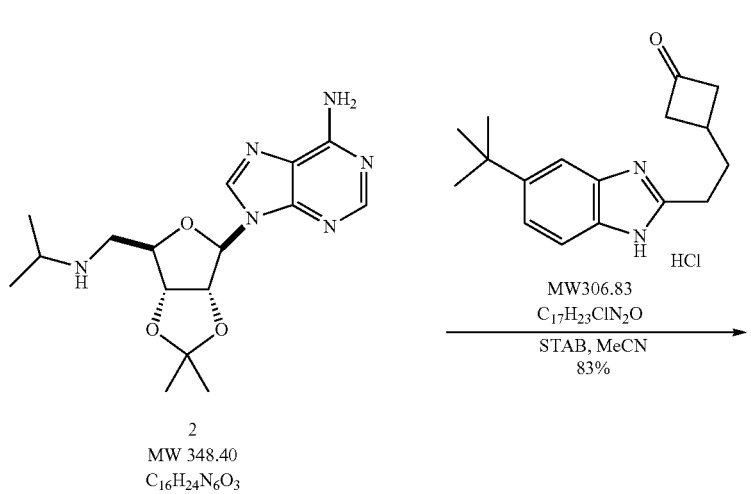

2
MW 348.40
$C_{16}H_{24}N_6O_3$

-continued
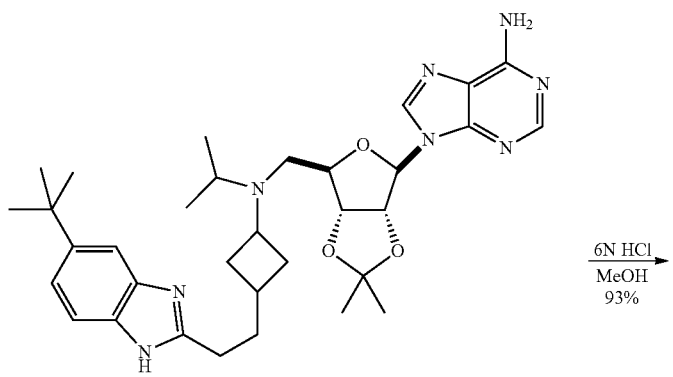
Cis/Trans = ~ 4:1
4
MW 602.77
C₃₃H₄₆N₈O₃
6N HCl
MeOH
93%
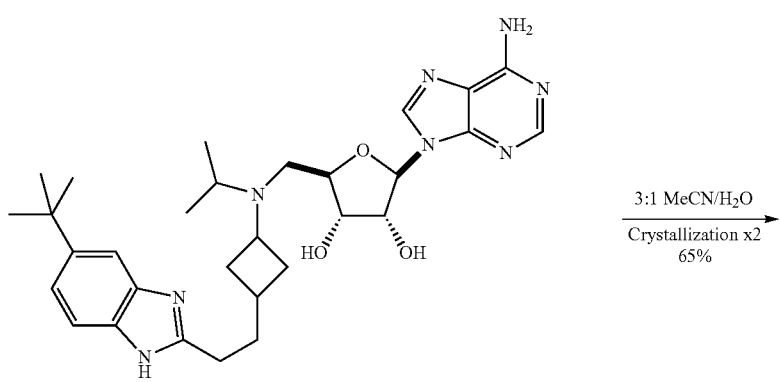
Cis/Trans = ~ 4:1
5
MW 562.71
C₃₀H₄₂N₈O₃
3:1 MeCN/H₂O
Crystallization x2
65%
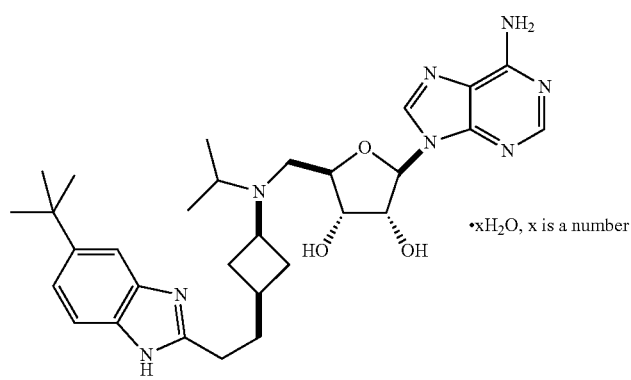
•xH₂O, x is a number
EP-1
(2R,3R,4S,5R)-2-(6-amino-9H-purin-9-yl)-5-((((1r, 3S)-3-(2-(5-(tert-butyl)-1H-benzo[d]imidazol-2-yl)ethyl)cyclobutyl)(isopropyl)amino)methyl) tetrahydrofuran-3,4-diol hydrate Step 1: Synthesis of 9-((3aR,4R,6R,6aR)-6-((isopropylamino)methyl)-2,2-dimethyltetrahydrofuro[3,4-d][1,3]dioxol-4-yl)-9H-purin-6-amine (2)

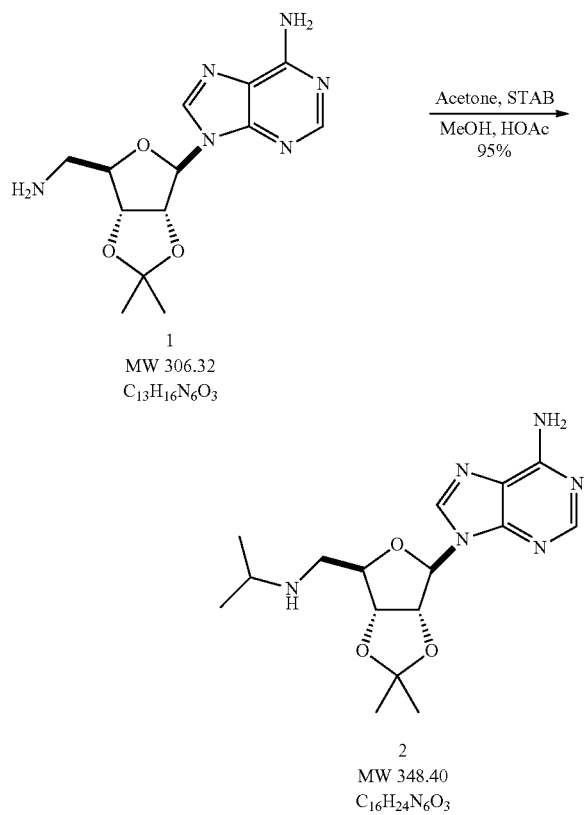

The materials employed for Step 1 are as follows:

| Reagents | MW (density) | Amount | Mol. | Equiv. | Grade and Comment |
|---|---|---|---|---|---|
| Compound 1 | 306.32 | 1100 g | 3.591 | 1.0 | N/A |
| Acetone | 58.08 (0.791) | 2.64 L | | 2.4 Vol | ACS, ≥99.5% |
| Acetic acid | 60.05 (1.049) | 206 mL | 3.591 | 1.0 | ACS |
| Sodium triacetoxy borohydride (STAB) | 211.94 | 1525 g | 7.182 | 1.9 | 95% |
| Solvents | | | | | |
| Methanol | | 8.8 L | | 8 Vol | ACS, ≥99.9% |
| Workup | | | | | |
| Acetonitrile | | 40 L | | | Chromasolv, ≥99.9% |

To a 30 L 3-neck jacketed vessel with a mechanical stirrer, a thermocouple, and a $N_2$ inlet were charged 1 (1100 g, 3.591 mol), acetone (2.64 L), acetic acid (206 mL), and methanol (8.8 L) at room temperature. The resulting mixture was stirred at room temperature for 5-10 min until all solids were dissolved. The solution was cooled to about 16-18° C., and STAB (305 g, 0.38 eq) was added over 1-2 min. The addition of STAB was moderately exothermic, the batch temperature should be cooled to about 16-18° C. prior to the STAB addition, so that the reaction mixture temperature was kept below 25° C. The rest of STAB was added in 4 equal portions (305 g, 0.38 eq each) over next 2 h, maintaining the batch temperature between 20-25° C. The batch as a solution was stirred at the same temperature for an additional 1-2 h. The batch appeared as a light yellow solution with a little bit of haziness. At this stage the reaction should give a full conversion monitored by HPLC. The reaction mixture was concentrated on rotavap under vacuum to remove all acetone and methanol, flushed with acetonitrile (4.4 L×2). Some inorganic solids were precipitated out during the concentration. The solid was removed by filtration, the wet cake was washed with MeCN (4.4 L). The combined filtrate was concentrated, flushed with MeCN (4.4 L). There was no 2 trapped in the inorganic solid. MeCN (18-20 L) was added to the concentrated oil, the resulting solution was analyzed by HPLC assay giving 2 (1188 g, 3.411 mol, 95% yield). The resulting solution was passed through an in-line filter (10 micron) to the reaction vessel (50 L size) for the next step of reaction. The line was rinsed with MeCN (1-2 L) so that the total volume reached to about 24 L. The solution was ready for the next reductive amination step without further purification. The mixture in $CH_3CN$ should be protected from atmospheric moisture.

Step 2: Synthesis of 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine (4)

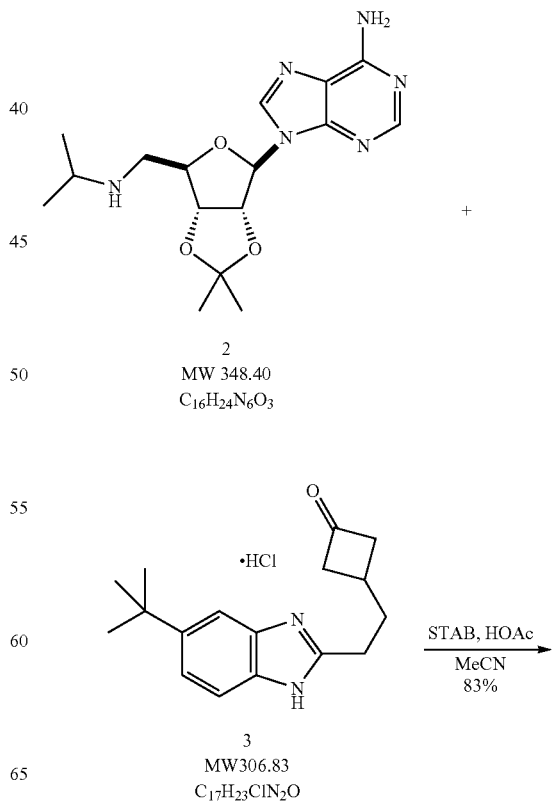

-continued

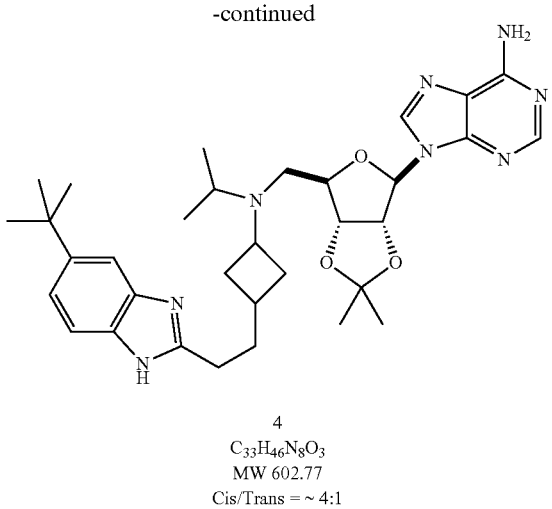

4
C₃₃H₄₆N₈O₃
MW 602.77
Cis/Trans = ~ 4:1

The materials employed for Step 2 are as follows:

| Reagents | MW (density) | Amount | Mol. | Equiv. | Grade and Comment |
|---|---|---|---|---|---|
| Compound 2 | 348.4 | 1188 g | 3.411 | 1.0 | In MeCN and HOAc solution (24 L) from step 1 |
| Acetic acid | 60.05 (1.049) | 390 mL | 6.822 | 2.0 | ACS |
| Compound 3 | 306.83 | 1047 g | 3.411 | 1.0 | Use test |
| Sodium triacetoxy borohydride (STAB) | 211.94 | 1446 g | 6.822 | 1.9 | 95% |
| Work-up |  |  |  |  |  |
| Water |  | 6 L |  |  | Chromasolv |
| MTBE |  | 8.5 L |  |  | ACS, ≥99.0% |
| Methanol |  | ~15 L |  |  | ACS, ≥99.9% |
| 3N NaOH* |  | ~10 L |  |  | ACS |
| 5% NaHCO₃ |  | 4 L |  |  | ≥99.7% |

*Preparation: NaOH (1200 g, pellets, Fisher Scientific, Lot# 093309) was diluted with Chromasolv water (Sigma-Aldrich, Lot# SHBB2917V) to 10 L to give 3N NaOH.

To a 50 L 3-neck jacketed vessel with a mechanical stirrer, a thermocouple, and a N₂ inlet were charged 2 (1188 g, 3.411 mol) in MeCN solution (total volume: 24 L) at room temperature (see step 1). Acetic acid (390 mL, 2.0 eq) and 3 (628 g, 0.6 eq) were added at room temperature under nitrogen. Since the reaction was water sensitive, the reaction mixture in CH₃CN should be protected from the moisture. The reaction mixture as slurry was heated to 55° C., STAB (145 g, 0.19 eq) was added over 1-2 min. The remaining 3 was added in the 3 portions over 4 h (209 g, 105 g, 105 g); and the remaining STAB was added over 9 portions (145 g×9) over 5 h. After the additions, the resulting slurry was stirred at 55° C. for 14-16 h. At this stage the conversion should be 98A % or higher (relative to API-1) monitored by HPLC. The LC ratio at the end of reaction: conversion by area % was >98% by HPLC, the ratio of EP-API-2-mix to RSM-2-OH was at the range of 8-9:1.

The reaction mixture was cooled to room temperature, water (6 L) was added over 1-2 min with stirring. The addition of water to the batch in MeCN solution was endothermic, the temperature was dropped from 25° C. to around 15° C. after the water addition. The batch was warmed to room temperature, the bottom aqueous layer was removed. There was no product loss in the aqueous layer. The product in MeCN solution was stable at ambient temperature for up to a week, which was confirmed by HPLC analysis. The resulting product in MeCN solution obtained was analyzed by HPLC assay, giving 4 (1.7 kg, 2.83 mol, 83% assay yield). The organic layer was concentrated to remove most of MeCN. MTBE (8.5 L) and MeOH (1.7 L) was added. The resulting solution was cooled to 5-10° C. 3N NaOH (~10 L) was added slowly with stirring to adjust aqueous layer pH from 6 to 10, while the mixture temperature was maintained at 25-30° C. When the aqueous layer reached to pH 10, the stirring was stopped and the layers were separated. The aqueous layer was removed, and the organic layer was washed 5% NaHCO₃ (4 L). The aqueous layer was removed again, the used aqueous layer pH should be 9. The product loss in combined aqueous layers should be less than 1.5%. The organic layer was concentrated, flushed with MeOH (4 L×2) to remove all MTBE. The resulting thick oil was diluted with MeOH to about 8.5 L as a clear light brown solution. The solution was ready for the next step directly without further purification.

Further note that the reason for the portion wise addition of 3 and STAB was to maintain the concentration of these two components at relatively low concentration in the reaction mixture, which would minimize the formation of the side product A by direct 3 reduction by STAB.

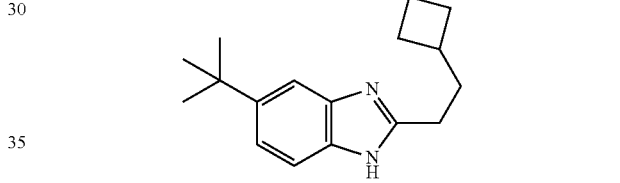

A

A complex formed during the reductive amination reaction, which was corresponding to several late eluting peaks by HPLC analysis. These peaks were confirmed to be a complex of 4 mixture and diacetoxyborohydride by LC/MS (B, see the structure below). This complex was converted to the product upon treating with base (LC sample was treated with NH₄OH to pH 10, and the complex peaks disappeared). Most of complex was broken back to the product after overnight heating (55° C.) and the remaining residual amounts of complex would be broken down to the desired product during the basic aqueous workup.

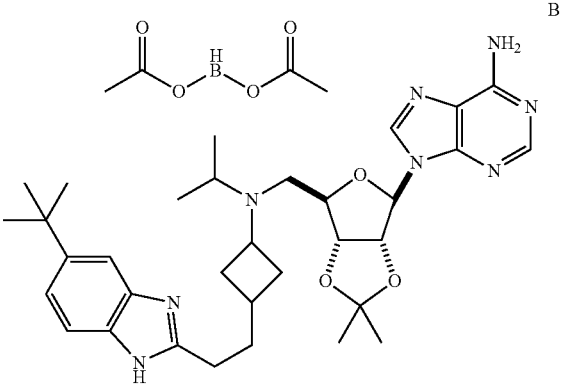

B

Step 3: Synthesis of (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol (5)

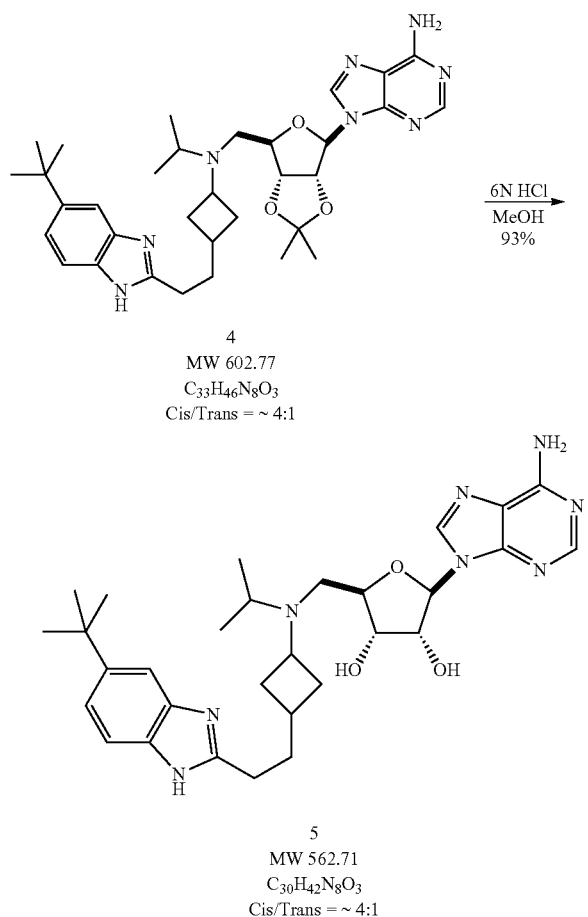

4
MW 602.77
C$_{33}$H$_{46}$N$_8$O$_3$
Cis/Trans = ~ 4:1

5
MW 562.71
C$_{30}$H$_{42}$N$_8$O$_3$
Cis/Trans = ~ 4:1

The materials employed for Step 3 are as follows:

| Reagents | MW (density) | Amount | | Mol. | Equiv. | Grade and Comment |
|---|---|---|---|---|---|---|
| Compound 4 | 602.77 | 851 | g | 1.412 | 1.0 | As solution in MeOH (1979 g, 43 wt %) |
| 6N HCl* | | 1.18 | L | 7.06 | 5.0 | 37%, ACS |
| Solvents | | | | | | |
| Methanol | | 2.9 | L | | | ACS, ≥99.8% |
| Work-up | | | | | | |
| MTBE | | 4.5 | L | | | ACS |
| 3N NaOH** | | 2.4 | L | 7.2 | 5.1 | ACS |
| Sat'd NaHCO$_3$*** | | 500 | mL | | | ACS |
| Acetonitrile | | 6 | L | | | Chromasolv |
| Acetonitrile/water (3:1)**** | | 6 | L | | | |

To a 10-L jacketed vessel with a mechanical stirrer, a thermocouple, and a N$_2$ inlet were charged 4 (1979 g, 43%, 1.412 mol), MeOH (2.9 L), and 6N HCl (1.18 L, 5 eq). The resulting solution was heated at 45° C. for 7-9 h and ambient temperature for 12-16 h (overnight). The reaction was almost complete after stirring at 45° C. for 7-9 h, the overnight aging was just for the convenience. It gave the same result that the reaction was stirred at 40° C. for 16 h. The reaction gave a full conversion at this stage.

The reaction mixture was cooled to 5-10° C., 3N NaOH (1 L) was added slowly keeping the temperature at the range of 25-30° C. The aqueous layer pH should be at the range of 3-4. MTBE (3 L) was added with stirring. 3N NaOH (~1.4 L) was added slowly with stirring keeping the temperature at the same range of 25-30° C. The target pH should be 10. The last 10% (~240 mL) of 3N NaOH addition should be very slow, so that the aqueous layer pH would be controlled to 10 without difficulty. Saturated aqueous NaHCO$_3$ (500 mL) was added with stirring. The aqueous layer pH should be around 9. The layers were separated, the aqueous layer was extracted with MTBE (1.5 L) and MeOH (375 mL) once. The combined organic layers were concentrated to about 1.5 L, the concentrated residue was flushed with MeCN (2.0 L×3) to remove all MTBE and MeOH. Caution should be taken, that foaming or bumping was possible during the concentration. To reduce such possible foaming or bumping batch temperature should be kept low (<25-30° C.) during the concentration. The resulting sticky residue was mixed with 3:1 MeCN/water (4.0 L) and warmed to 45° C., obtaining a clear solution. The assay yield of this solution (4.95 Kg, 14.56 wt %) was 91.5% as 5 (726 g, 1.29 mol). The solution was transferred to a 20 L jacketed vessel via an inline filter (Polycap 36 TC, 1.0 micron) to remove all fibers and dusts. The line was rinsed with 3:1 MeCN/water (1-2 L). The solution in the vessel was ready for the crystallization without any further purification.

*Preparation: HCl (590 mL, 37%) was mixed with Chromasolv water (Sigma-Aldrich, Lot# SHBB2917V) to 1.18 L to give 6N HCl
**Preparation: NaOH (1200 g, pellets, Fisher Scientific, Lot# 093309) was diluted with Chromasolv water (Sigma-Aldrich, Lot# SHBB2917V) to 10 L to give 3N NaOH.
***Preparation: NaHCO$_3$ (Solid powder, 150 g) was mixed with water (1 L, Sigma-Aldrich, Lot# SHBB2917V) to give saturated aqueous sodium bicarbonate solution.
****Preparation: MeCN (4.5 L, Sigma-Aldrich, Lot# HSBB0358V) and water (1.5 L, Sigma-Aldrich, Chromasolv, Lot# SHBB2917V) were premixed before use.

Step 4: Crystallization to isolate pure EP-1

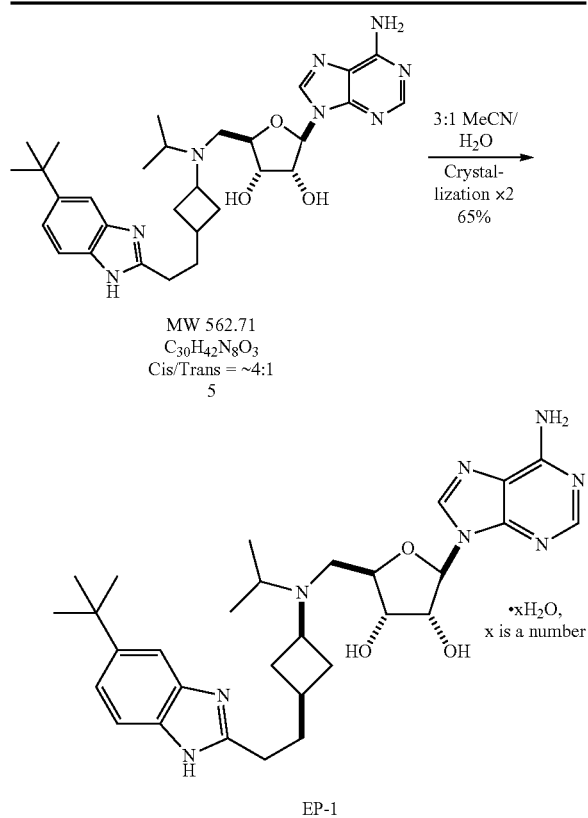

| Reagents | MW (density) | Amount | Mol. | Equiv. | Grade and Comment |
|---|---|---|---|---|---|
| EP-API-mix | 562.71 | 726 g | 1.29 | 1.0 | As solution in 3:1 MeCN/water (4.95 kg, 14.45 wt %) |
| Solvents | | | | | |
| Acetonitrile* | | 12 L | | | Chromasolv |
| Water* | | 4 L | | | Chromasolv |

*Acetonitrile and water were premixed in 3:1 ratio by volume before use.

1$^{st}$ Recrystallization: To a 20-L jacketed vessel equipped with a mechanical stirrer, a thermocouple, a N$_2$ inlet, and with 5 (4.95 Kg, 14.45 wt %, 1.29 mol) in 3:1 MeCN/water solution were charged additional 3:1 MeCN/water (3-4 L). The total volume of the batch was about 8 L and the batch temperature was kept around 30° C. The reaction mixture appeared as a clear light brown-yellow solution at 30° C. at this stage. If any solid was precipitated out, the mixture should be warmed to about 45° C. to dissolve all and cooled back to 30° C. EP-1 solid seeds (250 mg, >99.5A %, cis/trans=99.5:0.5) was added at 30° C. with stirring. White thin slurry was generated within 30 min, the mixture was stirred at 25-30° C. for 1 h. The resulting white slurry turned thicker gradually. The slurry was heated to 75° C. and stirred at the same temperature for 1-2 h. The slurry was cooled slowly back to 30° C. over 4-5 h, and stirred at the same temperature for an additional 12-16 h. The mixture was cooled to room temperature. After being stirred at the same temperature for 2-3 h, the slurry was filtered through coarse porosity sintered glass funnel. The wet cake was washed with 3:1 MeCN/water (1.5 L×2). The solid was dried in air at room temperature with a vacuum suction for 2-3 h to remove most of solvent. A filter paper was covered above funnel to protect from the dust from air. The isolated yield of this stage was about 68-70%, the purity of the solid was typically >99A % and 97:3 ratio of EPZ-5676/5677 (EPZ005677 was undesired trans-isomer, which was rejected mostly in mother liquor and during the wet cake wash). The product loss as EP-API-mix in mother liquor was 160 g, and 17 g in combined washes.

2$^{nd}$ Recrystallization: The partially dried solid (654 g) was transferred back to the cleaned 20 L vessel, 3:1 MeCN/water (5.5 L) was charged. The resulting slurry was heated to 75° C. and stirred at the same temperature for 1-2 h. The mixture was cooled slowly to 30° C. over 6 h, and stirred at the same temperature for an additional 12-16 h. The mixture was cooled to room temperature. After being stirred at the same temperature for 2-3 h, the slurry was filtered through coarse porosity sintered glass funnel (medium porosity should be fine). The wet cake was washed with 3:1 MeCN/water (1 L×2). The solid was dried in air at room temperature with a vacuum suction for 20-30 h to remove solvent. A filter paper was covered above funnel to protect from the dust from air. The solids were occasionally turned over to speed up the drying process. When the weight of batch remained as constant it was considered to be dry. EPZ-5676 trihydrate was obtained (537 g, >99A %, ration of EPZ-5676/5677=99.2:0.8, 66% over two crystallization). The product loss as EP-API-mix was 19 g, and 3.5 g in combined washes.

Example 2

Synthesis of 5-tert-Butyl-2-[2-(3-oxocyclobutyl)ethyl]-1H-1,3-benzodiazol-1-ium chloride (3)

Compound 3 was prepared as described below.

Step 1: Synthesis of Pent-4-enoic acid benzyl ester (7)

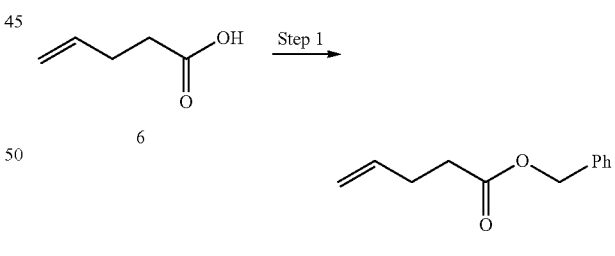

Benzyl bromide (7.19 g, 42.04 mmol) was added to a solution of 4-pentenoic acid (6) (5.05 g, 50.45 mmol, 1.2 eq.) in acetone (75 ml) at RT under N$_2$. Anhydrous potassium carbonate (29.05 g, 210.19 mmol, 5.0 eq.) and tetrabutylammonium iodide (0.776 g, 2.102 mmol, 0.05 eq.) were added and the resulting suspension was stirred over 2 days. LCMS analysis showed mainly product.

The solid was filtered and washed with acetone. The organic solvent evaporated and the residue was dissolved in EtOAc, washed with 2M HCl, sat NaHCO$_3$, brine, dried over Na$_2$SO$_4$, filtered and concentrated to yield 7.46 g (92% yield at 99% purity) of 7 as a colorless oil. LCMS analysis (on MS 19) and NMR analysis show clean product, no further purification was required. $^1$H NMR (500 MHz, CHLOROFORM-d) δ ppm 7.31-7.42 (5 H, m), 5.84 (1 H, ddt, J=16.98, 10.44, 6.23 Hz), 5.14 (2 H, s), 4.99-5.10 (2 H, m), 2.45-2.52 (2 H, m), 2.37-2.45 (2 H, m).

Step 2: Synthesis of 3-(2,2-Dichloro-3-oxo-cyclobutyl)-propionic acid benzyl ester (8)

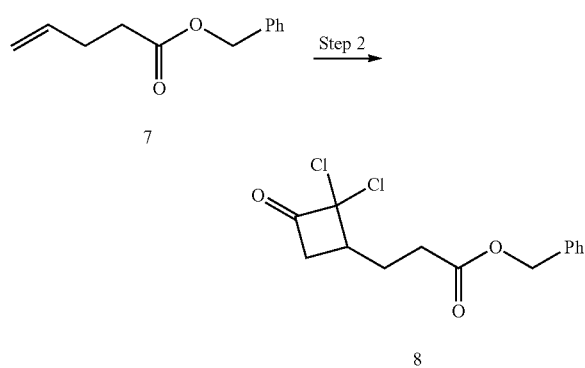

7 (7.46 g, 39.21 mmol) and zinc-copper couple (7.125 g, 98.03 mmol, 2.5 eq.) in diethyl ether (128 ml) and 1,2-dimethoxyethane (19 ml) was treated dropwise with trichloroacetyl chloride (17.83 g, 98.03 mmol, 2.5 eq.). The mixture was stirred at 50° C. for 3 days. The mixture reaction was cooled to RT, celite (~10 g) was added and mixture stirred for ~5 min. then filtered through a plug of celite. The solid/celite were washed with TBME (3×100 ml). The combined organic were washed with water (3×150 ml), NaHCO$_3$ sat sol (2×150 ml), brine (100 ml), dried over Na$_2$SO$_4$, filtered and concentrated to yield a brown oil.

The brown oil was stirred with 50 ml of heptane for 10-15 min, stirring stopped and the heptane layer was removed. This was repeated until oil turn into solid (~350-450 ml of Heptane used). The combined heptane layers were concentrated to yield 11.29 g (96% yield at 100% purity) of 8 as a yellow oil. NMR analysis shows clean product, no further purification was required. $^1$H NMR (500 MHz, CHLOROFORM-d) δ ppm 7.32-7.43 (5 H, m), 5.12-5.21 (2 H, m), 3.28-3.39 (1 H, m), 2.91-3.06 (2 H, m), 2.49-2.65 (2 H, m), 2.18-2.28 (1 H, m), 2.00-2.10 (1 H, m).

Step 3: Synthesis of 3-(3-Oxo-cyclobutyl)-propionic acid benzyl ester (9)

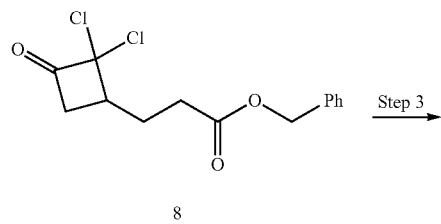

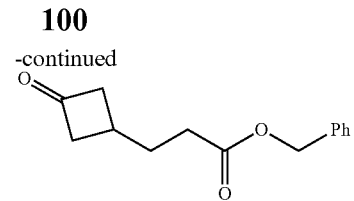

A solution of benzyl 3-(2,2-dichloro-3-oxocyclobutyl)propanoate (8) (11.29 g, 37.49 mmol) in AcOH (100 ml) was treated in small portions with zinc powder (12.26 g, 187.44 mmol, 5 eq.) at RT. After addition, the reaction mixture was stirred at 80° C. for 2 h. LCMS analysis after 2 h shows complete consumption of starting material. The reaction was cooled to RT, diluted with TBME (~100 ml), filtered and concentrated in vacuo. Heptane (250 ml) was added to remove most of the acetic acid azeotropically. Water (100 ml) was added to the resultant viscous liquid and the mixture was extracted with EtOAc (100 ml×2). The combined organic phase was washed with saturated NaHCO$_3$ (100 ml×1), brine, dried over Na$_2$SO$_4$, filtered and concentrated to yield 8.12 g (93% yield at >95% purity by NMR) of 9 as a clear yellow oil. LCMS analysis on MS 19 shows 92% purity. $^1$H NMR (500 MHz, CHLOROFORM-d) δ ppm 7.30-7.43 (5 H, m), 5.14 (2 H, s), 3.08-3.21 (2 H, m), 2.64-2.76 (2 H, m), 2.34-2.48 (3 H, m), 1.96 (2 H, q, J=7.62 Hz):

Step 4: Synthesis of 3-(3-Oxo-cyclobutyl)-propionic acid (10)

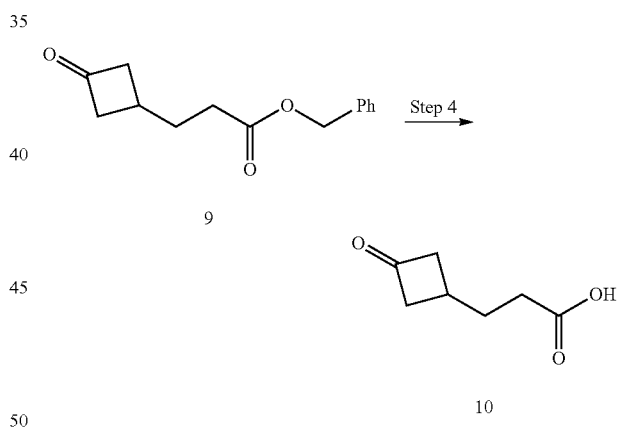

A solution of 3-(3-Oxo-cyclobutyl)-propionic acid benzyl ester (9) (8.12 g, 34.96 mmol) in ethyl acetate (80 ml) was purged 3× with N$_2$ before 10% Pd/C (800 mg, 0.077 mmol, ~2 mol %) was added. The reaction mixture was purged again 3× with N$_2$ then twice with H$_2$ before leaving the reaction under an atmosphere of H$_2$. The reaction was monitored by LCMS until no more sign of starting material was observed (~10 h). The reaction was purged with 3 times N$_2$, filtered through celite and Pd/C was washed 3× with ~25 ml of EtOAc. The combined organic were concentrated to yield 4.94 g (99%) of 10 as a light yellow oil. NMR analysis shows clean product, no further purification was required. $^1$H NMR (500 MHz, CHLOROFORM-d) δ ppm 11.46 (1 H, br. s.), 3.09-3.29 (2 H, m), 2.63-2.80 (2 H, m), 2.35-2.53 (3 H, m), 1.95 (2 H, q, J=7.57 Hz).

After overnight under high vacuum, 10 solidified as a white wax with a m.p. of 43° C.

Step 5: Synthesis of N-(4-tert-Butyl-2-nitrophenyl)-3-(3-oxocyclobutyl)propanamide (12)

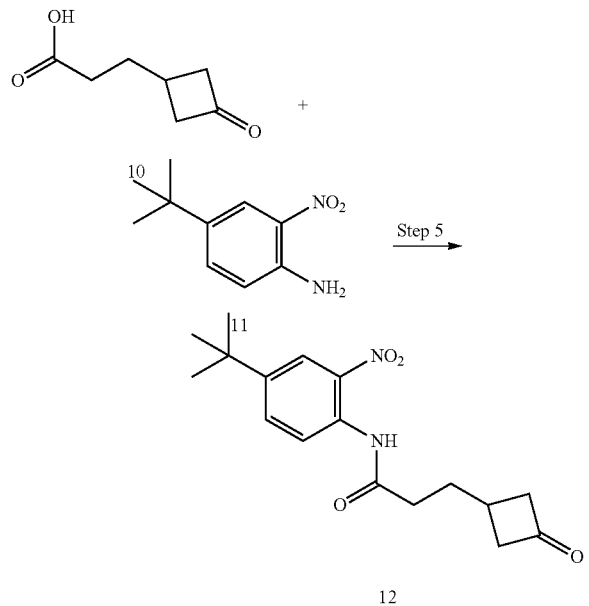

3-(3-Oxocyclobutyl)propanoic acid (10) (1.610 g, 11.3 mmol) and 4-tert-butyl-2-nitroaniline (11) (2.000 g, 10.3 mmol) were dissolved in 1,4-dioxane (20 ml) and pyridine (2.6 ml, 30.9 mmol) and T3P (50% solution in EtOAc) (9.1 ml, 15.5 mmol) was added at r.t. The reaction was heated to 100° C. and left for 7 hrs. The reaction was cooled to r.t., diluted with EtOAc (20 ml) and washed with 2M NaOH (2×20 ml), 2M HCl (20 ml), brine (20 ml), dried over MgSO$_4$ and concentrated in vacuo to give the crude product. The product was purified by silica flash column chromatography using between 100% heptanes to 40% EtOAc:60% heptanes as eluent to give 12 as a yellow oil (2.776 g, 85%): MS (ESI$^+$) for C$_{17}$H$_{22}$N$_2$O$_4$ m/z 319.25 [M+H]$^+$, 341.00 [M+Na]$^+$; LC purity 99% (UV) (ret. time, 2.11 min); $^1$H NMR (500 MHz, CDCl$_3$) δ 10.28 (s, 1H), 8.66 (d, J=8.9 Hz, 1H), 8.20 (d, J=2.3 Hz, 1H), 7.70 (dd, J=8.9, 2.3 Hz, 1H), 3.30-3.12 (m, 2H), 2.86-2.69 (m, 2H), 2.50 (ddd, J=30.3, 14.9, 7.6 Hz, 3H), 2.07 (q, J=7.6 Hz, 2H), 1.34 (s, 9H).

Step 6: Synthesis of 5-tert-Butyl-2-[2-(3-oxocyclobutyl)ethyl]-1H-1,3-benzodiazol-1-ium chloride (3)

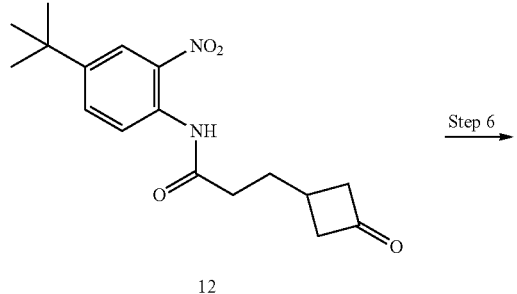

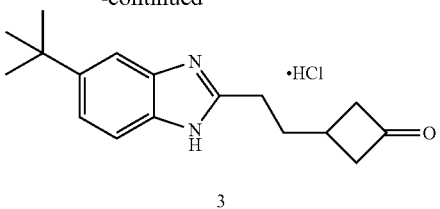

N-(4-tert-Butyl-2-nitrophenyl)-3-(3-oxocyclobutyl)propanamide (12) (2.776 g, 8.72 mmol) was dissolved in AcOH (55 ml) and iron powder was added (2.922 g, 52.3 mmol) at r.t. The reaction was heated to 80° C. and left for 1 hr. The reaction was cooled to r.t. and the mixture filtered through GF (glass fibre) filter paper under suction and the solid was washed with EtOAc. The solvents were removed in vacuo and the residue was dissolved in DCM (50 ml) and sat. Na$_2$CO$_3$ solution (100 ml) was added until the mixture was no longer acidic. The mixture was filtered through Celite under suction and the plug washed with DCM. The layers were separated and the aqueous layer was extracted with DCM (2×50 ml). The combined organic layers were dried over MgSO$_4$, filtered and concentrated in vacuo to give the crude product. The product was salted by dissolving the residue in DCM (10 ml) and adding 2M HCl in ether (10 ml). After about 30 seconds of swirling the solvent a white precipitate formed. The precipitate was filtered under suction, washed with ether and dried under vacuum at 50° C. for 2 hrs to give the pure 3, which was pure enough for use without subsequent purification, as a white powder (2.135 g, 80%): MS (ESI$^+$) for C$_{17}$H$_{22}$N$_2$O m/z 271.45 [M+H]$^+$, 293.20 [M+Na]$^+$; LC purity 97% (UV) (ret. time, 1.42 min); $^1$H NMR (500 MHz, CDCl$_3$) δ 7.67 (ddd, J=9.2, 6.4, 2.3 Hz, 3H), 3.25-3.15 (m, 4H), 2.86-2.68 (m, 2H), 2.57-2.35 (m, 1H), 2.19 (dd, J=15.6, 7.7 Hz, 2H), 1.40 (s, 9H).

Example 3

Polymorph Screening

A screening strategy using different crystallization methods in different solvents was applied to maximize the probabilities of finding as many crystal forms as possible. In the present study, five crystallization methods were utilized for polymorph screening, namely slow evaporation, solvent-mediated phase transition, anti-solvent addition, solvent sweeping, and vapor diffusion. The starting material used for the screening was lot EP-1 trihydrate (x is 3). This material was found to be Form B as indicated by solid state characterization.

Slow Evaporation

Slow evaporation experiments were performed in 32 solvents by dissolving ~15-20 mg of EP-1 trihydrate (x is 3) (Form B) in 0.4-2.0 ml of solvent in a 3-ml vial; the resulting clear solutions were left with the caps off and subjected to slow evaporation to produce precipitation. The solids were isolated for X-ray Powder Diffraction (XRPD) analysis and the results are summarized in Table 1. As shown in Table 1, either Form B or amorphous phase was produced in all tested solvents.

TABLE 1

Slow Evaporation

| Solvent | Solid Obtained | NB-Ref | Solvent | Solid Obtained |
|---|---|---|---|---|
| benzonitrile | Type B | 802401-37-A17 | 1:4 (v:v) EtOH/hexane | amorphous |
| trifluoroethanol | amorphous | 802401-37-A18 | 1:4 (v:v) acetone/$H_2O$ | Form B |
| THF[a] | Type B | 802401-37-A19 | 1:4 (v:v) ACN[h]/$H_2O$ | Form B |
| EtOAc[b] | Type B | 802401-37-A20 | 1:4 (v:v) acetone/MTBE | amorphous |
| 1,2-dichloroethane | Type B | 802401-37-A21 | 1:4 (v:v) IPAC/MTBE | Form B |
| $CH_2Cl_2$ | amorphous | 802401-37-A22 | 1:4 (v:v) ACN/MTBE | Form B |
| anisole | amorphous | 802401-37-A23 | 1:4 (v:v) THF/$H_2O$ | Form B |
| IPA[c] | amorphous | 802401-38-A1 | 1:4 (v:v) IPA/$H_2O$ | Form B |
| Me—THF[d] | amorphous | 802401-38-A2 | 1:4 (v:v) IPA/hexane | Form B |
| toluene | Type B | 802401-38-A3 | 1.4 (v:v) acetone/hexane | amorphous |
| IPAC[e] | Type B | 802401-38-A4 | 1:4 (v:v) THF/hexane | Form B |
| cyclohexanol | Type B | 802401-38-A5 | MTBE | Form B |
| acetic acid | amorphous | 802401-38-A6 | glycol | Form B |
| cyclohexane | amorphous | 802401-38-A7 | 1,2-dimethoxyethane | amorphous |
| 1:4 (v:v) EtOH[f]/$H_2O$ | Type B | 802401-39-A8 | 1:4 (v:v) EtOH/MTBE | Form B |
| 1:4 (v:v) THF/MTBE[g] | Type B | 802401-39-A9 | 1:4 (v:v) MeOH[i]/MTBE | Form B |

[a]THF: tetrahydrofuran;
[b]EtOAc: ethyl acetate;
[c]IPA: isopropyl alcohol;
[d]Me—THF: 2-methyltetrahydrofuran;
[e]IPAC: isopropyl acetate;
[f]EtOH: ethanol;
[g]MTBE: methyl t-butyl ether;
[h]ACN: acetonitrile;
[i]MeOH: methanol.

Solvent-Mediated Phase Transition

Solvent-Mediated phase transition experiments were conducted in twelve solvents by suspending ~20-30 mg EP-1 trihydrate (x is 3) (Form B) in 0.5-1.0 ml of solvent at both RT and 50° C. After the suspension was stirred for 3 days, the remaining solids were isolated for XRPD analysis. The results summarized in Table 2 indicate that either Type B or amorphous phase was generated.

TABLE 2

Solvent-Mediated Phase Transition

| Solvent | Temp. | Time | Remaining Solid |
|---|---|---|---|
| toluene | RT* | 3 days | Form B |
| $CHCl_3$ | RT | 3 days | Form B |
| ACN | RT | 3 days | Form B |
| IPAC | RT | 3 days | Form B |
| 1:4 (v:v) dioxane/heptane | RT | 3 days | Form B |
| 1:4 (v:v) acetone/heptane | RT | 3 days | Form B |
| 1:4 (v:v) THF/heptane | RT | 3 days | Form B |
| 1:4 (v:v) Me—THF/MTBE | RT | 3 days | Form B |
| 1:4 (v:v) THF/$H_2O$ | RT | 3 days | Form B |
| 1:4 (v:v) IPA/$H_2O$ | RT | 3 days | Form B |
| 1:4 (v:v) EtOH/MTBE | RT | 3 days | amorphous |
| 1:4 (v:v) MeOH/MTBE | RT | 3 days | Form B |
| toluene | 50° C. | 3 days | Form B |
| $CHCl_3$ | 50° C. | 3 days | Form B |
| ACN | 50° C. | 3 days | amorphous |
| IPAC | 50° C. | 3 days | Form B |
| 1:4 (v:v) dioxane/heptane | 50° C. | 3 days | Form B |
| 1:4 (v:v) acetone/heptane | 50° C. | 3 days | Form B |
| 1:4 (v:v) THF/heptane | 50° C. | 3 days | Form B |
| 1:4 (v:v) Me—THF/MTBE | 50° C. | 3 days | Form B |
| 1:4 (v:v) THF/$H_2O$ | 50° C. | 3 days | Form B |
| 1:4 (v:v) IPA/$H_2O$ | 50° C. | 3 days | Form B |

*RT: Room Temperature (25 ± 3° C.)

Anti-Solvent Addition

A total of twenty anti-solvent addition experiments were carried out by dissolving ~20 mg EP-1 trihydrate (x is 3) (Form B) in 0.3-3.0 ml good solvent to obtain saturated solution. 1.0-3.0 ml anti-solvent was added to the saturated solution to precipitate out solids. XRPD was then used to analyze the precipitated solids and the results are summarized in Table 3. Either Form B or amorphous phase was formed.

TABLE 3

Anti-Solvent Addition

| Solvent | Anti-solvent | Temperature | Solid Obtained |
|---|---|---|---|
| acetone | hexane | RT* | amorphous |
| THF | hexane | RT | Form B |
| IPA | hexane | RT | amorphous |
| dioxane | hexane | RT | Form B |
| acetone | heptane | RT | amorphous |
| THF | heptane | RT | Form B |
| IPA | heptane | RT | Form B |
| dioxane | heptane | RT | Form B |
| MeOH | $H_2O$ | RT | Form B |
| Acetone | $H_2O$ | RT | Form B |
| ACN | $H_2O$ | RT | Form B |
| THF | $H_2O$ | RT | Form B |
| Dioxane | $H_2O$ | RT | Form B |
| IPA | $H_2O$ | RT | Form B |
| EtOH | $H_2O$ | RT | Form B |
| acetic acid | $H_2O$ | RT | Form B |
| acetone | MTBE[f] | RT | amorphous |
| ACN | MTBE[f] | RT | No precipitation observed |
| THF | MTBE[f] | RT | amorphous |
| acetic acid | MTBE[f] | RT | amorphous |

*RT: Room Temperature (25 ± 3° C.)

Vapor Sweeping

Vapor sweeping experiments in eleven solvents at RT were conducted by placing ~10 mg amorphous EP-1 trihydrate (x is 3) (Form B) into a 1-ml vial which was put inside a 20-ml vial filled with ~5 ml volatile solvents. The bigger vials were sealed with a cap and kept at room temperature for 7 days allowing sufficient time for organic vapor to interact with the solids. The solids were analyzed at the end of the experiment and the results are listed in Table 4. Either Form B or amorphous phase was generated.

TABLE 4

Results from Vapor Sweeping

| NB-Ref | Solvent | Temperature | Time | Solid Obtained |
|---|---|---|---|---|
| 802401-45-A1 | Me—THF | RT* | 7 days | Form B |
| 802401-45-A2 | butanol | RT | 7 days | solid deliquesced |
| 802401-45-A3 | THF | RT | 7 days | Form B |
| 802401-45-A4 | EtOAc | RT | 7 days | Form B |
| 802401-45-A5 | MeOH | RT | 7 days | Form B |
| 802401-45-A6 | toluene | RT | 7 days | amorphous |
| 802401-45-A7 | acetone | RT | 7 days | amorphous |
| 802401-45-A8 | ACN | RT | 7 days | Form B |
| 802401-45-A9 | hexane | RT | 7 days | amorphous |
| 802401-45-A10 | $CH_2Cl_2$ | RT | 7 days | amorphous |
| 802401-45-A11 | IPAC | RT | 7 days | amorphous |

*RT: Room Temperature (25 ± 3° C.)

Vapor Diffusion

Vapor diffusion experiments in eleven solvents at RT were conducted by dissolving ~10 mg amorphous EP-1 trihydrate (x is 3) (Form B) in ~0.5 ml appropriate solvent to obtain a clear solution in a 3-ml vial, this solution was placed inside a 20-ml vial filled with ~5 ml volatile solvents. The larger vials were sealed with a cap and kept at room temperature for 14 days, allowing sufficient time for organic vapor of the anti-solvent to diffuse into the solution of EP-1 trihydrate (x is 3) to precipitate out solids. The solids obtained were separated and analyzed with XRPD. The results are summarized in Table 5. Only amorphous phase was formed in these experiments.

TABLE 5

Results from Vapor Diffusion Experiments

| NB-Ref | Starting Material | Solvent | Anti-Solvent | Solid Obtained |
|---|---|---|---|---|
| 802401-50-A1 | amorphous | THF | heptane | amorphous |
| 802401-50-A2 | amorphous | THF | MTBE | no precipitation observed |
| 802401-50-A3 | amorphous | THF | toluene | amorphous |
| 802401-50-A4 | amorphous | IPA | heptane | amorphous |
| 802401-50-A5 | amorphous | IPA | MTBE | amorphous |
| 802401-50-A6 | amorphous | IPA | toluene | amorphous |
| 802401-50-A7 | amorphous | IPA | EtOAc | amorphous |
| 802401-50-A8 | amorphous | n-butanol | heptane | amorphous |
| 802401-50-A9 | amorphous | n-butanol | MTBE | no precipitation observed |
| 802401-50-A10 | amorphous | n-butanol | toluene | amorphous |
| 802401-50-A11 | amorphous | n-butanol | EtOAc | no precipitation observed |

Example 4

Physical Characterization and Thermodynamic Phase Relationships

Three crystalline forms have been observed for free base EPZ-5676: Type A and Type B are hydrates while Type C is an anhydrate. All three solid forms have been fully characterized and their thermodynamic relationships have been investigated.

Form A

Figure 2:
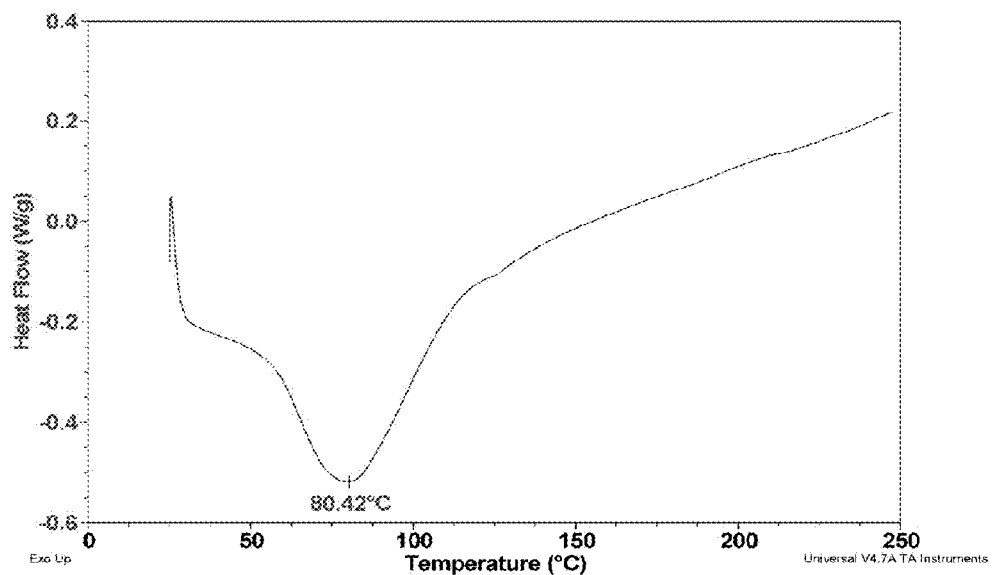
FIG. 2 is a graph indicating the DSC curve of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol hydrate (Form A).
Figure 3:
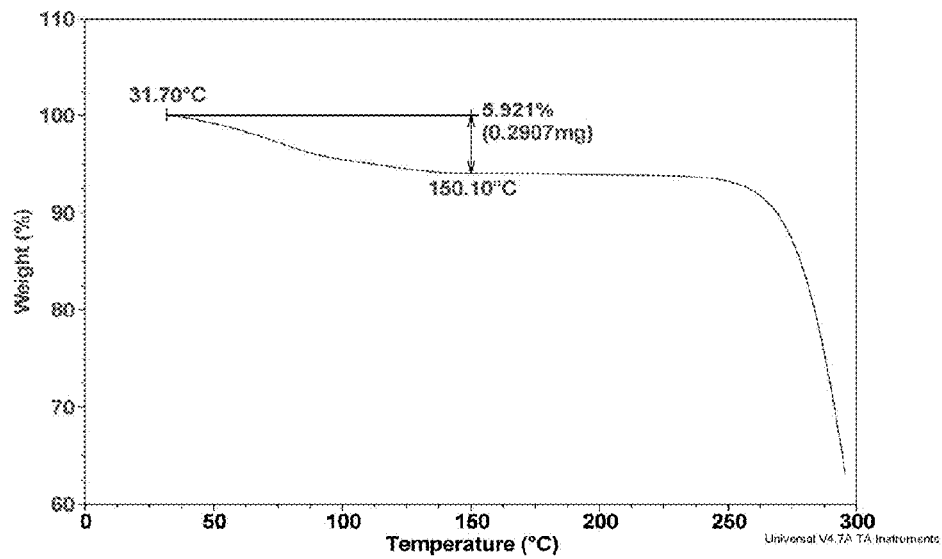
FIG. 3 is a graph indicating the TGA curve of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol hydrate (Form A).
Figure 4:
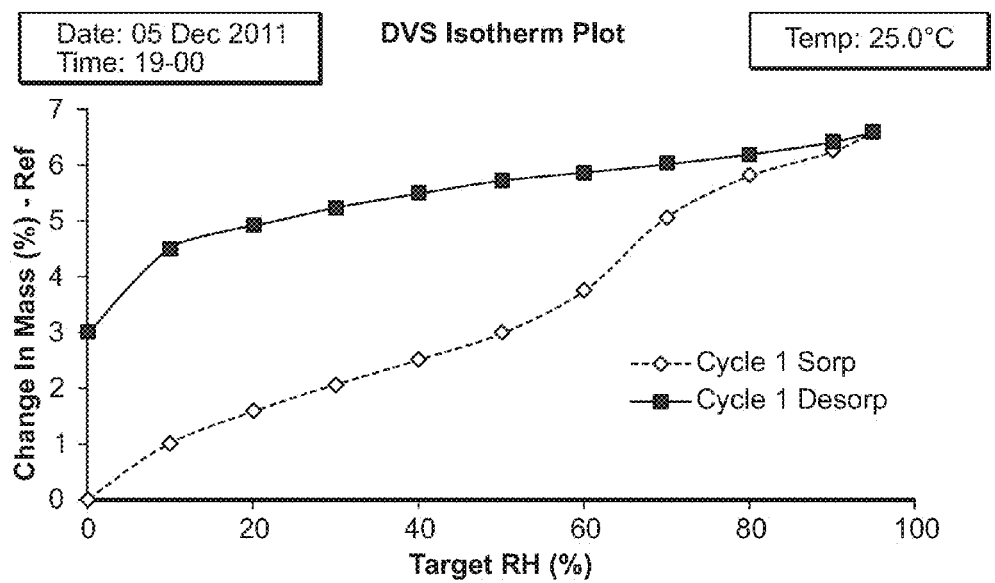
FIG. 4 is a graph indicating the adsorption/desorption isotherm at 25° C. of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl) tetrahydrofuran-3,4-diol hydrate (Form A).
Figure 5:
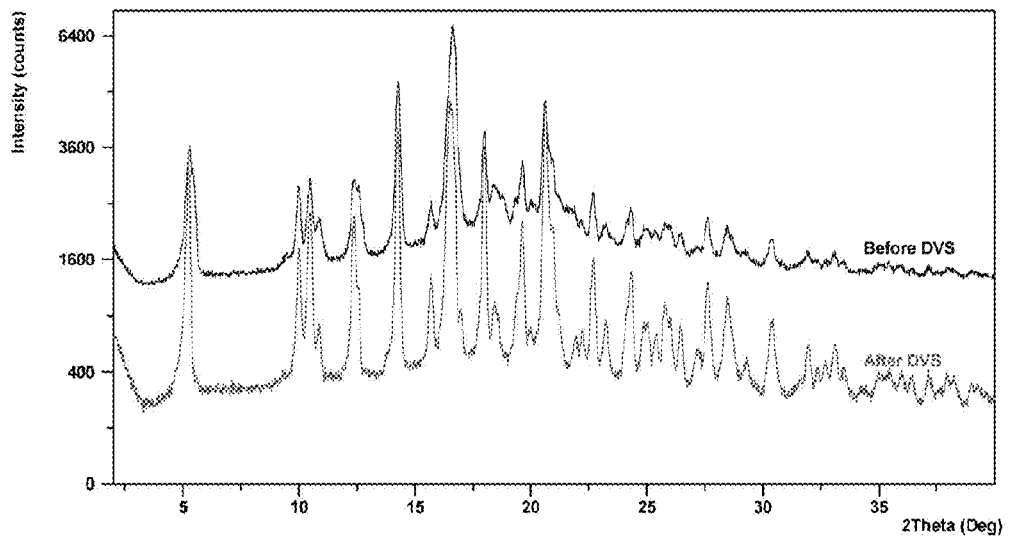
FIG. 5 is a graph indicating the XRPD overlay before and after DVS analysis of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol hydrate (Form A).

Form A may be observed EP-1. EP-1 may be crystalline but contains a certain amount of amorphous phase as evidenced by the halo displayed in the XRPD pattern (FIG. 1). The DSC curve (FIG. 2) of Form A exhibits a dehydration endotherm at ~80° C. (peak temperature) which is accompanied by 5.9 wt % weight loss up to ~150° C. in the TGA curve (FIG. 3). The water content was found to be 6.4 wt % as determined by a Mettler Toledo DL31 KF Titrator. This data confirms that Form A is a hydrate. Form A is hygroscopic as indicated by water adsorption of 5.8 wt % at 80% RH measured by dynamic vapor sorption (DVS) (FIG. 4). A solid is considered moderately hygroscopic when water uptake at 25° C./80% RH is between 2-15 wt % based on criteria of European Pharmacopeia. The hysteresis in the DVS plot suggests that Form A partially converts to Form B during the experiment, although it converts back to Form A when RH goes back down to zero, therefore no significant change in XRPD pattern was observed post DVS experiment (FIG. 5).

Form B

Figure 6:
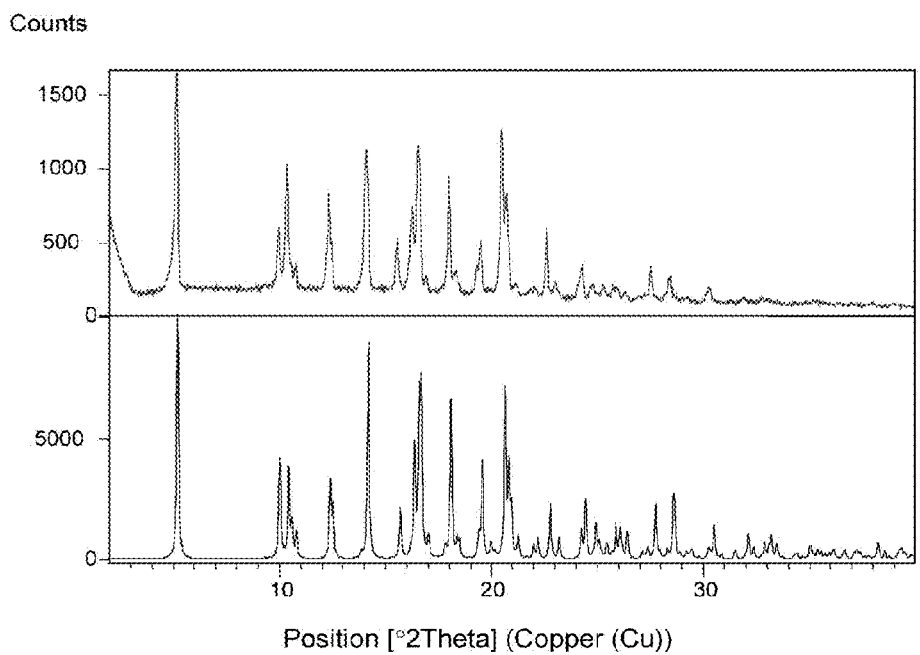
FIG. 6 is a graph indicating the XRPD overlay (top: experimental; bottom: simulated) of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino) methyl)tetrahydrofuran-3,4-diol trihydrate (Form B).
Figure 7:
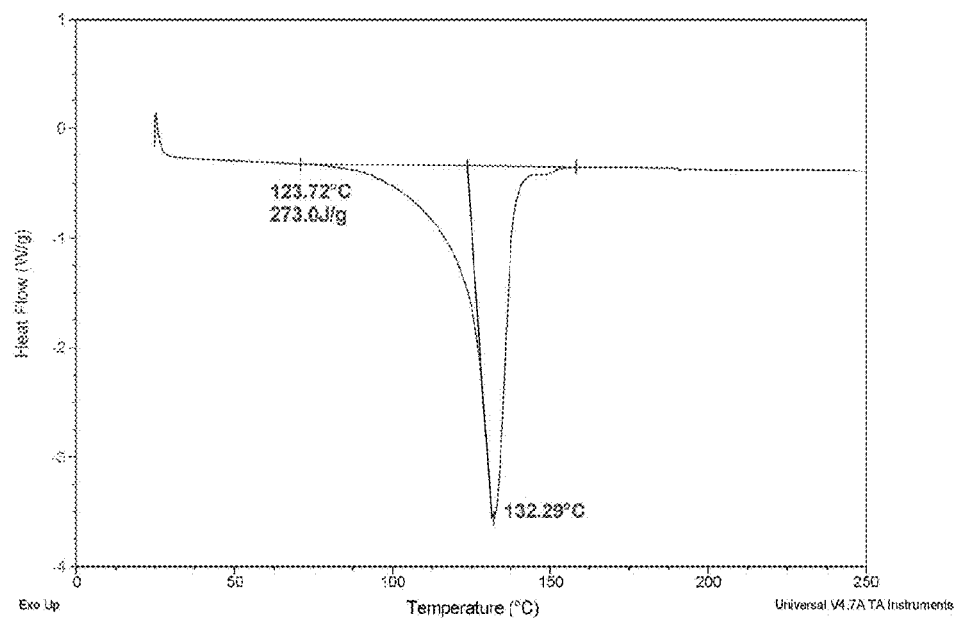
FIG. 7 is a graph indicating the DSC curve of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol trihydrate (Form B).
Figure 8:
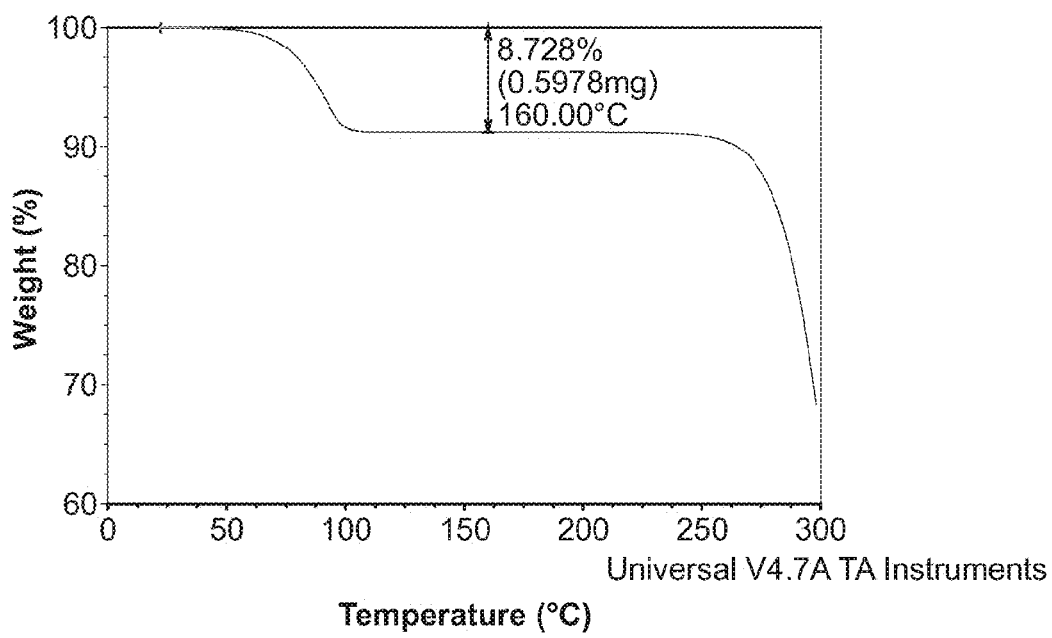
FIG. 8 is a graph indicating the TGA curve of (2R,3R,4S,5R)-2-(6-amino-9H-purin-9-yl)-5-((((1r,3S)-3-(2-(5-(tert-butyl)-H-benzo[d]imidazol-2-yl)ethyl)cyclobutyl) (isopropyl)amino)methyl)tetrahydrofuran-3,4-diol trihydrate (Form B).
Figure 9:
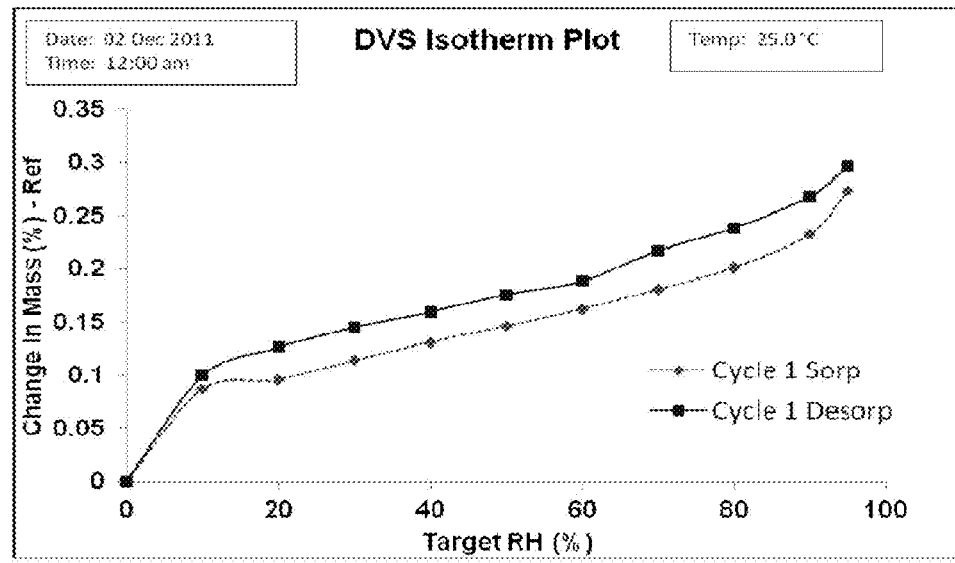
FIG. 9 is a graph indicating the water adsorption/desorption isotherm at 25° C. of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol trihydrate (Form B).
Figure 10:
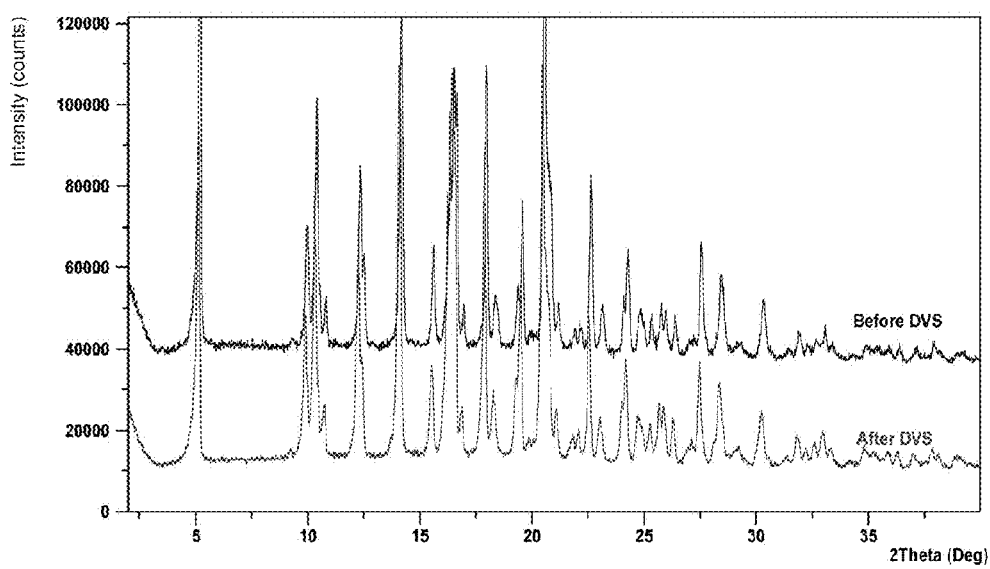
FIG. 10 is a graph indicating the XRPD overlay before and after DVS analysis of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol trihydrate (Form B).

Form B of EP-1 trihydrate (x is 3) is a trihydrate as confirmed by single crystal analysis. The experimental XRPD pattern of Form B matches well with the simulated one from single crystal data (FIG. 6). This was also confirmed by DSC and TGA data (FIG. 7 and FIG. 8, respectively). DSC data indicates Form B dehydrates at ~132° C. (peak temperature) and TGA data displays a 8.73% weight loss up to 160° C. which is in good agreement with the theoretical value (8.75%) of a trihydrate. Form B is slightly hygroscopic as evidenced by a weight change of ~0.3% between 0% and 95% RH (FIG. 9), (data collection was programmed from 95% RH-0% RH-95% RH at a step size of 10% RH at 25° C.). XRPD results suggested that no form change was observed for Form B after the DVS experiment (FIG. 10).

Form C

Figure 11:
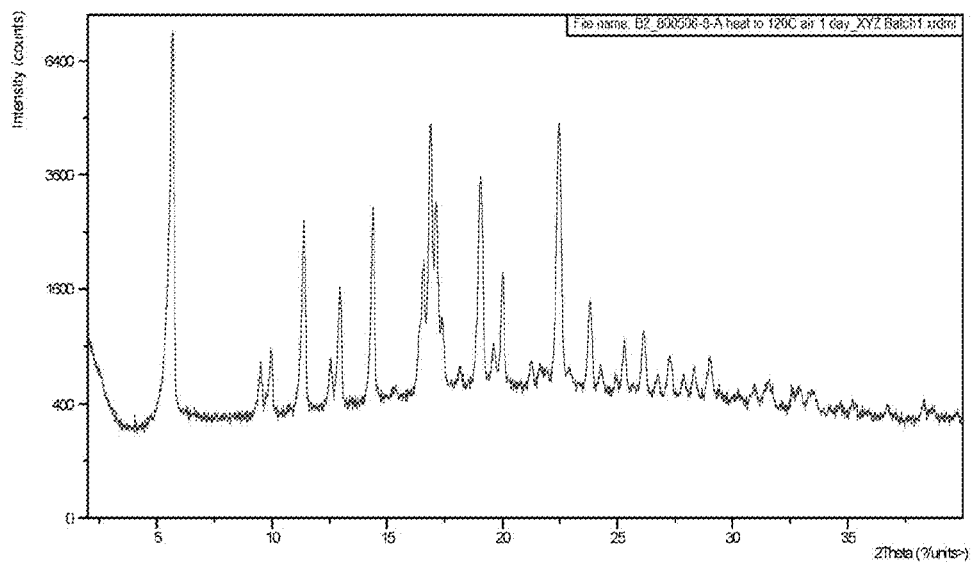
FIG. 11 is a graph indicating the XRPD of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol anhydrate (Form C).
Figure 12:
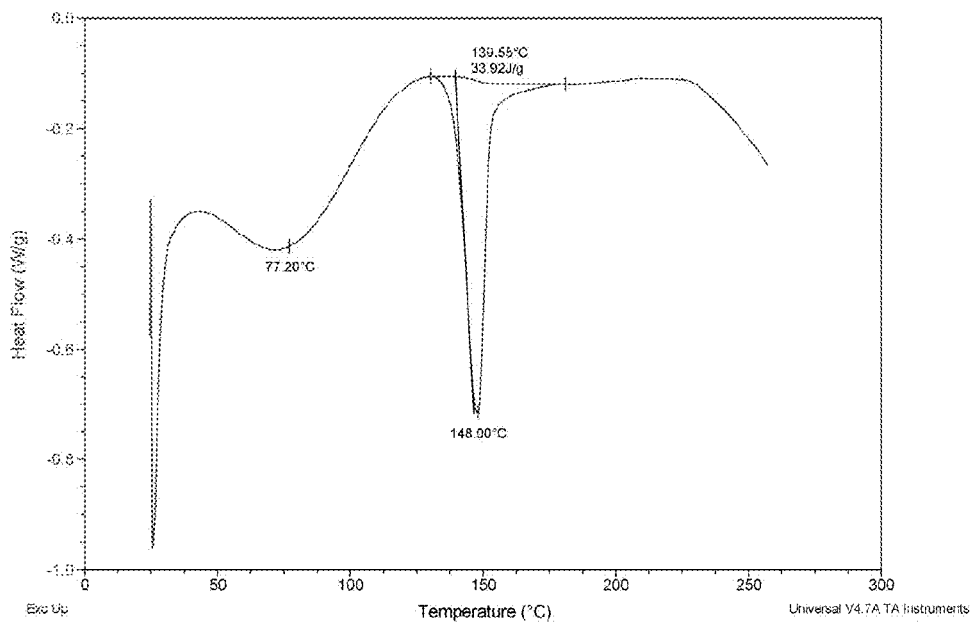
FIG. 12 is a graph indicating the DSC curve of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol anhydrate (Form C).
Figure 13:
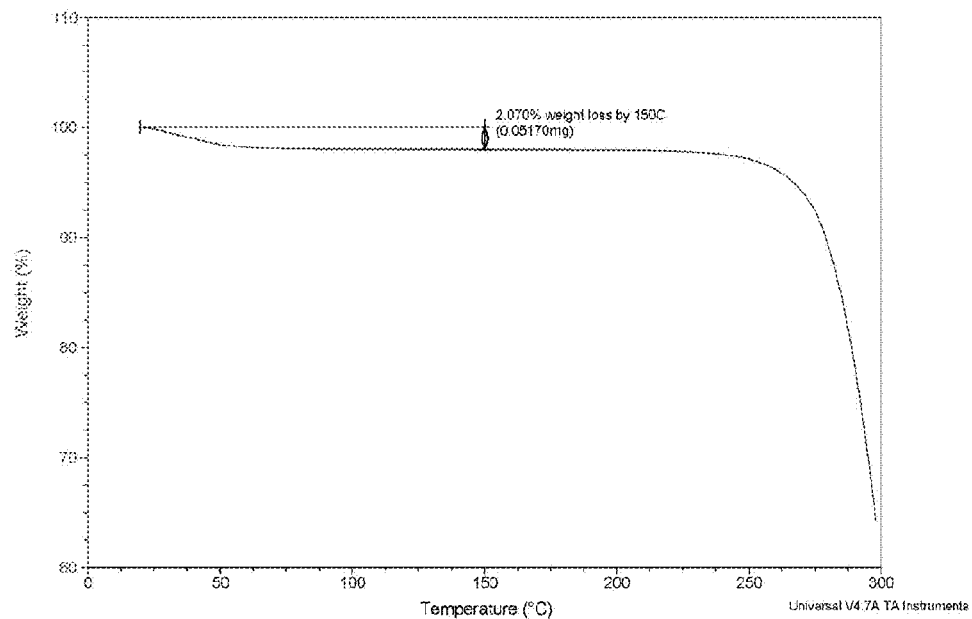
FIG. 13 is a graph indicating the TGA curve of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol anhydrate (Form C).

Form C was observed upon heating of Form B to 120° C. and cooling down to room temperature (FIG. 11). Its DSC and TGA characterization data are shown in FIG. 12 and FIG. 13, respectively. The results suggest it is a channel hydrate.

Thermodynamic Phase Relationships

Figure 14:
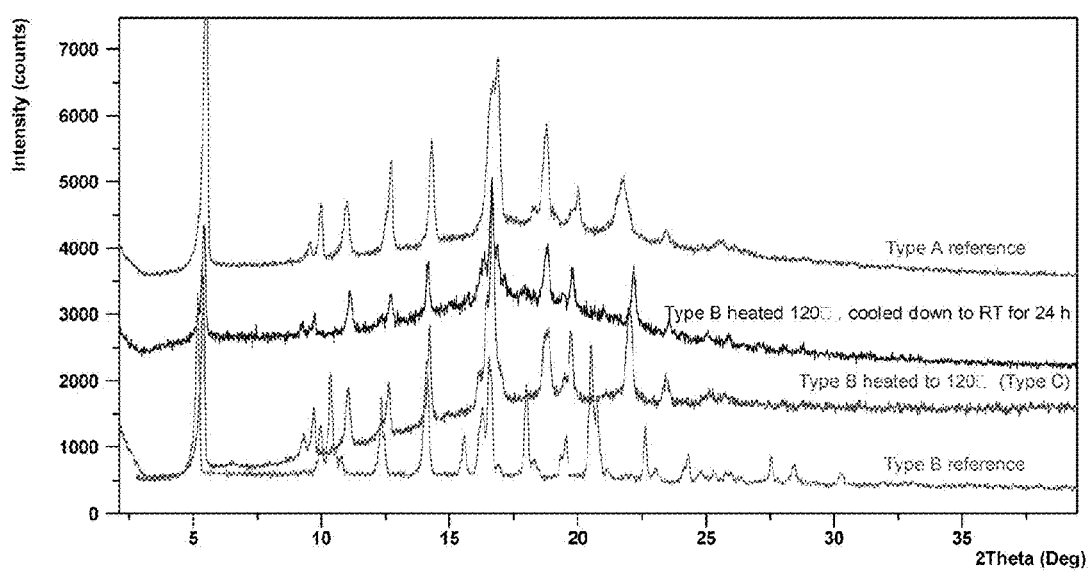
FIG. 14 is a graph indicating the VT-XRPD of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol trihydrate (Form B).

Variable temperature XRPD indicates that Form B converts to Form C upon heating to 120° C., and cooling down to RT in the presence of ambient moisture (FIG. 14). Form C is an anhydrate form whose XRPD pattern is very similar to that of Form A.

Figure 15:
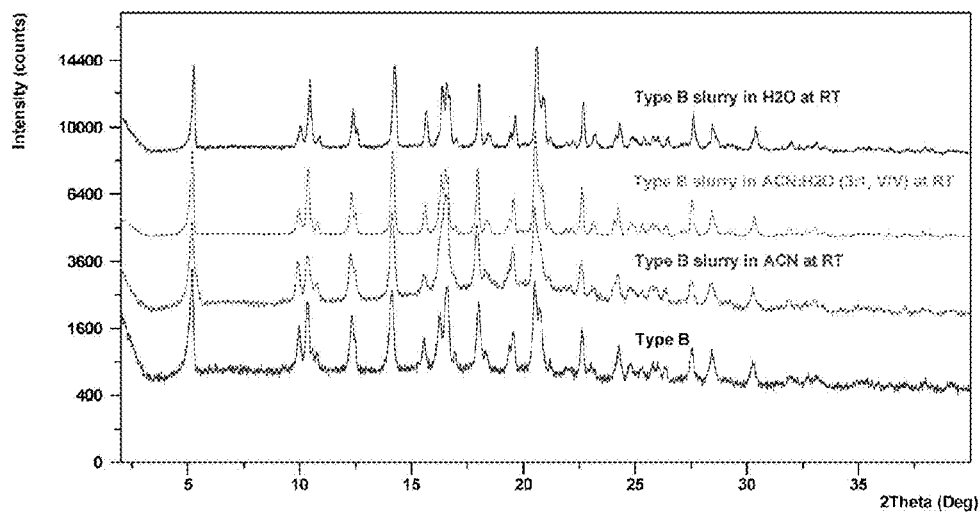
FIG. 15 is a graph indicating XRPD samples from slurry experiments using a mixture of Form A and Form B at room temperature of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol trihydrate.
Figure 16:
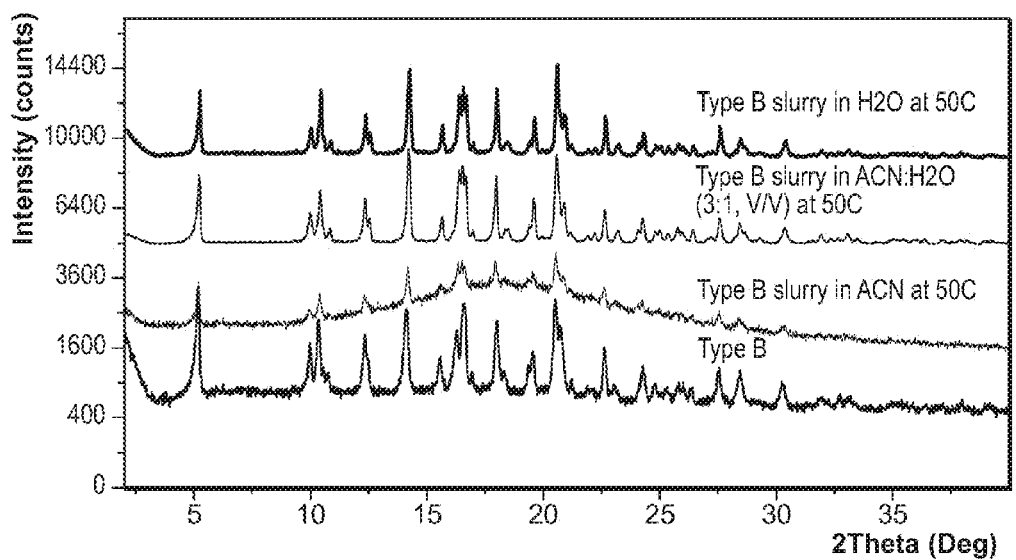
FIG. 16 is a graph indicating XRPD samples from slurry experiments using a mixture of Form A and Form B at 50° C. of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol trihydrate.

The relative stability between Form A and Form B was investigated by slurry experiments in ACN (containing less than 0.3 wt % water), ACN/$H_2O$ (v/v, 3;1), and $H_2O$ at room temperature and 50° C. In general, about 10-30 mg Form A was added to a 5-ml glass vial with 0.5 ml corresponding solvents to get suspensions at room temperature and 50° C., respectively. Then 10-30 mg Form B was added to the suspensions which were kept stirring for 24 h. The water activity was calculated using the UNIFAC model. The results summarized in Table 6 indicate that Form B is thermodynamically more stable than Form A at water activity equal to or greater than 0.09 at RT and 0.08 at 50° C. as evidenced by form conversion of Form A to Form B in ACN (containing less than 0.3 wt % water), ACN/$H_2O$ (v/v, 3:1), and $H_2O$ (FIG. 15 and FIG. 16).

TABLE 6

Results of Slurry Experiments Using Form A and Form B

| Solvent | Water Activity | Starting Form | Temperature | Ending Form |
|---|---|---|---|---|
| ACN | <0.09§ | A + B | RT* | Form B |
| 3:1 ACN/H₂O | 0.93 | A + B | RT | Form B |
| H₂O | 1.00 | A + B | RT | Form B |
| ACN | <0.08 | A + B | 50° C. | Form B |
| 3:1 ACN/H₂O | 0.90 | A + B | 50° C. | Form B |
| H₂O | 1.00 | A + B | 50° C. | Form B |

§ACN contains less than 0.3 wt % water.
*RT: Room Temperature, 25 ± 3° C.

Figure 17:
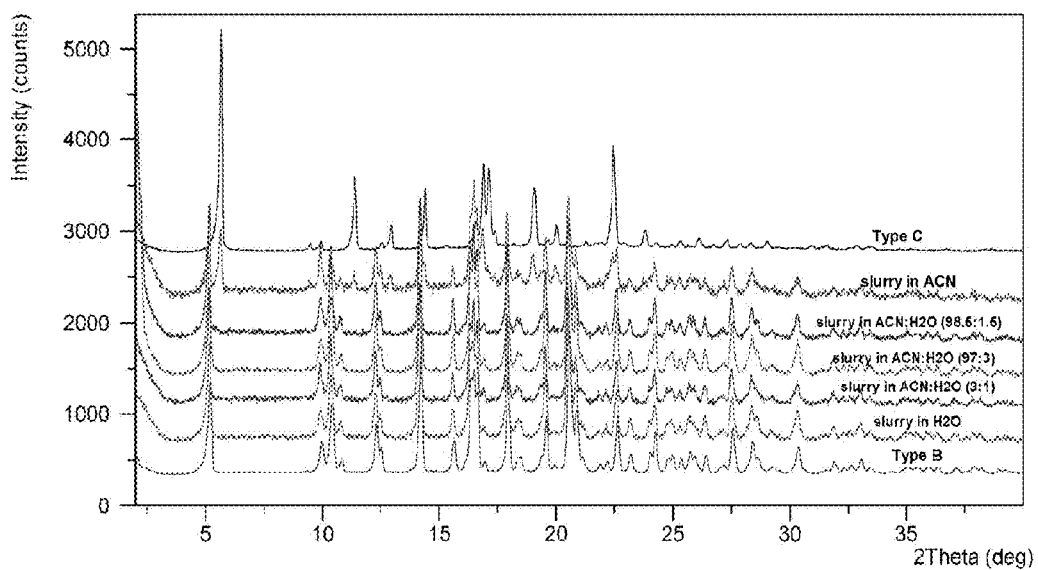
FIG. 17 is a graph indicating XRPD samples from slurry experiments using a mixture of Form B and Form C at room temperature of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol anhydrate and trihydrate, respectively.

The relative stability between Form B and Form C was investigated as a function of water activity at room temperature using ACN/H₂O. In general, about 10-30 mg Form B was added to a 5-ml glass vial with 0.5 ml corresponding solvents to get suspensions at room temperature. Then 10-30 mg Form C was added to the suspensions which were kept stirring for 24 h. The water activity was calculated using the UNIFAC model. The results summarized in Table 7 indicate that Form B is thermodynamically more stable than Form C at water activity equal to or greater than 0.30 at RT (FIG. 17).

TABLE 7

Results of Slurry Experiments Using Form B and Form C

| Solvent | Water Activity | Starting Form | Temperature | Ending Form |
|---|---|---|---|---|
| ACN | <0.09§ | B + C | RT* | B + C |
| 98.5:1.5 ACN/H₂O | 0.30 | B + C | RT | B |
| 97:3 ACN/H₂O | 0.50 | B + C | RT | B |
| 3:1 ACN/H₂O | 0.93 | B + C | RT | B |
| H₂O | 1.00 | B + C | RT | B |

§ACN contains less than 0.3 wt % water.
*RT: Room Temperature, 25 ± 3° C.

Figure 18:
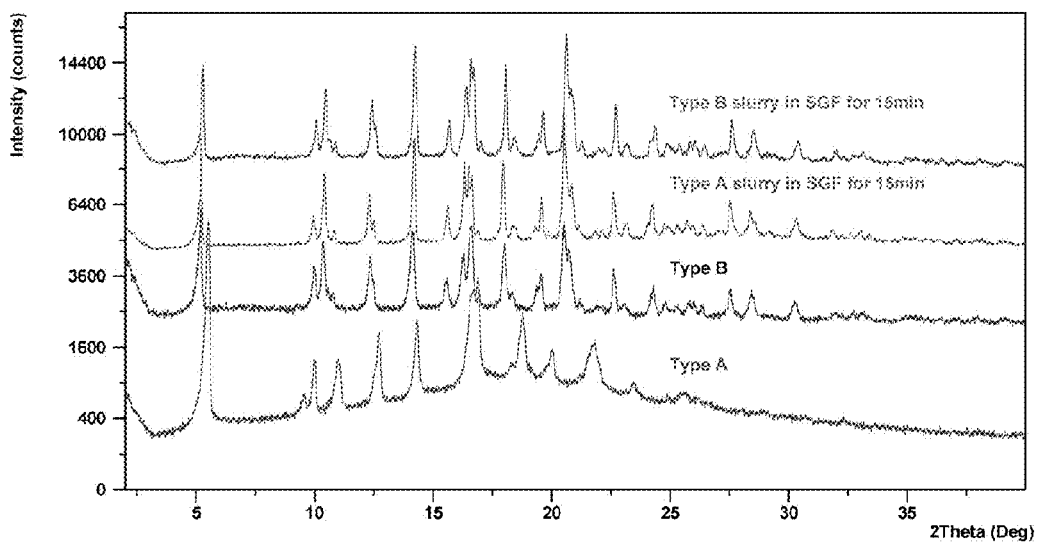
FIG. 18 is a graph indicating XRPD samples from slurry experiments of Form A and Form B of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol trihydrate in SGF at 37° C.

To study if Form A and Form B would perform differently in stomach, the solubilities of Form A and Form B were measured in Simulated Gastric Fluid (SGF, see below for SGF preparation) at 37° C. In these experiments, about 100 mg Form A and 50 mg Form B were weighed into 20-ml glass vials, followed by addition of 4 ml SGF into each vial and the samples were stirred at 37° C. Aliquots were taken for solubility determination using HPLC after 15, 30, and 60 min, respectively. The remaining solids after each time point were subject to XRPD analysis. The results are summarized in Table 8 and FIG. 18 which indicate that Form A converts to Form B in SGF within 15 min, suggesting Form A and Form B will behave the same after 15 min in the stomach.

TABLE 8

Solubility of Form and Form in SGF at 37° C.

| | 15 min | | 30 min | | 60 min | | |
|---|---|---|---|---|---|---|---|
| Starting Form | Solubility* mg/ml | Resulting Solid | Solubility mg/ml | Resulting Solid | Solubility mg/ml | Resulting Solid | Final pH |
| Type A | 5.4 | Type B | 5.5 | Type B | 5.3 | Type B | 5.1 |
| Type B | 5.4 | Type B | 5.4 | Type B | 5.6 | Type B | 5.3 |

*Solubility of Form A and Form B was both calculated using free base content

Figure 19:
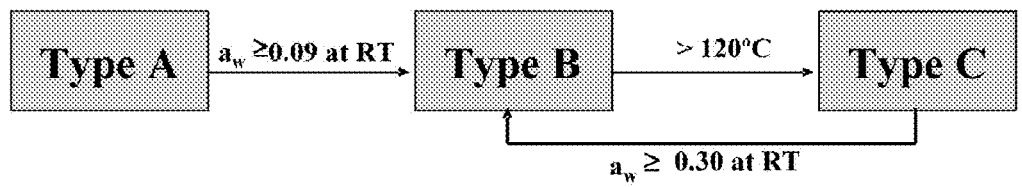
FIG. 19 is a graph indicating the XRPD overlay of Form A, Form B, and Form C of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol hydrate, trihydrate, and anhydrate, respectively.
Figure 20:
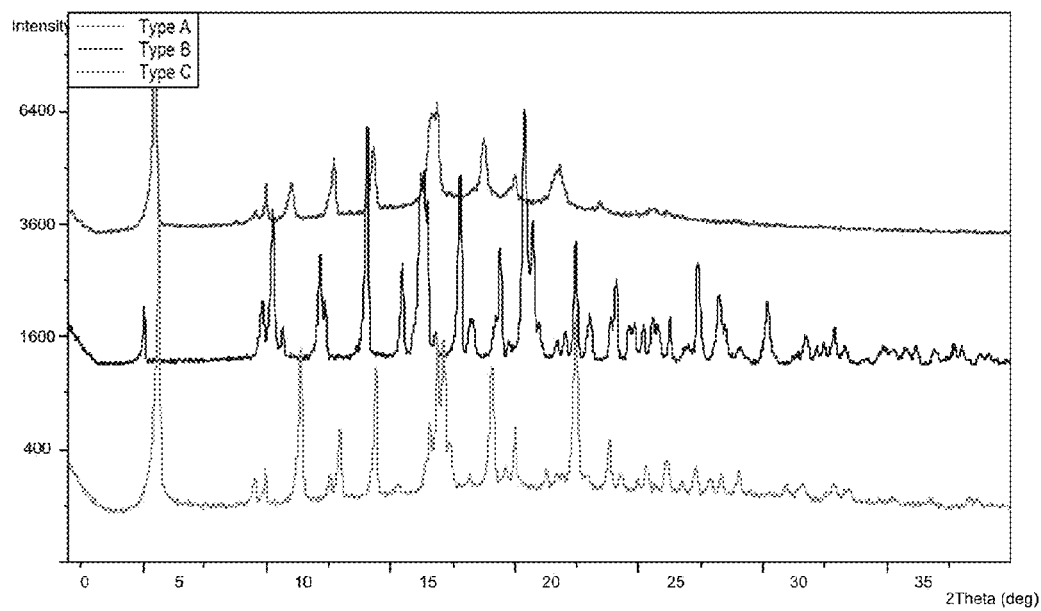
FIG. 20 is a picture indicating the morphology of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol trihydrate (Form B).

Based on the above results, among the three observed crystalline forms, Form B is the most thermodynamically stable form under ambient conditions. The relationships of these three crystalline forms are summarized in FIG. 19. An XRPD overlay for Form A, Form B, and Form C is shown in FIG. 20.

Example 5

Further Evaluation of Form B

Based on the physical characterization data (DSC, TGA, XRPD, and DVS) and relative thermodynamic stability, Form B was deemed most suitable for pharmaceutical development. Thus additional characterization and preformulation evaluation is focused on Form B.

Particle Morphology

Figure 21:
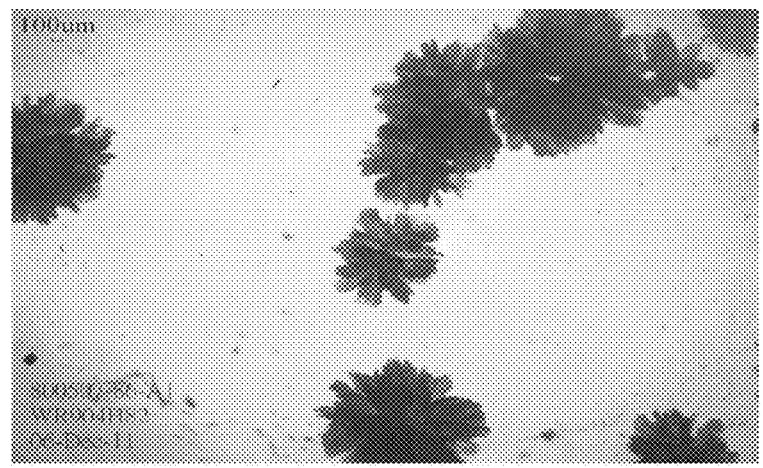
FIG. 21 is a graph indicating the XRPD of remaining solids in solubility determination of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol trihydrate (Form B).

The morphology of Form B obtained by recrystallization in MeOH/H₂O is shown in FIG. 21. Form B grows as thin plate-like crystals in MeOH/H₂O.

Solubility

Approximately 10 mg of Form B was weighed into a 1-ml glass vial followed by addition of 0.5 ml relevant media. Each sample was continuously stirred using a magnetic stir bar at 25° C. for 24 h. The suspension was then filtered using a nylon membrane with a pore diameter of 0.22 μm. The filtrates were diluted for HPLC analysis and final pH was measured. The solid residue of each sample was collected for XRPD analysis.

Equilibrium Solubility in Aqueous Media

Figure 22:
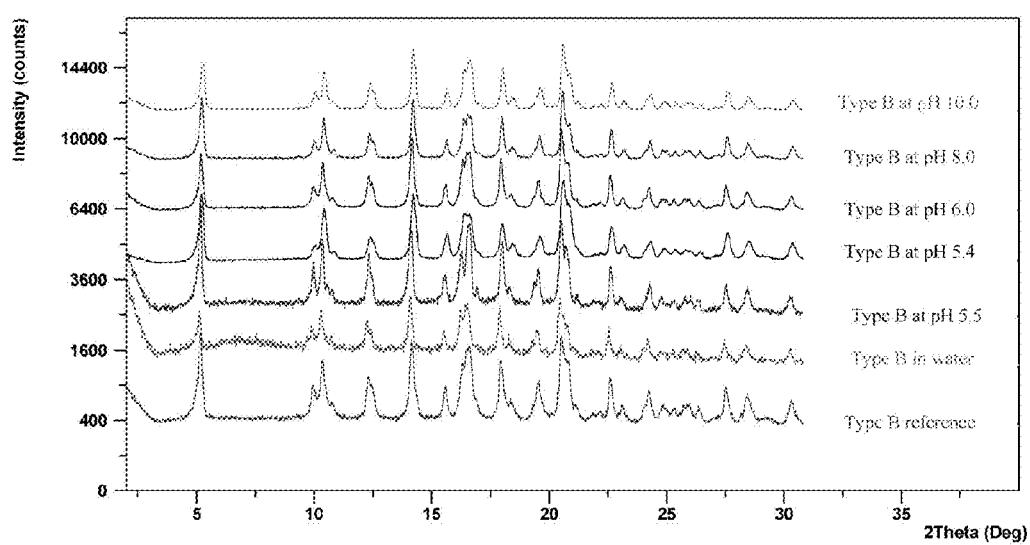
FIG. 22 is a scheme indicating the pKa plot of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol.

The solubilities of Form B in water and five different pH values at 25° C. were determined by HPLC after 24 h equilibration. Solubility data for Form B was obtained across the physiological pH by using buffer solutions from pH 2 to pH 10. The results are summarized in Table 9. The solubility of Form B at RT in unbuffered water was found to be 1.2 μg/ml. Data in Table 9 indicated that Form B has pH-dependent solubility, namely, Form B shows satisfactory solubilities at pH≤4 (i.e., 3.4 mg/ml at pH 2 and 9.8 mg/ml at pH 4). No crystal form change was observed in all solubility experiments (FIG. 22).

TABLE 9

Solubility of Form B in Aqueous Media at RT

| Buffer | pH (initial) | pH (final) | Solubility (mg/ml) | Remaining Solid |
|---|---|---|---|---|
| Water | Not measured | 5.6 | $1.2 \times 10^{-3}$ | Form B |
| 0.01N HCl | 2.0 | 5.5 | 3.4 | Form B |
| 50 mM sodium citrate | 4.0 | 5.4 | 9.7 | Form B |
| 50 mM sodium citrate | 6.0 | 6.0 | 0.08 | Form B |

TABLE 9-continued

Solubility of Form B in Aqueous Media at RT

| Buffer | pH (initial) | pH (final) | Solubility (mg/ml) | Remaining Solid |
|---|---|---|---|---|
| 50 mM Na phosphate buffer | 8.0 | 8.0 | <LOD[§] | Form B |
| 50 mM Na carbonate buffer | 10.0 | 10.0 | <LOD | Form B |

[§]LOD was determined to be 0.1 µg/ml

Equilibrium Solubility in Organic Solvents

The solubility of Form B was also determined in commonly used organic solvents (diluents or HPLC mobile phase). The solubility data summarized in Table 10 indicates Form B is quite soluble in MeOH, EtOH, and IPA.

TABLE 10

Solubility of Form B in Organic Solvents at RT

| Solvent | Solubility (mg/ml) | Remaining Solid |
|---|---|---|
| Acetone | 23.9 | Form B |
| Methanol | >200 | No solid obtained |
| Ethanol | >87 | No solid obtained |
| Isopropanol | >129 | No solid obtained |
| Acetonitrile | 1.5 | Form B | pKa Studies

Figure 23:
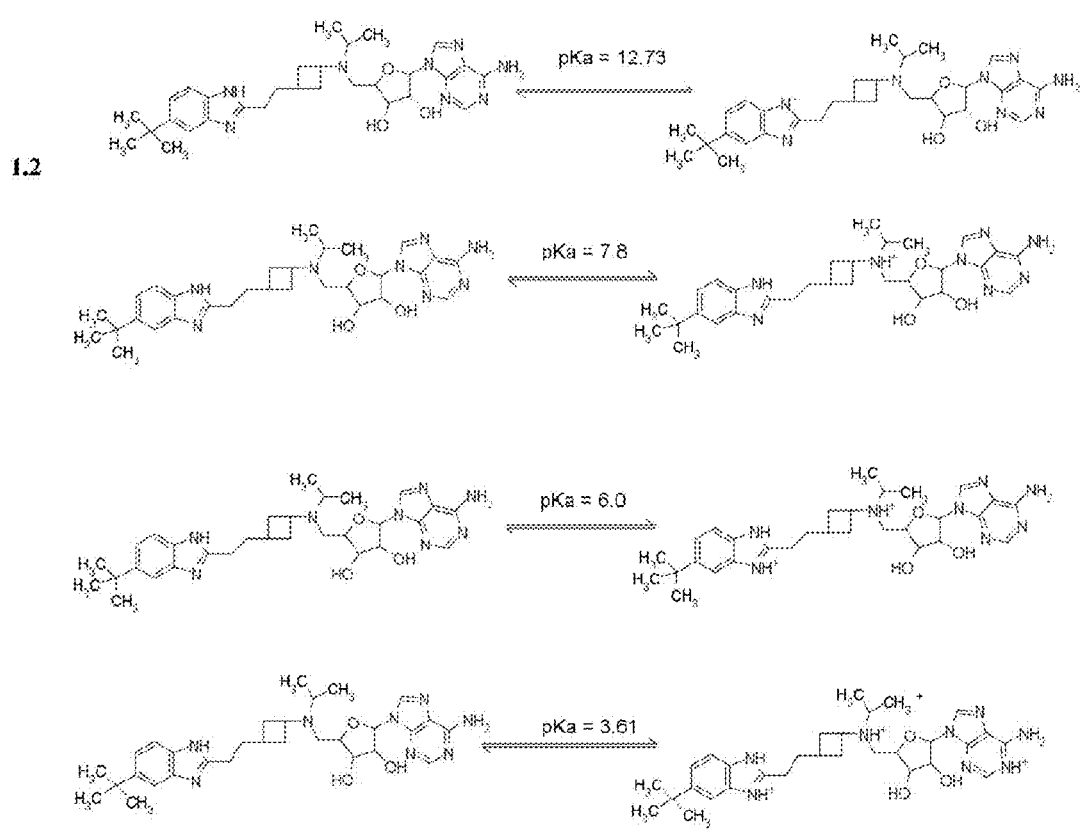
FIG. 23 is a graph indicating the XRPD of samples from physical stability of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol trihydrate (Form B).

The pKa and log P were calculated use software ADMET Predictor, Version 5.5 from Simulation Plus Inc. Lancaster, Calif. The predicted major pKas of EP-1 are 12.73, 7.80, 6.00 and 3.61 (the aliphatic-OH groups were ignored by the software). The microstates of the compound in different pKa are plotted in FIG. 23.

Solid-State Stability

Chemical Stability: Accurately weighed ~10 mg Form B was placed into four 10-ml volumetric flasks. The samples were stored at 5° C. closed dish, 25° C./57% RH open dish, 40° C./75% RH open dish, and 60° C. closed dish for 7 days. The sample stored at 5° C. was used as a control. Assay and total related substances for each sample were checked at the end of 7 days.

Figure 24:
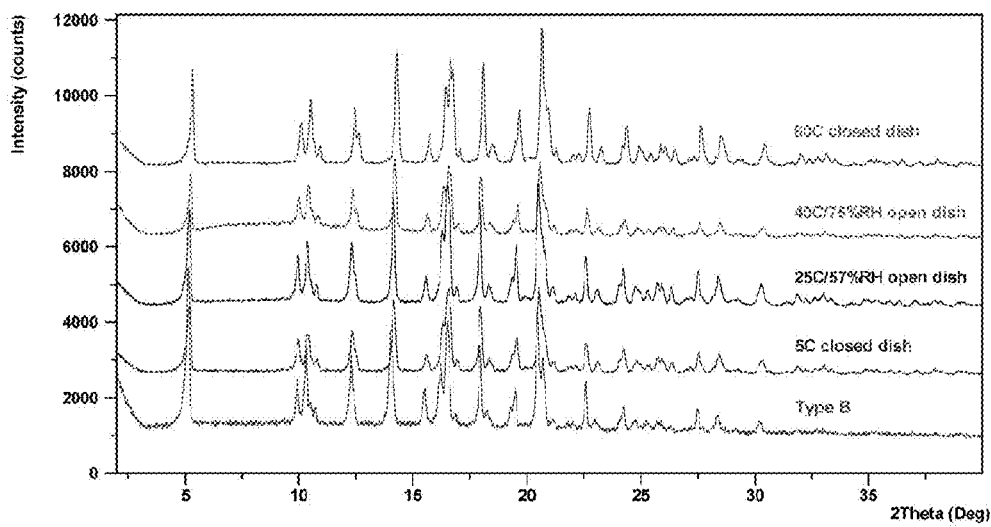
FIG. 24 is an XRPD of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol trihydrate (Form B) from physical stability study.

Physical Stability: Accurately weighed ~15 mg of Form B was placed into 5-ml glass vials and the samples were stored at 5° C. closed dish, 25° C./57% RH open dish, 40° C./75% RH open dish, and 60° C. closed dish for 7 days. Samples were analyzed by XRPD and TGA (FIG. 24).

No detectable physical change and no significant degradation were observed after 7 days under 5° C. closed dish, 25° C./57% RH open dish, 40° C./75% RH open dish and 60° C. closed dish (results summarized in Table 11). This was also confirmed by the water content determination by TGA (theoretical water content of a trihydrate is 8.75 wt %).

TABLE 11

Solid-state Stability of Form B

| | 7 Days | | | |
|---|---|---|---|---|
| | Chemical | | Physical | |
| Conditions | Area %* | % Claim[§] | TGA (%) | XRPD |
| 5° C. Closed Dish | 99.1 | 100.0[&] | 8.63 | Form B |
| 25° C./57% RH Open Dish | 99.0 | 100.7 | 8.66 | Form B |
| 40° C./75% RH Open Dish | 99.0 | 101.0 | 8.64 | Form B |
| 60° C. Closed Dish | 99.1 | 100.7 | 8.49 | Form B |

*Area % = 100% − TRS %; TRS: Total related substance
[§]Claim % = Cs/Ci × 100%; Cs: Concentration of stability sample; Ci: Concentration of initial sample
[&]The sample was used as standard for the calculation Solution Stability 0.1 mg/ml solutions of Form B were prepared in five buffers, including 0.01N HCl (pH 2), 50 mM sodium citrate (pH 4), 50 mM sodium citrate (pH 6), 50 mM sodium phosphate (pH 8), and 50 mM sodium carbonate (pH 10). Methanol was added as a co-solvent to dissolve Form B in buffers (i.e., 10% (v/v) in pH 2, 4, and 6 buffers, 20% (v/v) in pH 8 buffer, and 30% (v/v) in pH 10 buffer). Each buffer solution containing Form B was stored at 3 different temperatures: 25° C., 37° C., and 50° C. Aliquots were taken for HPLC analysis after 1 day and 7 days. pH values were also measured before and after the stability experiments.

Solution stability data are summarized in Table 12. EP-1 trihydrate (x is 3) shows good stability in solution since less than 5% degradation was observed.

TABLE 12

Solution Stability of EP-1 trihydrate (x is 3)

| | pH 2 | | | | | |
|---|---|---|---|---|---|---|
| | 24 h | | | 7 days | | |
| Temp. | % area* | % claim[§] | pH | % area | % claim | pH |
| 25° C. | 98.7 | 97.1 | 2.1 | 98.5 | 99.1 | 2.1 |
| 37° C. | 98.7 | 96.8 | 2.1 | 98.4 | 97.5 | 2.1 |
| 50° C. | 98.3 | 97.0 | 2.1 | 98.4 | 97.0 | 2.1 |

| | 24 h | | | 7 days | | |
|---|---|---|---|---|---|---|
| Temp. | % area | % claim | pH | % area | % claim | pH |
| | | | pH 4 | | | |
| 25° C. | 99.4 | 97.4 | 4.2 | 99.6 | 100.2 | 4.2 |
| 37° C. | 99.4 | 97.6 | 4.1 | 99.5 | 99.0 | 4.1 |
| 50° C. | 99.4 | 97.6 | 4.1 | 99.5 | 98.7 | 4.2 |
| | | | pH 6 | | | |
| 25° C. | 99.2 | 98.0 | 6.2 | 99.5 | 100.0 | 6.2 |
| 37° C. | 99.3 | 97.9 | 6.2 | 99.4 | 99.0 | 6.3 |
| 50° C. | 99.3 | 98.1 | 6.2 | 99.5 | 98.9 | 6.2 |
| | | | pH 8 | | | |
| 25° C. | 99.2 | 98.0 | 8.2 | 99.5 | 99.8 | 8.2 |
| 37° C. | 99.5 | 98.4 | 8.2 | 99.5 | 99.3 | 8.3 |
| 50° C. | 99.5 | 98.0 | 8.3 | 99.5 | 98.8 | 8.3 |
| | | | pH 10 | | | |
| 25° C. | 99.4 | 98.0 | 10.9 | 99.4 | 99.7 | 10.9 |
| 37° C. | 99.4 | 98.2 | 10.9 | 99.4 | 99.0 | 10.9 |
| 50° C. | 99.5 | 97.9 | 11.0 | 99.4 | 98.9 | 10.9 |

*Area % = 100%−TRS %; TRS: Total related substances.
[§]Claim % = Cs/Ci × 100%; Cs: Concentration in stability sample; Ci: Concentration in initial sample Photostability Solid-State Photostability The solid-state photostability of EP-1 trihydrate (x is 3) was assessed upon exposure to UV/Vis light according to ICH guidelines. Loss of claim %, loss of area %, and degradates were evaluated versus dark control samples.

Solid-State Photostability: Weighed ~5 mg Form B into glass vials with 2 vials covered with foil as the controls. Put these 2 samples with their controls into chamber and expose them to Vis (10 Kilo lux) for 120 hrs followed by UV (10 W/m$^2$) for 20 hrs (per ICH guidelines). At the end of Vis, take 1 sample and 1 control out for analysis and the others were taken out after both Vis and UV exposure.

Solid state photostability data are summarized in Table 13. No loss of claim %, area %, or degradates were detected as compared to the dark control samples, indicating the bulk Form B is stable upon exposure to full ICH photostability requirement.

TABLE 13

Solid State Photostability of EP-1 trihydrate (x is 3) - Form B

| Sample | Vis Stability (1.2 Mil lux-hours) | | Vis-UV stability (1.2 Mil lux-hours + 200 Watt-hours/m$^2$) | |
|---|---|---|---|---|
| | % area* | % claim$^\&$ | % area* | % claim$^\&$ |
| Bulk | 99.8 | 101.1 | 99.8 | 99.6 |
| Bulk control | 99.7 | 100.0 | 99.8 | 100.0 |

*Area % = 100% − TRS %; TRS: Total related substances
$^\&$Claim % = Cs/Ci × 100%; Cs: Concentration in stability sample; Ci: Concentration in initial sample Solution Photostability Solution Photostability: Weighed ~1 mg of Form B and dissolved in 3 solutions at different pHs (0.01 N HCl, 0.01 N NaOH and water). Methanol was added as a co-solvent to dissolve Form B in solutions (i.e., 10% (v/v) methanol in 0.01 N HCl, 20% (v/v) in water and 30% (v/v) in 0.01 N NaOH), the final concentration was 0.1 mg/mL. For each solution, 1 sample and 1 control covered in foil were put into the photo chamber for Vis study (2 vials total for each solution). Measure the concentration and monitor the degradation.

Figure 25:
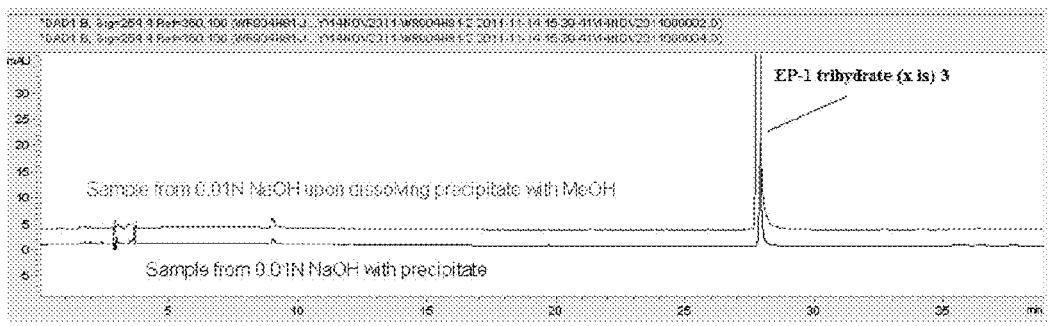
FIG. 25 is an HPLC chromatogram of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol hydrate and trihydrate (Form A and Form B, respectively).
Figure 26:
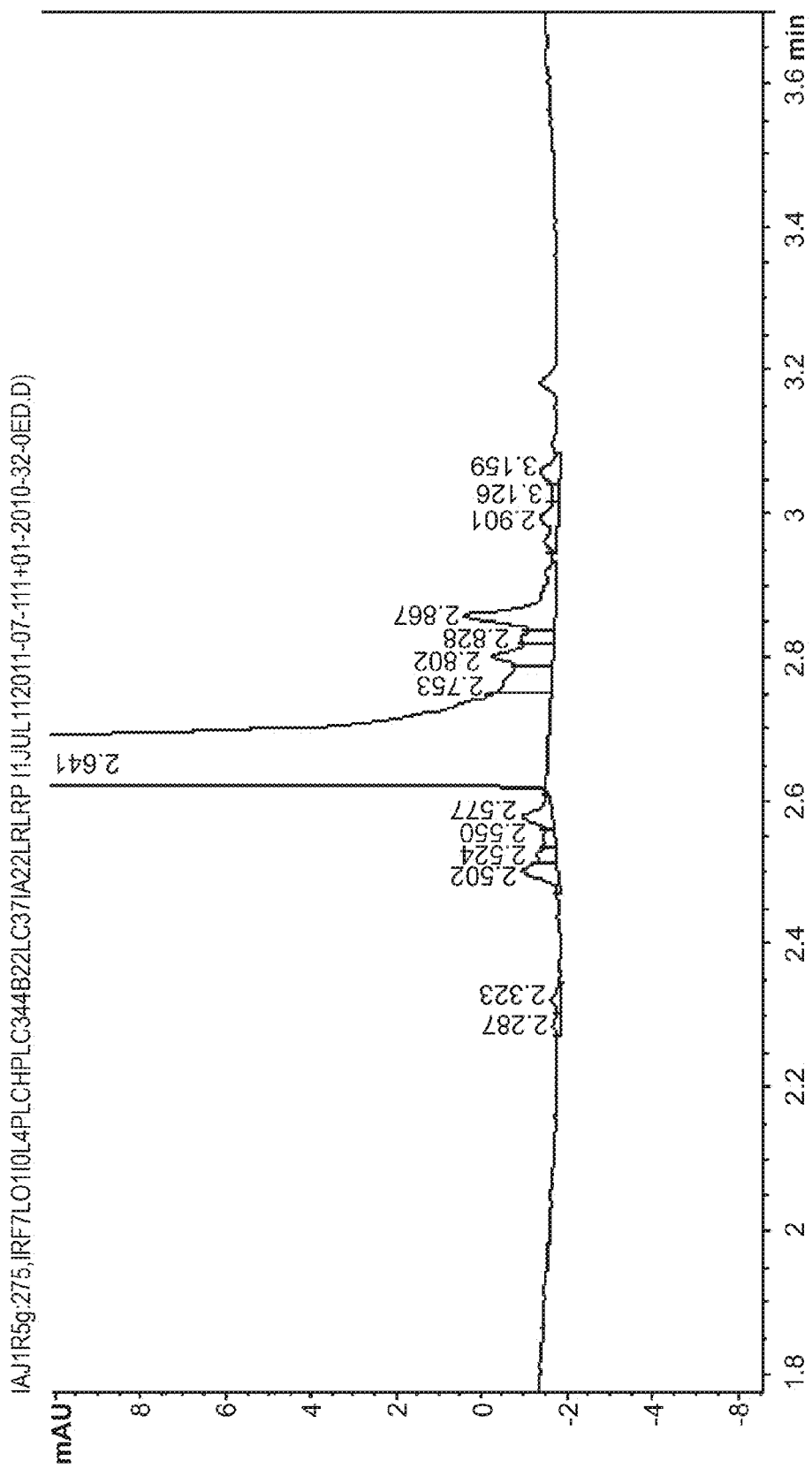
FIG. 26 is a HPLC chromatogram of EP-1 trihydrate (x is 3) free base.
Figure 27:
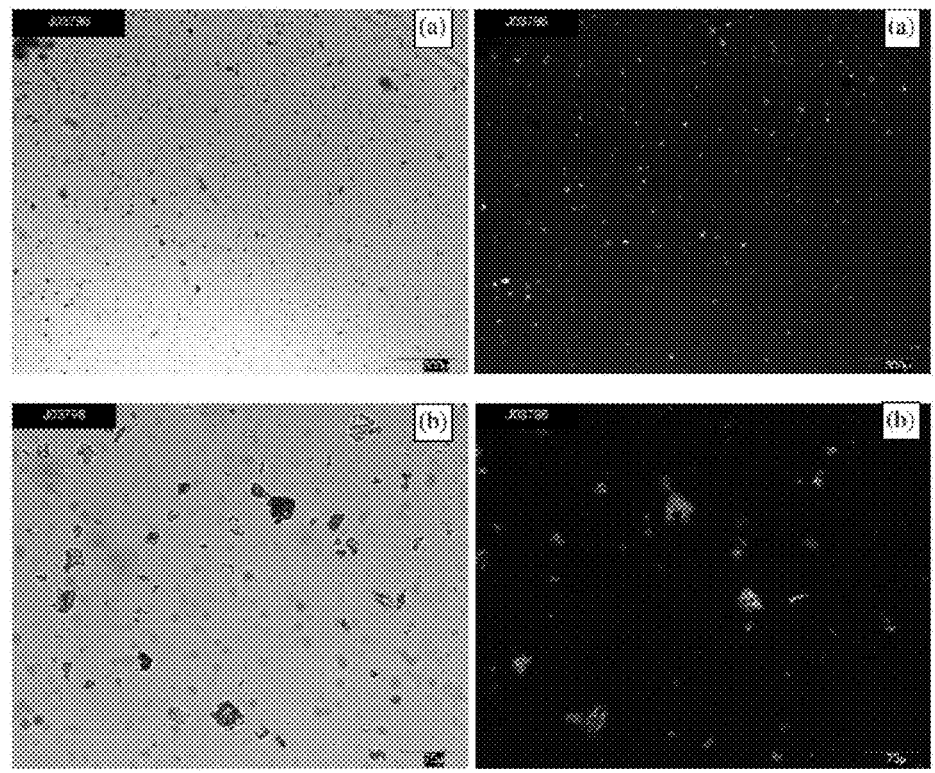
FIG. 27A is an image of EP-1 trihydrate (x is 3) at ×5 magnification.
FIG. 27B is an image of EP-1 trihydrate (x is 3) at ×20 magnification.
Figure 28:
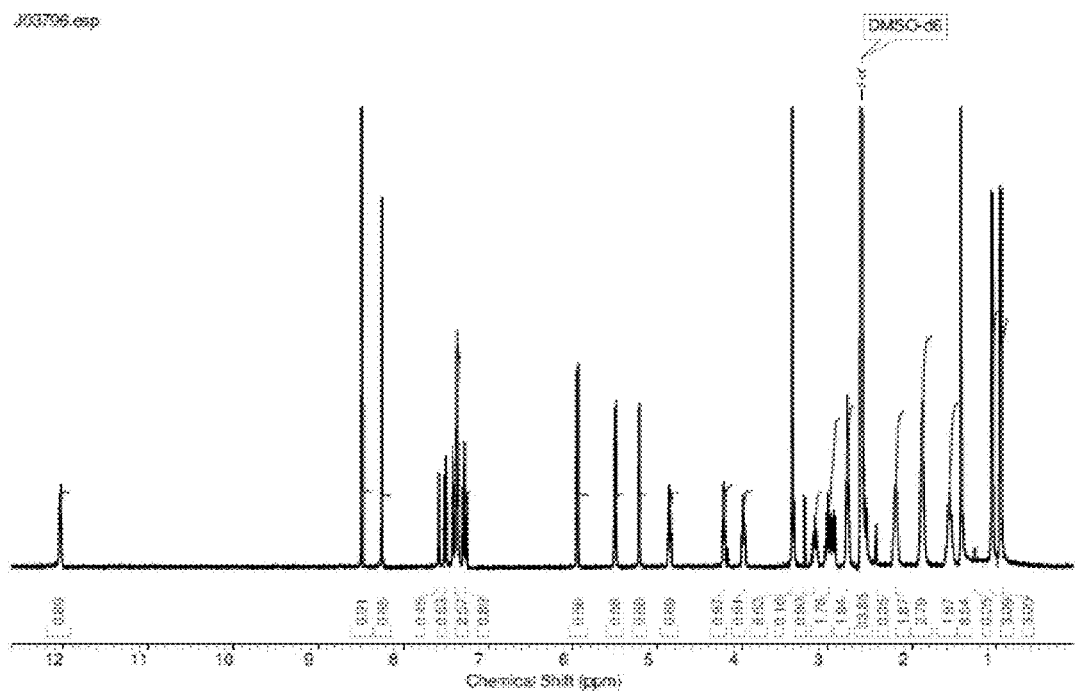
FIG. 28 is a $^1$H NMR spectrum of EP-1 trihydrate (x is 3).
Figure 29:
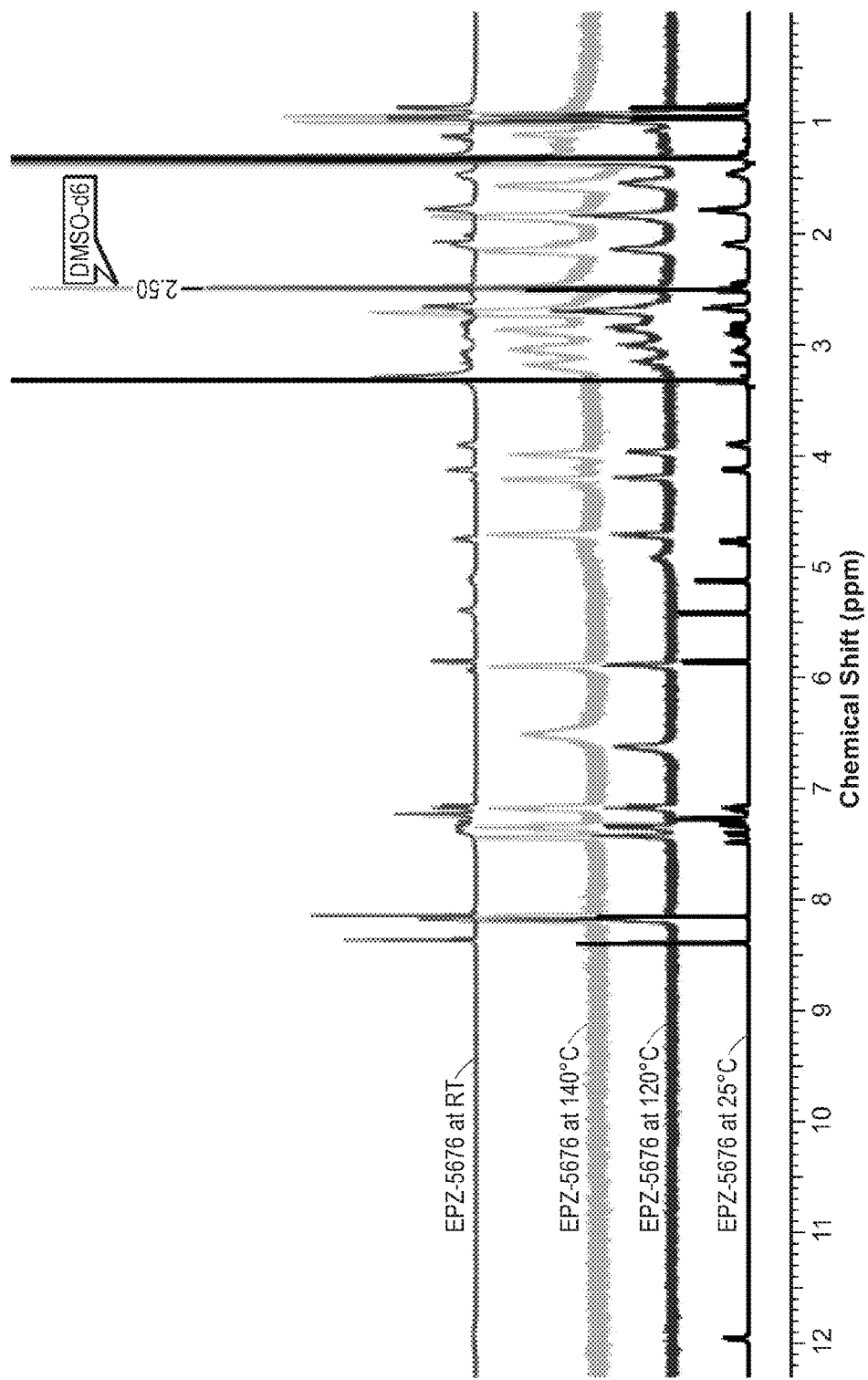
FIG. 29 is a variable temperature (VT)$^1$H NMR spectrum of EP-1 trihydrate (x is 3).
Figure 30:
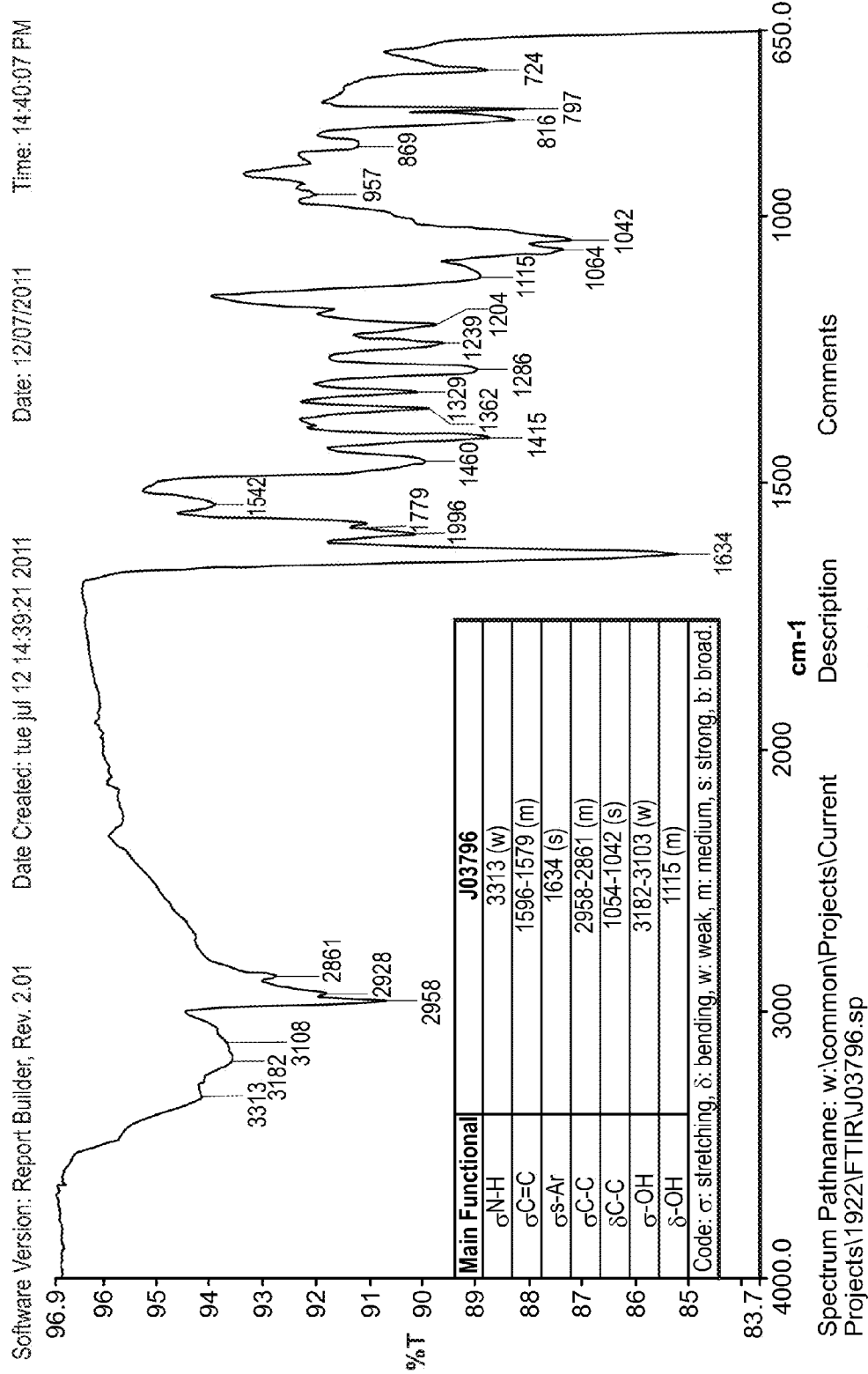
FIG. 30 is FTIR of EP-1 trihydrate (x is 3) free base.
Figure 31:
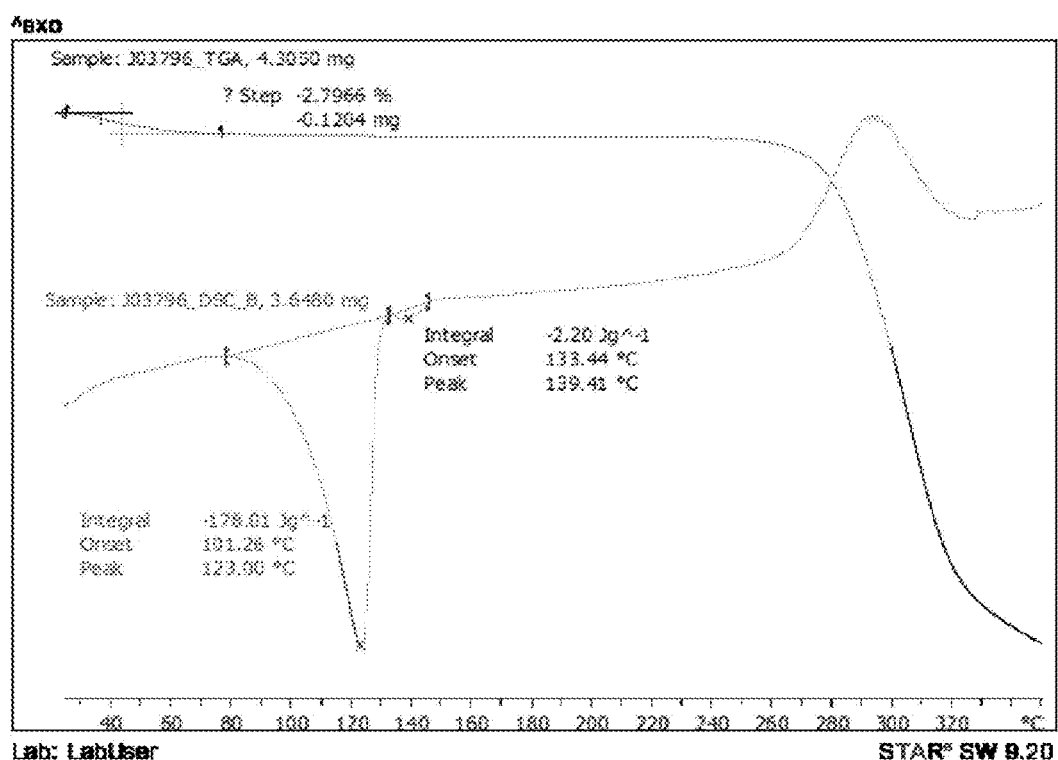
FIG. 31 is a graph indicating the TGA and DSC of EP-1 trihydrate (x is 3) free base.
Figure 32:
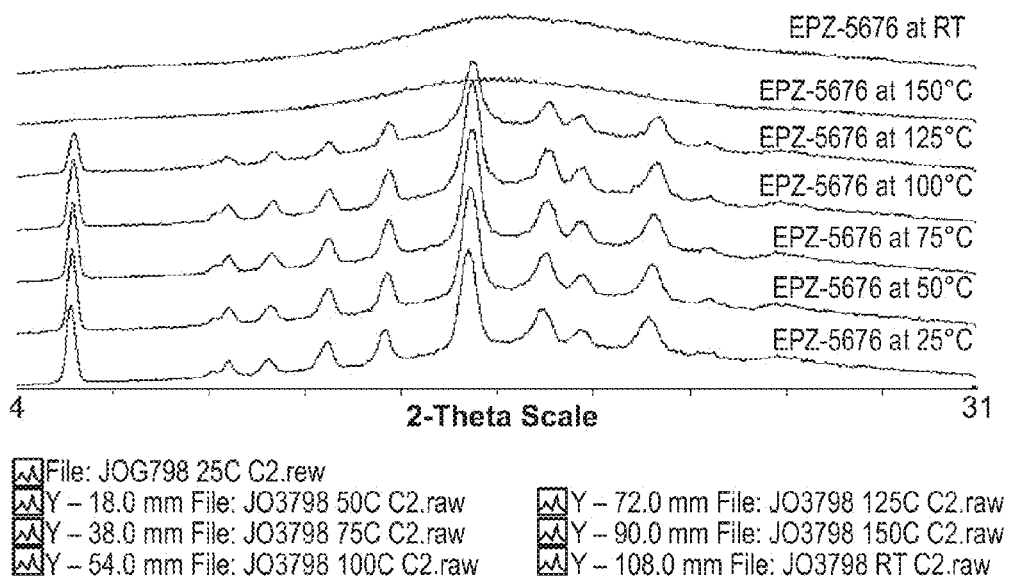
FIG. 32 is a VT-XRPD diffractogram of EP-1 trihydrate (x is 3) free base.
Figure 33:
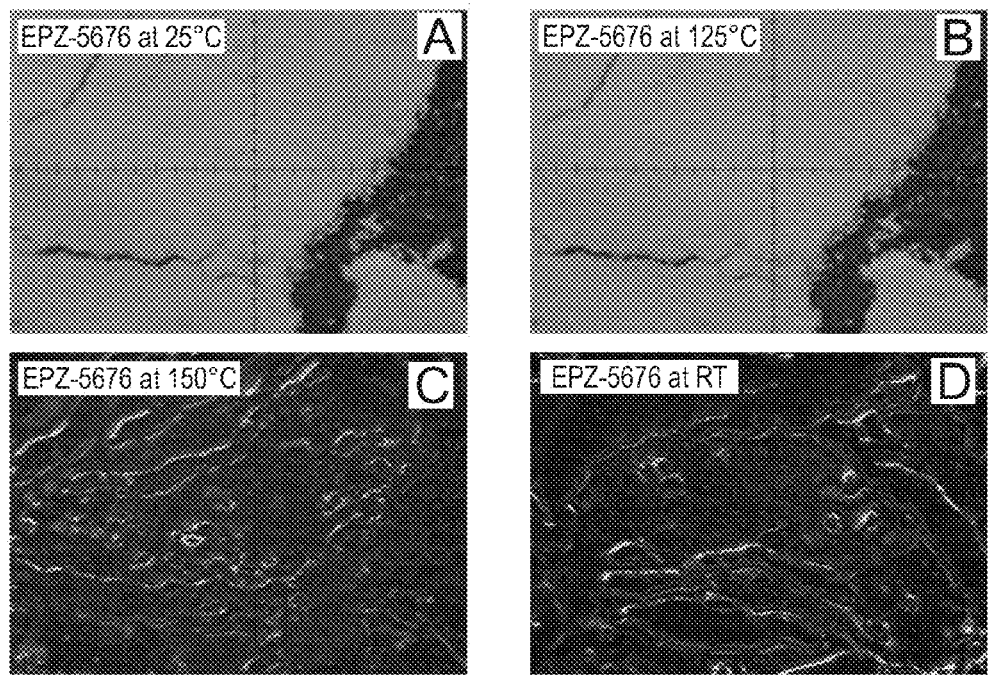
FIG. 33A is an image of EP-1 trihydrate (x is 3) free base at 25° C. taken during a VT-XRPD experiment.
FIG. 33B is an image of EP-1 trihydrate (x is 3) free base at 125° C. taken during a VT-XRPD experiment.
FIG. 33C is an image of EP-1 trihydrate (x is 3) free base at 150° C. taken during a VT-XRPD experiment.
FIG. 33D is an image of EP-1 trihydrate (x is 3) free base at room temperature taken during a VT-XRPD experiment.
Figure 34:
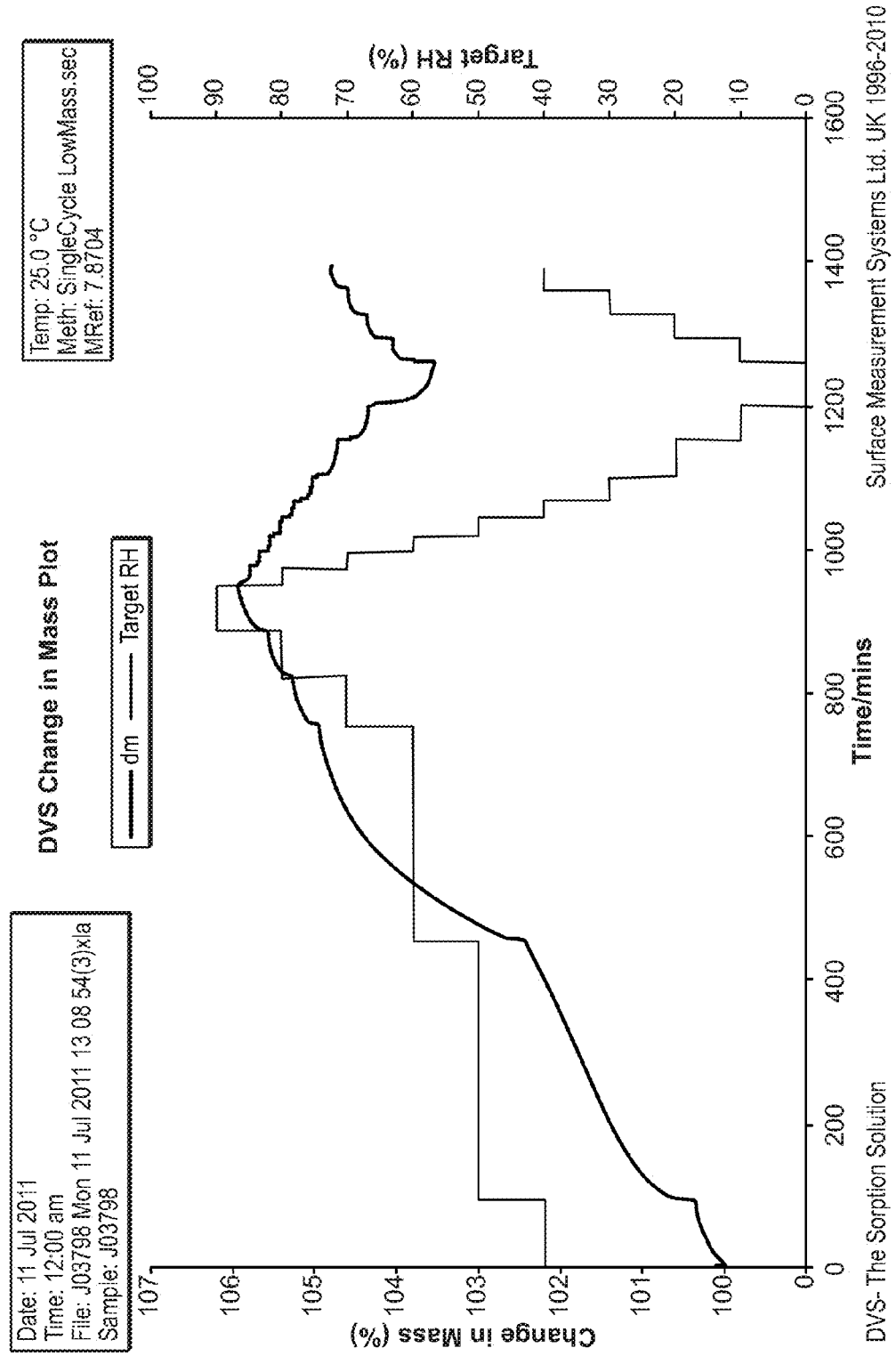
FIG. 34 is a GVS kinetic plot of EP-1 trihydrate (x is 3) free base.
Figure 35:
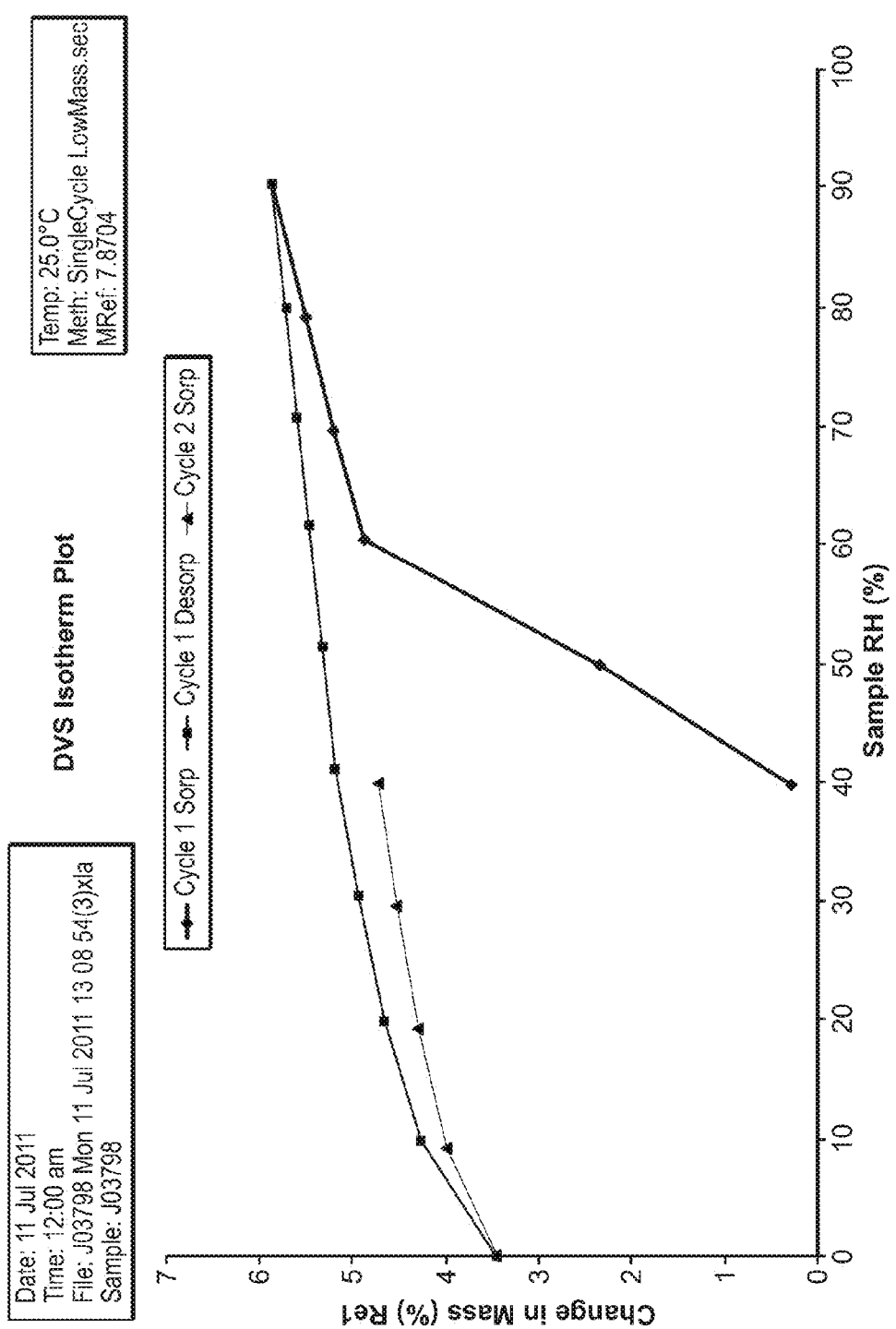
FIG. 35 is a GVS isotherm of EP-1 trihydrate (x is 3) free base.
Figure 36:
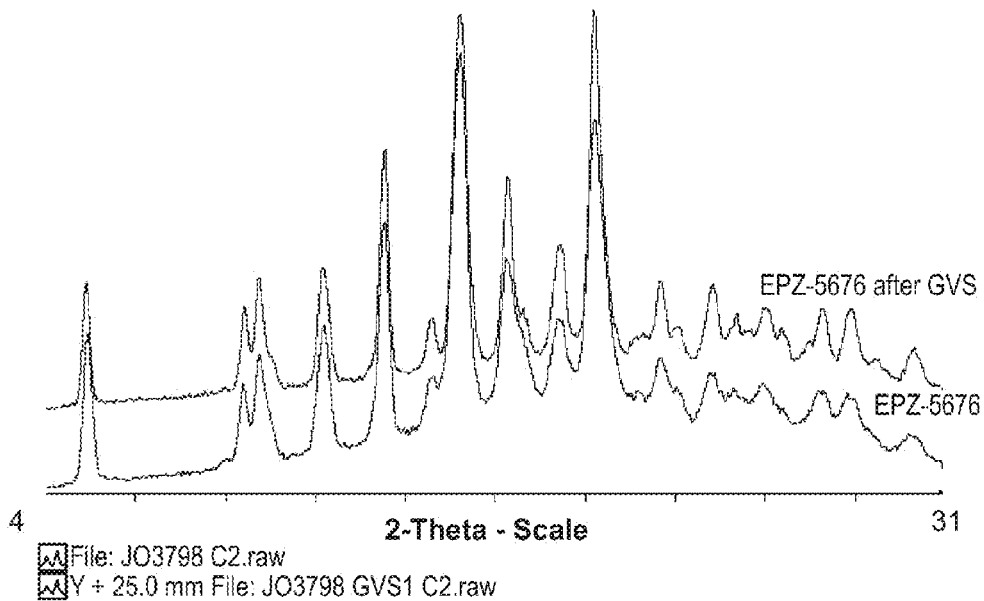
FIG. 36 is an XRPD diffractogram of EP-1 trihydrate (x is 3) free base post GVS.
Figure 37:
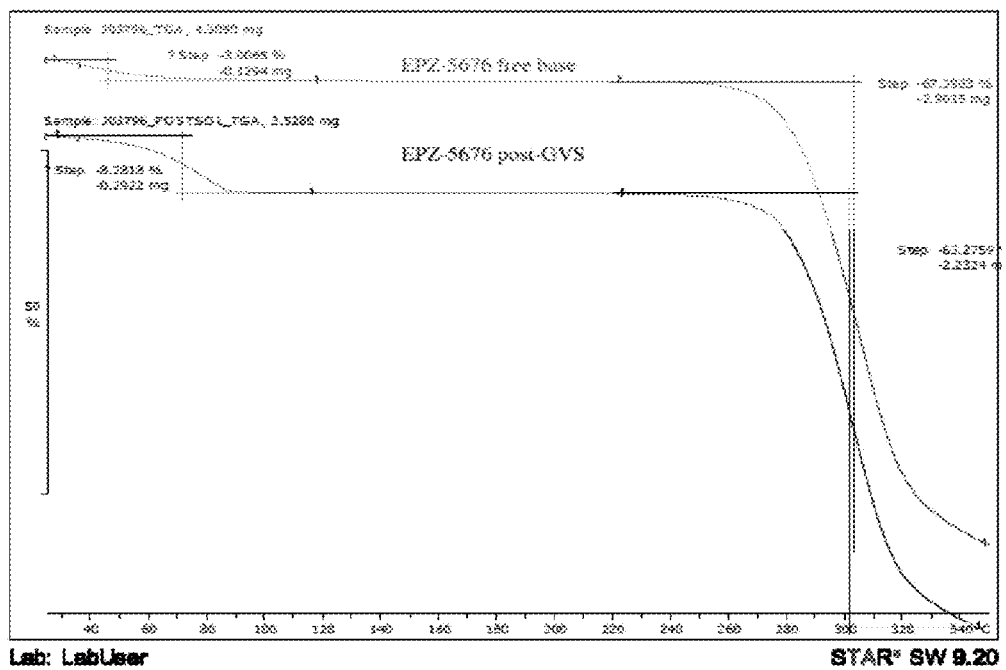
FIG. 37 is a TGA plot of EP-1 trihydrate (x is 3) free base post-GVS.
Figure 38:
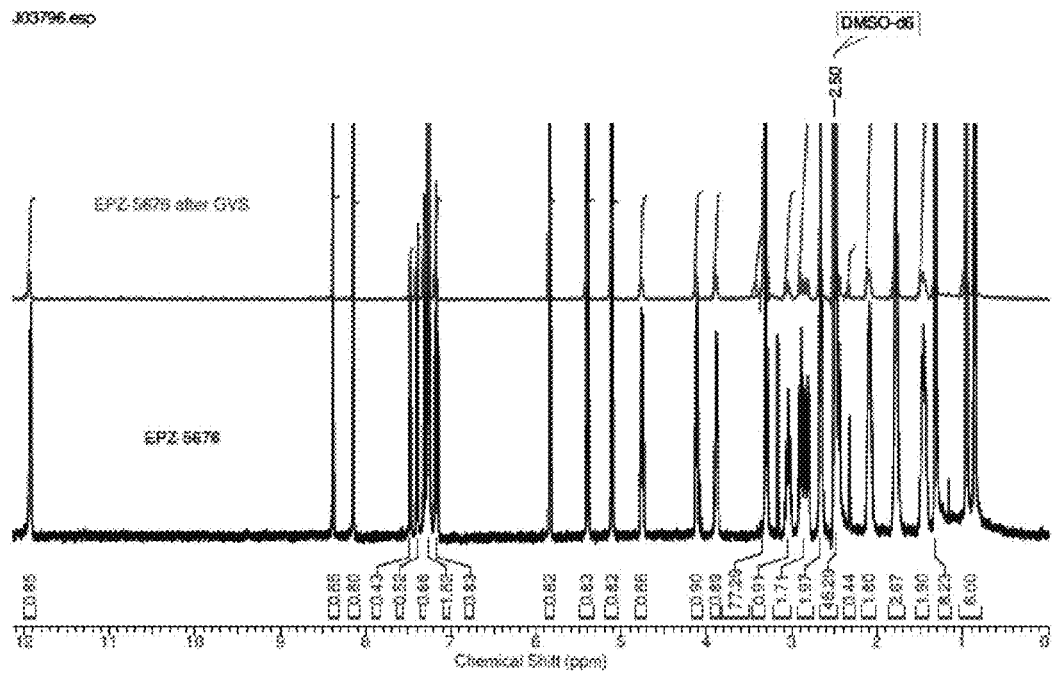
FIG. 38 is a $^1$H NMR spectrum of EP-1 trihydrate (x is 3) free base post-GVS.
Figure 39:
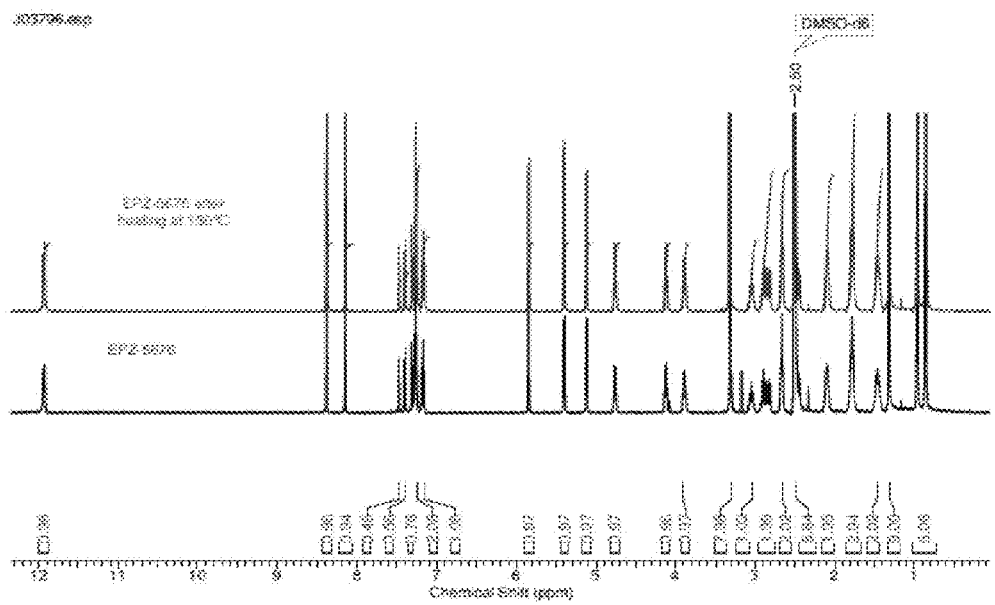
FIG. 39 is a $^1$H NMR spectrum of EP-1 trihydrate (x is 3) free base after heating EP-1 trihydrate (x is 3) free base at 180° C.
Figure 40:
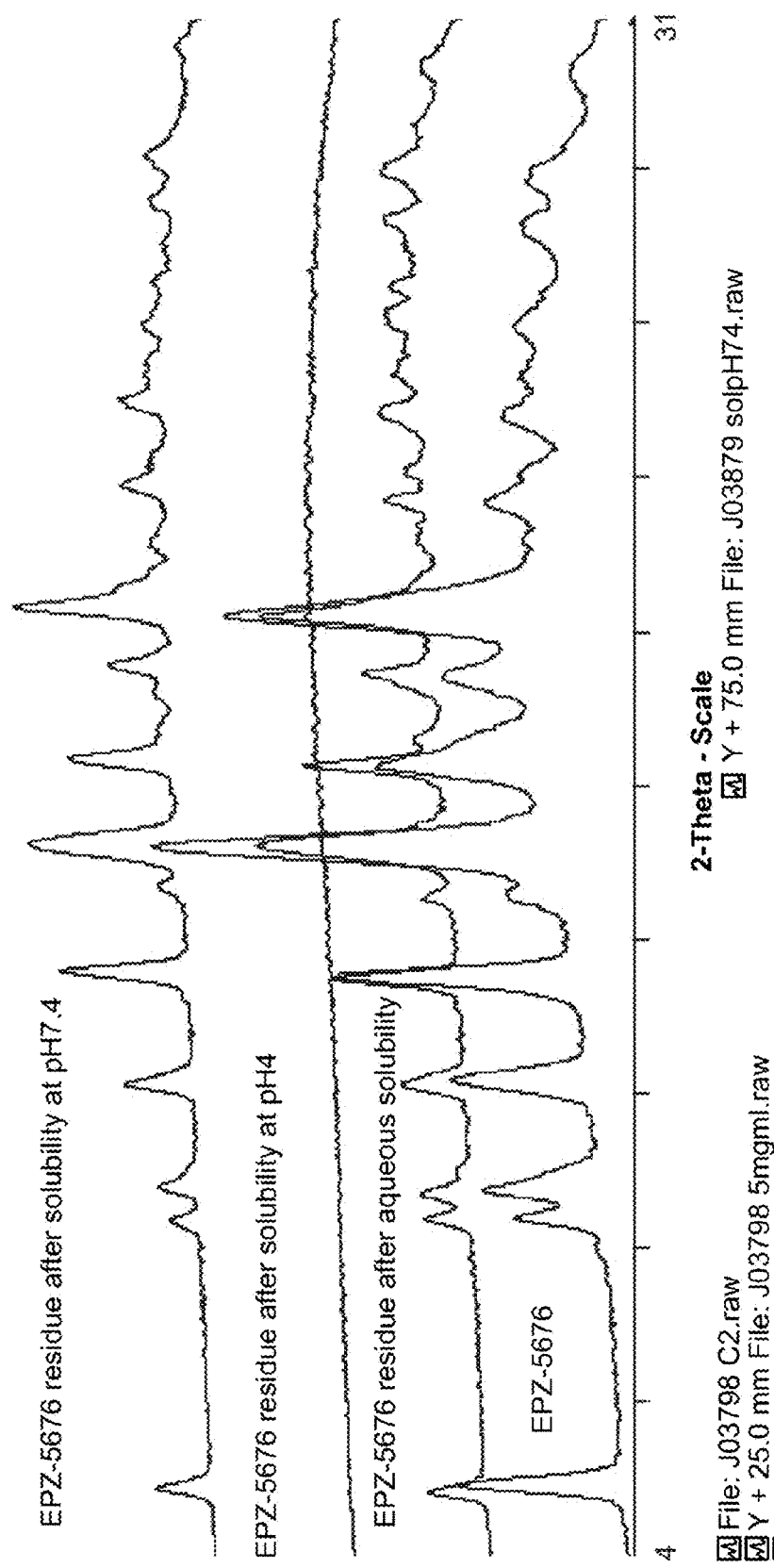
FIG. 40 is an overlay of the XRPD diffractograms of EP-1 trihydrate (x is 3) free base after solubility analysis.
Figure 41:
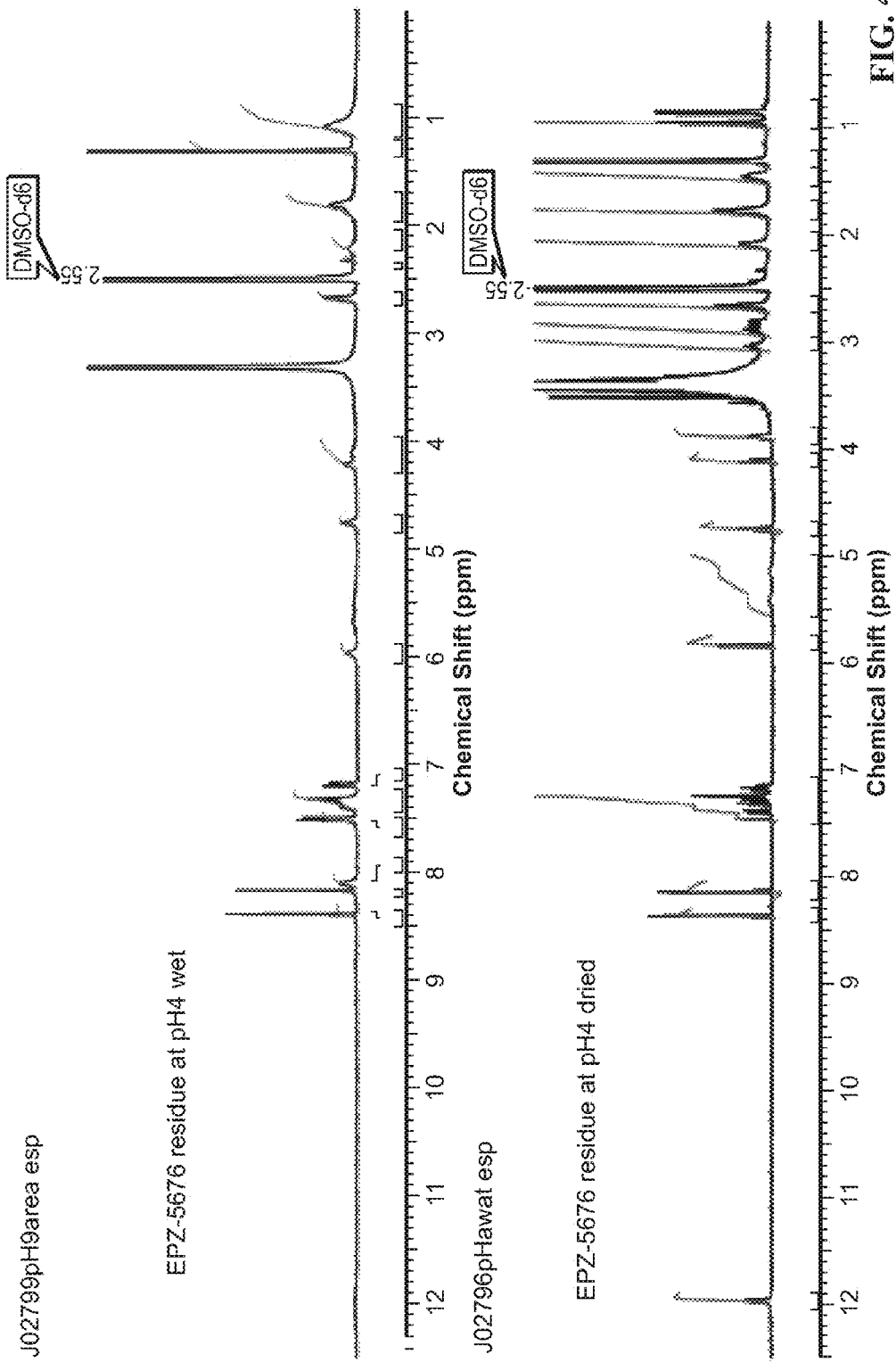
FIG. 41 is an overlay of $^1$H NMR spectra of EP-1 trihydrate (x is 3) residue at pH4 wet vs. at pH4 dry.
Figure 42:
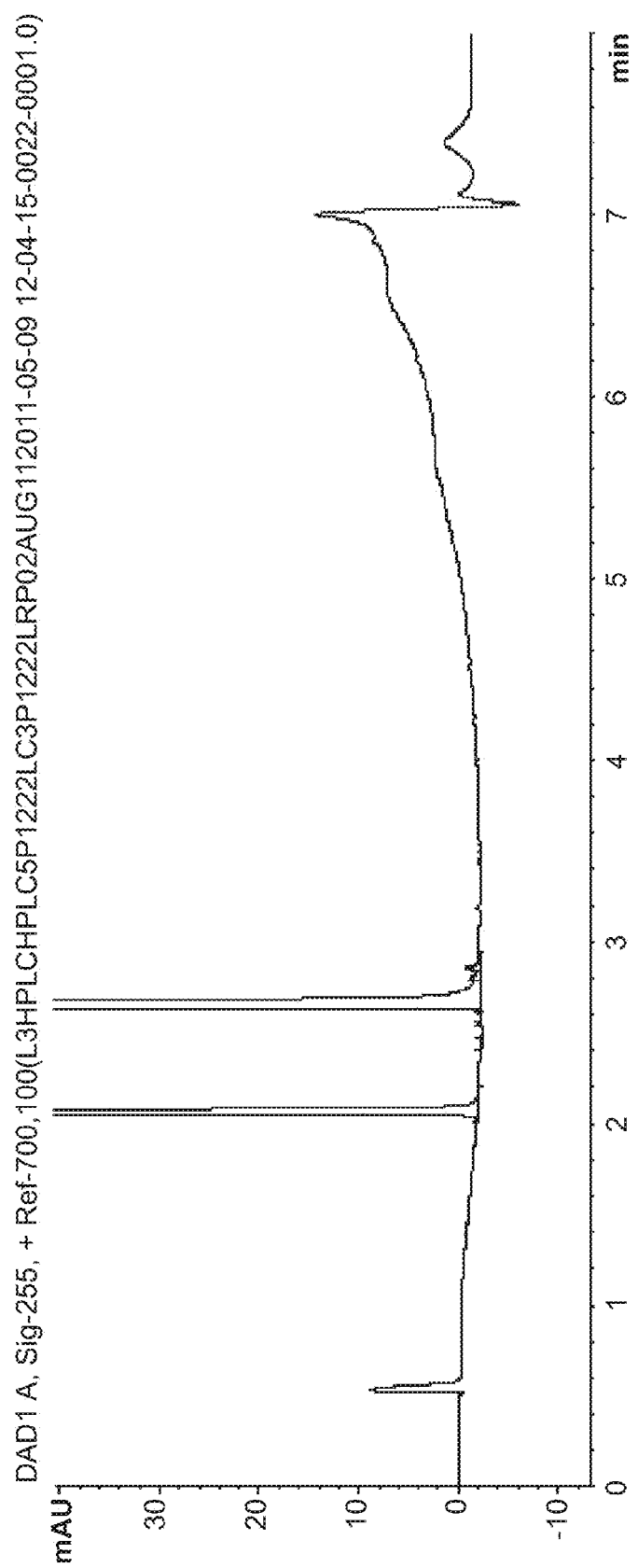
FIG. 42 is a HPLC chromatogram of EP-1 trihydrate (x is 3) residue at pH 4 after a few days.
Figure 43:
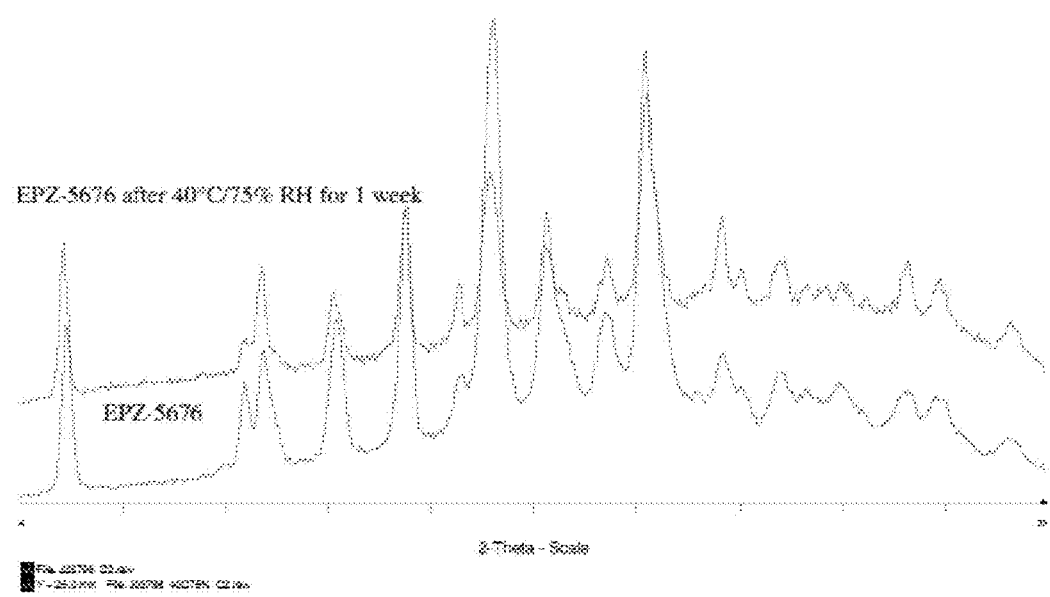
FIG. 43 is an overlay of XRPD diffractograms of EP-1 trihydrate (x is 3) free base at 40° C./75% RH after a week.
Figure 44A:
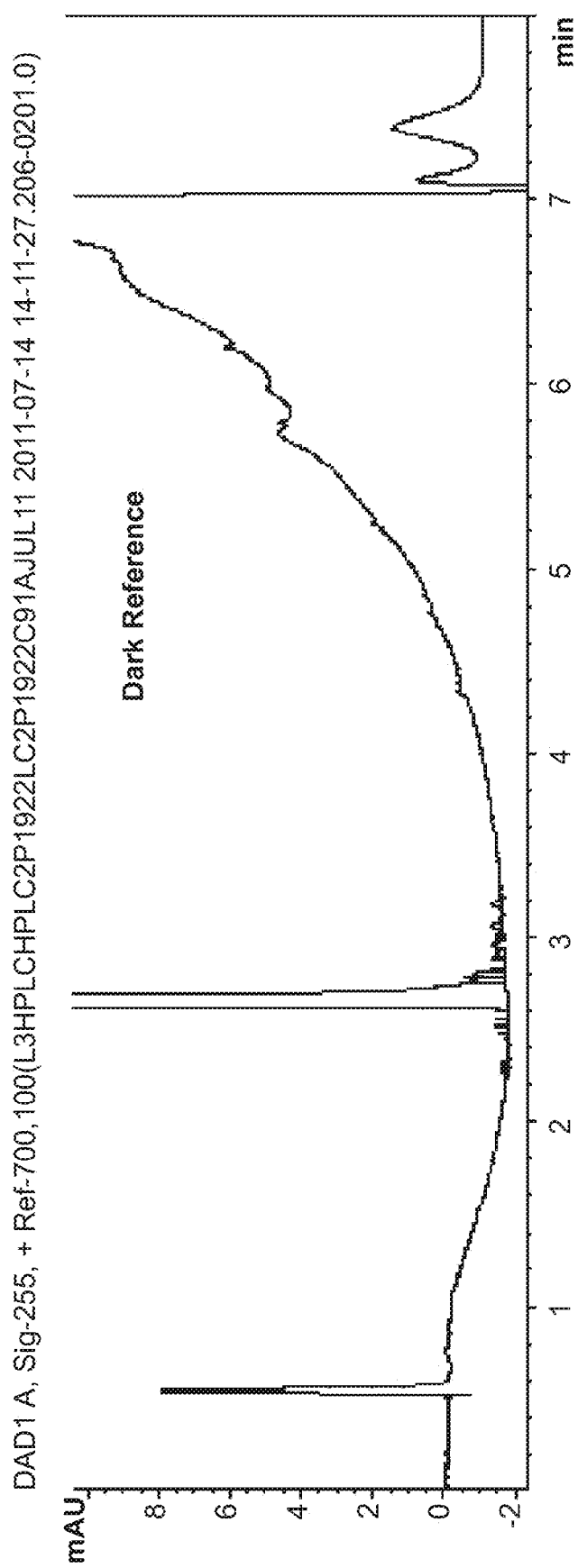
FIGS. 44A-C are a set of HPLC chromatograms of EP-1 trihydrate (x is 3) free base: dark reference (i.e., no UV exposure as in FIG. 44A), surface exposure (as in FIG. 44B), and bulk exposure (as in FIG. 44C) after 24 h of UV light exposure.
Figure 44B:
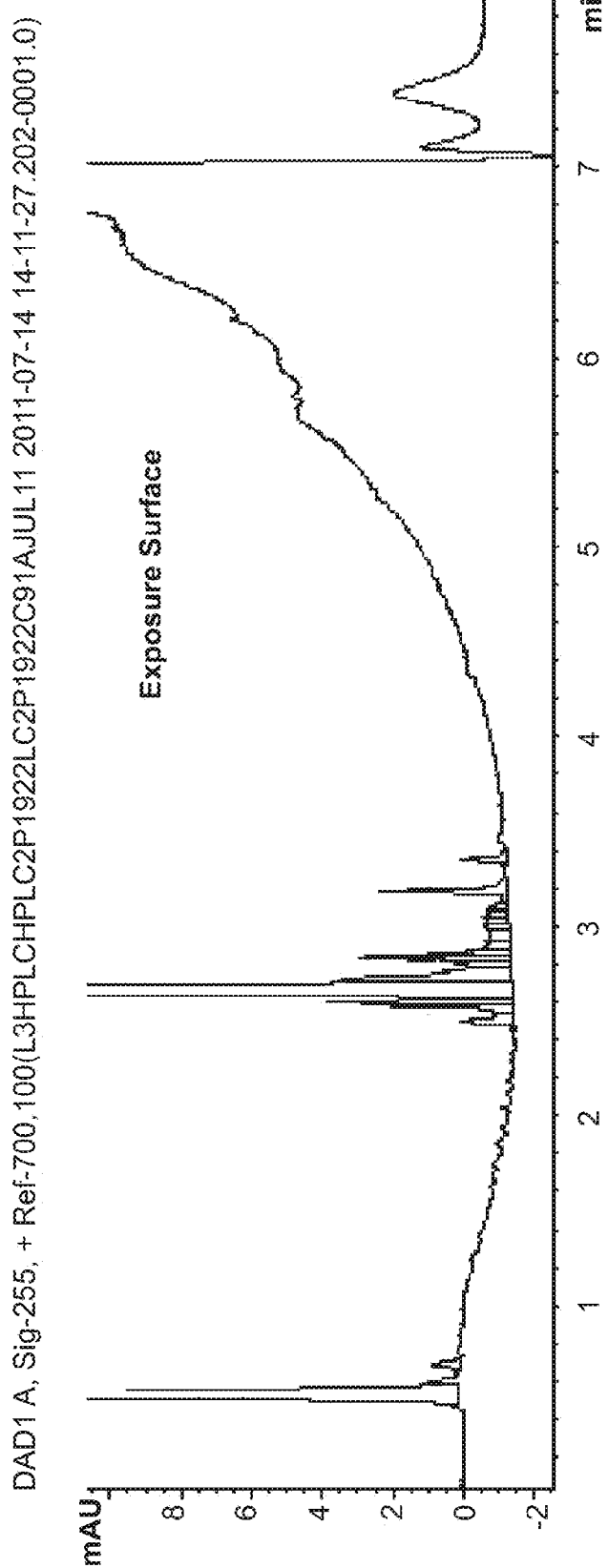
Figure 44C:
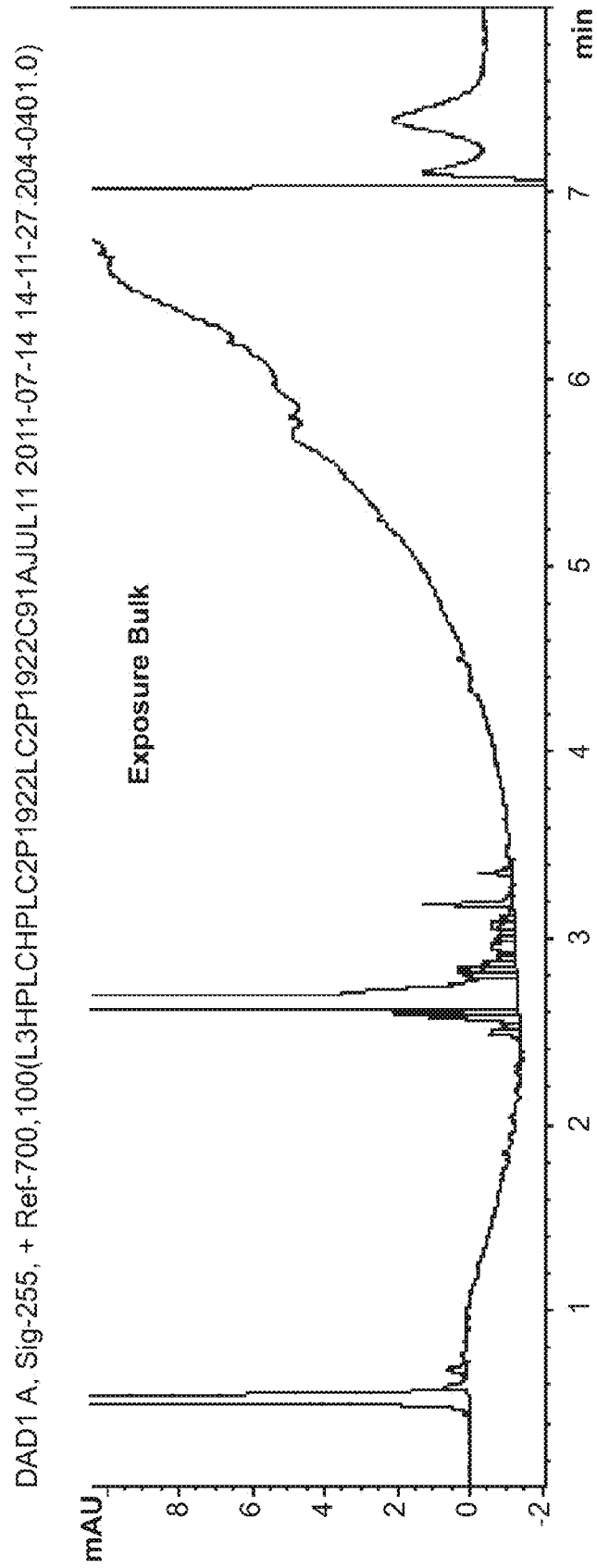
Figure 45:
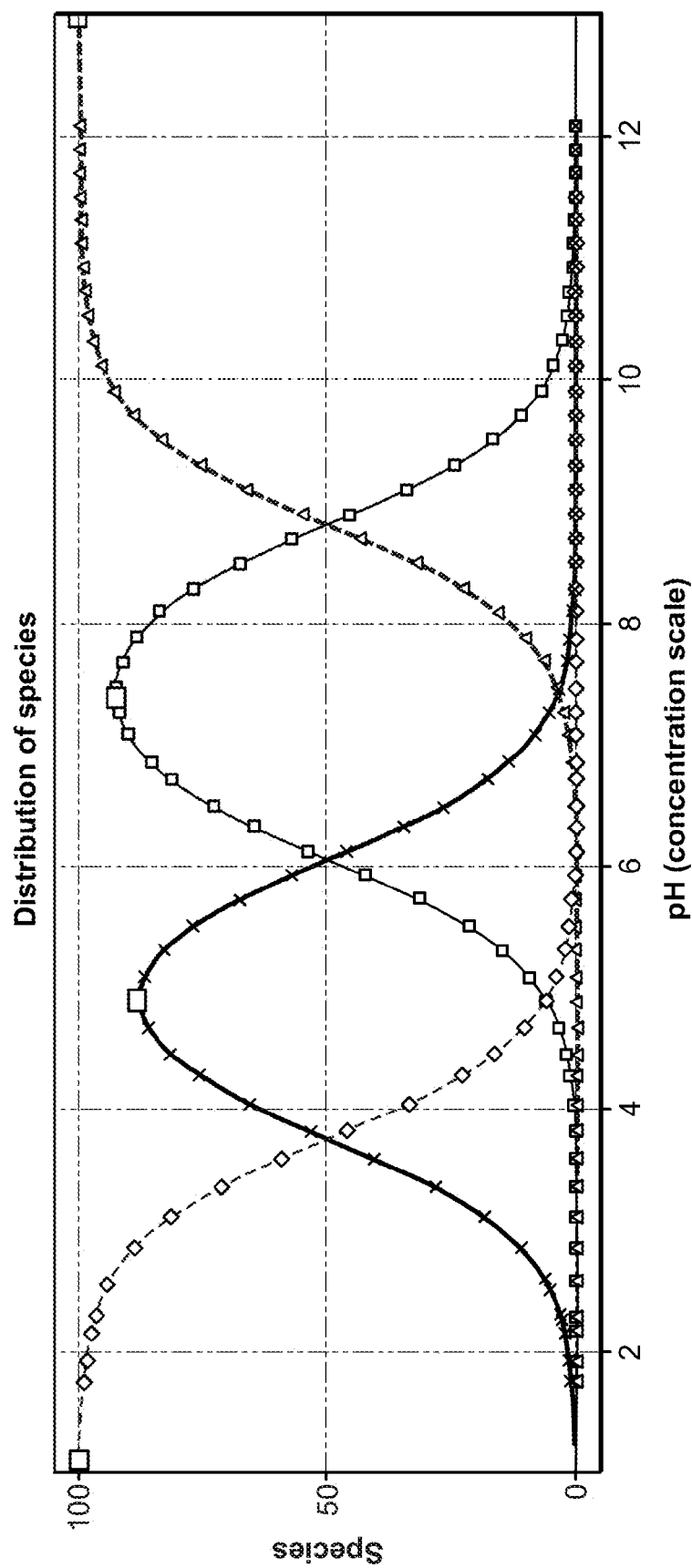
FIG. 45 is a graph indicating the distribution of species from EP-1 trihydrate (x is 3) free base with the pH calculated from the extrapolated aqueous result. pKa can be calculated from the intersection of the different species (free base as triangles, mono-protonated form as squares, bis-protonated form as crosses and tri- protonated form as diamonds).
Figure 46:
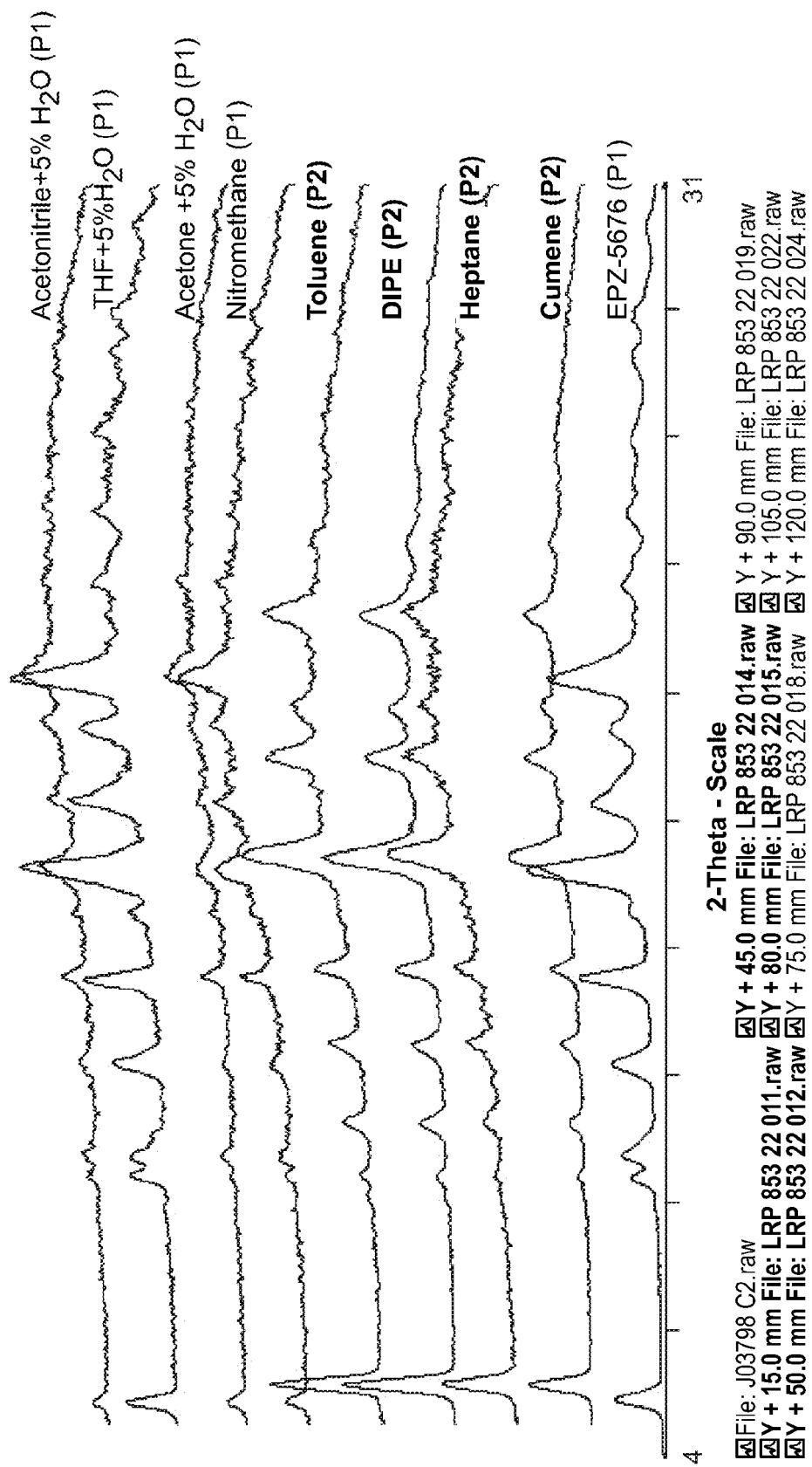
FIG. 46 is a XRPD overlay of EP-1 trihydrate (x is 3) solids obtained in the polymorphism assessment.
Figure 47:
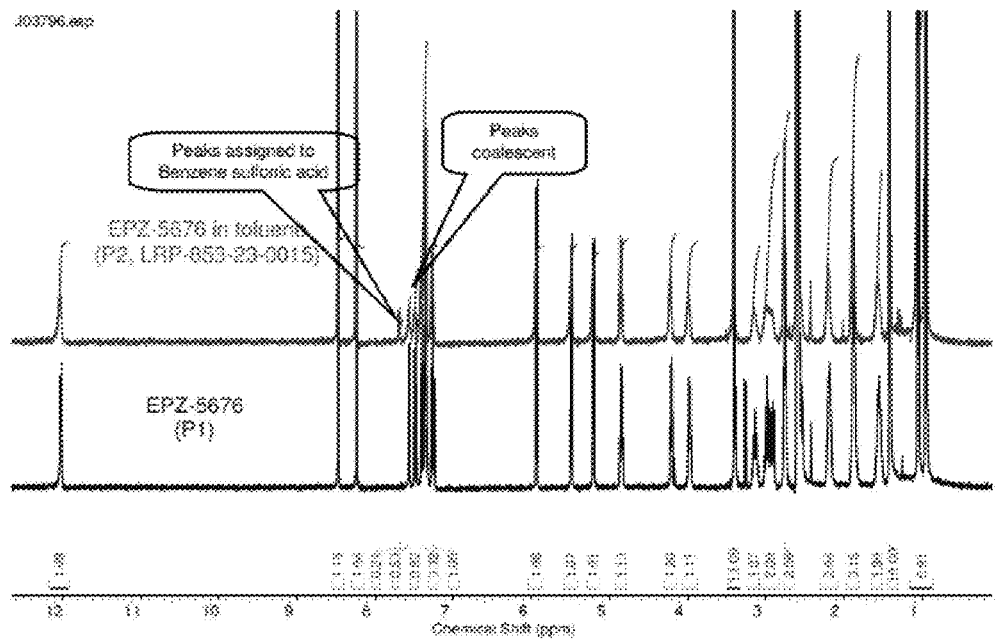
FIG. 47 is an overlay of $^1$H NMR spectra of Form 1 (P1) and Form 2 (P2) of EP-1 trihydrate (x is 3) free base.
Figure 48:
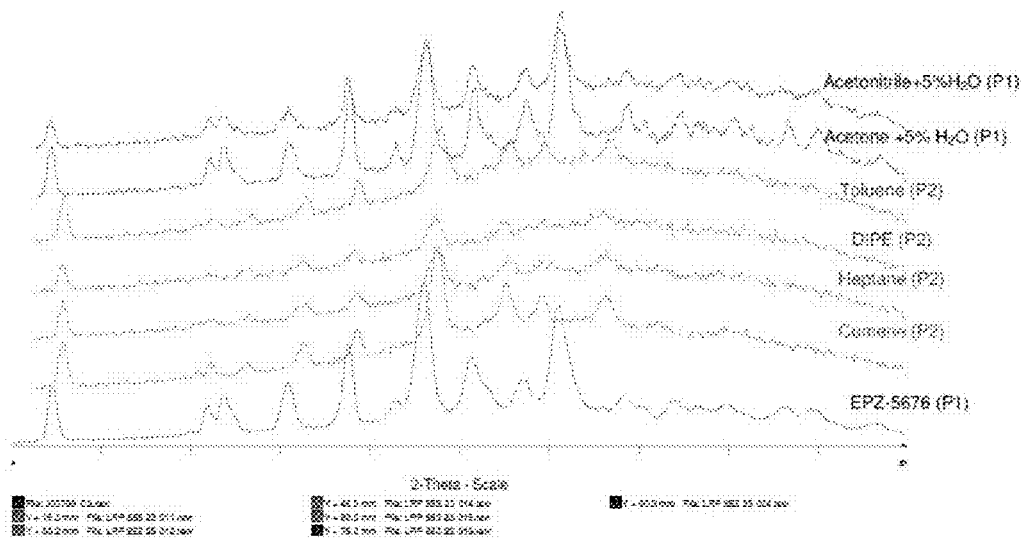
FIG. 48 is a XRPD overlay of EP-1 trihydrate (x is 3) solids from the salt assessment.
Figure 49:
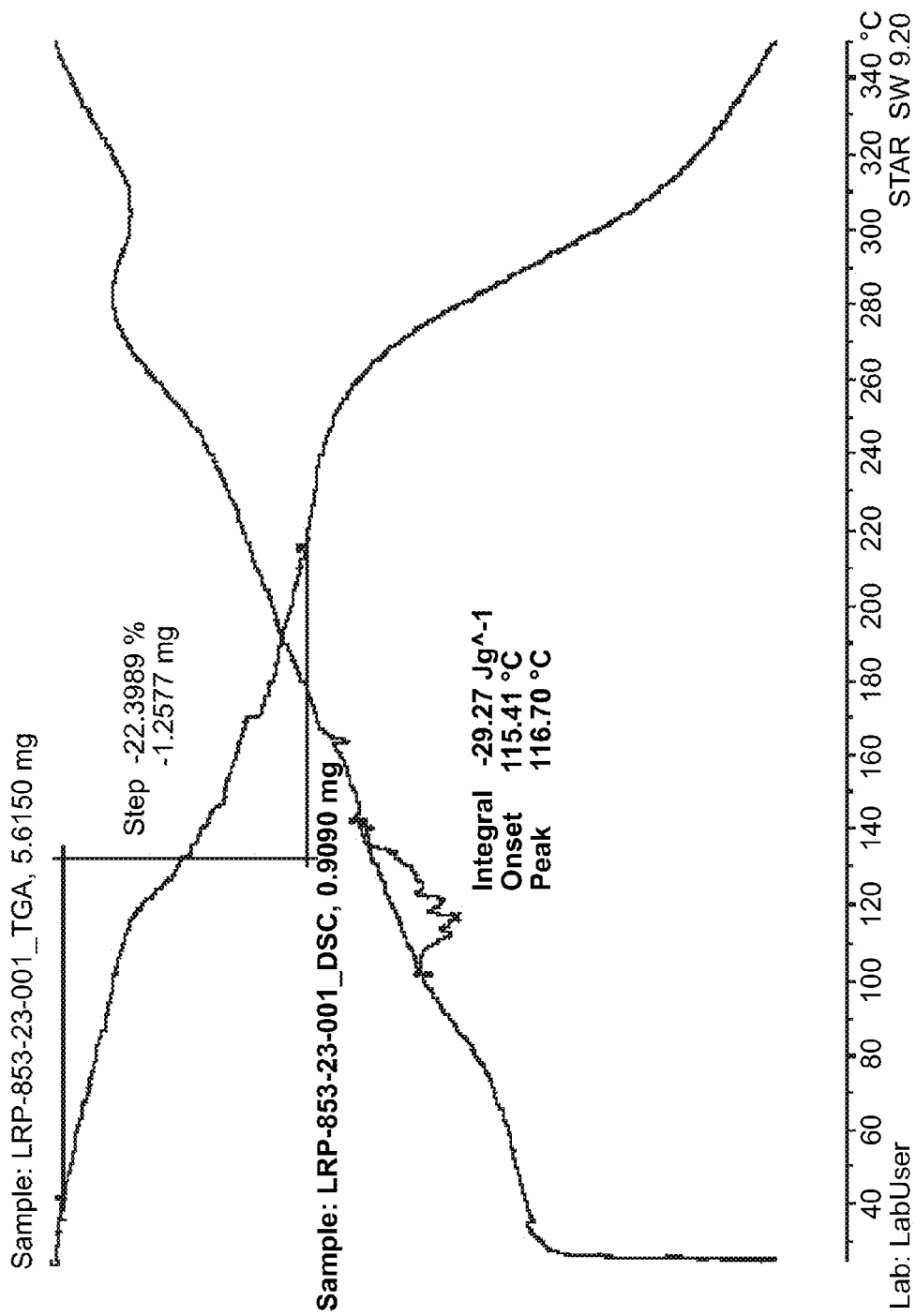
FIG. 49 is TGA/DSC plot of EP-1 trihydrate (x is 3) obtained after treatment with benzene sulfonic acid in 1,4-dioxane.
Figure 50:
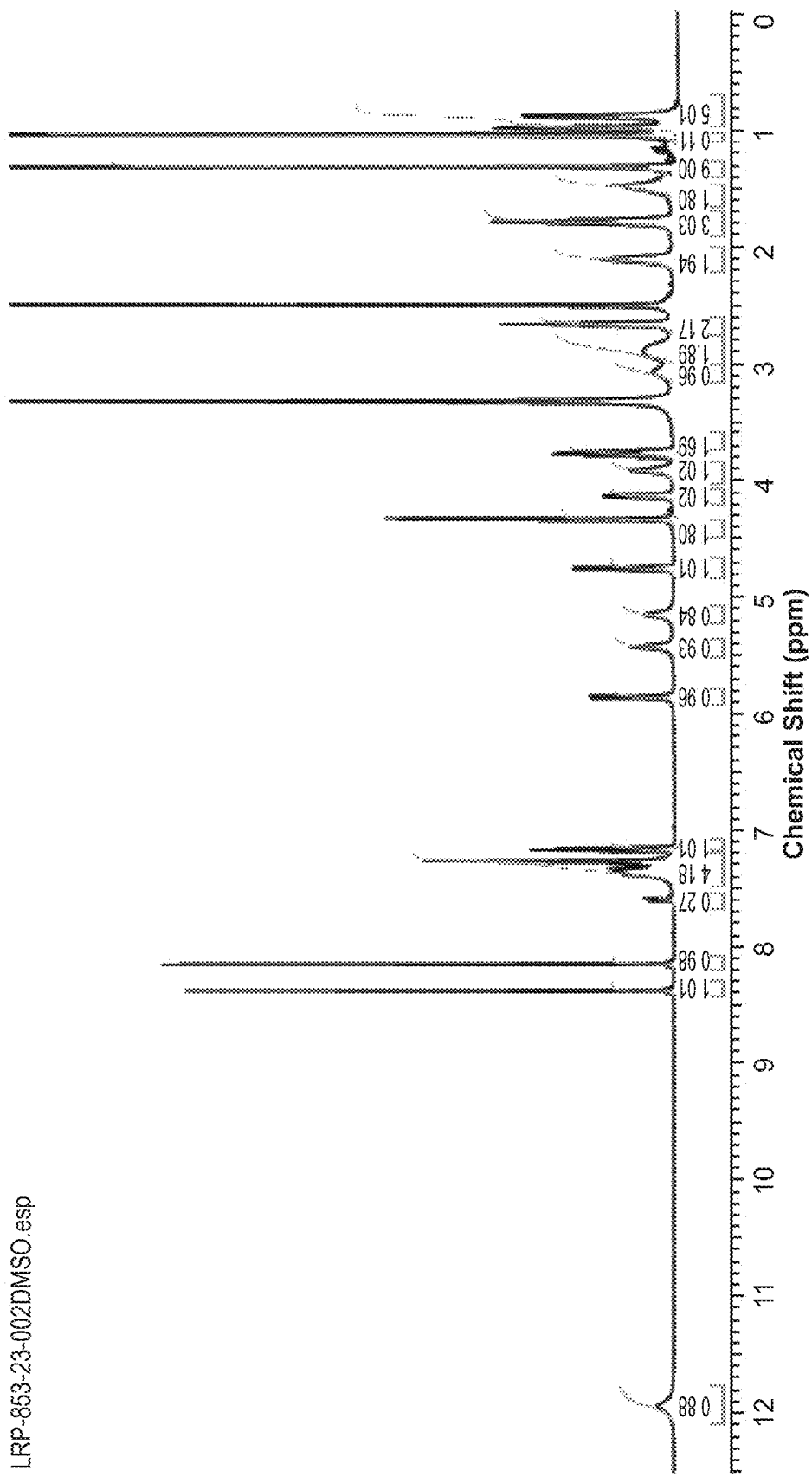
FIG. 50 is a $^1$H NMR spectrum of EP-1 trihydrate (x is 3) obtained after treatment with benzene sulfonic acid in IPA.
Figure 51:
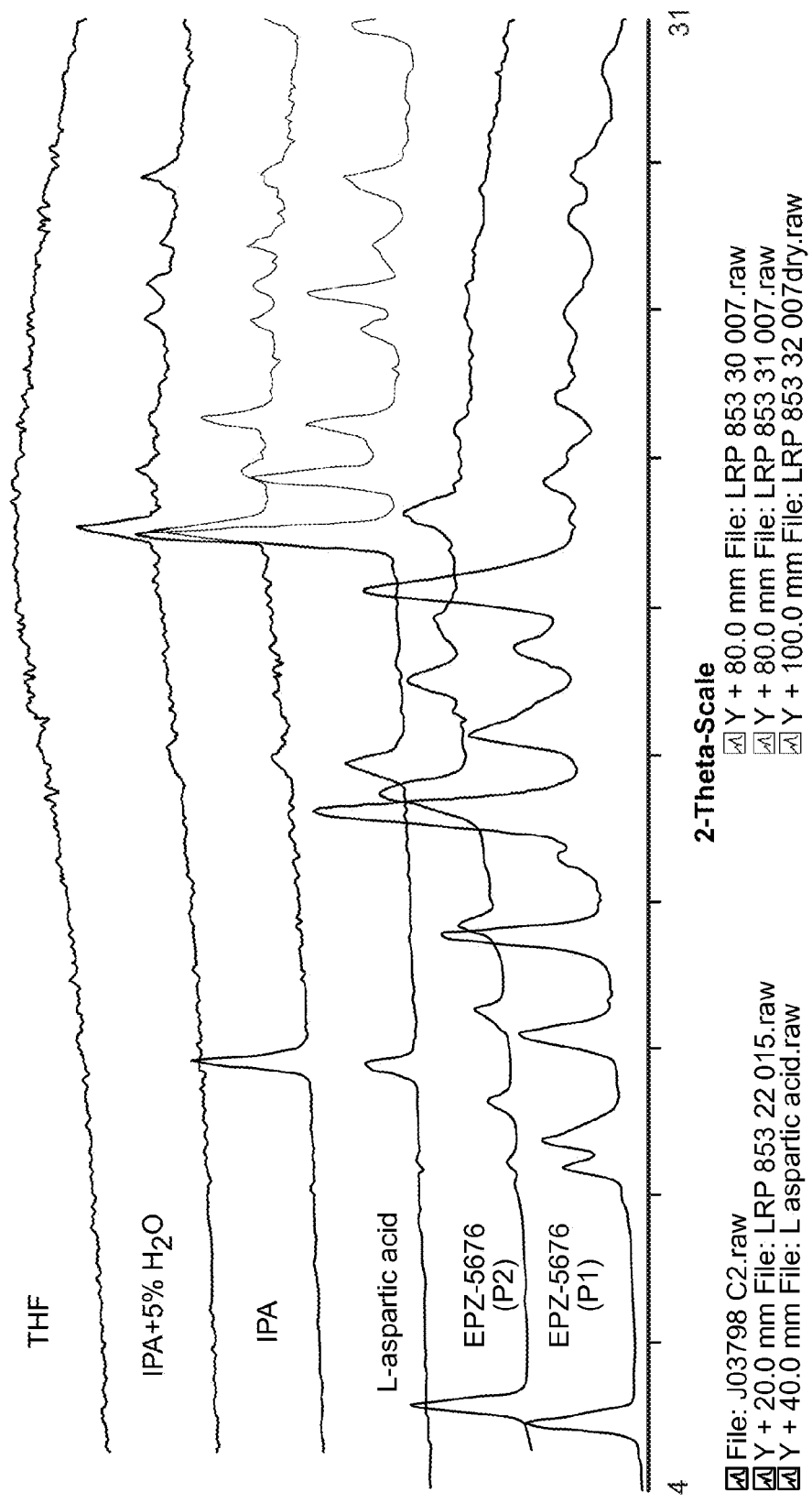
FIG. 51 is a XRPD overlay of EP-1 trihydrate (x is 3) solids obtained from L-aspartic acid.
Figure 52:
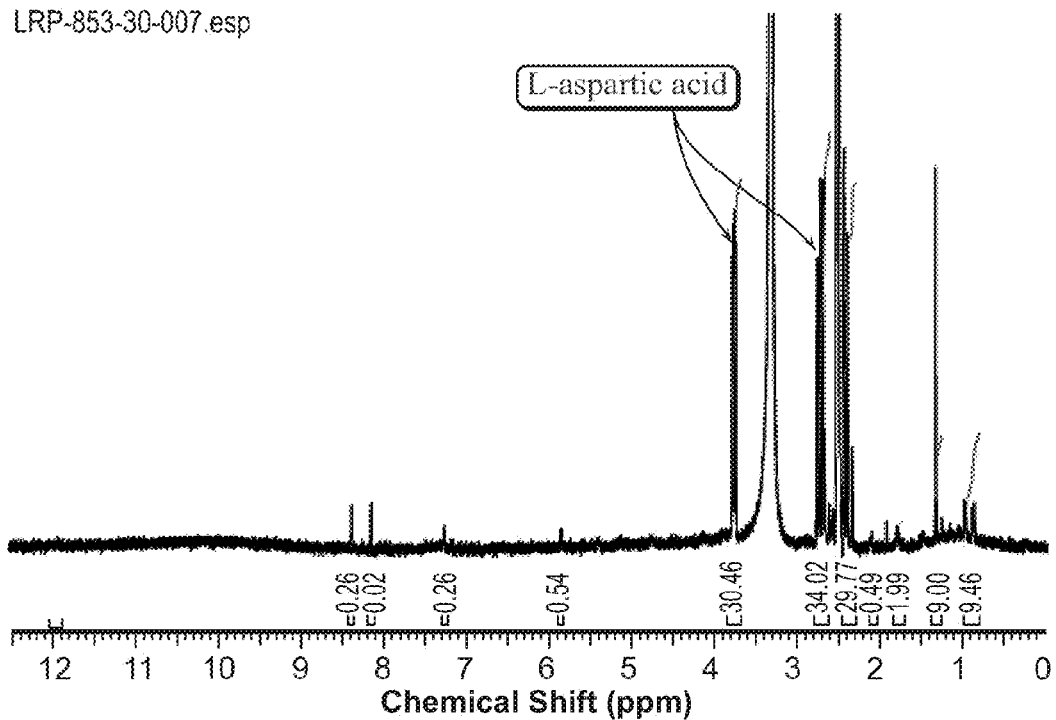
FIG. 52 is a $^1$H NMR spectrum of EP-1 trihydrate (x is 3) obtained after treatment with L-aspartic acid.
Figure 53:
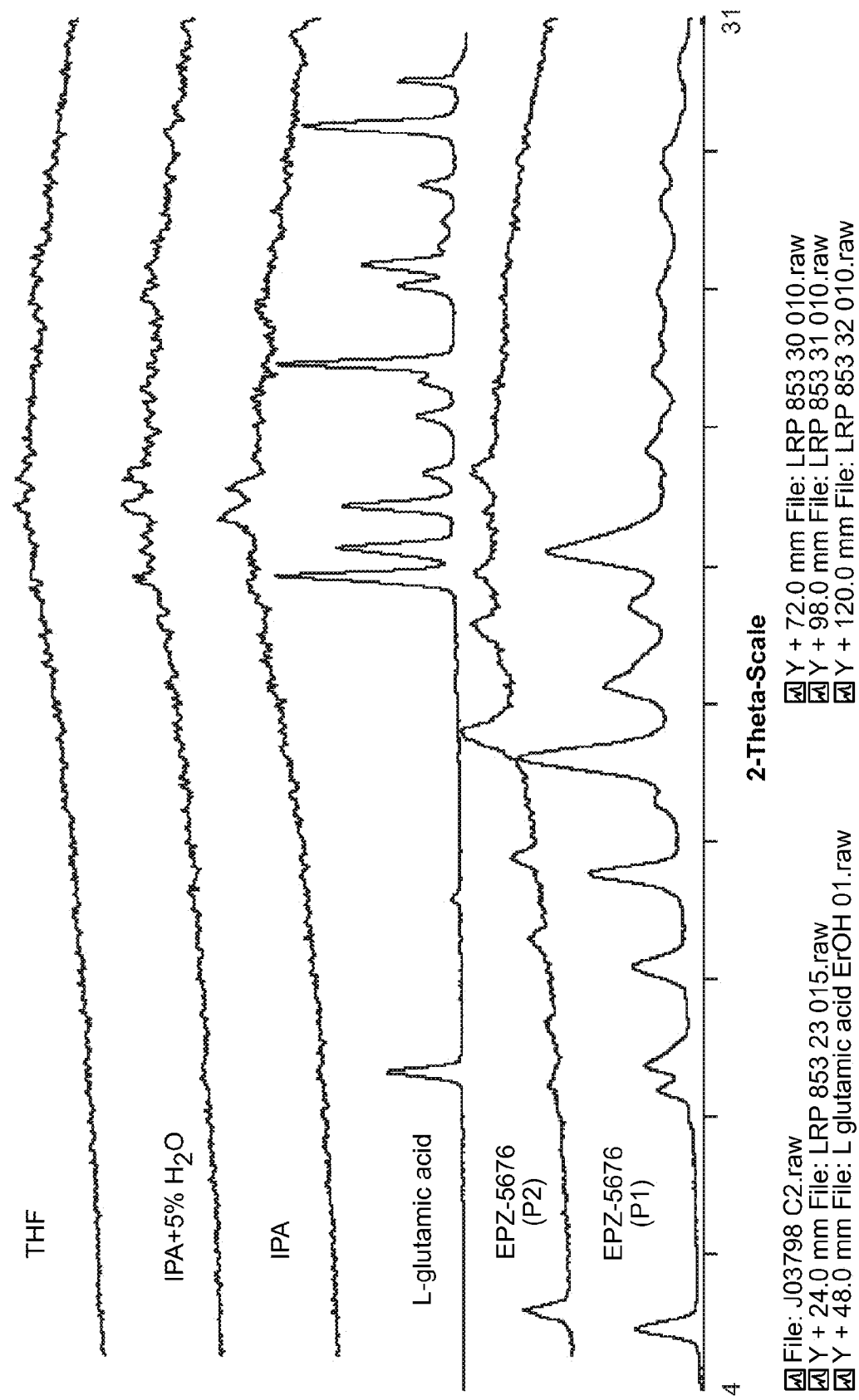
FIG. 53 is a XRPD overlay of EP-1 trihydrate (x is 3) solids obtained from L-glutamic acid.
Figure 54:
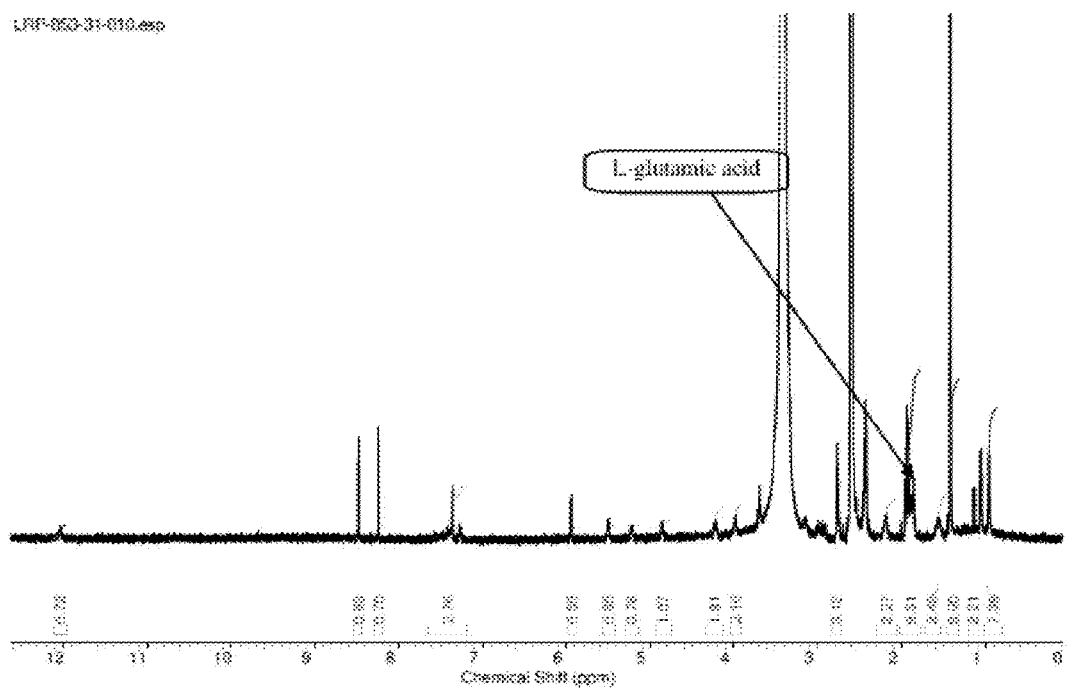
FIG. 54 is a $^1$H NMR spectrum of EP-1 trihydrate (x is 3) obtained after treatment with L-glutamic acid.
Figure 55:
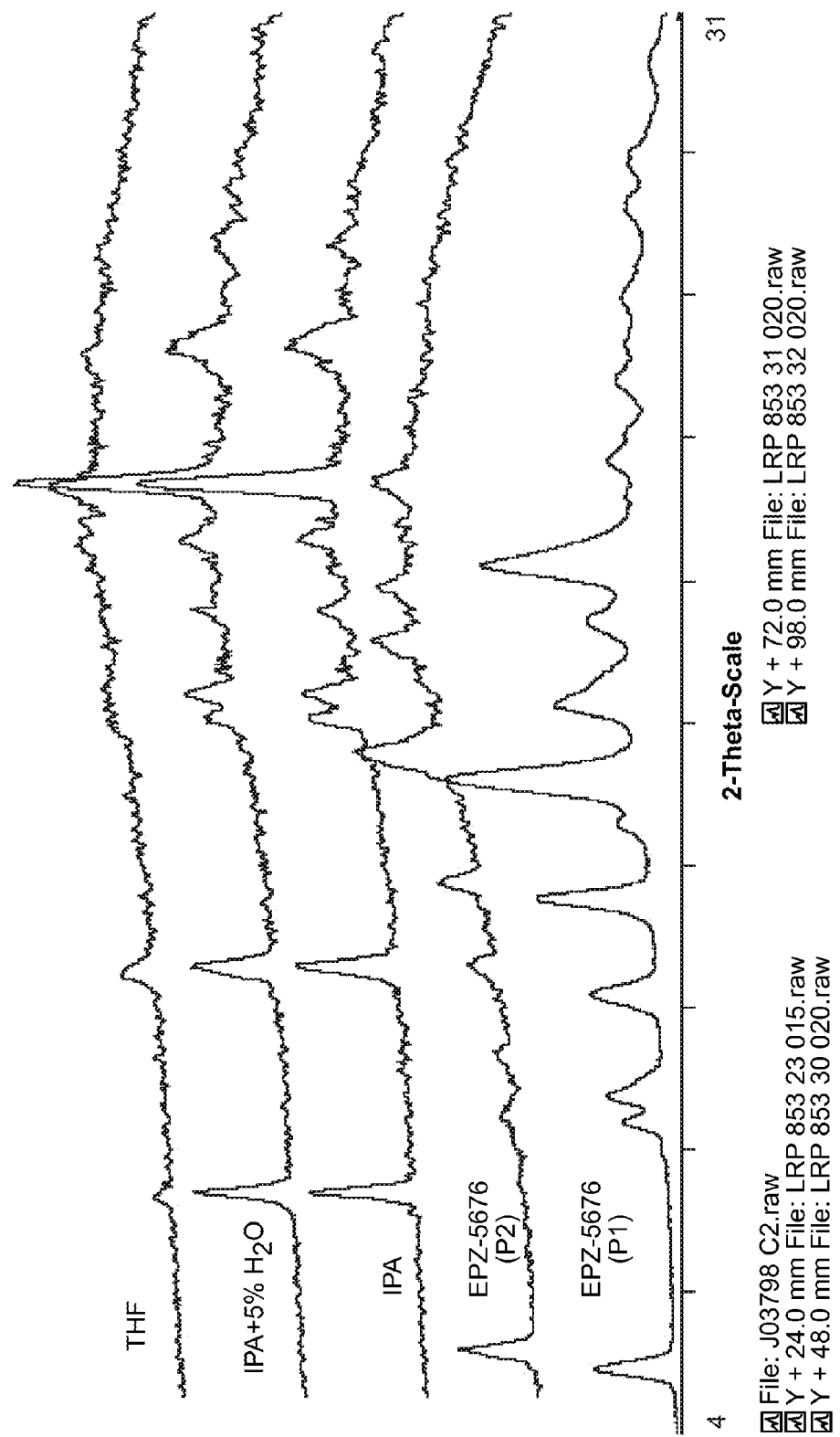
FIG. 55 is a XRPD overlay of EP-1 trihydrate (x is 3) solids obtained from D-glucoheptonic acid.
Figure 56:
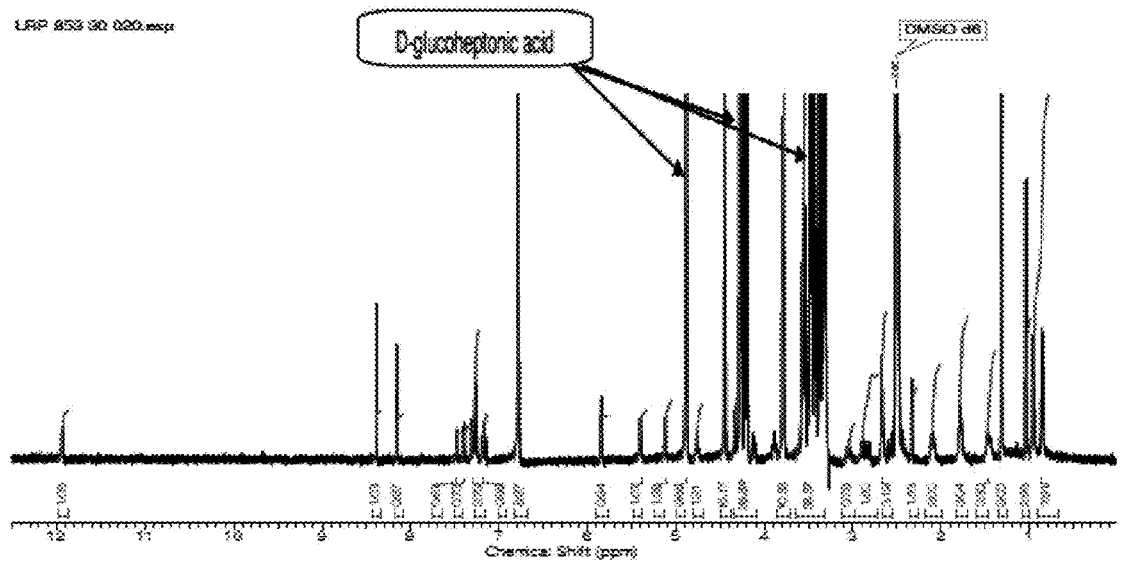
FIG. 56 is a $^1$H NMR spectrum of EP-1 trihydrate (x is 3) obtained after treatment with D-glucoheptonic acid.
Figure 57:
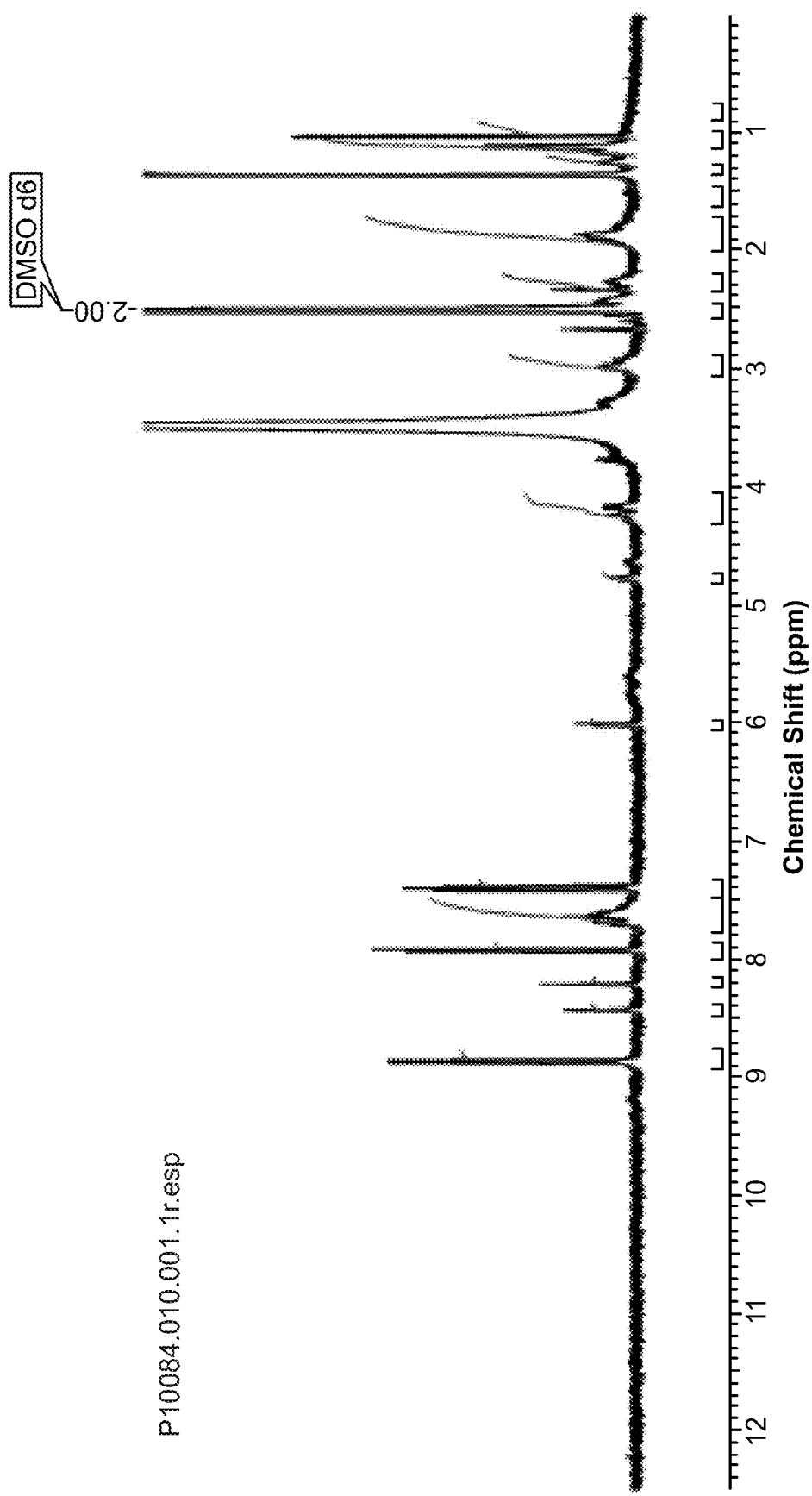
FIG. 57 is a $^1$H NMR spectrum of EP-1 trihydrate (x is 3) obtained after treatment with 1,5-naphthalene disulfonic acid.
Figure 58:
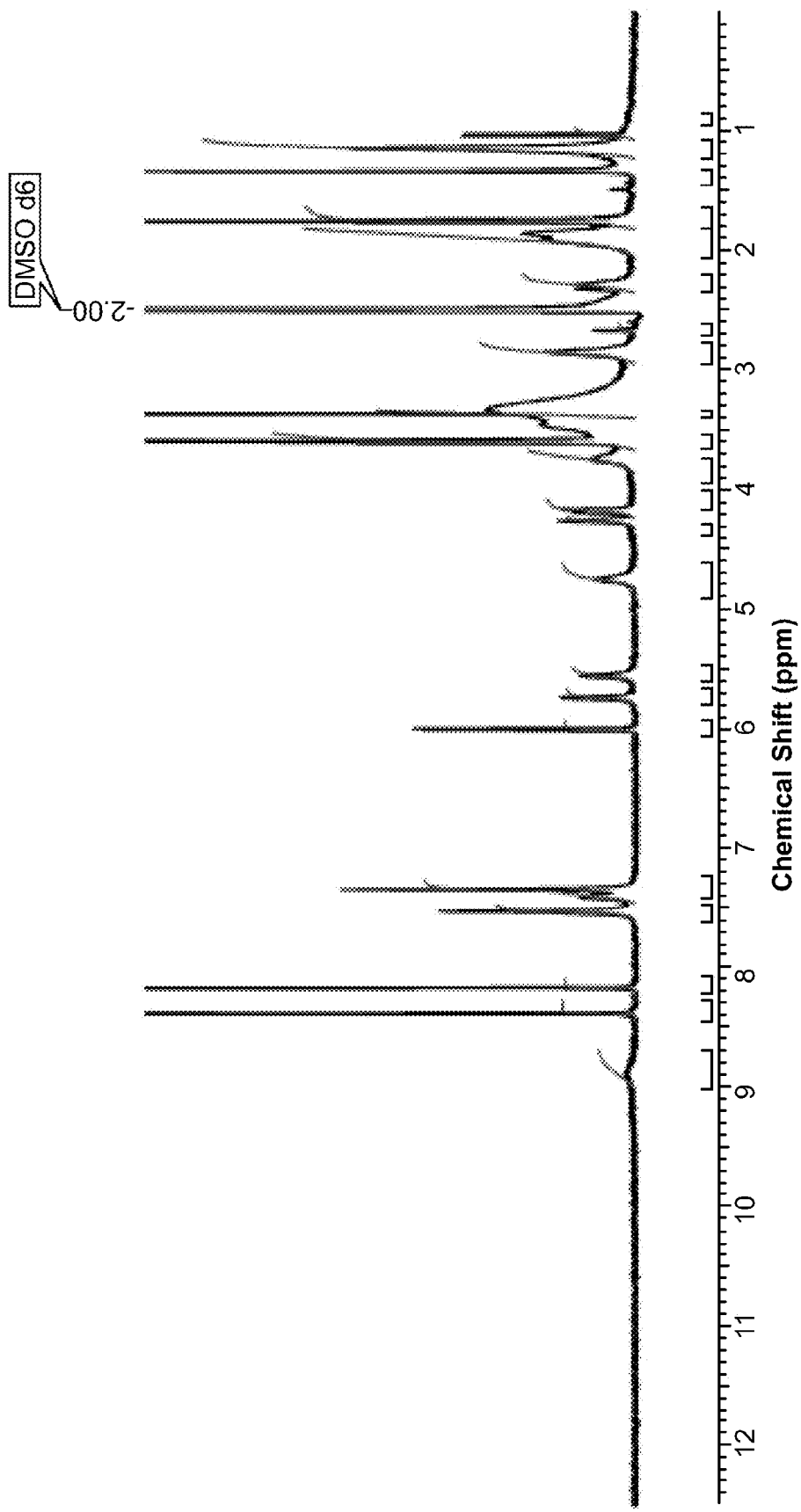
FIG. 58 is a $^1$H NMR spectrum of EP-1 trihydrate (x is 3) obtained after treatment with $H_2SO_4$.
Figure 59:
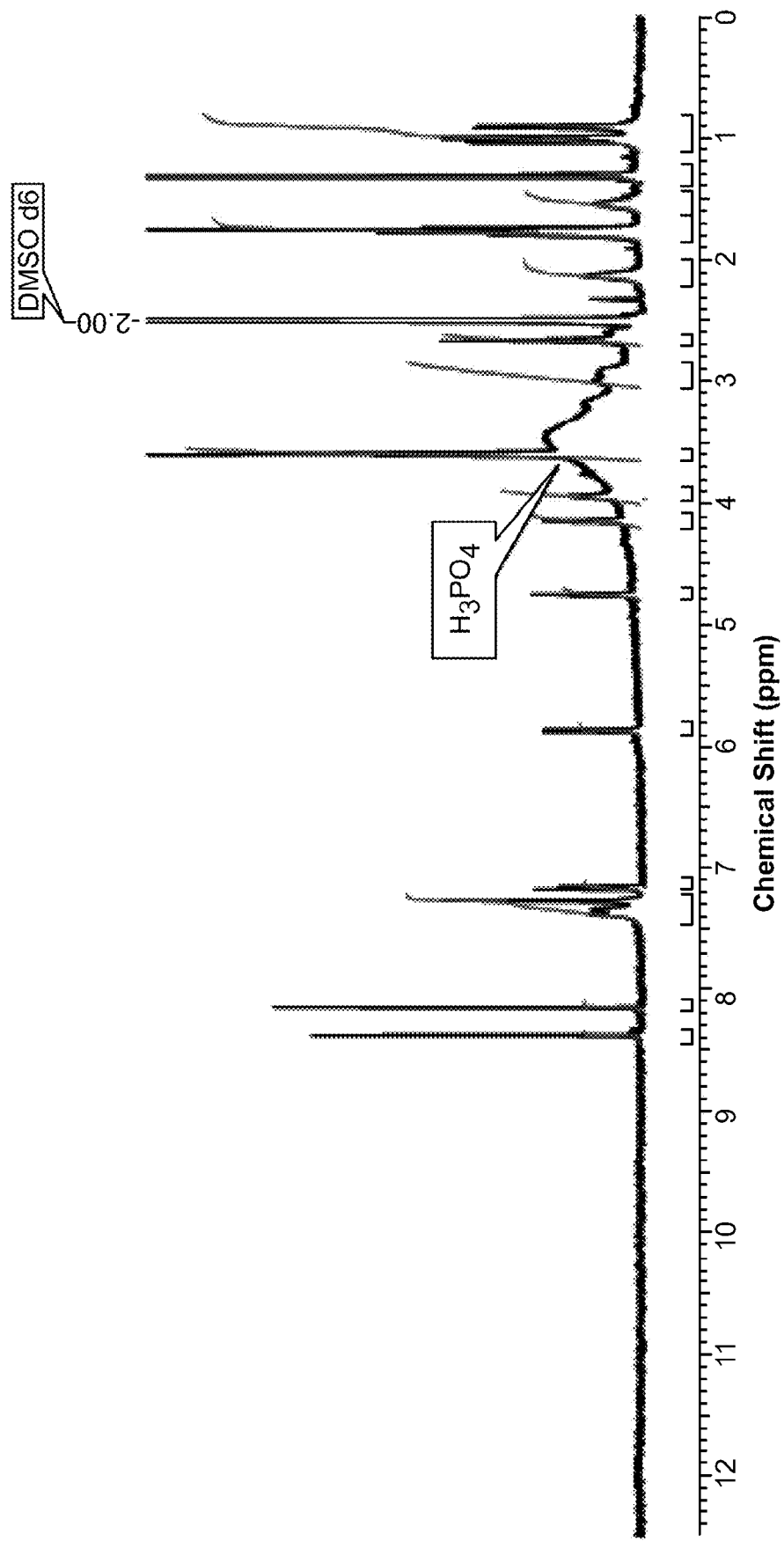
FIG. 59 is a $^1$H NMR spectrum of EP-1 trihydrate (x is 3) obtained after treatment with $H_3PO_4$.
Figure 60:
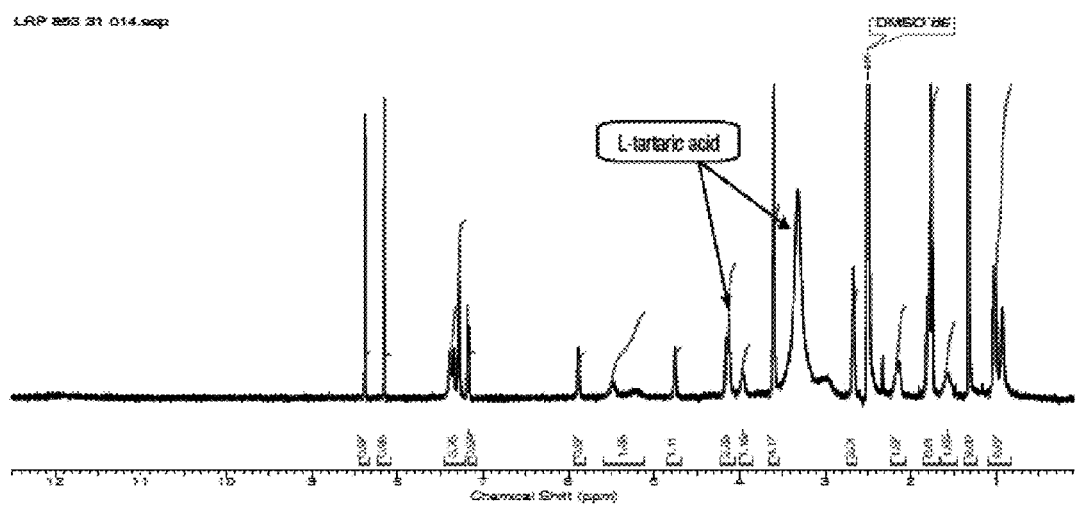
FIG. 60 is a $^1$H NMR spectrum of EP-1 trihydrate (x is 3) obtained after treatment with L-tartaric acid.
Figure 61:
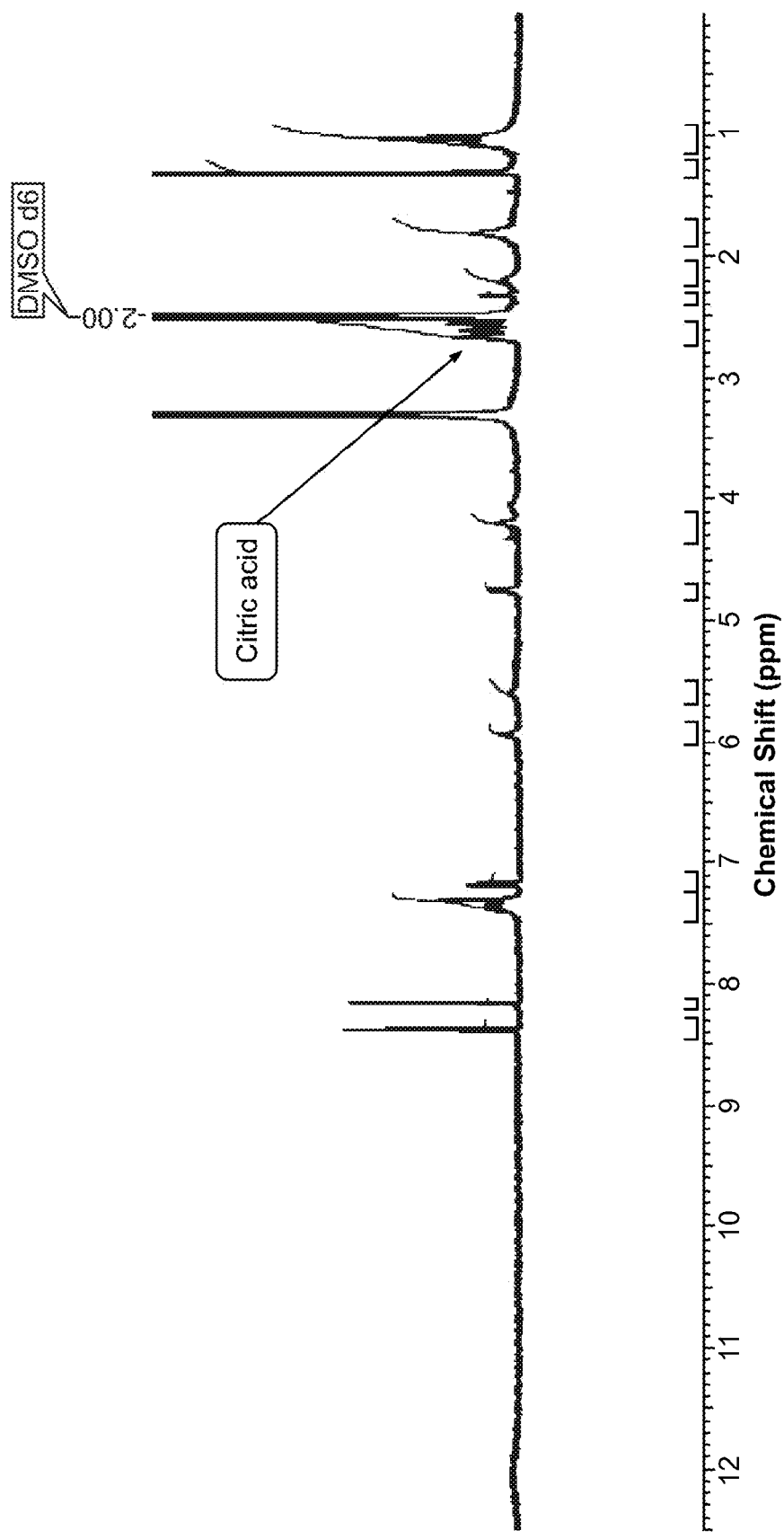
FIG. 61 is a $^1$H NMR spectrum of EP-1 trihydrate (x is 3) obtained after treatment with citric acid.
Figure 62:
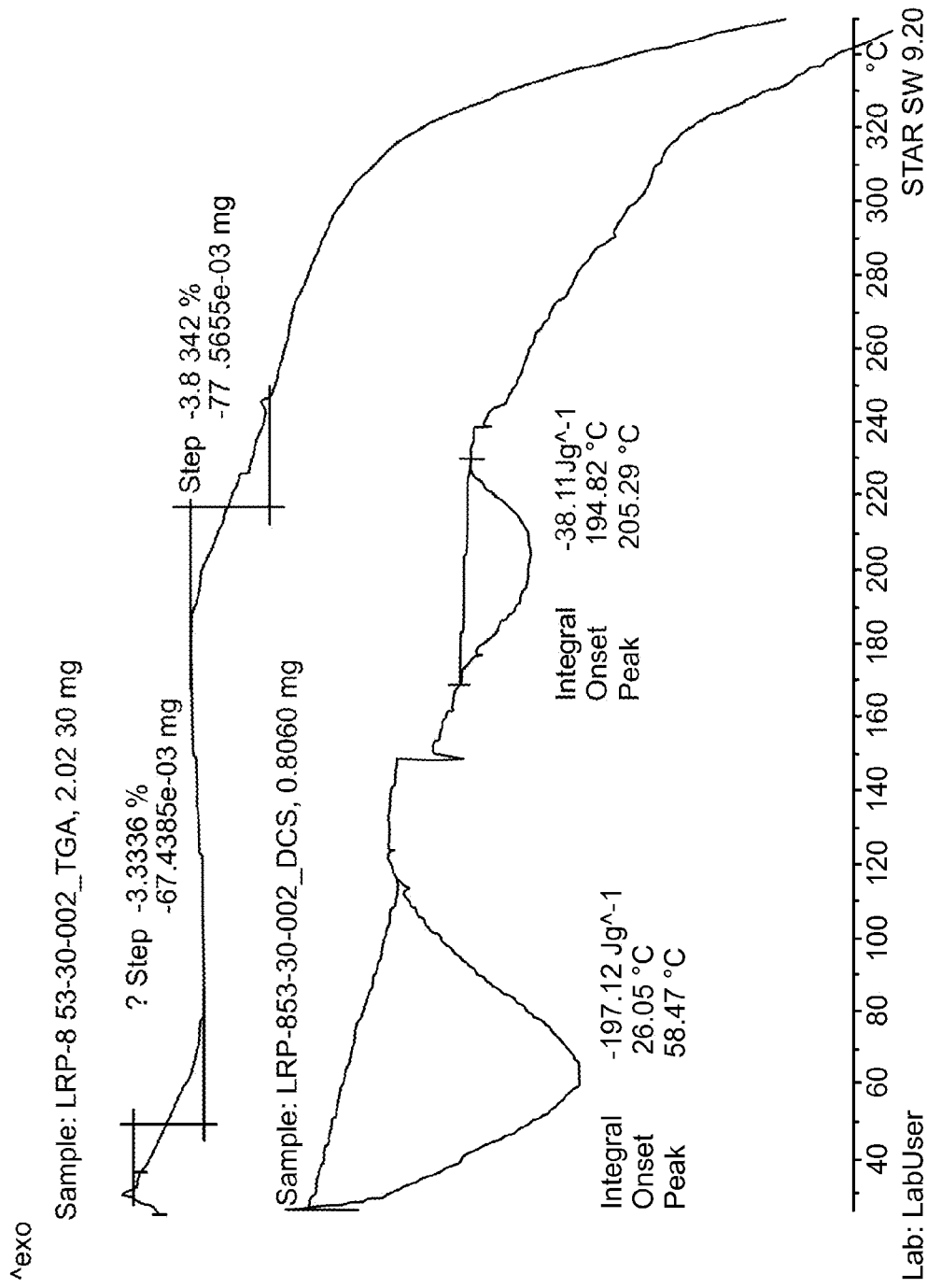
FIG. 62 is a TGA/DSC plot of EP-1 trihydrate (x is 3) obtained after treatment with 1,5-naphthalene disulfonic acid.
Figure 63:
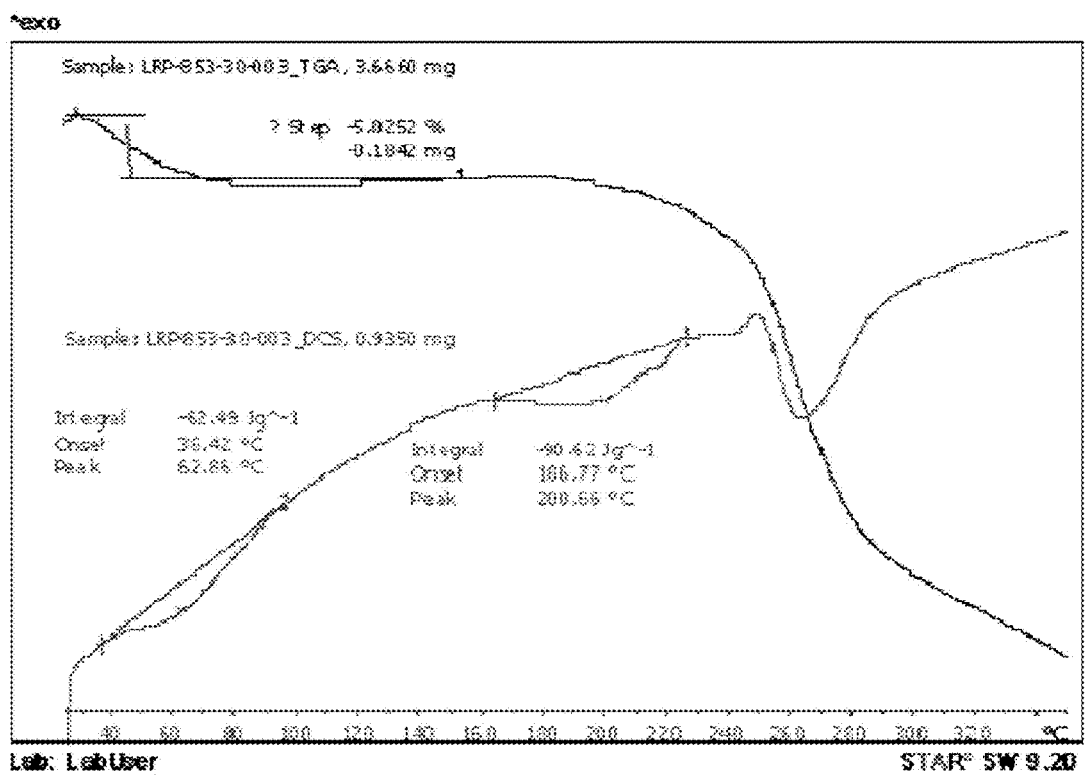
FIG. 63 is a TGA/DSC plot of EP-1 trihydrate (x is 3) obtained after treatment with $H_2SO_4$.
Figure 64:
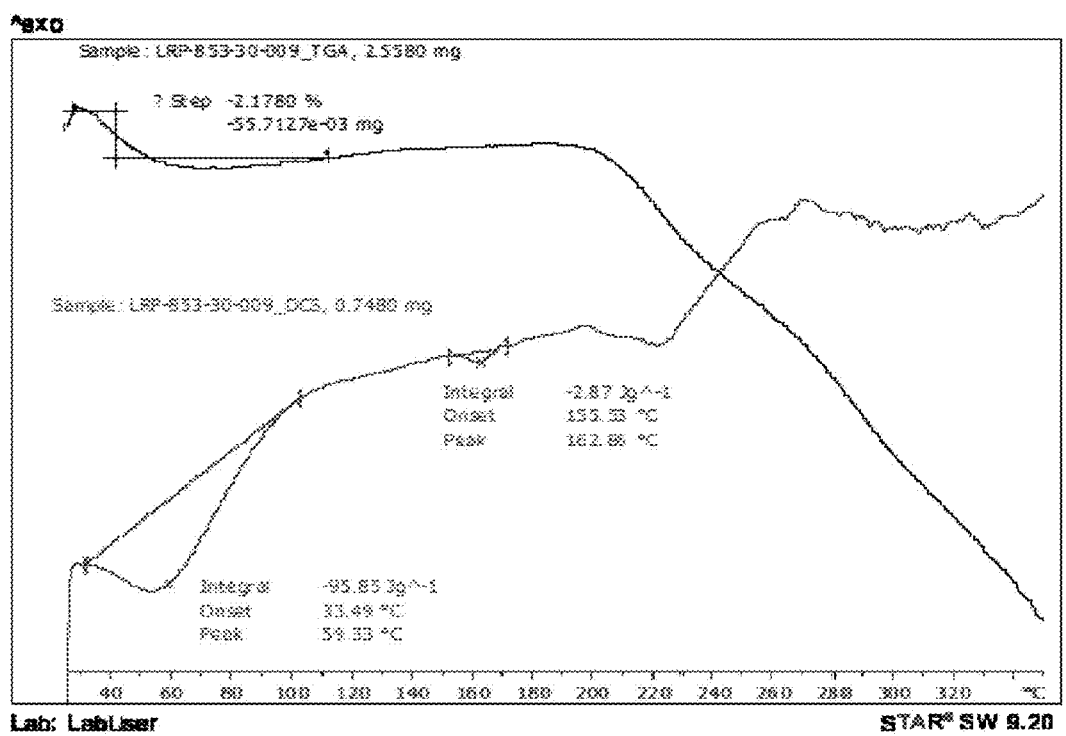
FIG. 64 is a TGA/DSC plot of EP-1 trihydrate (x is 3) obtained after treatment with $H_3PO_4$.
Figure 65:
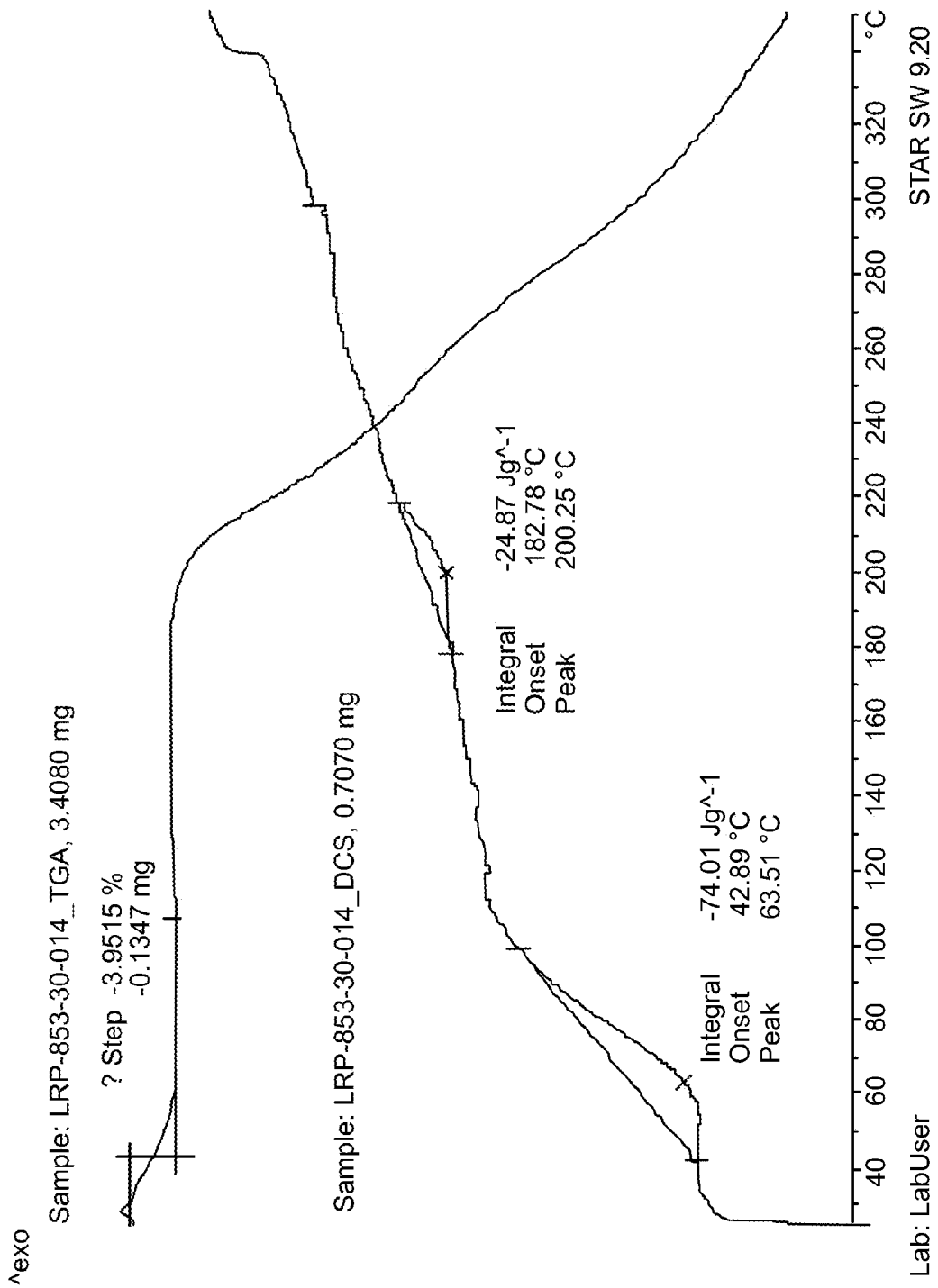
FIG. 65 is a TGA/DSC plot of EP-1 trihydrate (x is 3) obtained after treatment with L-tartaric acid.
Figure 66:
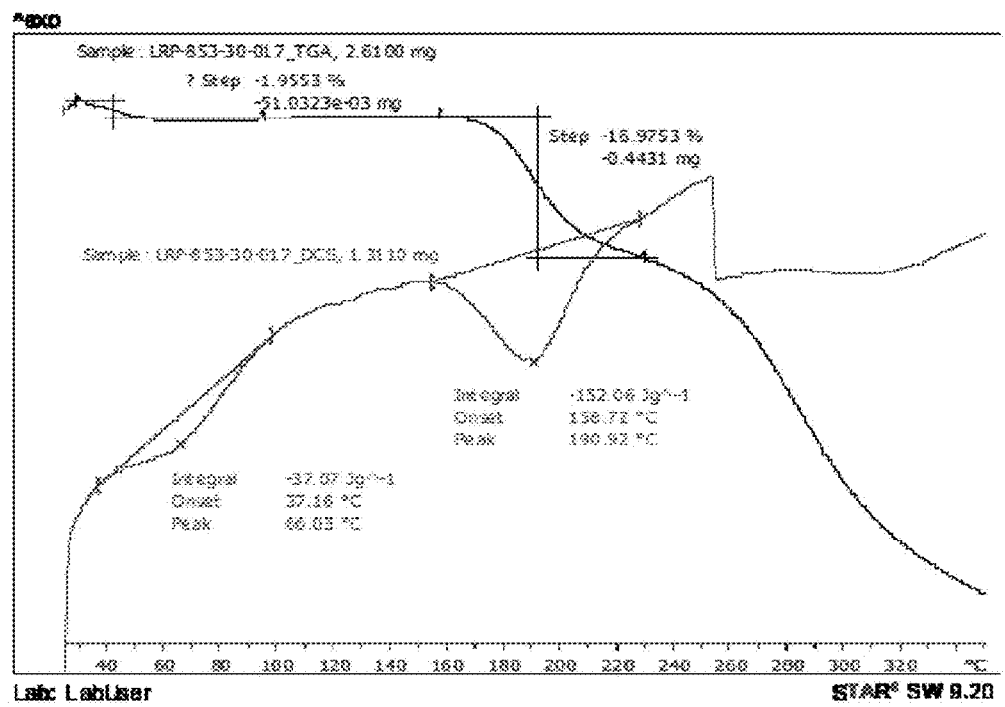
FIG. 66 is a TGA/DSC plot of EP-1 trihydrate (x is 3) obtained after treatment with citric acid.
Figure 67:
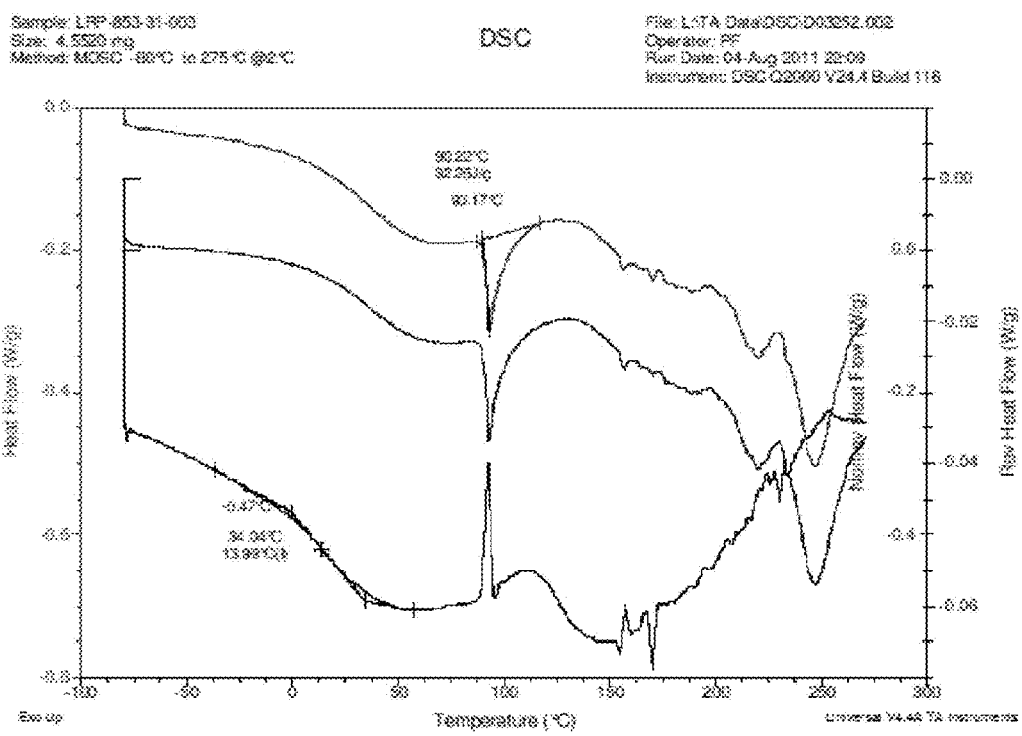
FIG. 67 is a mDSC plot of EP-1 trihydrate (x is 3) obtained after treatment with $H_2SO_4$.
Figure 68:
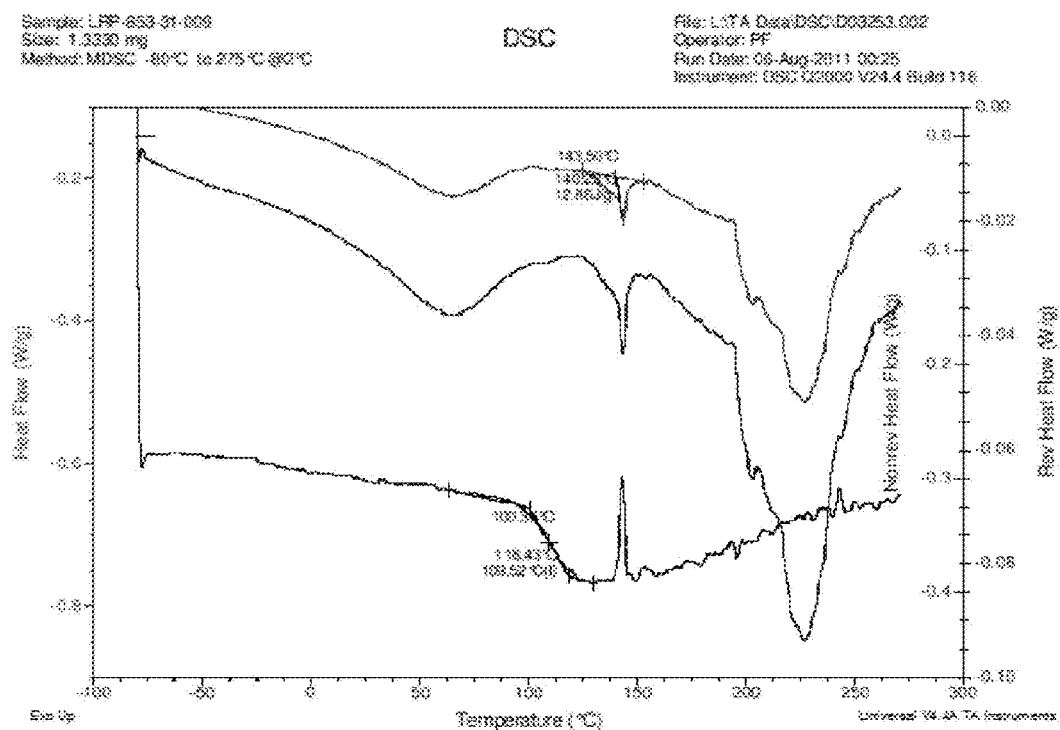
FIG. 68 is a mDSC plot of EP-1 trihydrate (x is 3) obtained after treatment with $H_3PO_4$.
Figure 69:
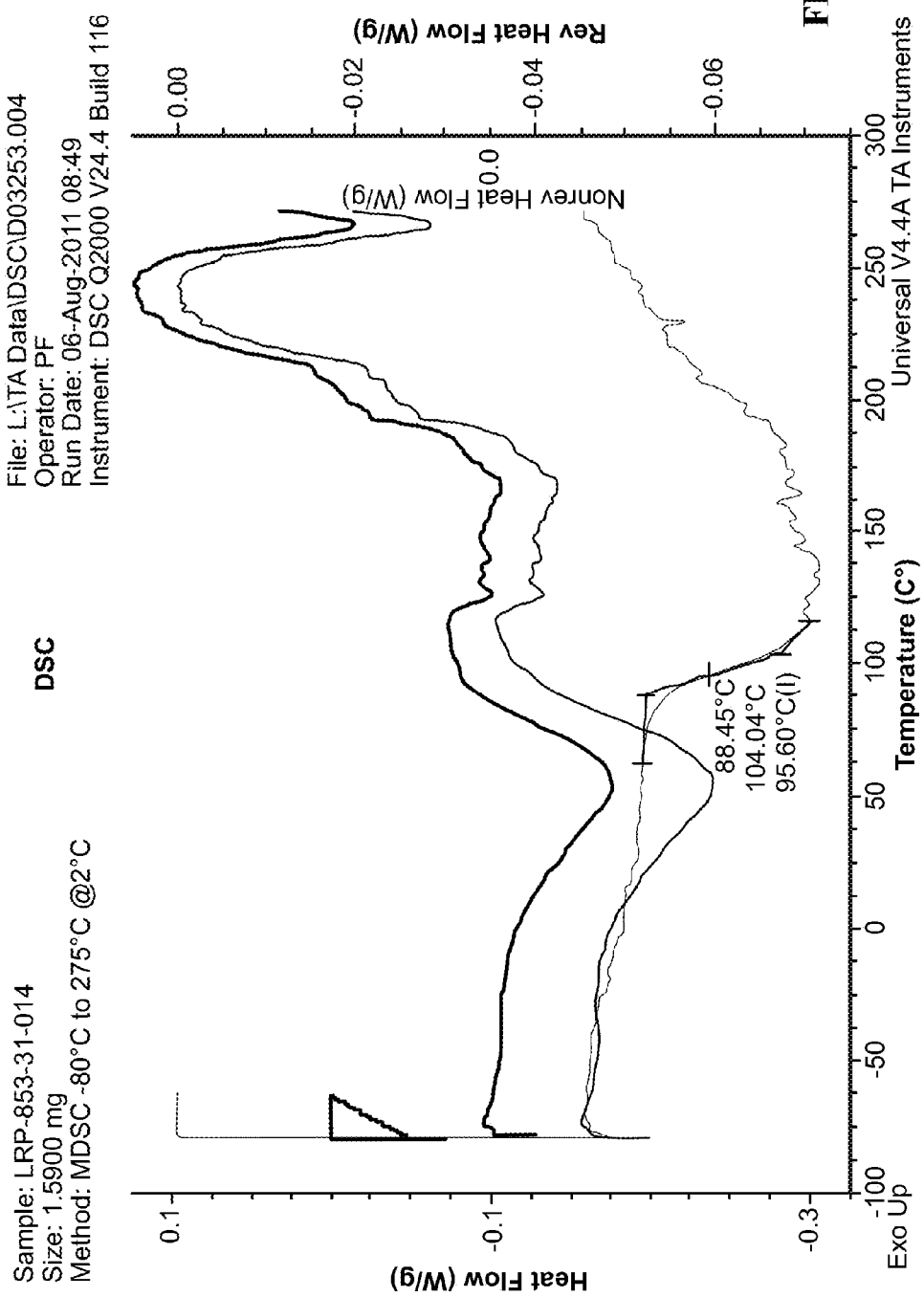
FIG. 69 is a mDSC plot of EP-1 trihydrate (x is 3) obtained after treatment with L-tartaric acid.
Figure 70:
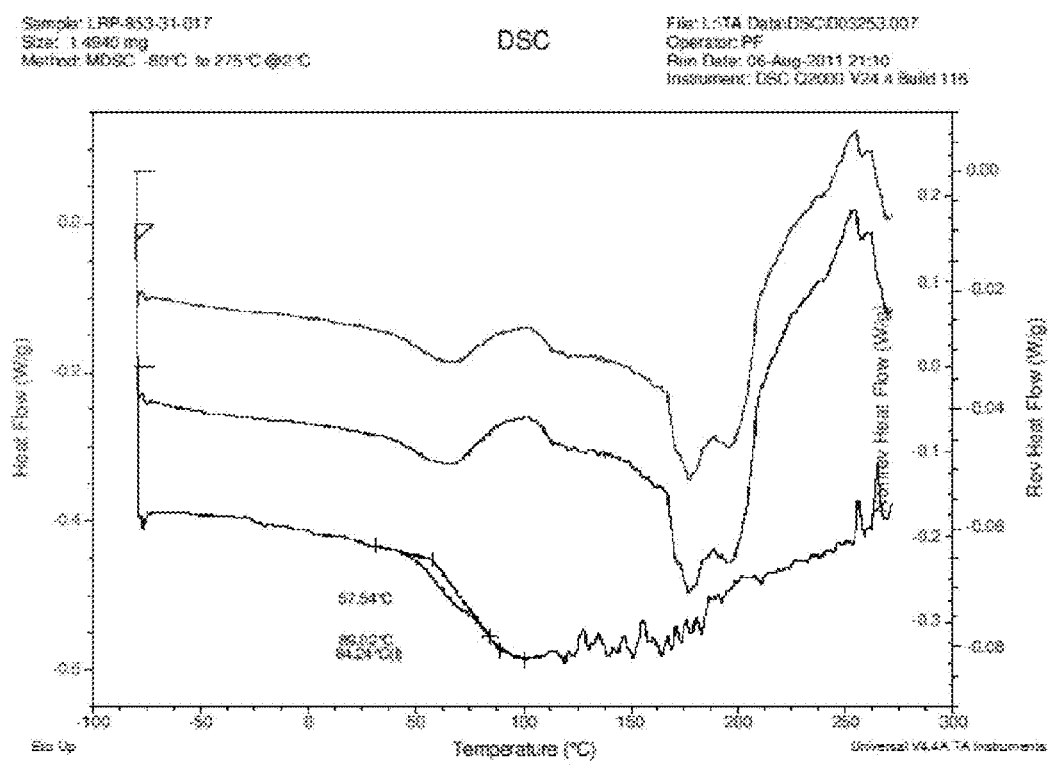
FIG. 70 is a mDSC plot of EP-1 trihydrate (x is 3) obtained after treatment with citric acid.
Figure 71:
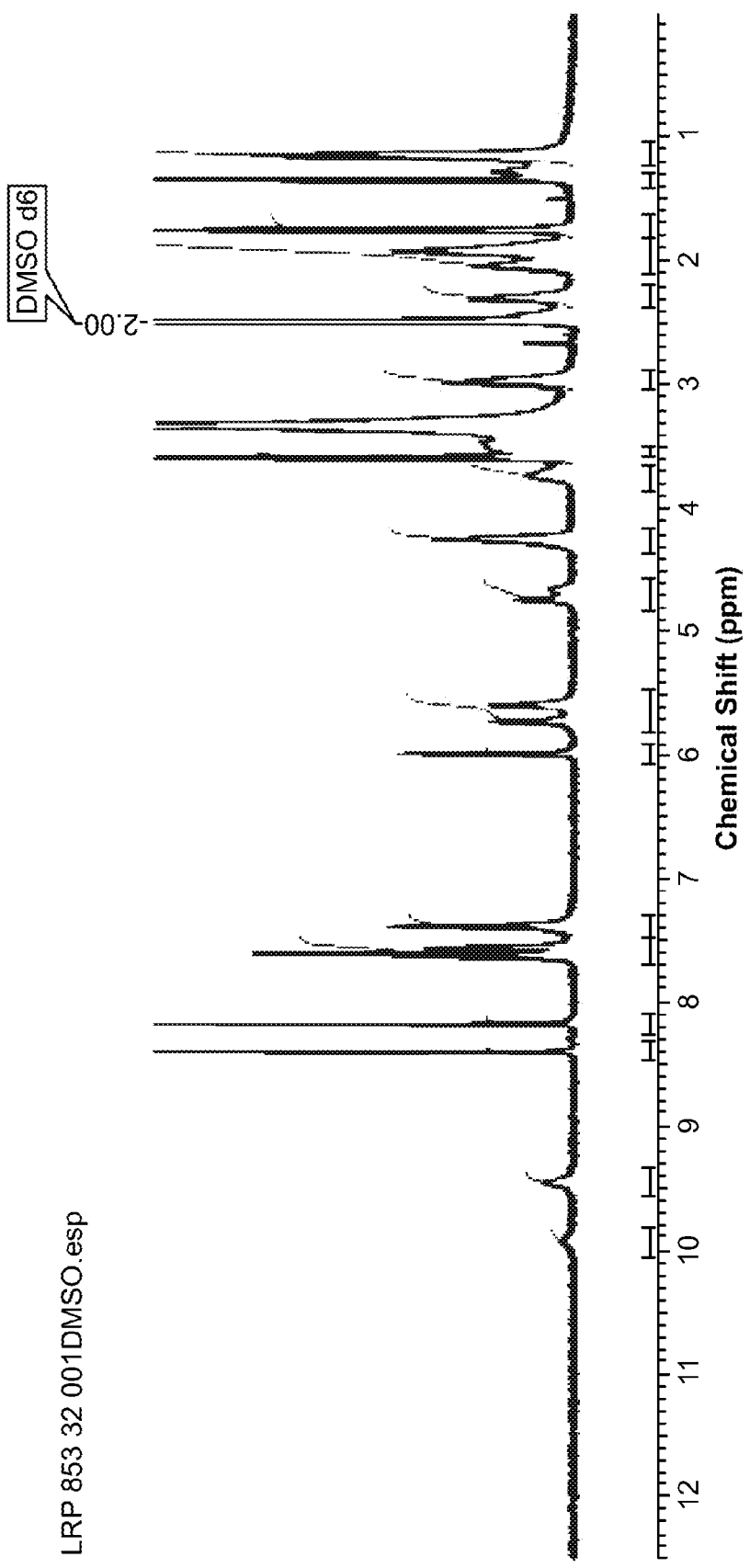
FIG. 71 is a $^1$H NMR spectrum of EP-1 trihydrate (x is 3) obtained after treatment with HCl.
Figure 72:
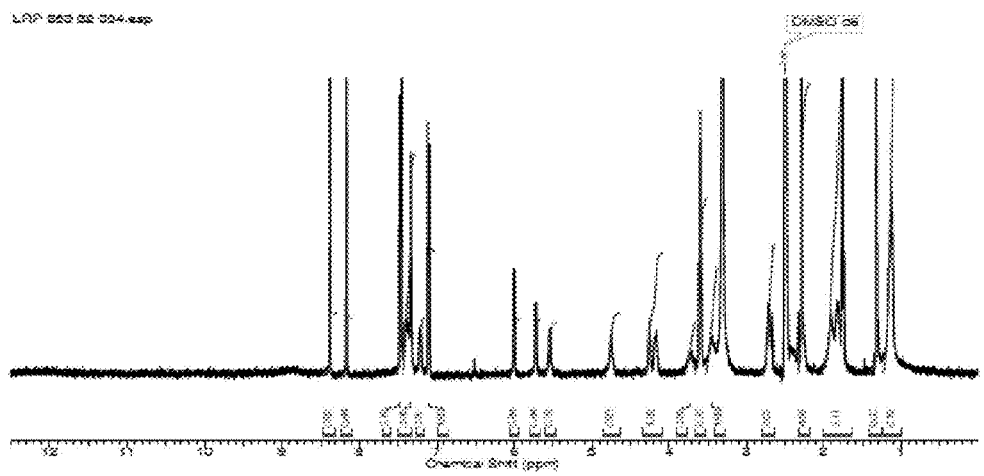
FIG. 72 is a $^1$H NMR spectrum of EP-1 trihydrate (x is 3) obtained after treatment with p-toluene sulfonic acid.
Figure 73:
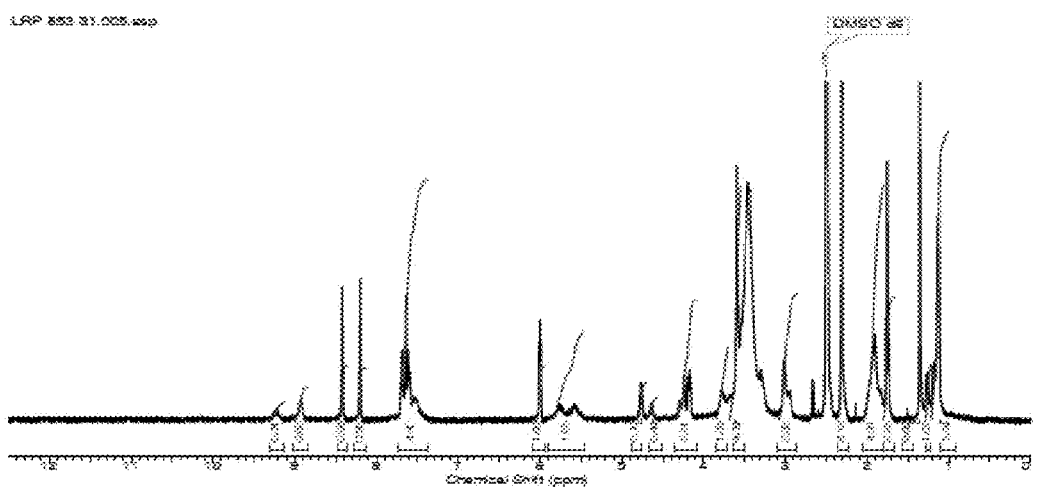
FIG. 73 is a $^1$H NMR spectrum of EP-1 trihydrate (x is 3) obtained after treatment with methane sulfonic acid.
Figure 74:
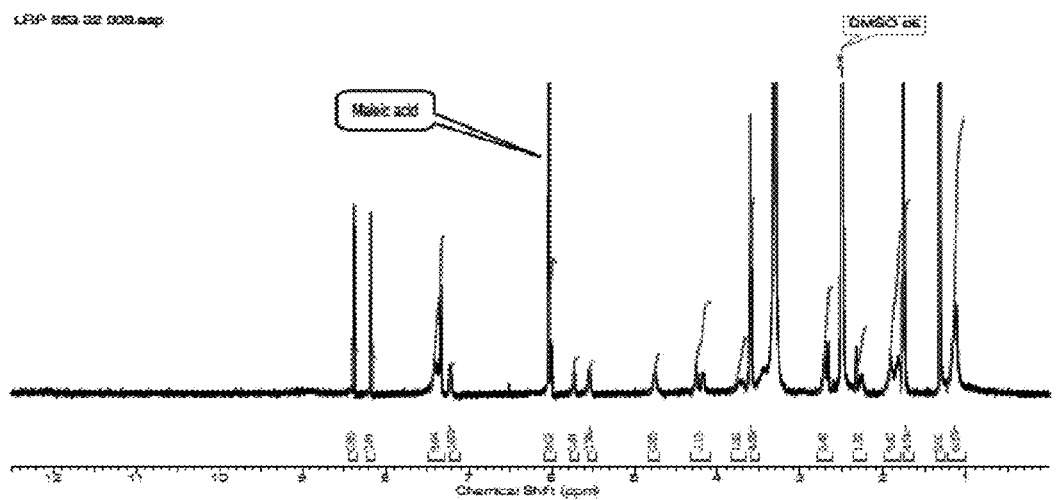
FIG. 74 is a $^1$H NMR spectrum of EP-1 trihydrate (x is 3) obtained after treatment with maleic acid.
Figure 75:
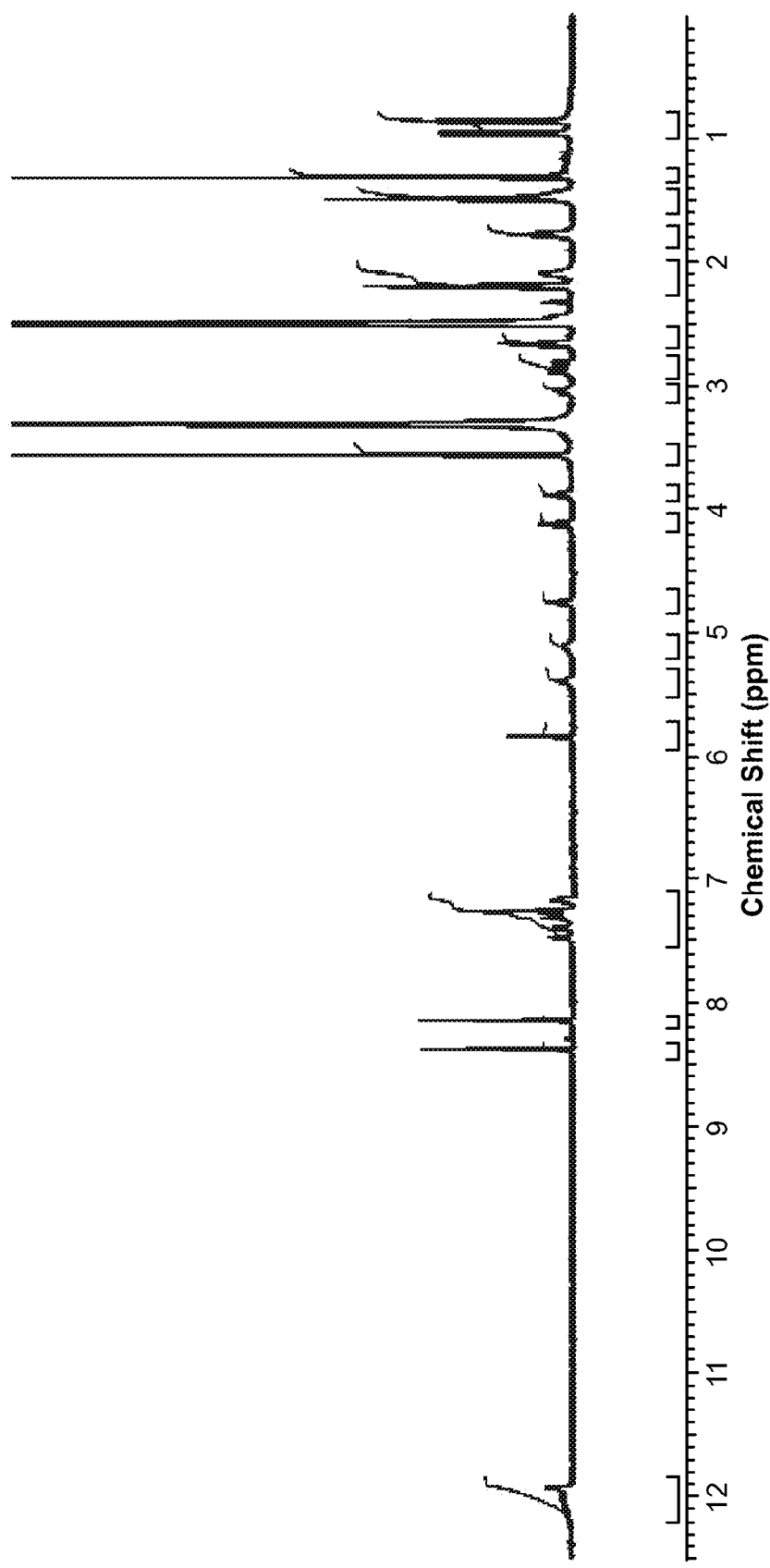
FIG. 75 is a $^1$H NMR spectrum of EP-1 trihydrate (x is 3) obtained after treatment with adipic acid.
Figure 76:
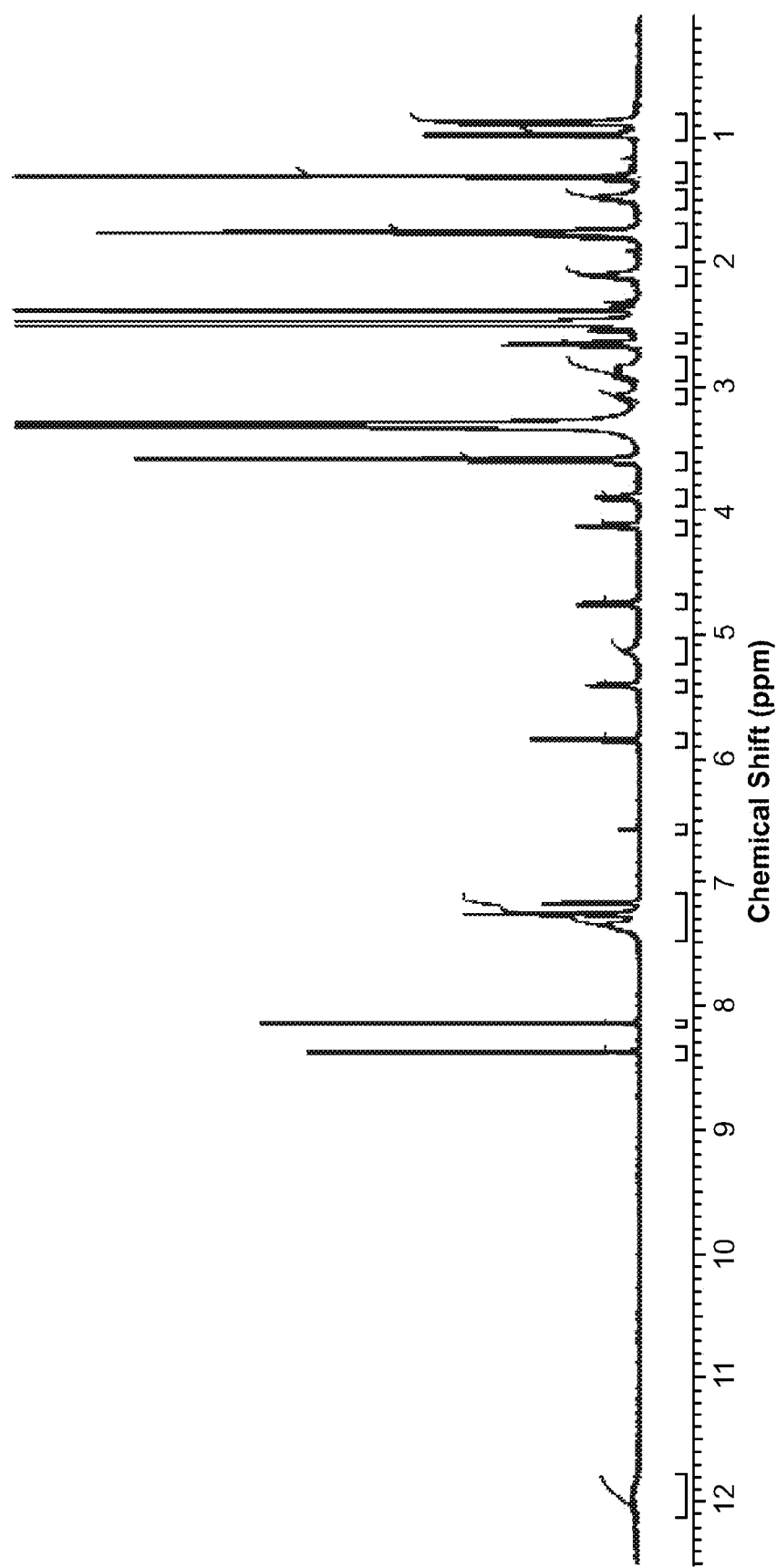
FIG. 76 is a $^1$H NMR spectrum of EP-1 trihydrate (x is 3) obtained after treatment with succinic acid.
Figure 77:
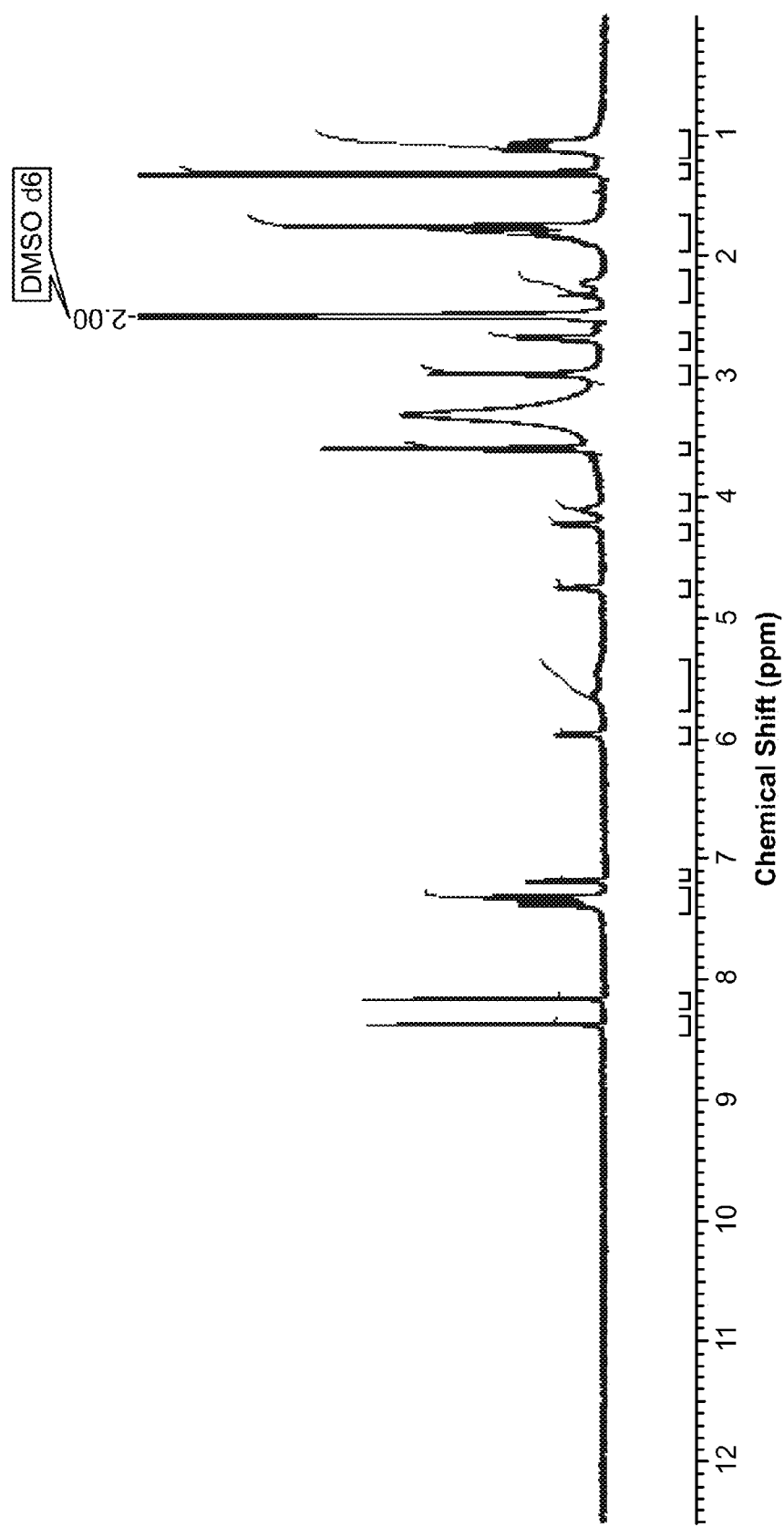
FIG. 77 is a $^1$H NMR spectrum of EP-1 trihydrate (x is 3) obtained after treatment with malonic acid.
Figure 78:
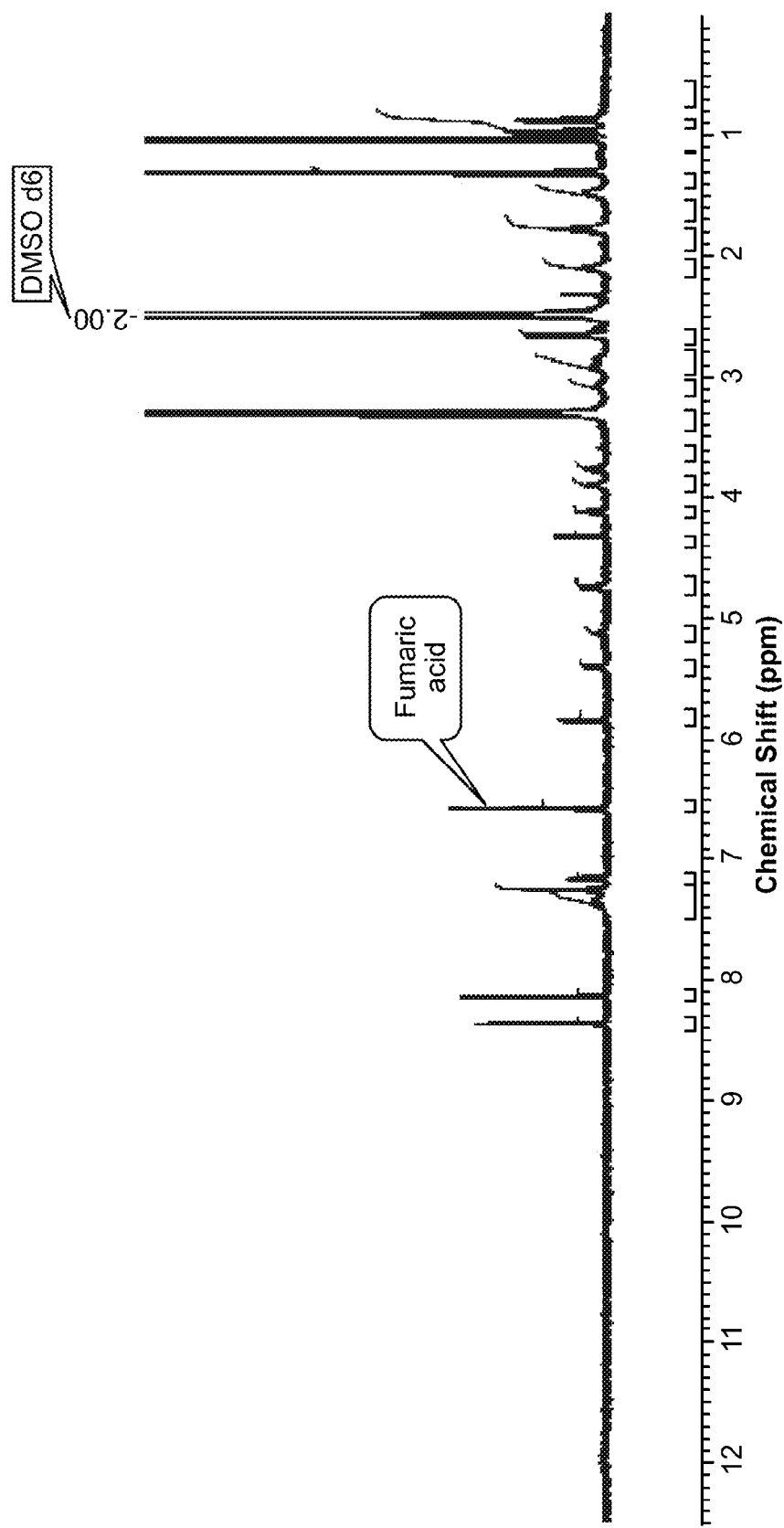
FIG. 78 is a $^1$H NMR spectrum of EP-1 trihydrate (x is 3) obtained after treatment with fumaric acid.
Figure 79:
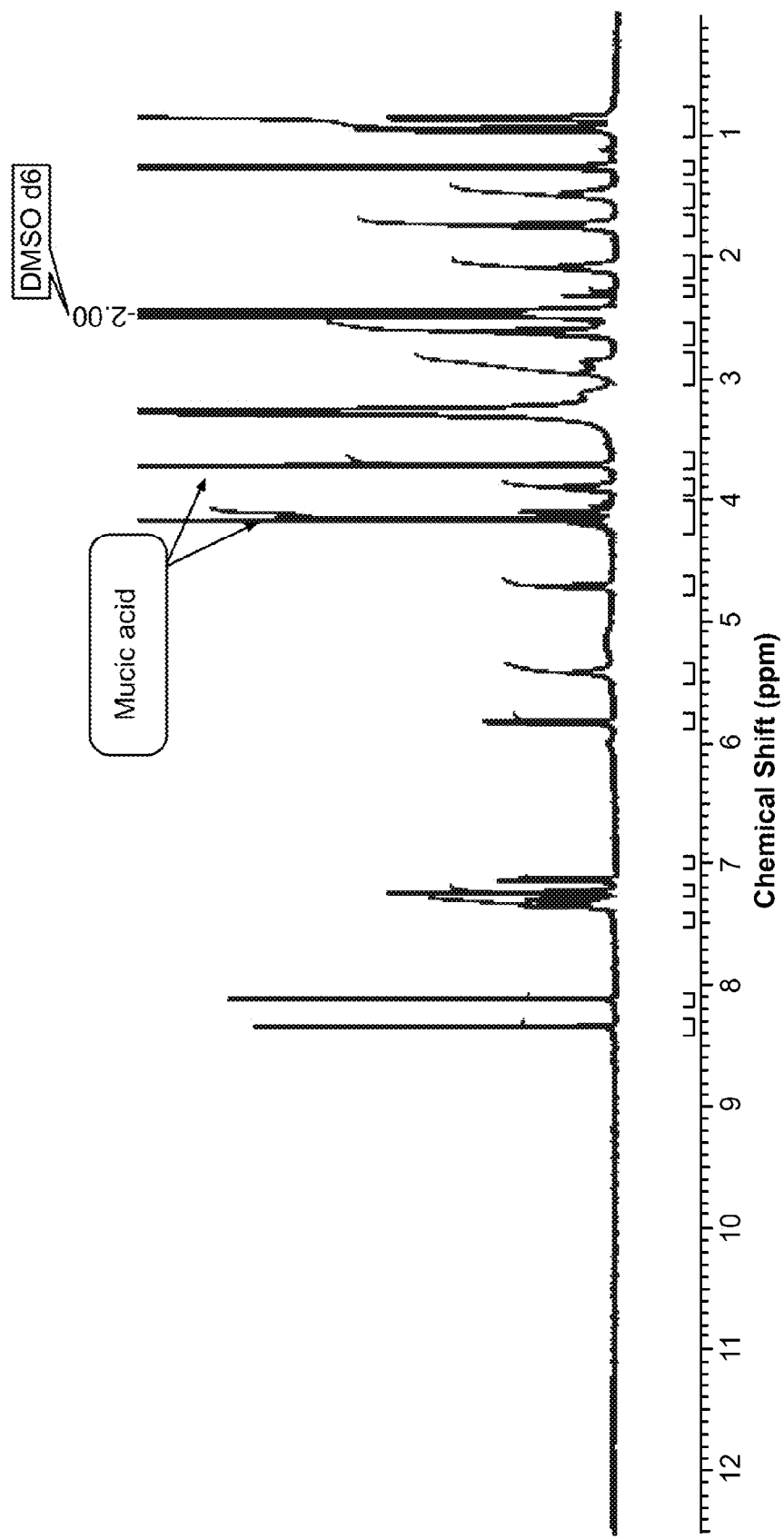
FIG. 79 is a $^1$H NMR spectrum of EP-1 trihydrate (x is 3) obtained after treatment with galactaric acid.
Figure 80:
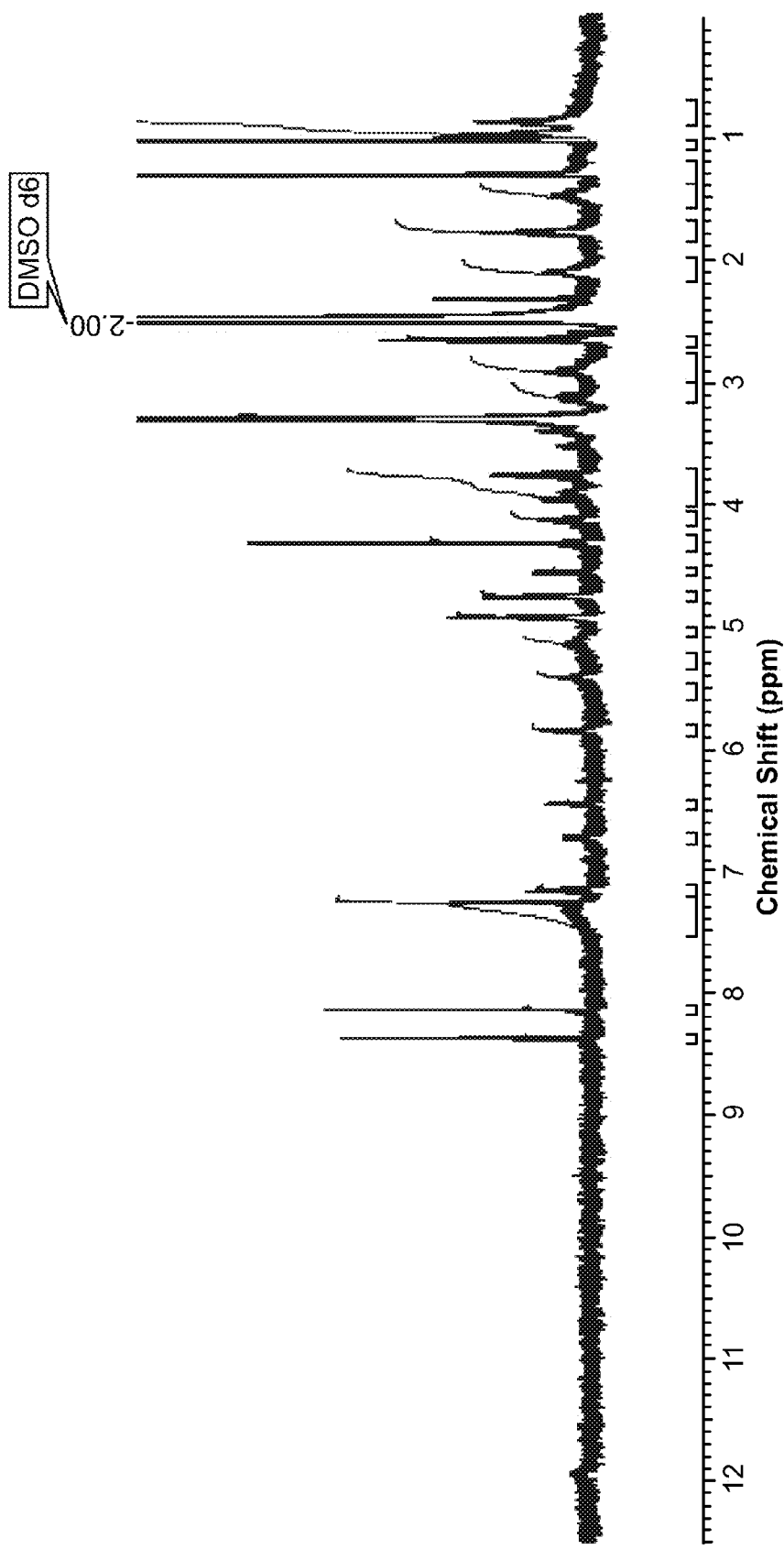
FIG. 80 is a $^1$H NMR spectrum of EP-1 trihydrate (x is 3) obtained after treatment with D-glucuronic acid.
Figure 81:
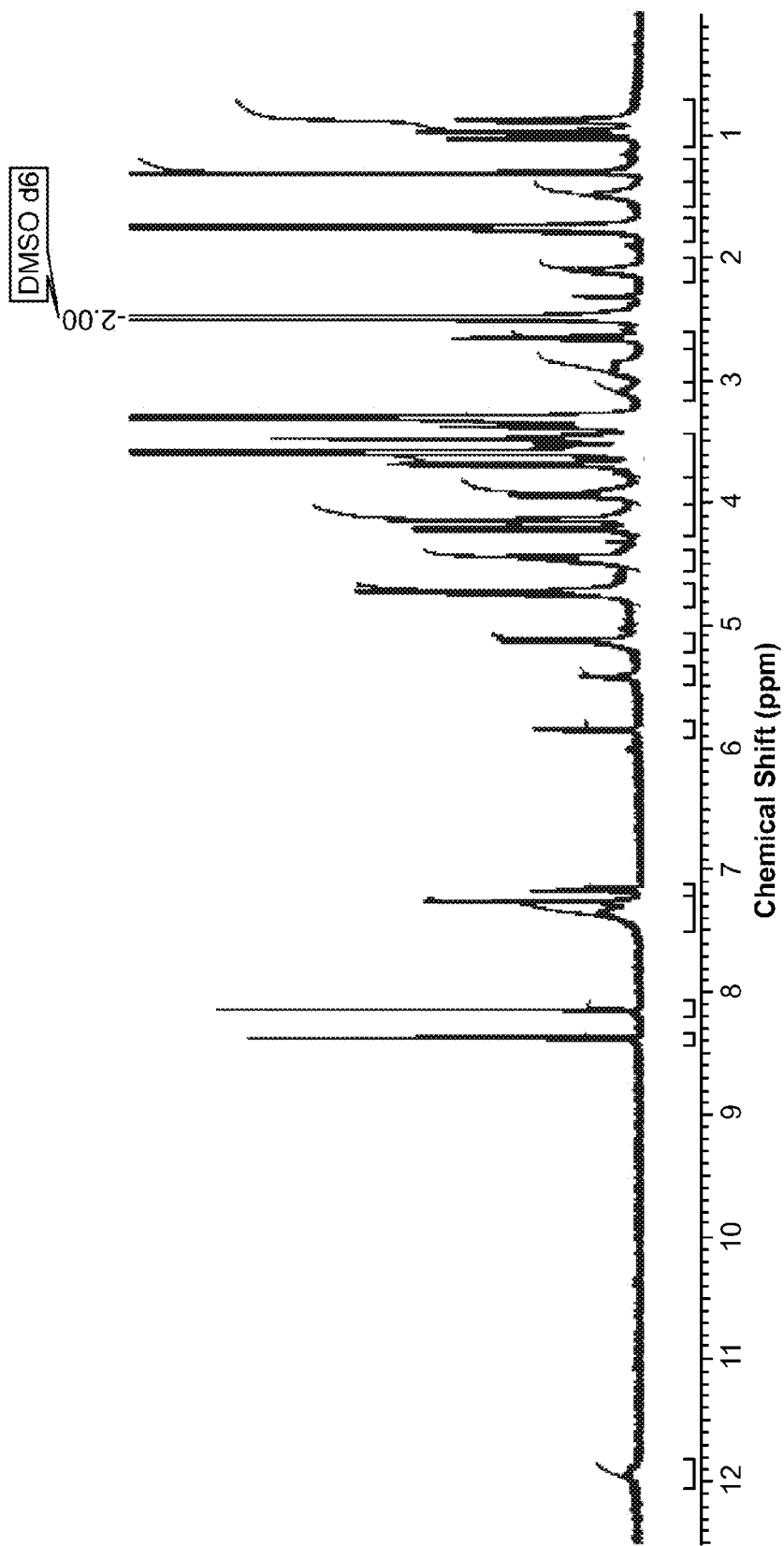
FIG. 81 is a $^1$H NMR spectrum of EP-1 trihydrate (x is 3) obtained after treatment with lactobionic acid.
Figure 82:
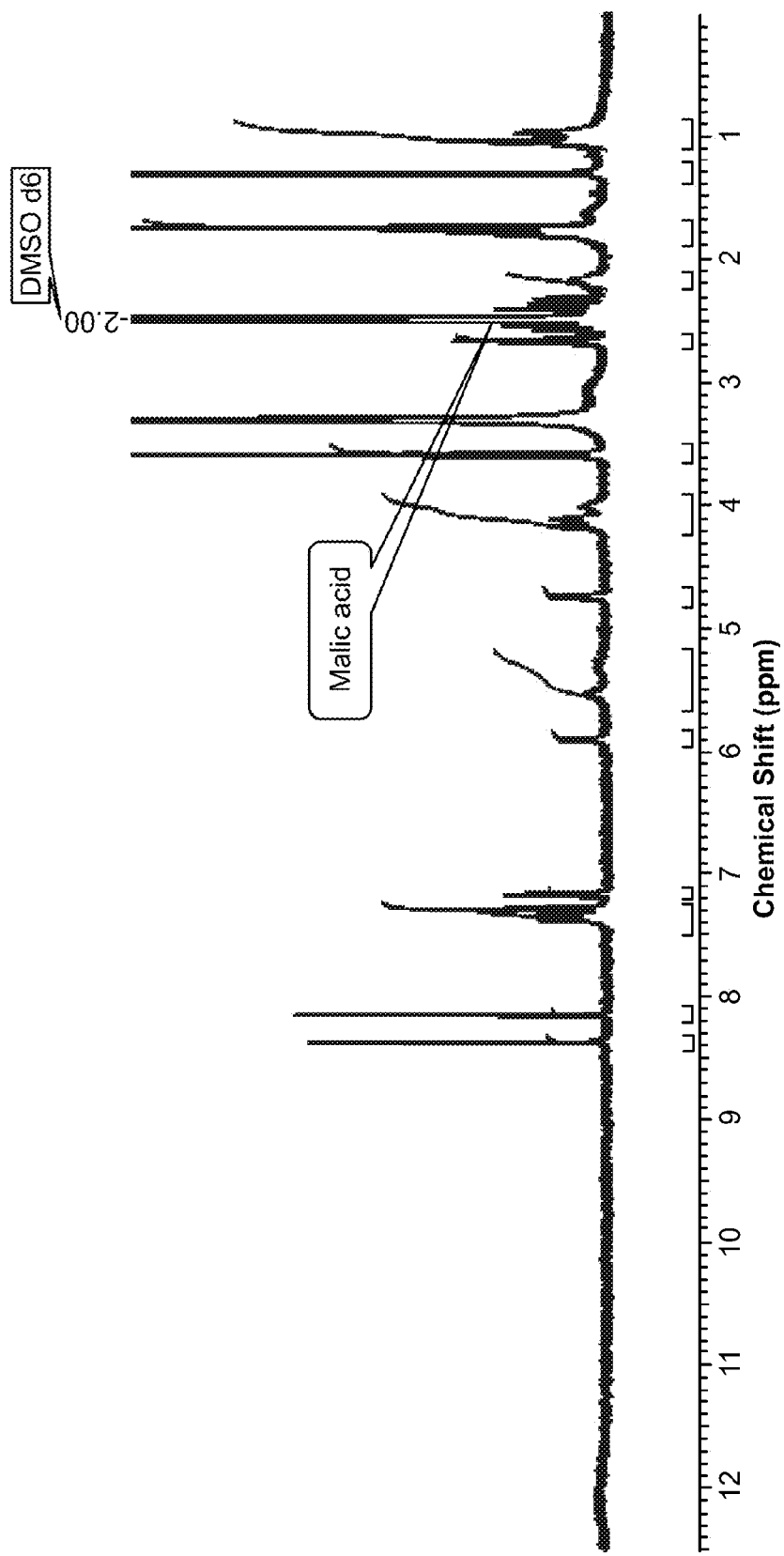
FIG. 82 is a $^1$H NMR spectrum of EP-1 trihydrate (x is 3) obtained after treatment with malic acid.
Figure 83:
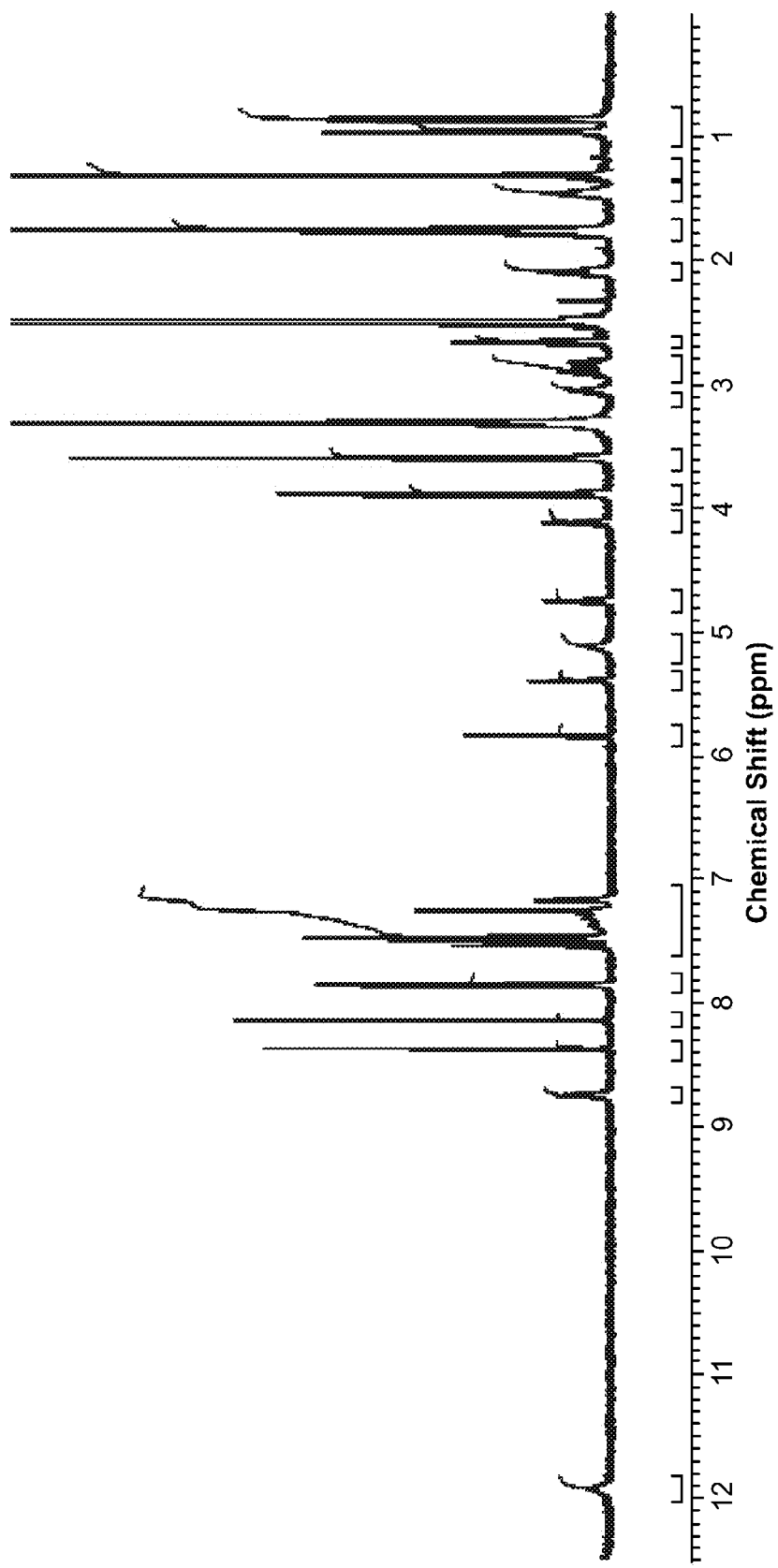
FIG. 83 is a $^1$H NMR spectrum of EP-1 trihydrate (x is 3) obtained after treatment with hippuric acid.
Figure 84:
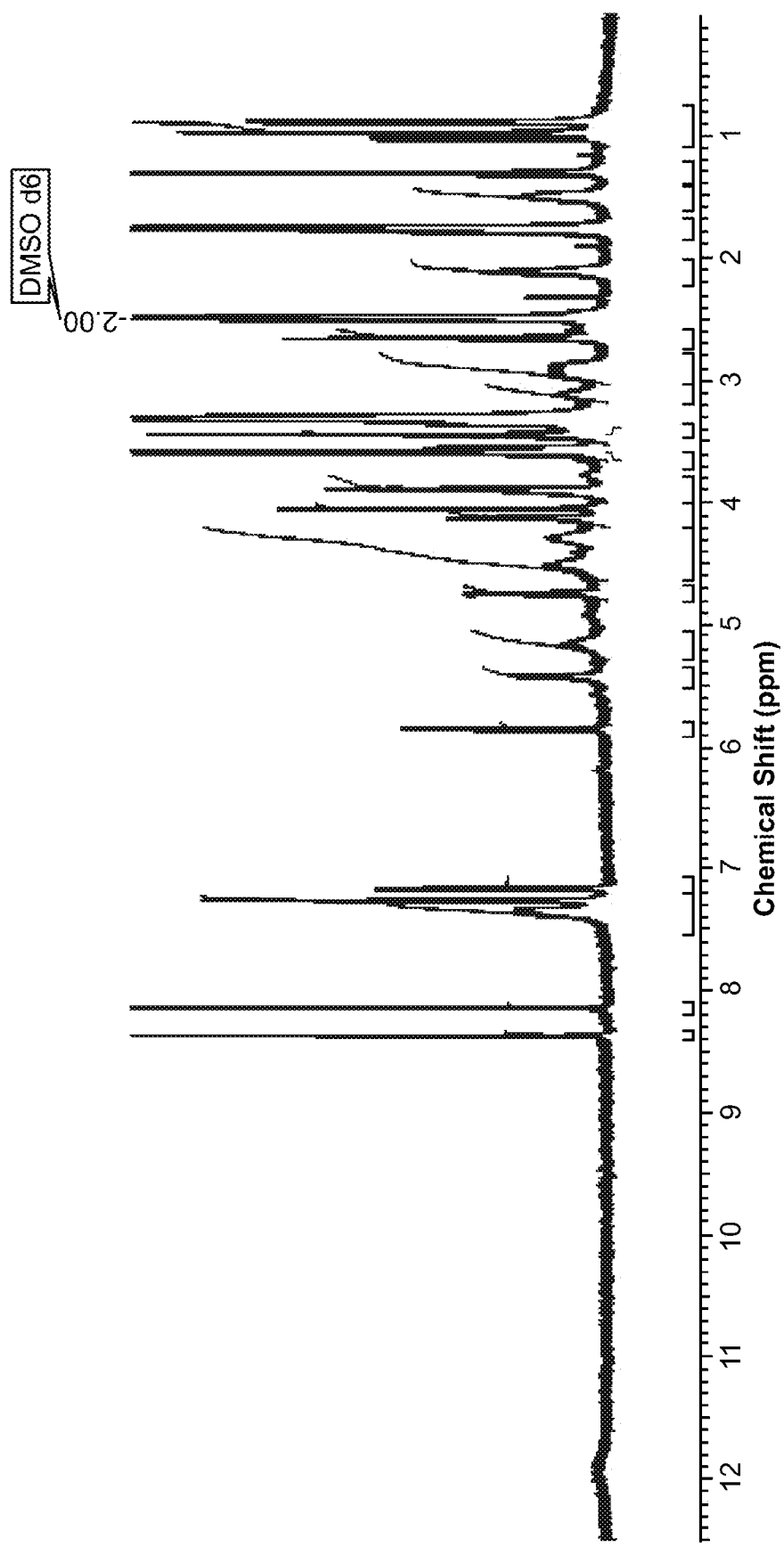
FIG. 84 is a $^1$H NMR spectrum of EP-1 trihydrate (x is 3) obtained after treatment with gluconic acid.
Figure 85:
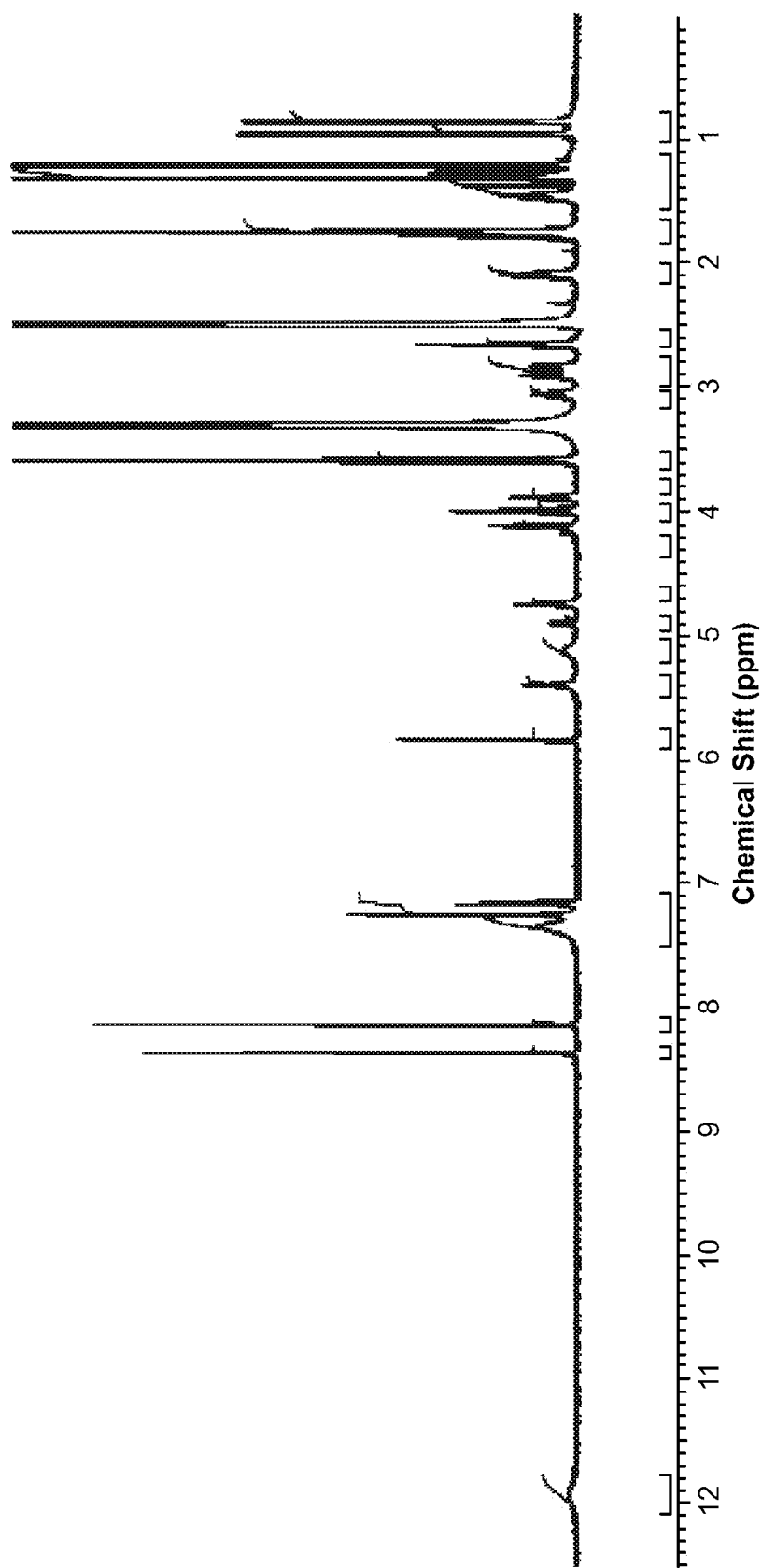
FIG. 85 is a $^1$H NMR spectrum of EP-1 trihydrate (x is 3) obtained after treatment with lactic acid.
Figure 86:
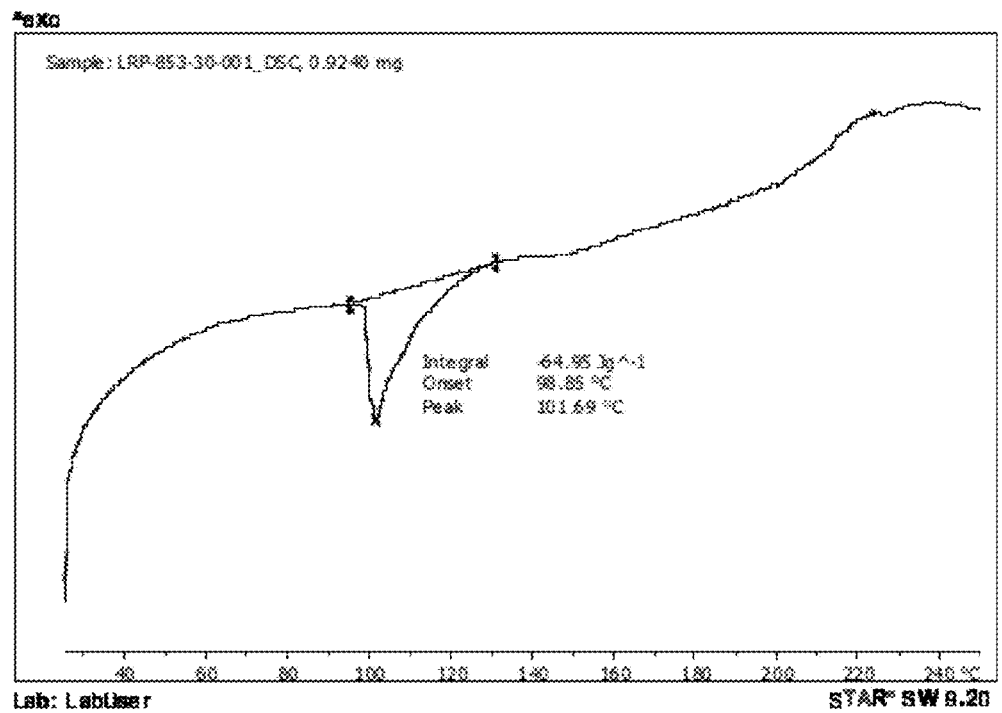
FIG. 86 is a DSC plot of EP-1 trihydrate (x is 3) obtained after treatment with HCl.
Figure 87:
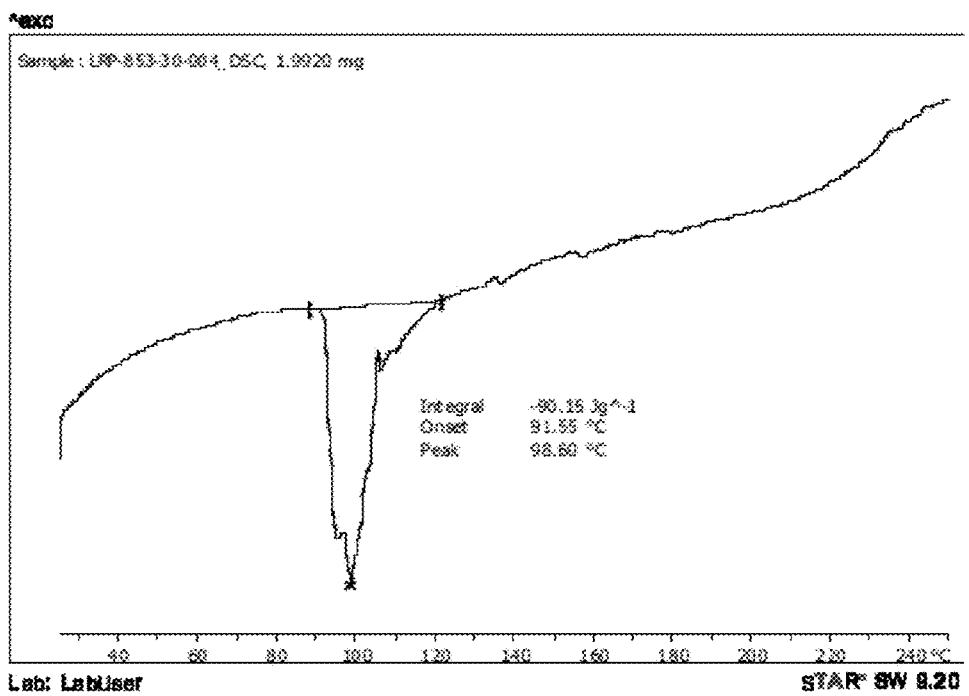
FIG. 87 is a DSC plot of EP-1 trihydrate (x is 3) obtained after treatment withp-toluene sulfonic acid.
Figure 88:
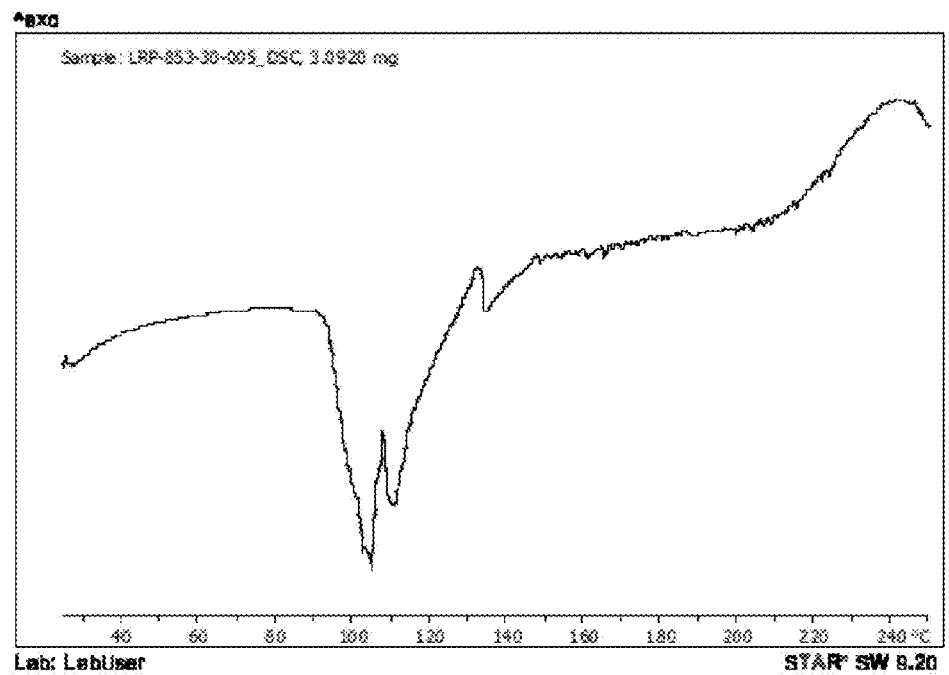
FIG. 88 is a DSC plot of EP-1 trihydrate (x is 3) obtained after treatment with methane sulfonic acid.
Figure 89:
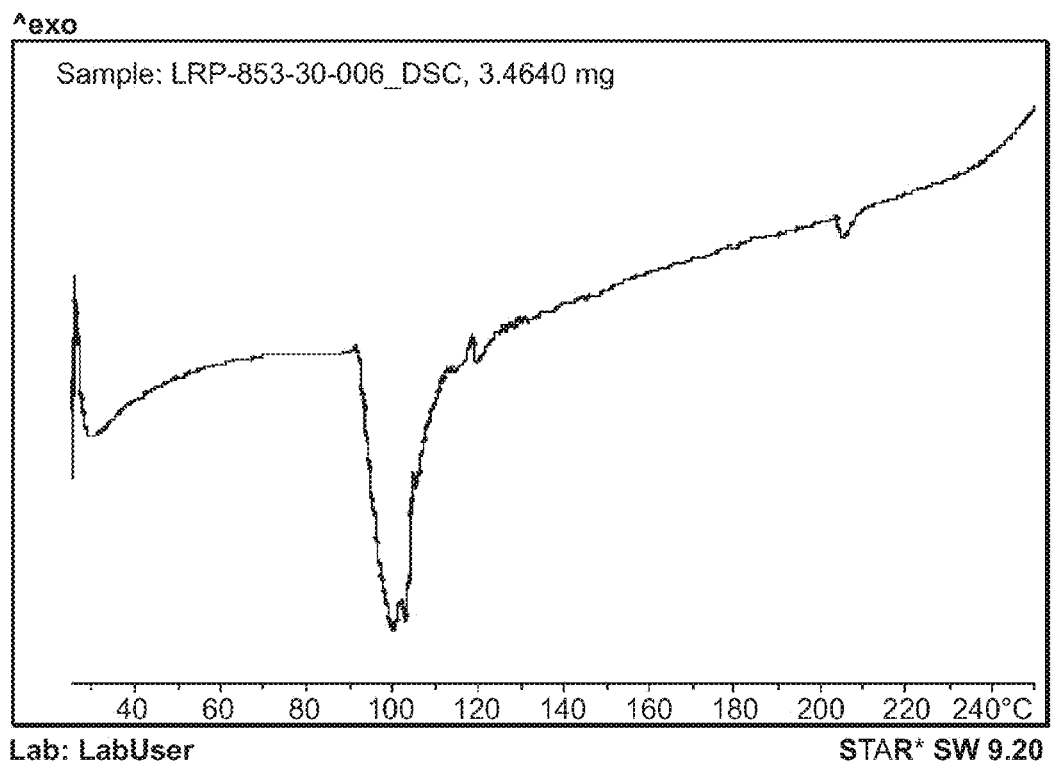
FIG. 89 is a DSC plot of EP-1 trihydrate (x is 3) obtained after treatment with benzene sulfonic acid.
Figure 90:
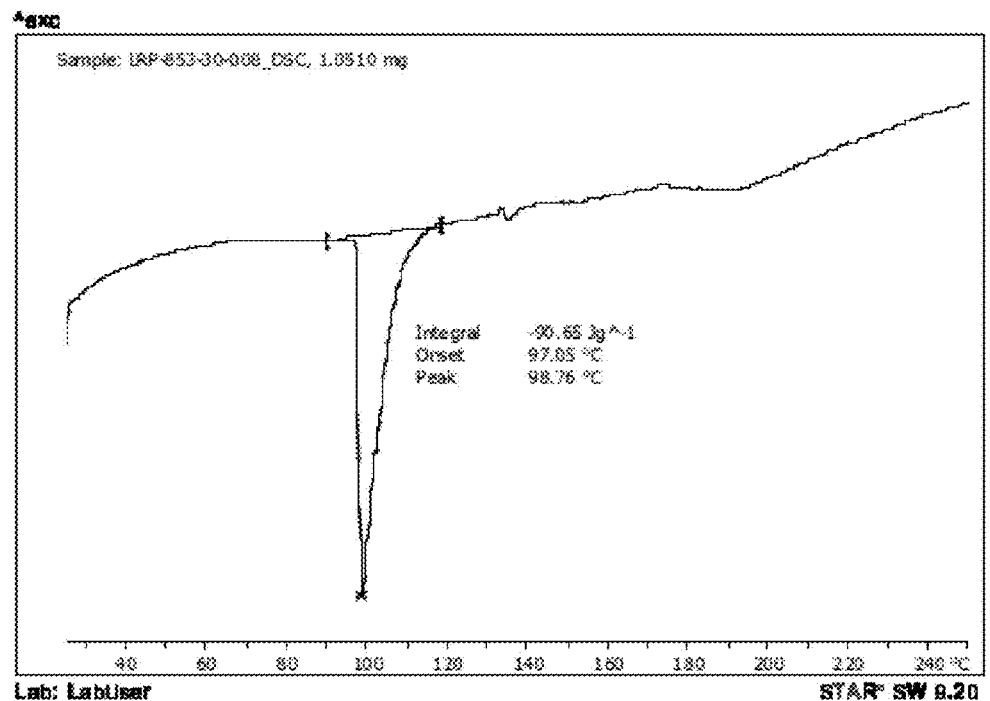
FIG. 90 is a DSC plot of EP-1 trihydrate (x is 3) obtained after treatment with maleic acid.
Figure 91:
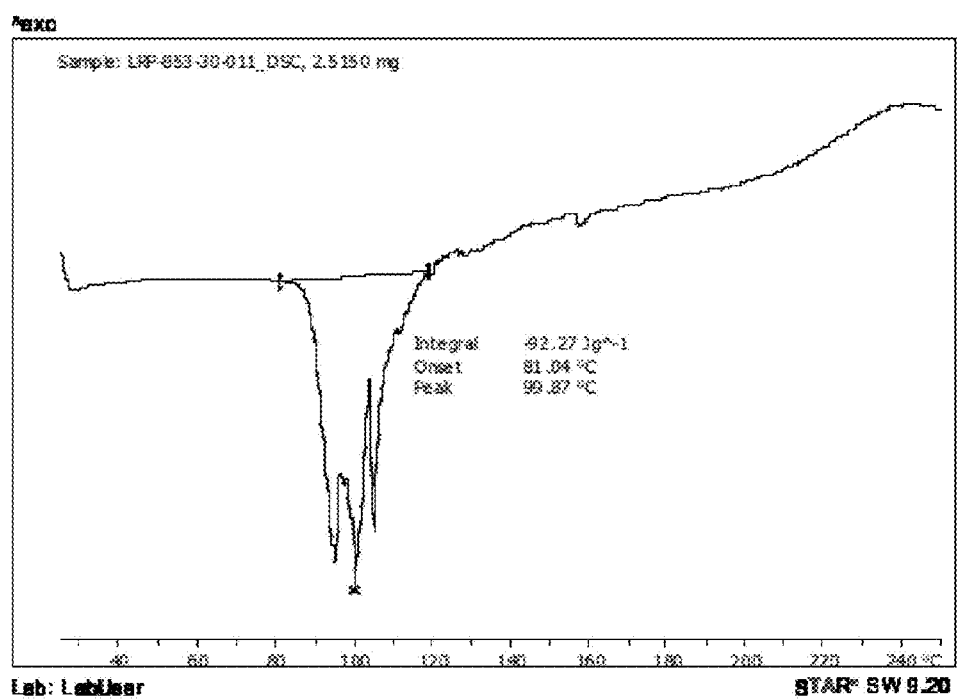
FIG. 91 is a DSC plot of EP-1 trihydrate (x is 3) obtained after treatment with adipic acid.
Figure 92:
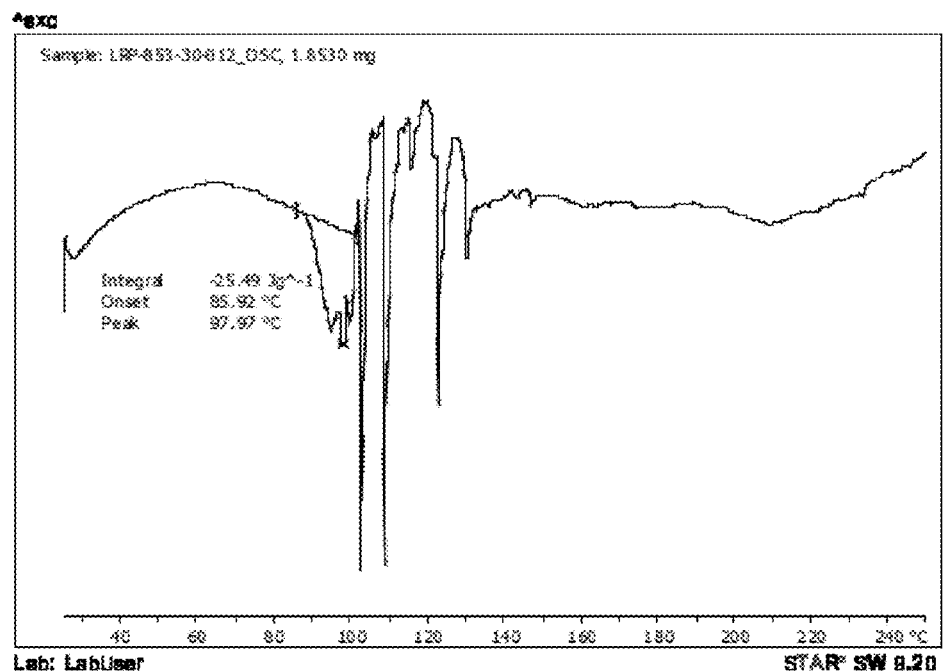
FIG. 92 is a DSC plot of EP-1 trihydrate (x is 3) obtained after treatment with succinic acid.
Figure 93:
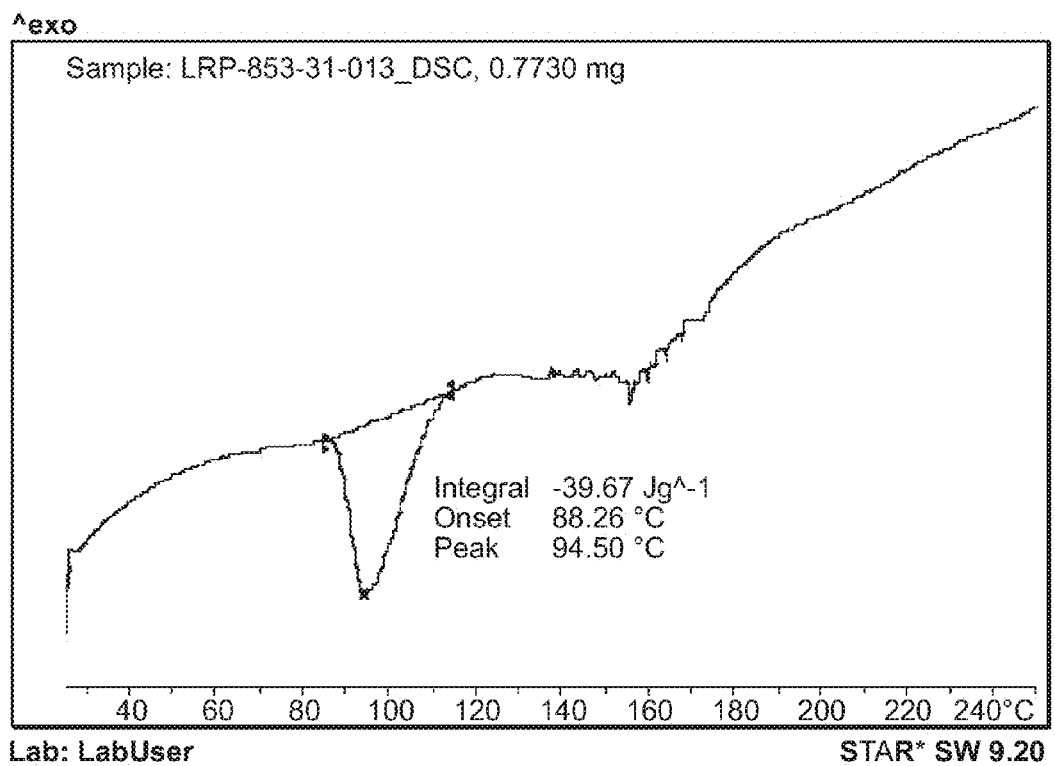
FIG. 93 is a DSC plot of EP-1 trihydrate (x is 3) obtained after treatment with malonic acid.
Figure 94:
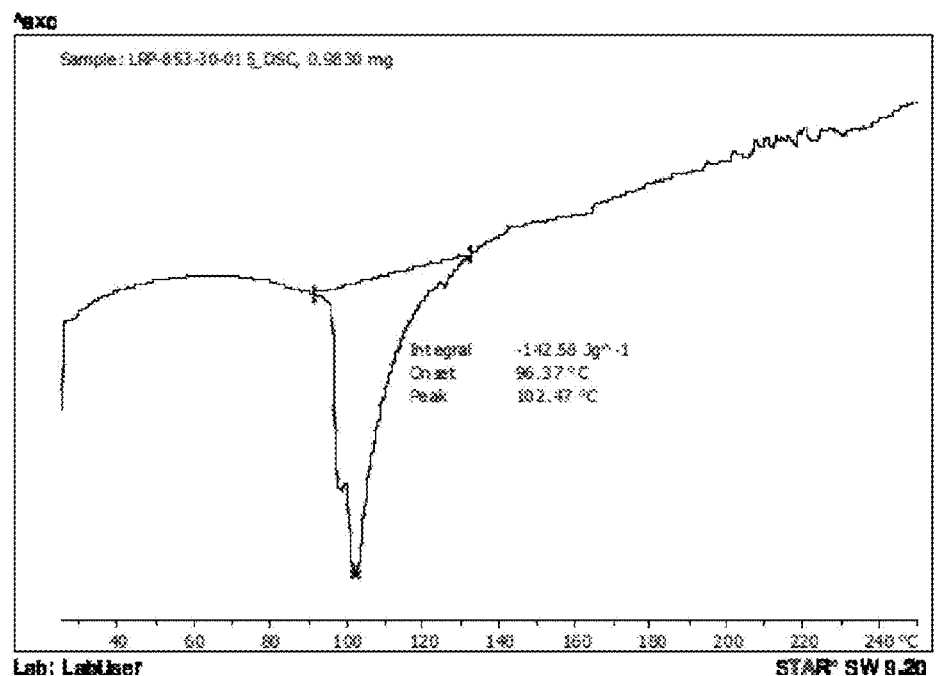
FIG. 94 is a DSC plot of EP-1 trihydrate (x is 3) obtained after treatment with fumaric acid.
Figure 95:
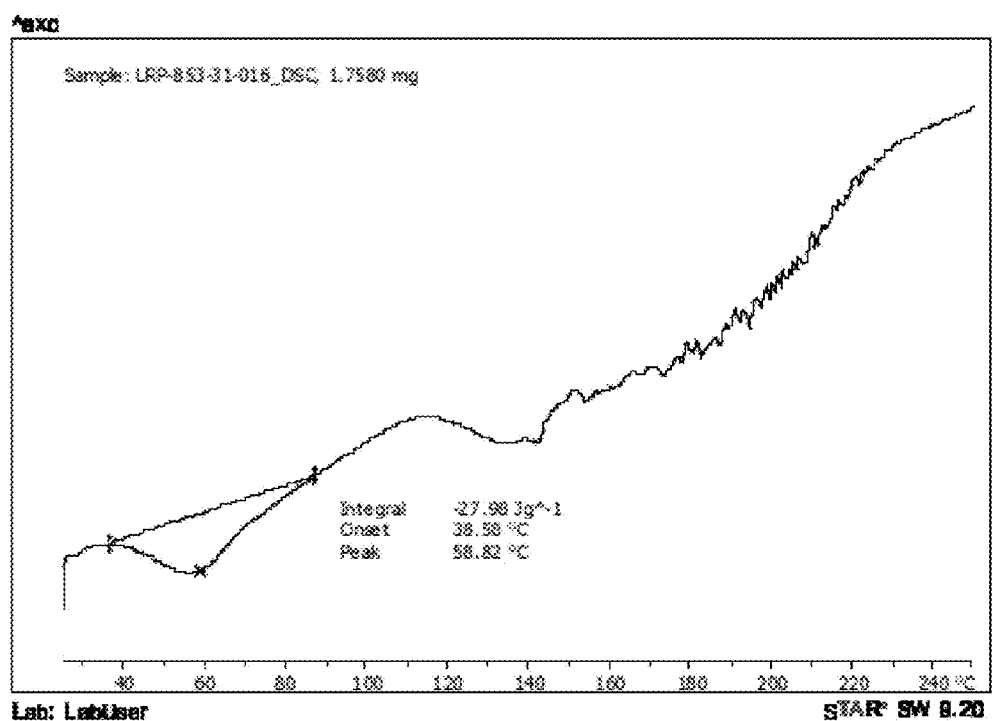
FIG. 95 is a DSC plot of EP-1 trihydrate (x is 3) obtained after treatment with galactaric acid.
Figure 96:
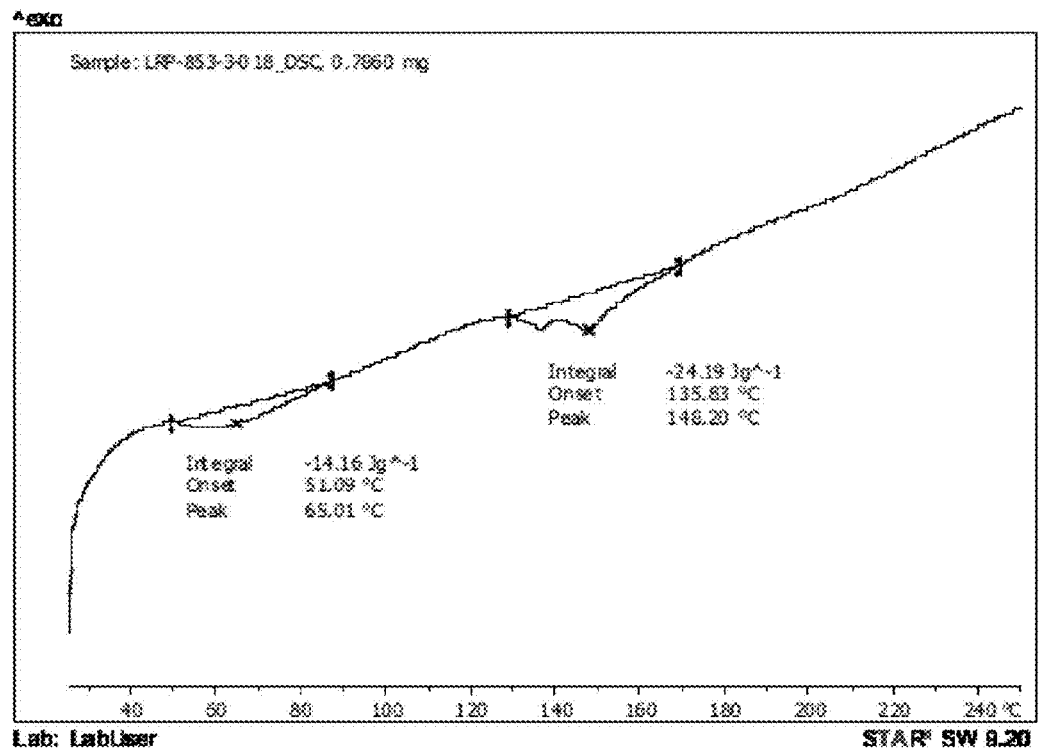
FIG. 96 is a DSC plot of EP-1 trihydrate (x is 3) obtained after treatment with D-glucuronic acid.
Figure 97:
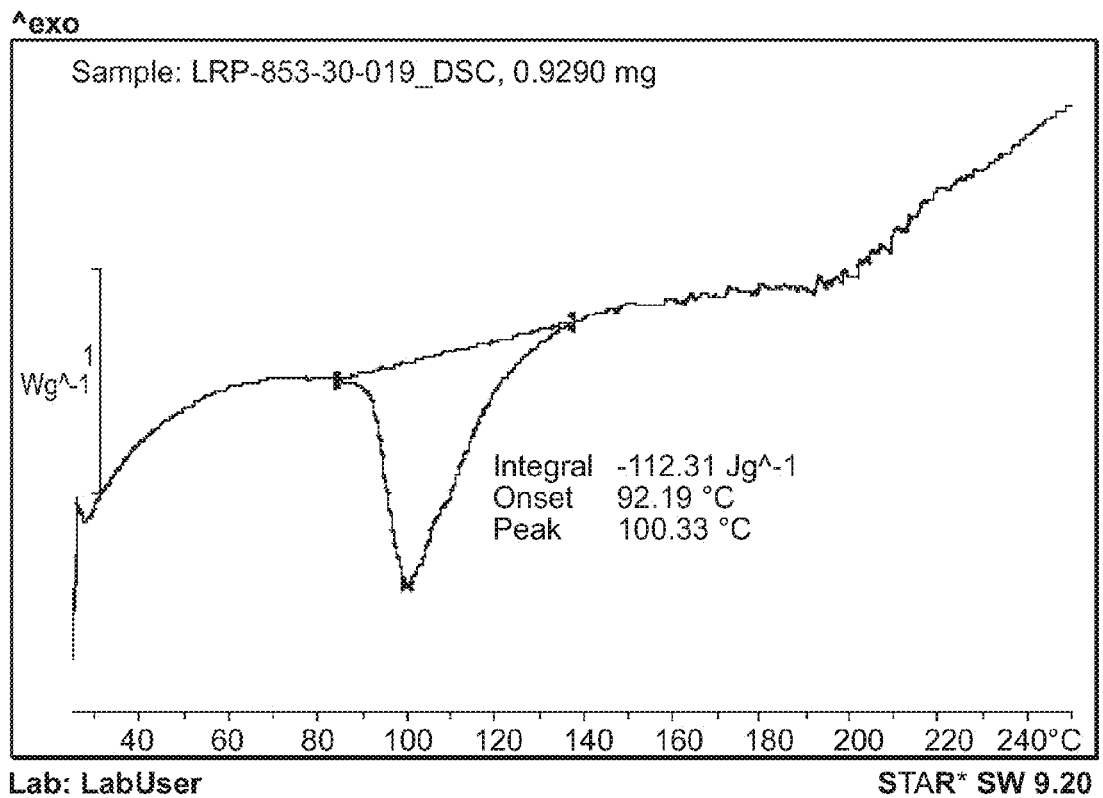
FIG. 97 is a DSC plot of EP-1 trihydrate (x is 3) obtained after treatment with lactobionic acid.
Figure 98:
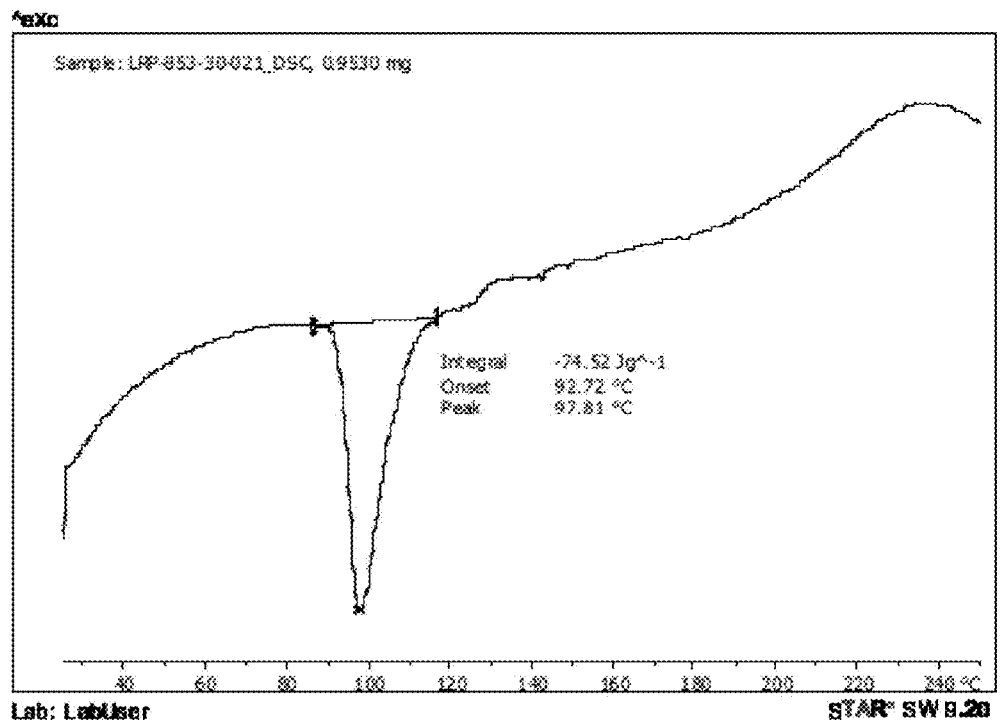
FIG. 98 is a DSC plot of EP-1 trihydrate (x is 3) obtained after treatment with L-malic acid.
Figure 99:
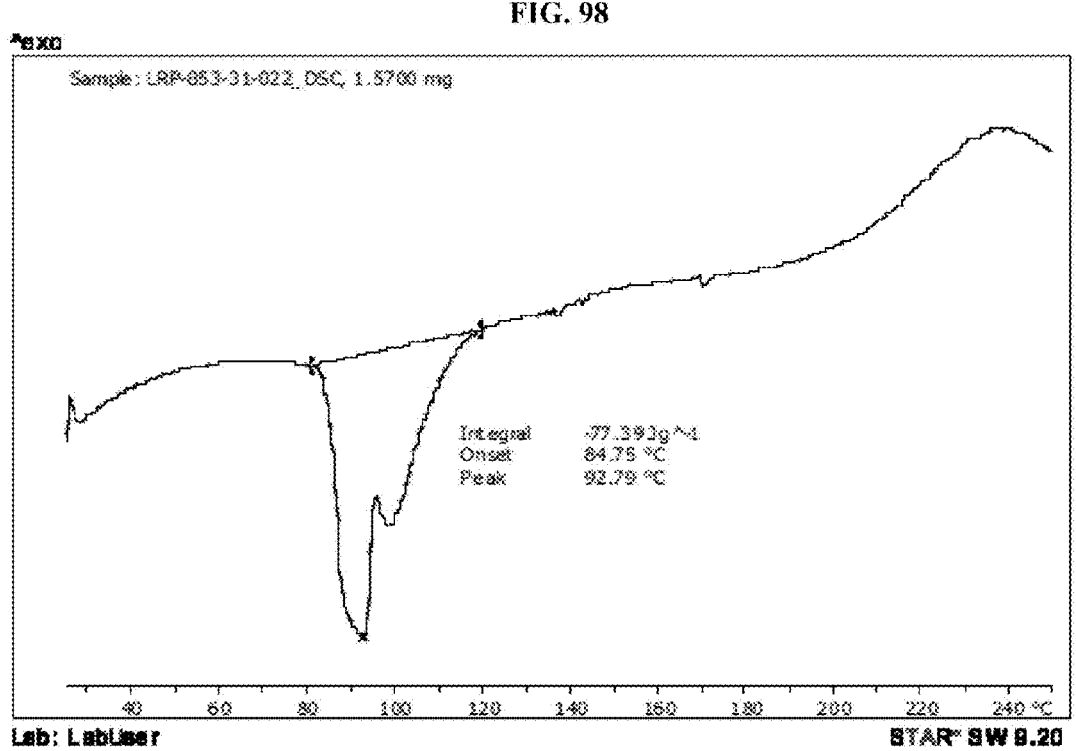
FIG. 99 is a DSC plot of EP-1 trihydrate (x is 3) obtained after treatment with hippuric acid.
Figure 100:
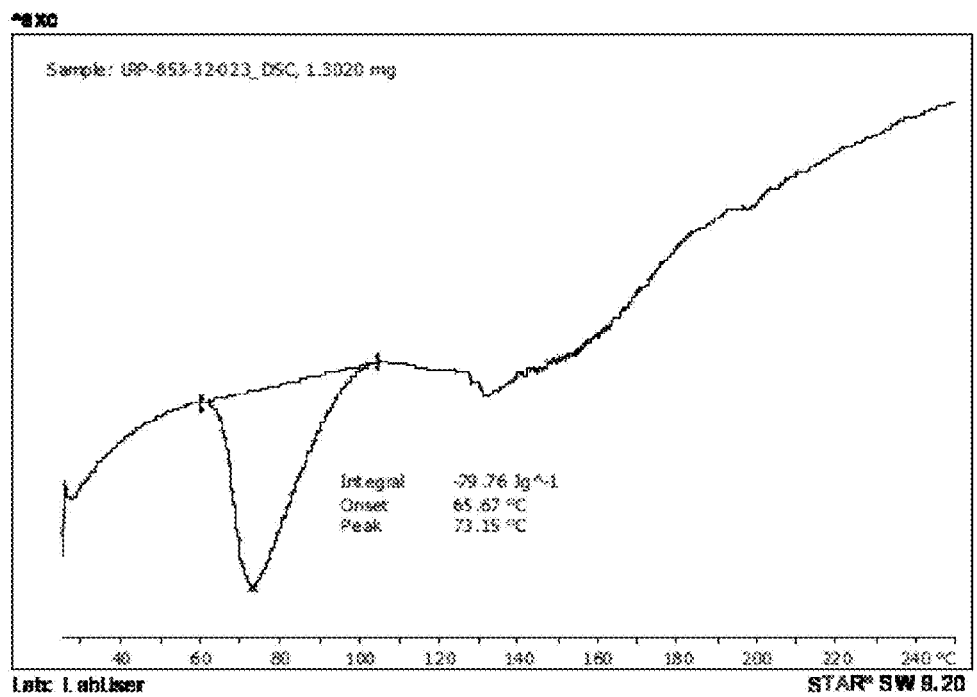
FIG. 100 is a DSC plot of EP-1 trihydrate (x is 3) obtained after treatment with D-gluconic acid.
Figure 101:
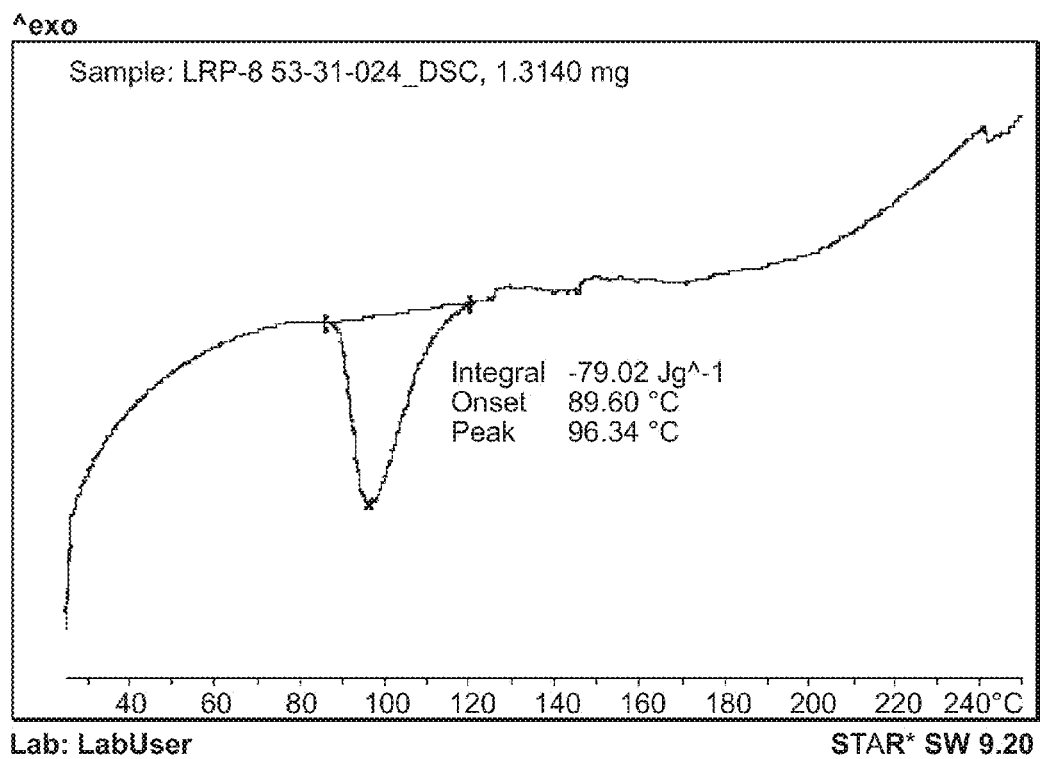
FIG. 101 is a DSC plot of EP-1 trihydrate (x is 3) obtained after treatment with lactic acid.
Figure 102:
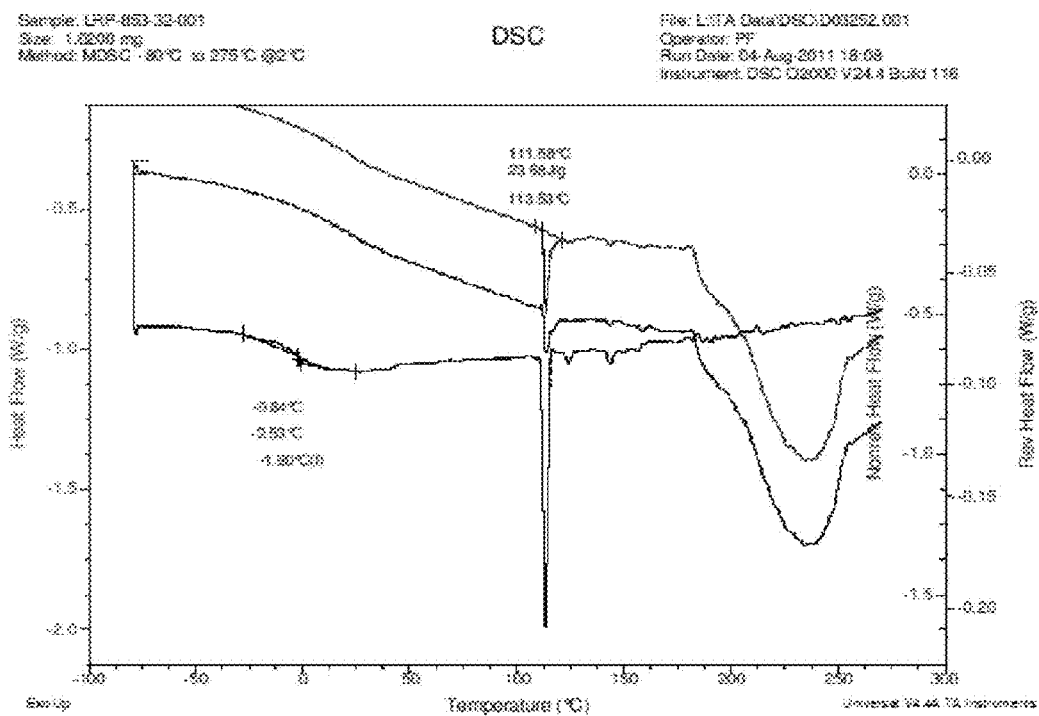
FIG. 102 is a mDSC plot of EP-1 trihydrate (x is 3) obtained after treatment with HCl.
Figure 103:
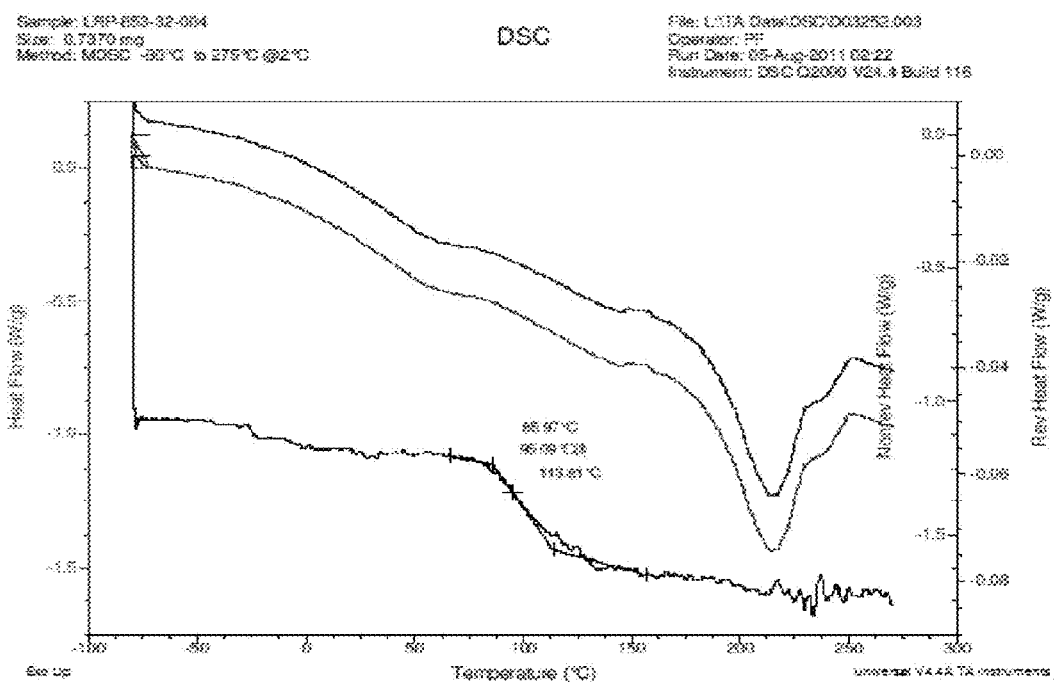
FIG. 103 is a mDSC plot of EP-1 trihydrate (x is 3) obtained after treatment with p-toluene sulfonic acid.
Figure 104:
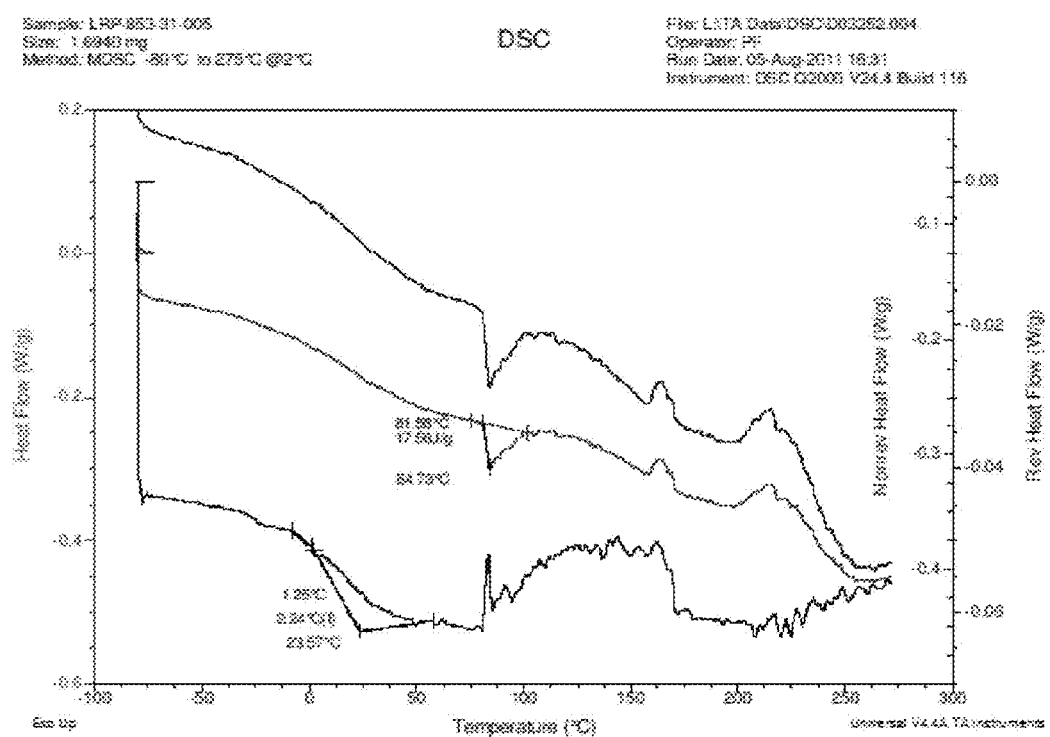
FIG. 104 is a mDSC plot of EP-1 trihydrate (x is 3) obtained after treatment with methane sulfonic acid.
Figure 105:
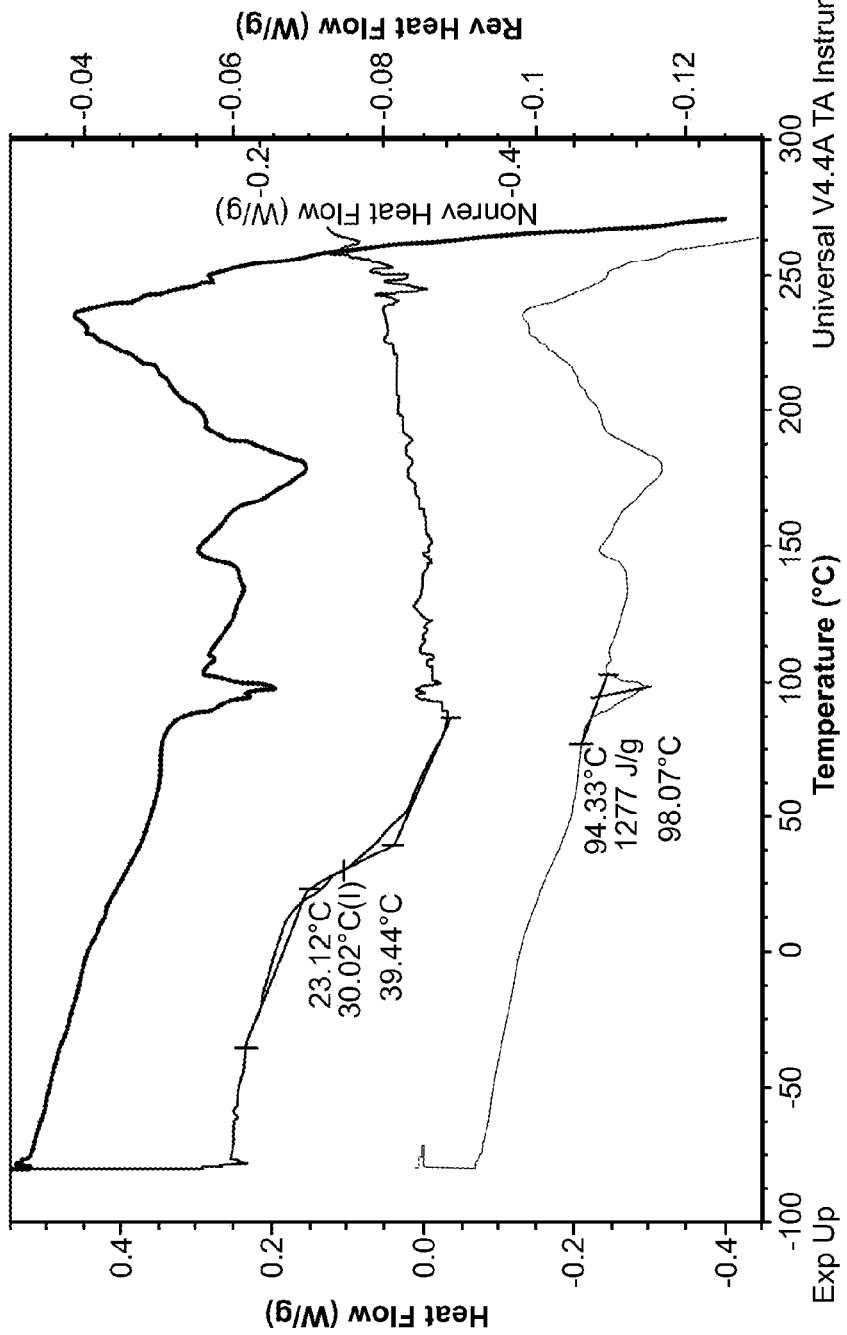
FIG. 105 is a mDSC plot of EP-1 trihydrate (x is 3) obtained after treatment with maleic acid.
Figure 106:
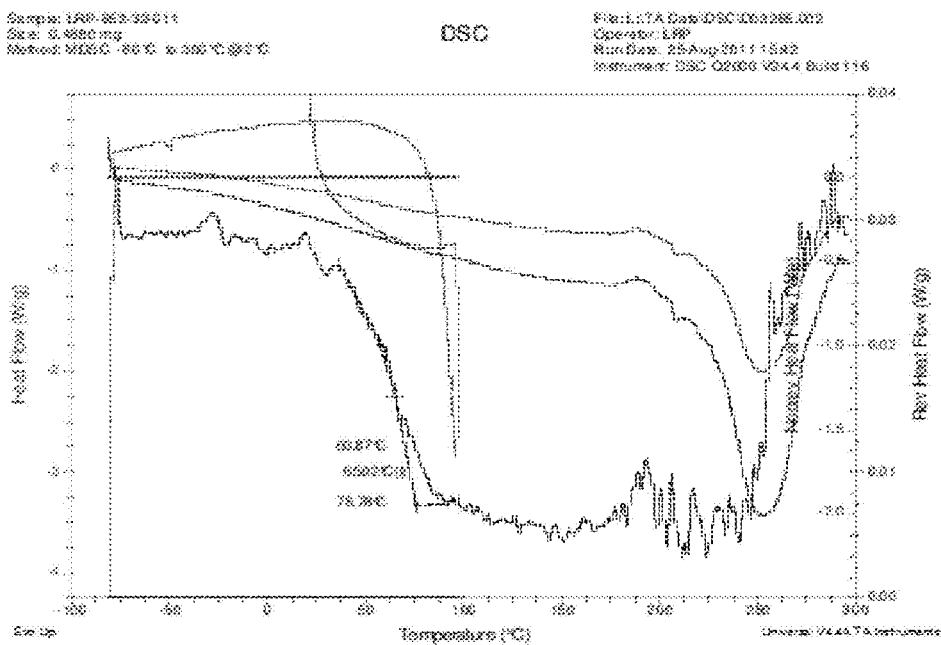
FIG. 106 is a mDSC plot of EP-1 trihydrate (x is 3) obtained after treatment with adipic acid.
Figure 107:
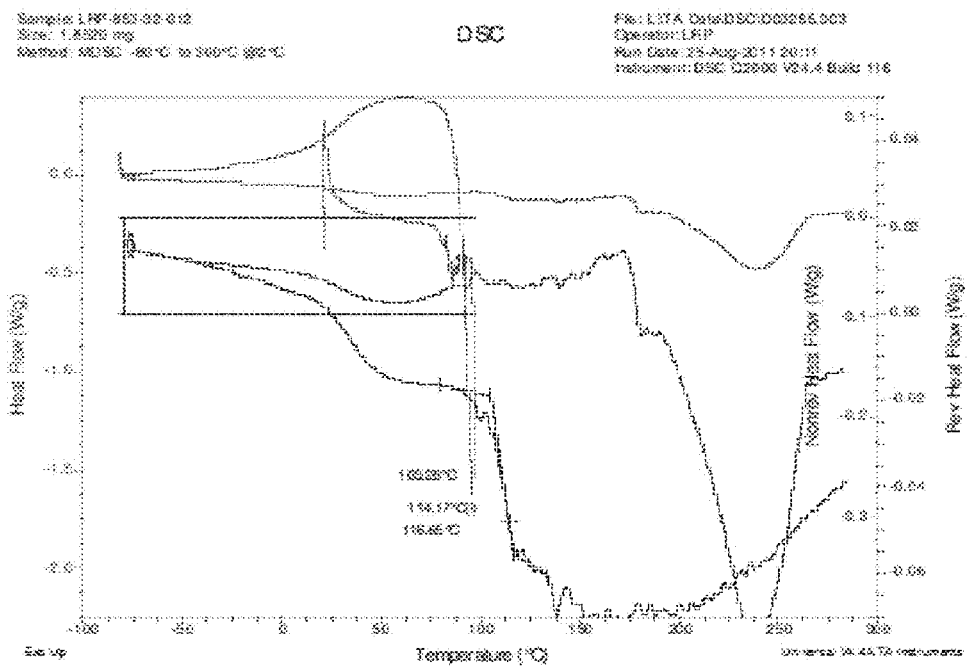
FIG. 107 is a mDSC plot of EP-1 trihydrate (x is 3) obtained after treatment with succinic acid.
Figure 108:
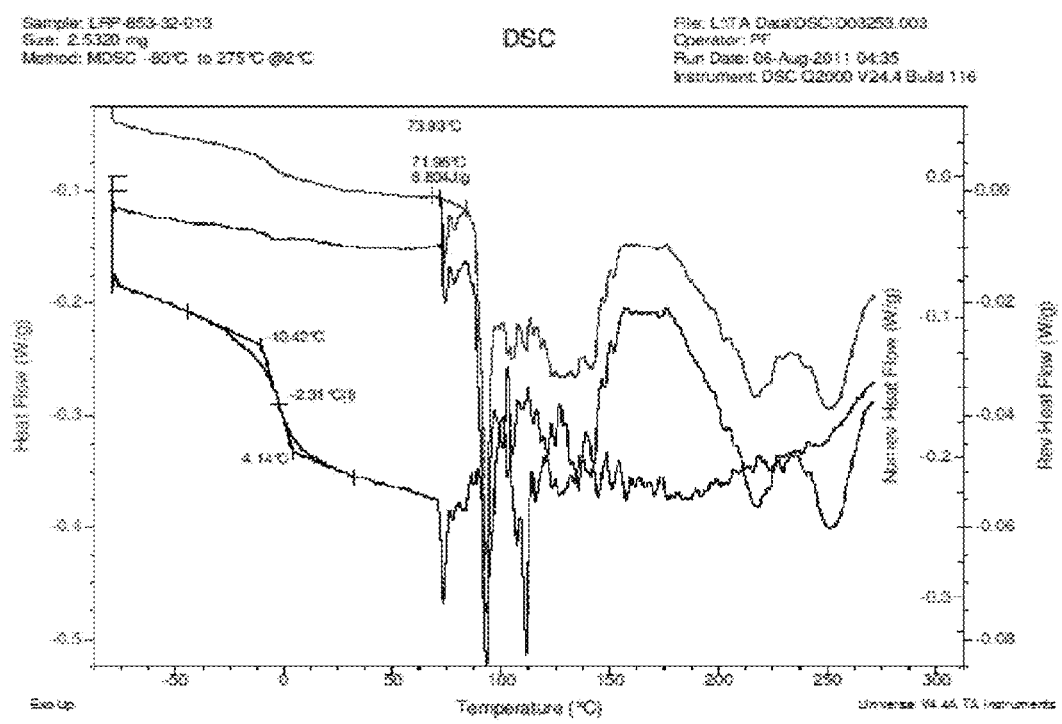
FIG. 108 is a mDSC plot of EP-1 trihydrate (x is 3) obtained after treatment with malonic acid.
Figure 109:
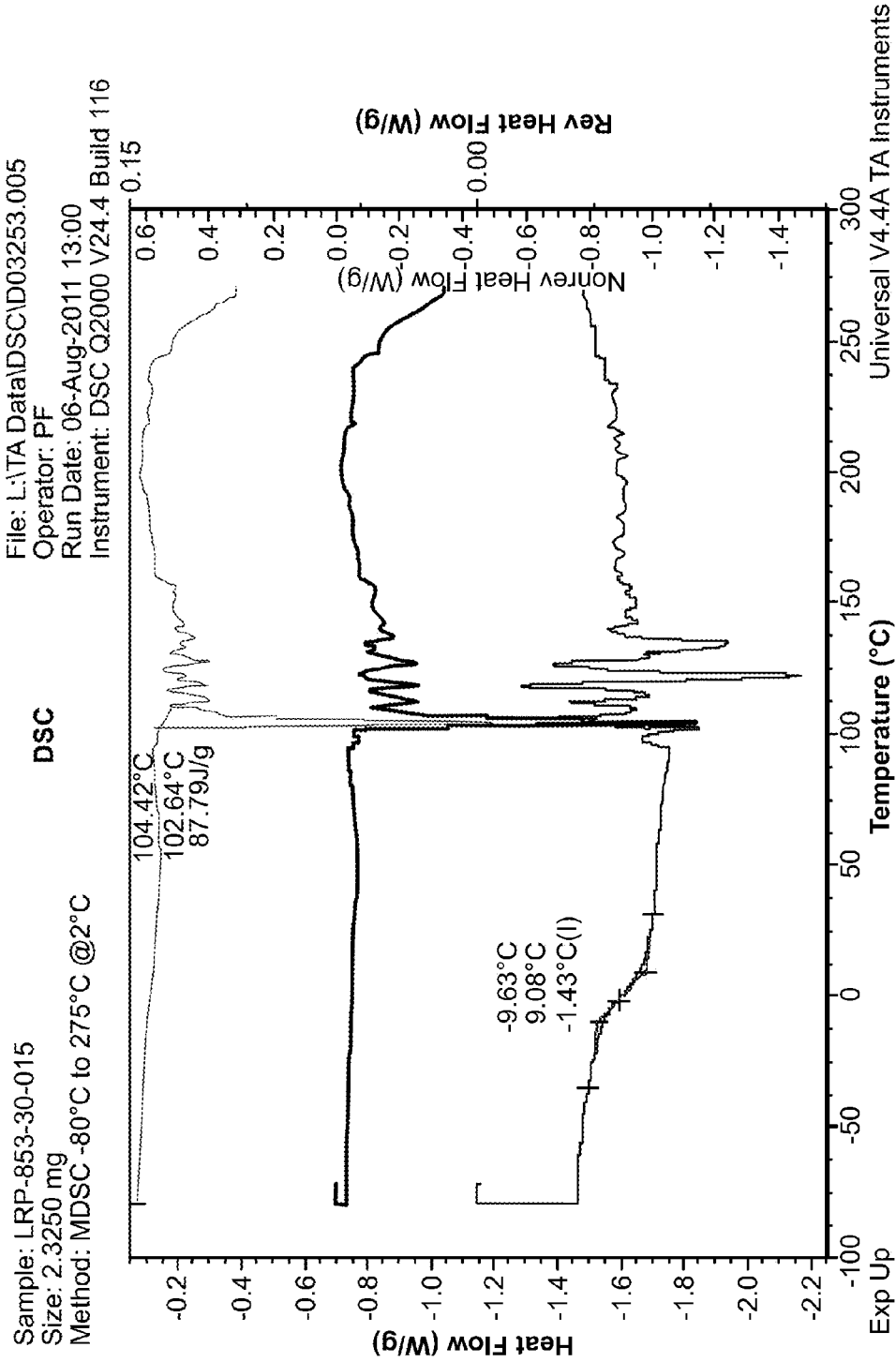
FIG. 109 is a mDSC plot of EP-1 trihydrate (x is 3) obtained after treatment with fumaric acid.
Figure 110:
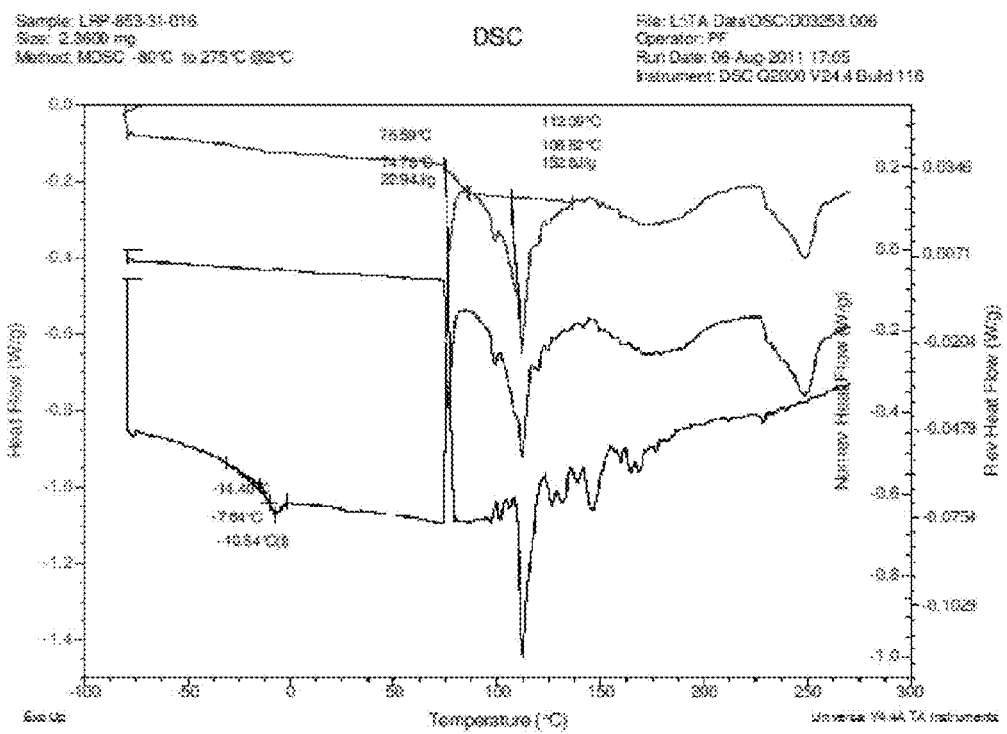
FIG. 110 is a mDSC plot of EP-1 trihydrate (x is 3) obtained after treatment with galactaric acid.
Figure 111:
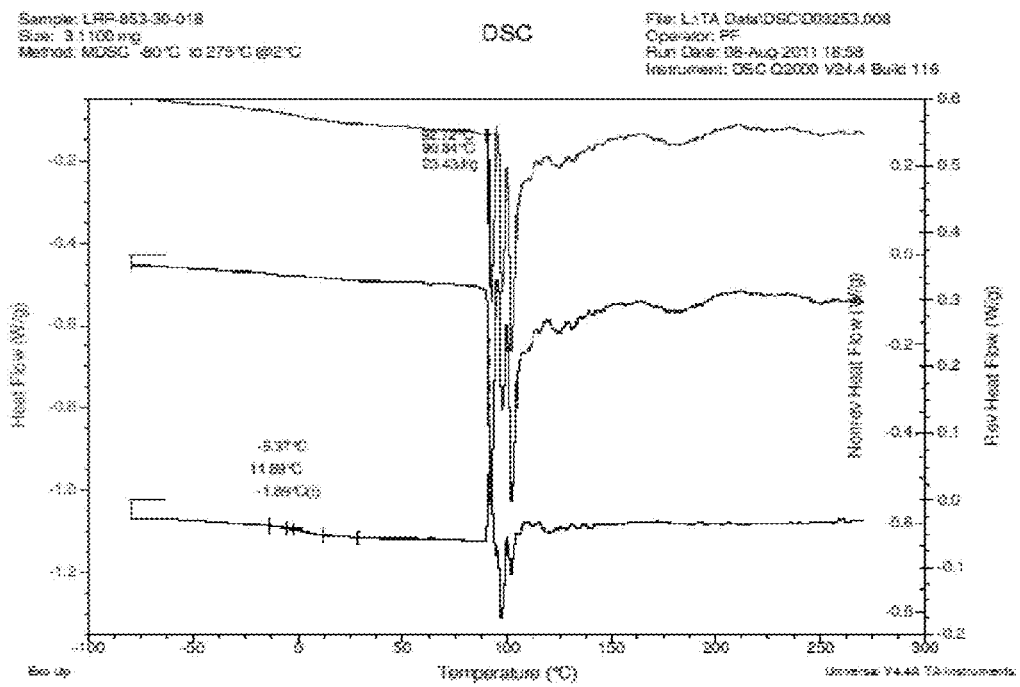
FIG. 111 is a mDSC plot of EP-1 trihydrate (x is 3) obtained after treatment with D-glucuronic acid.
Figure 112:
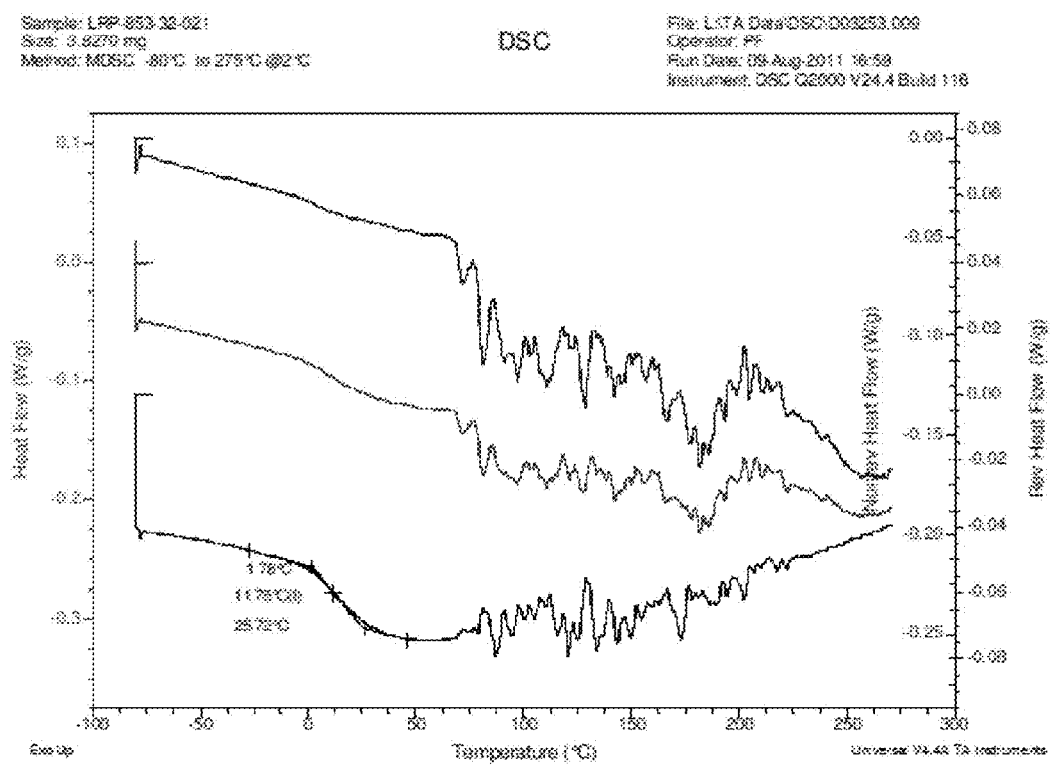
FIG. 112 is a mDSC plot of EP-1 trihydrate (x is 3) obtained after treatment with L-malic acid.
Figure 113:
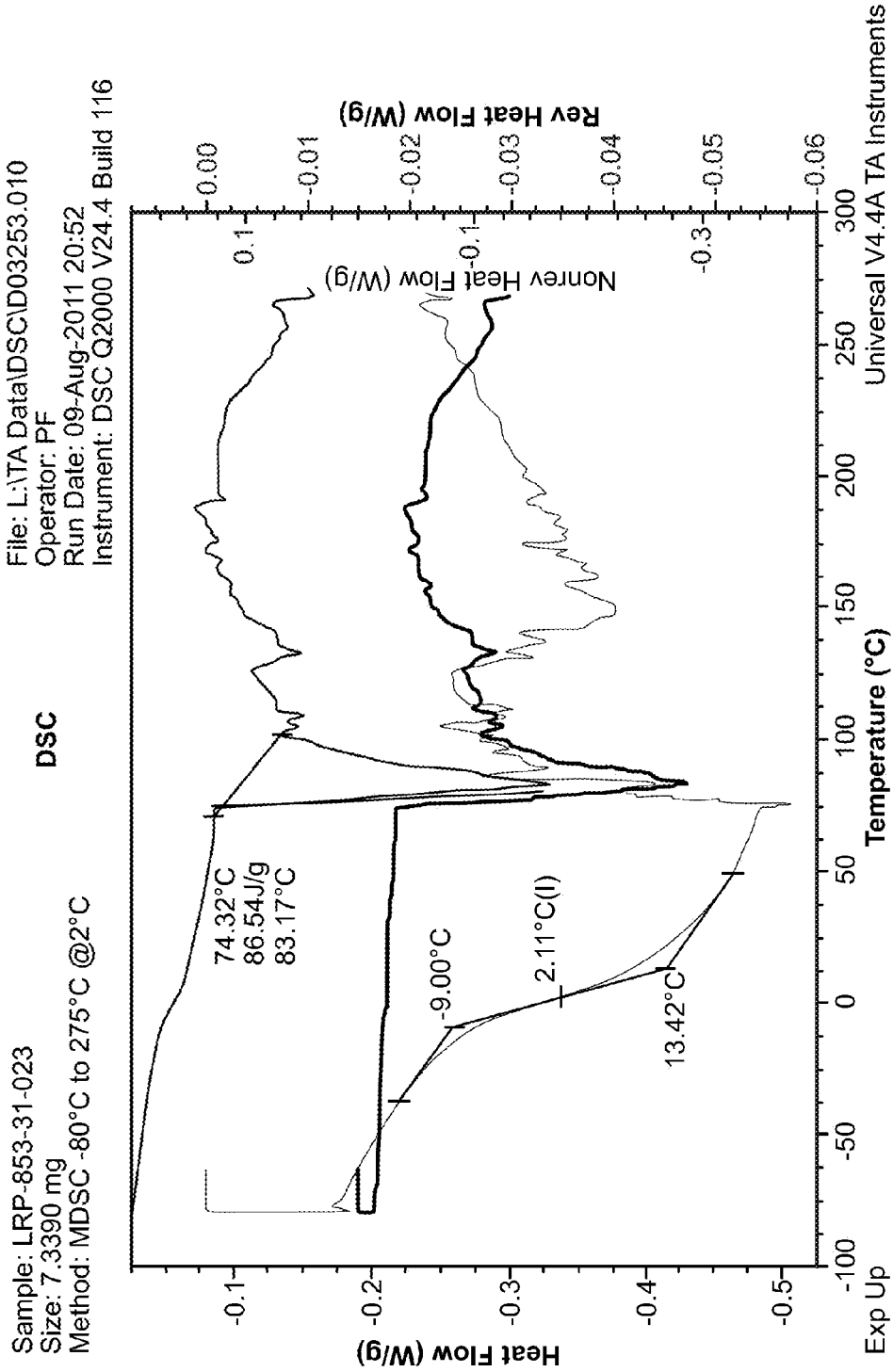
FIG. 113 is a mDSC plot of EP-1 trihydrate (x is 3) obtained after treatment with gluconic acid.
Figure 114:
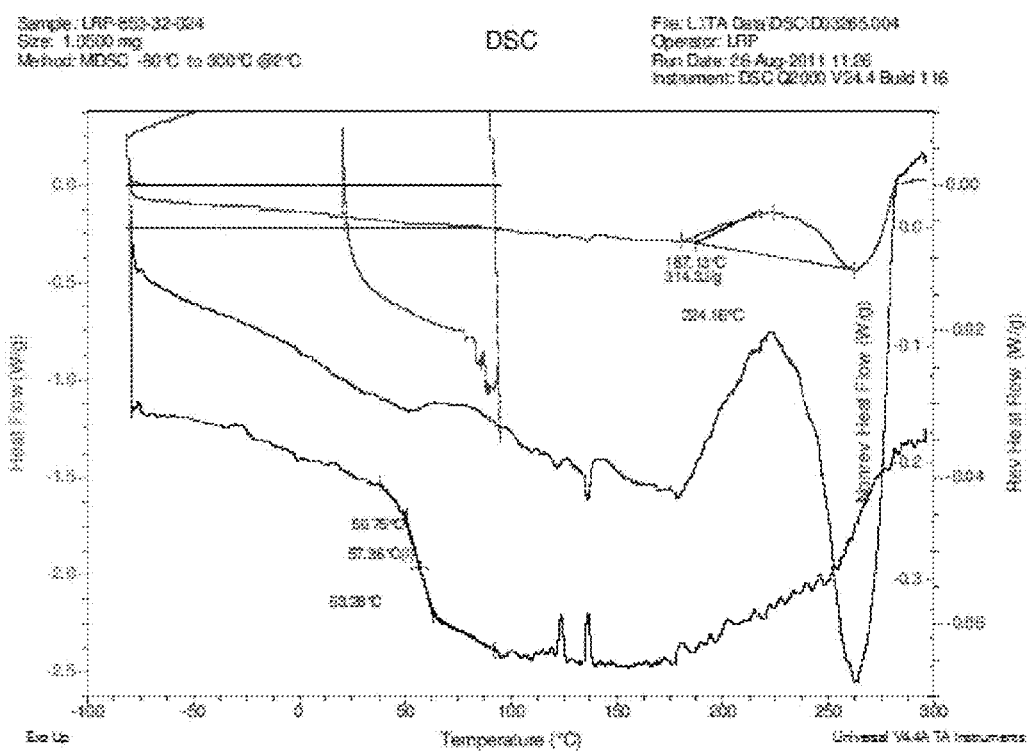
FIG. 114 is a mDSC plot of EP-1 trihydrate (x is 3) obtained after treatment with lactic acid.
Figure 115:
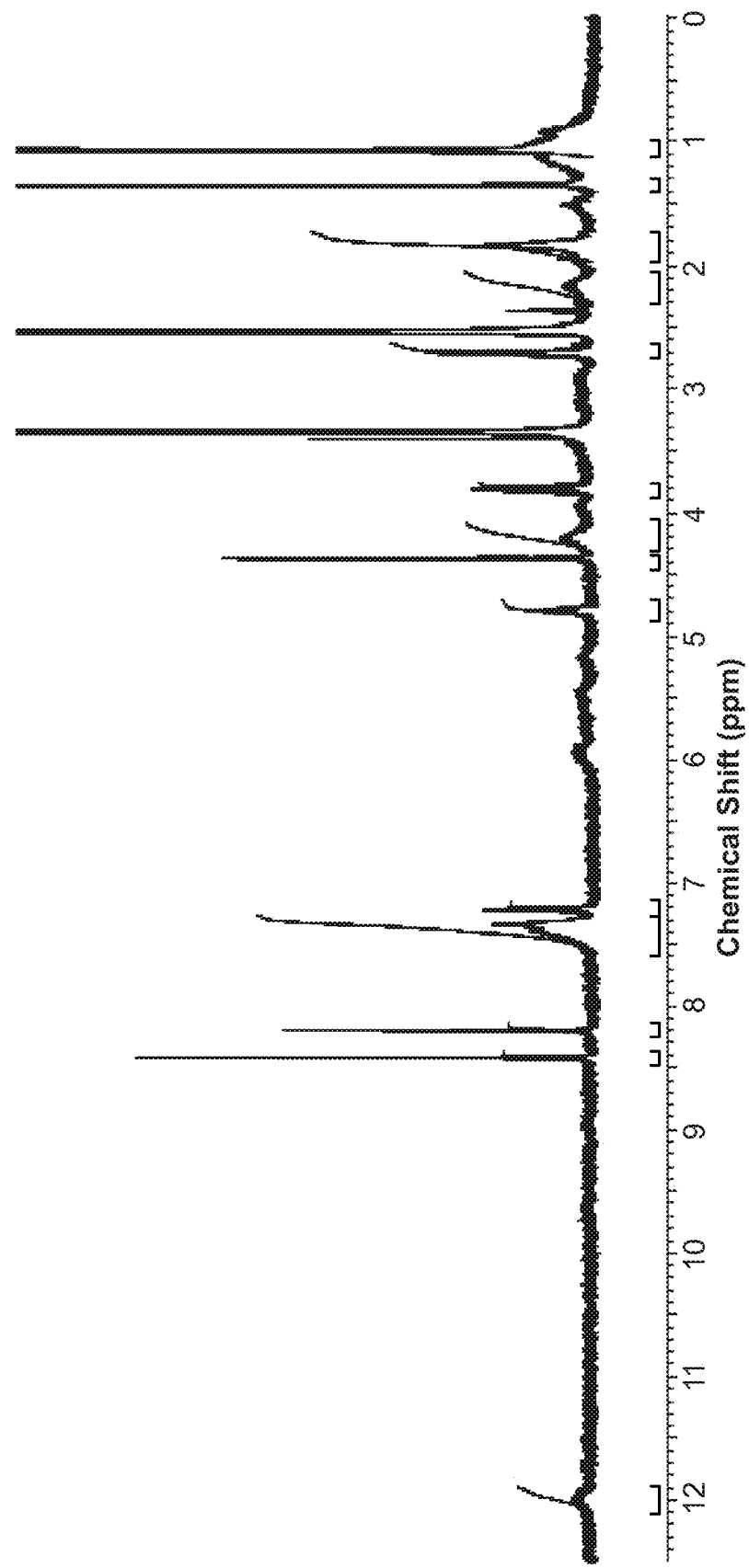
FIG. 115 is a $^1$H NMR spectrum of EP-1 trihydrate (x is 3) $H_2SO_4$ hemi-salt.
Figure 116:
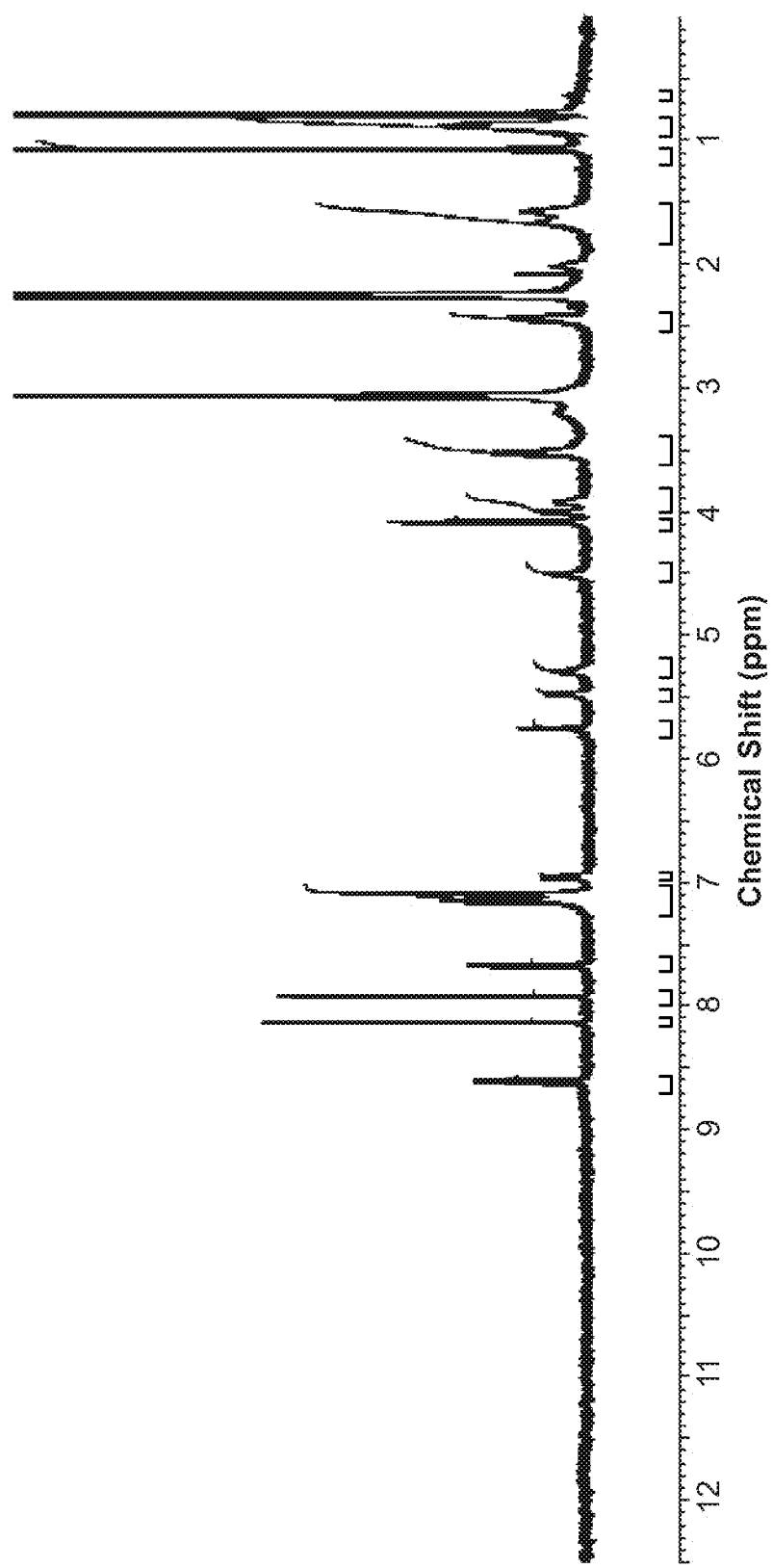
Figure 117:
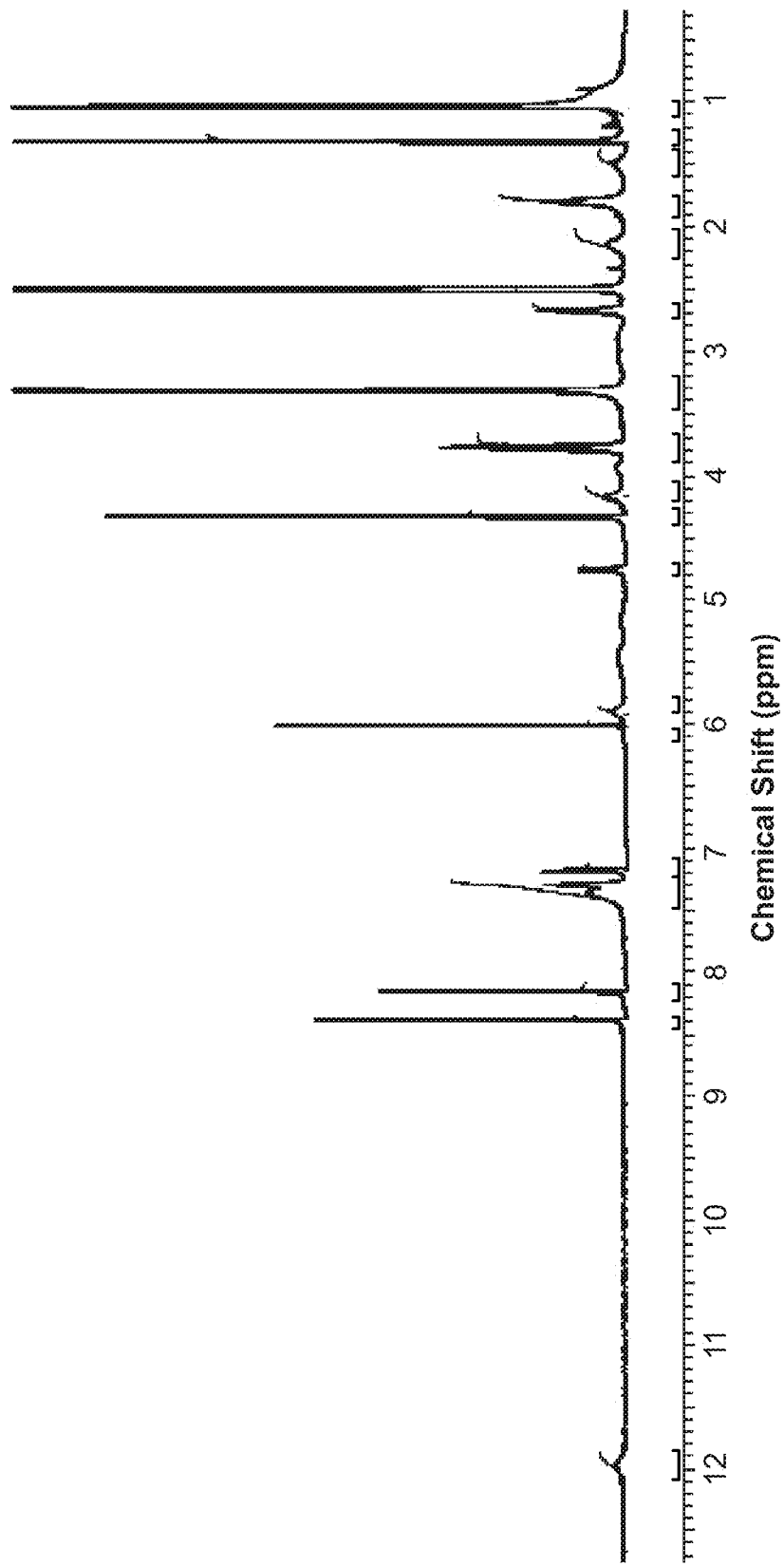
Figure 118:
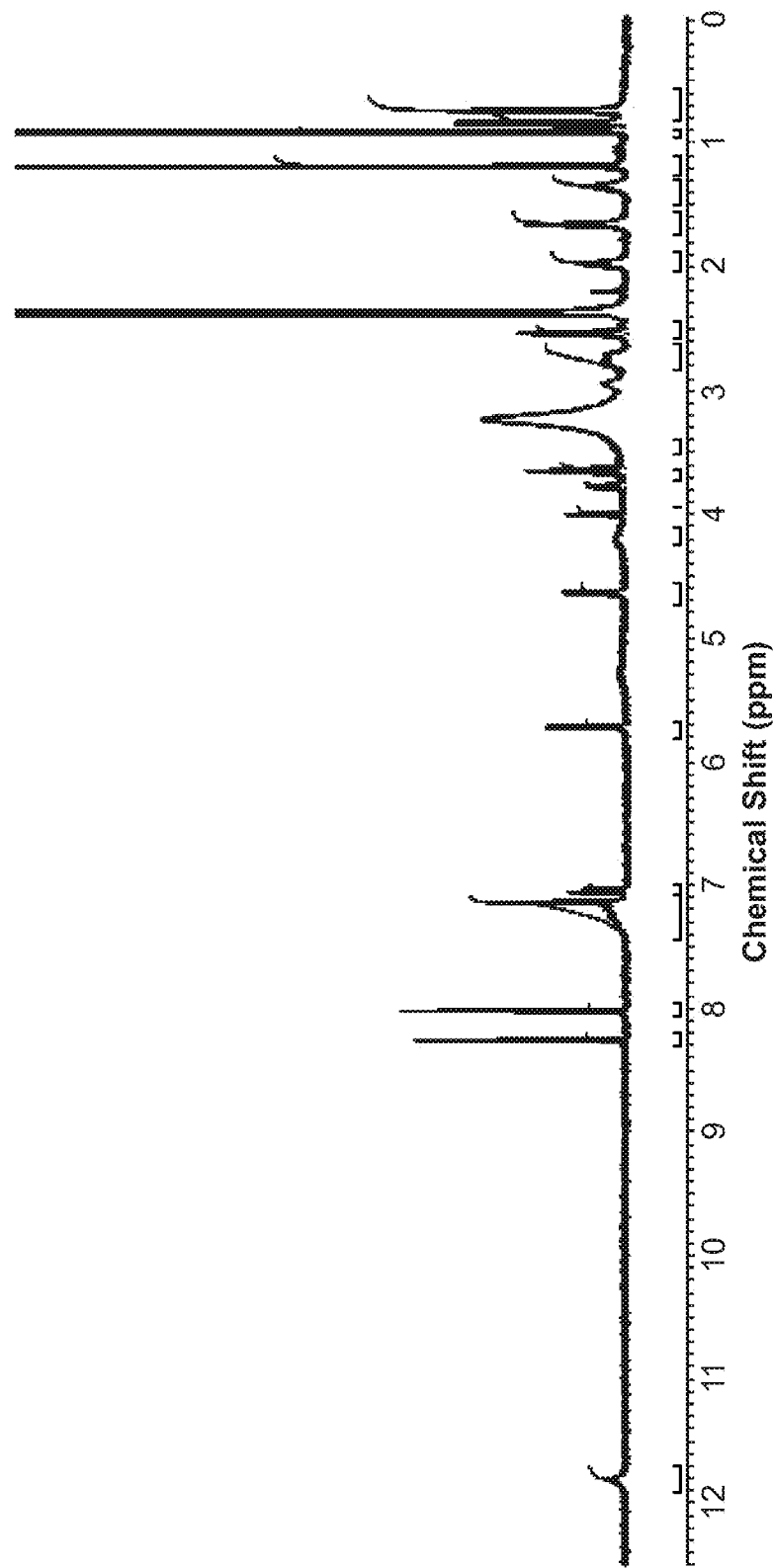
Figure 119:
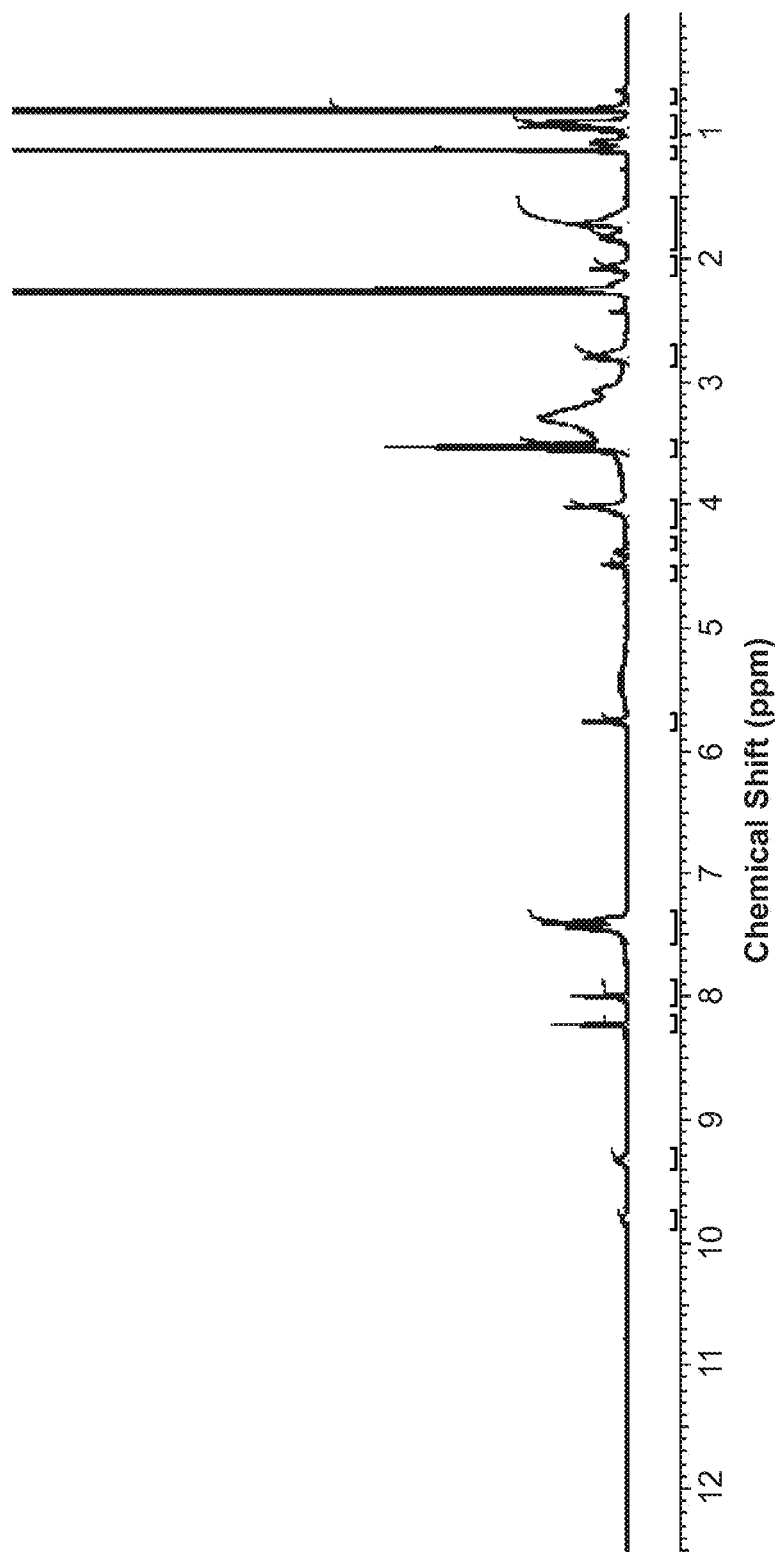
Figure 120:
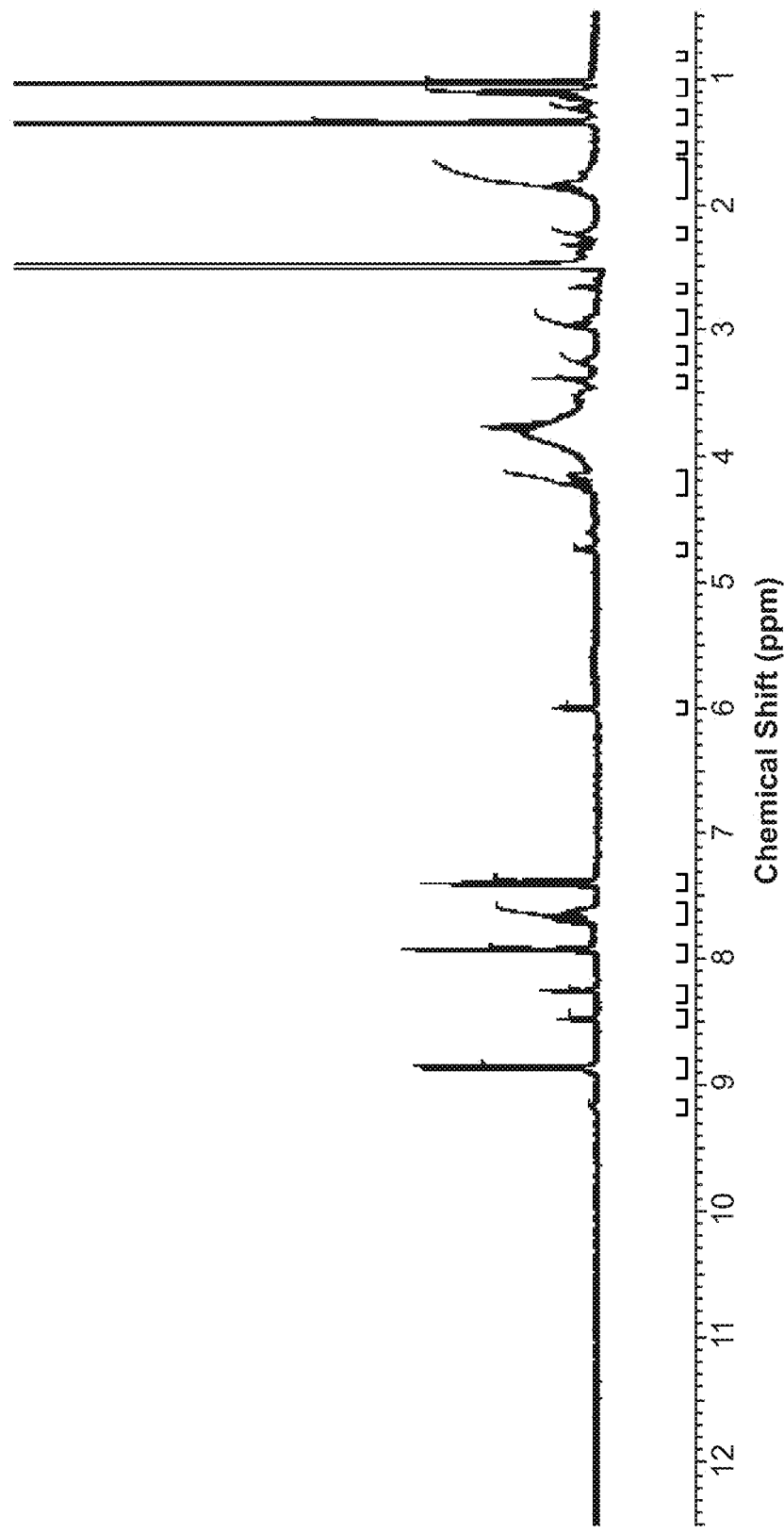
Figure 121:
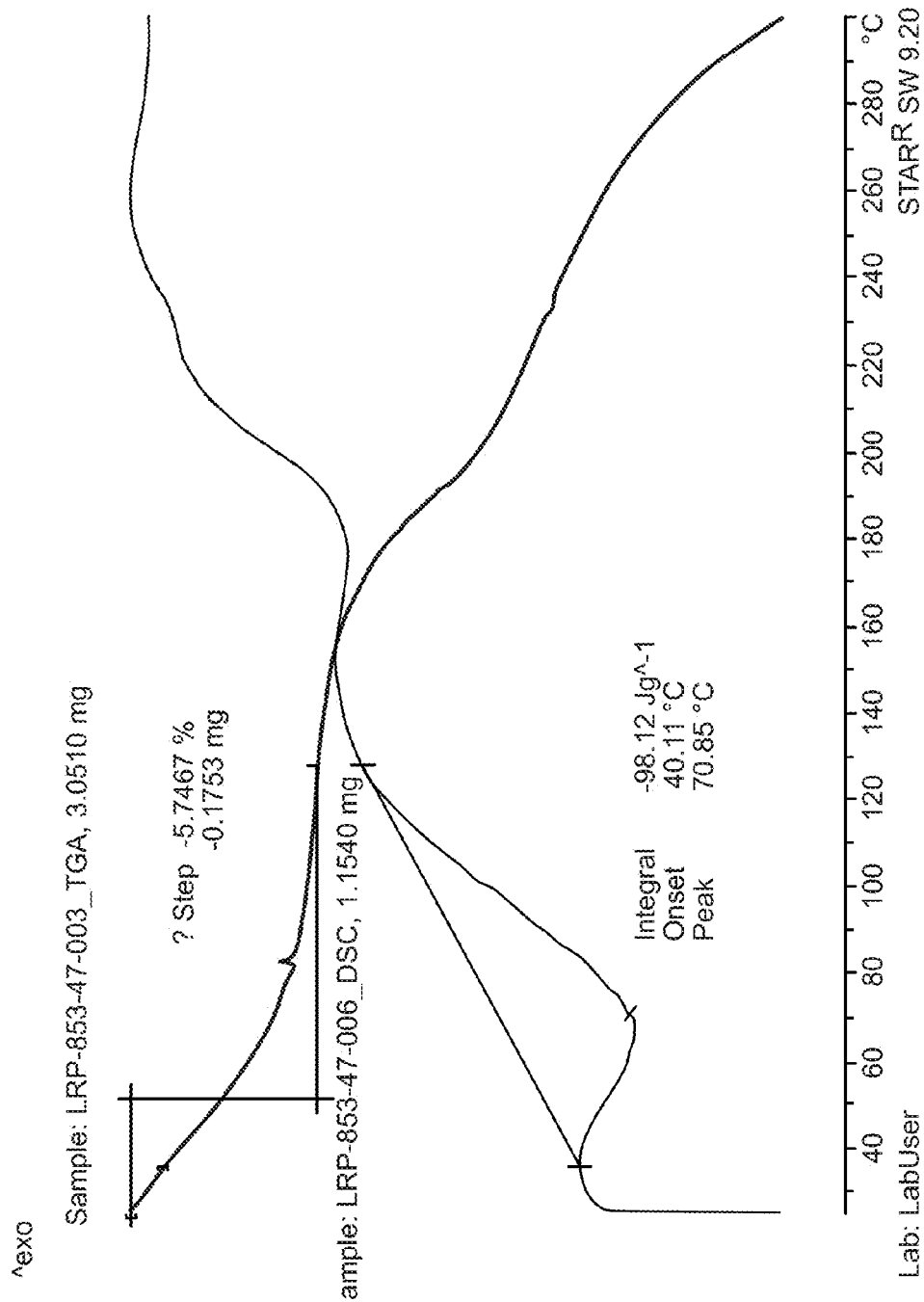
Figure 122:
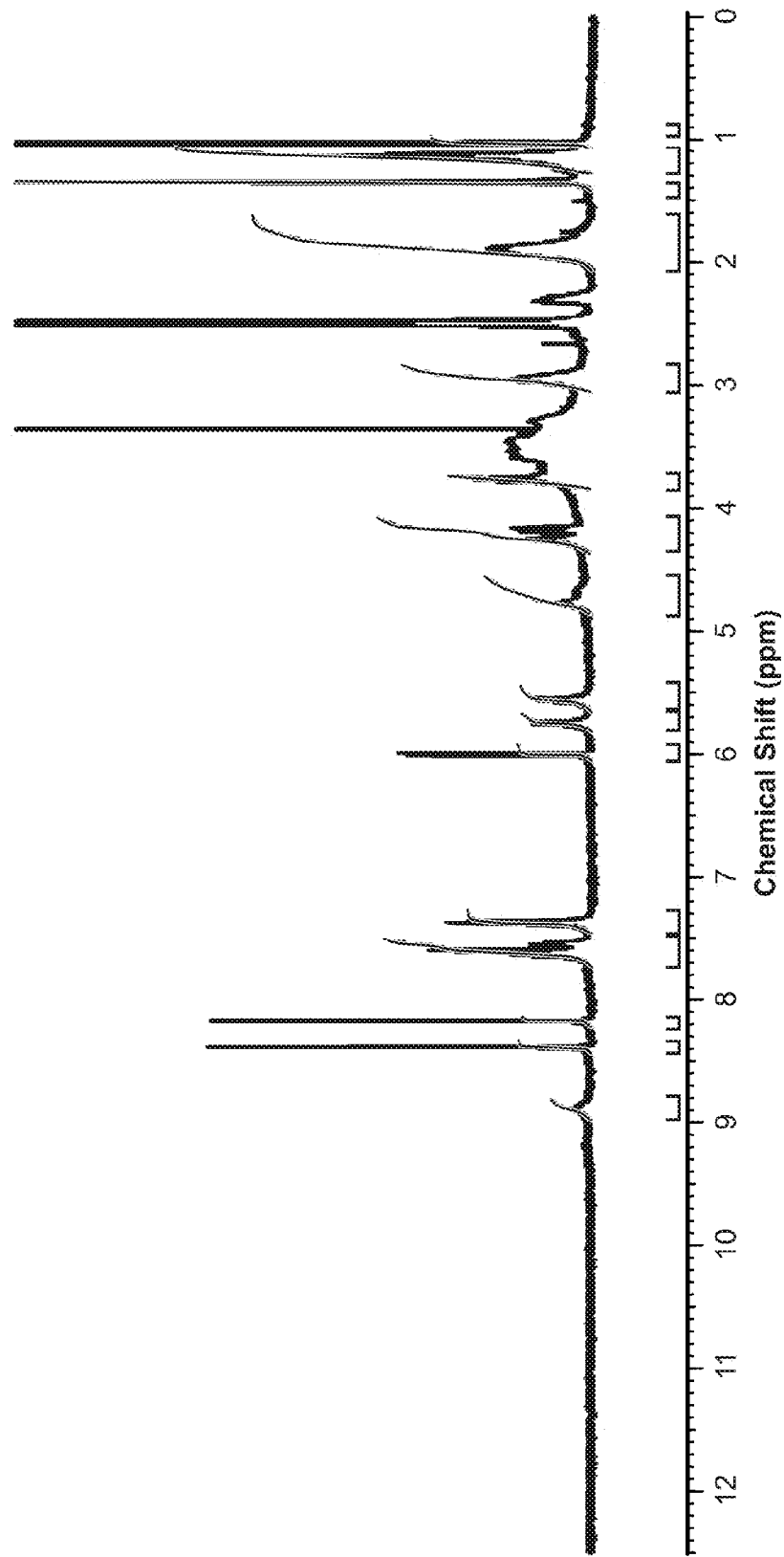
Figure 123:
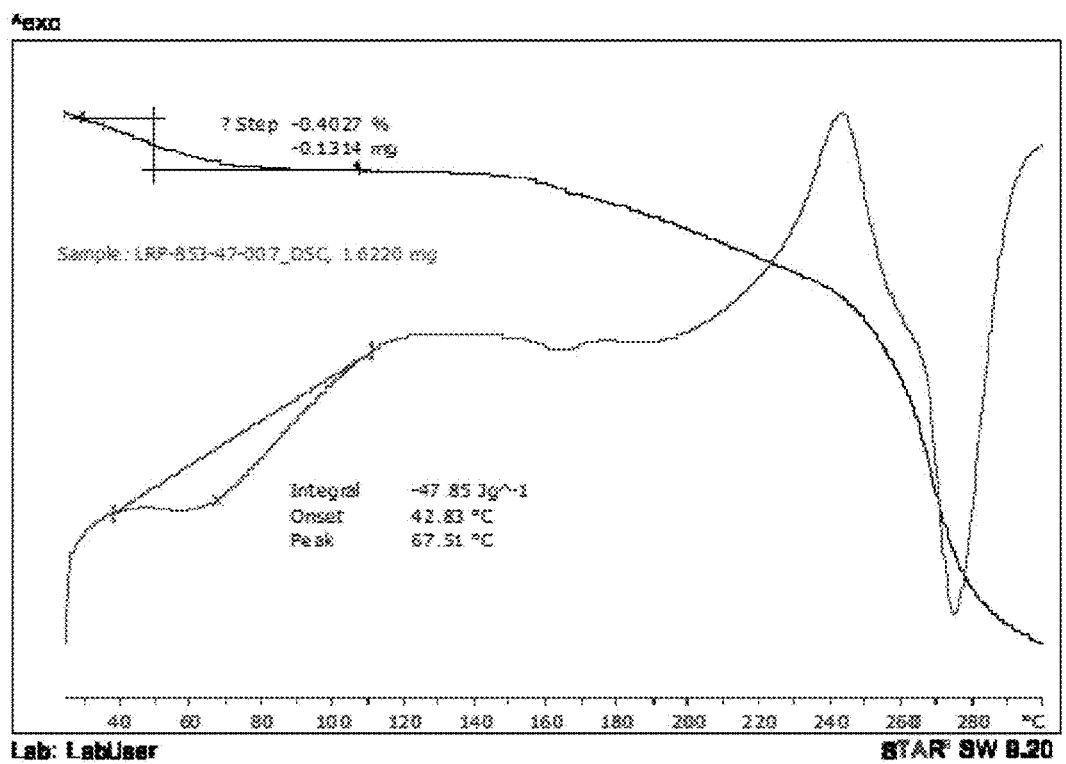
Figure 124:
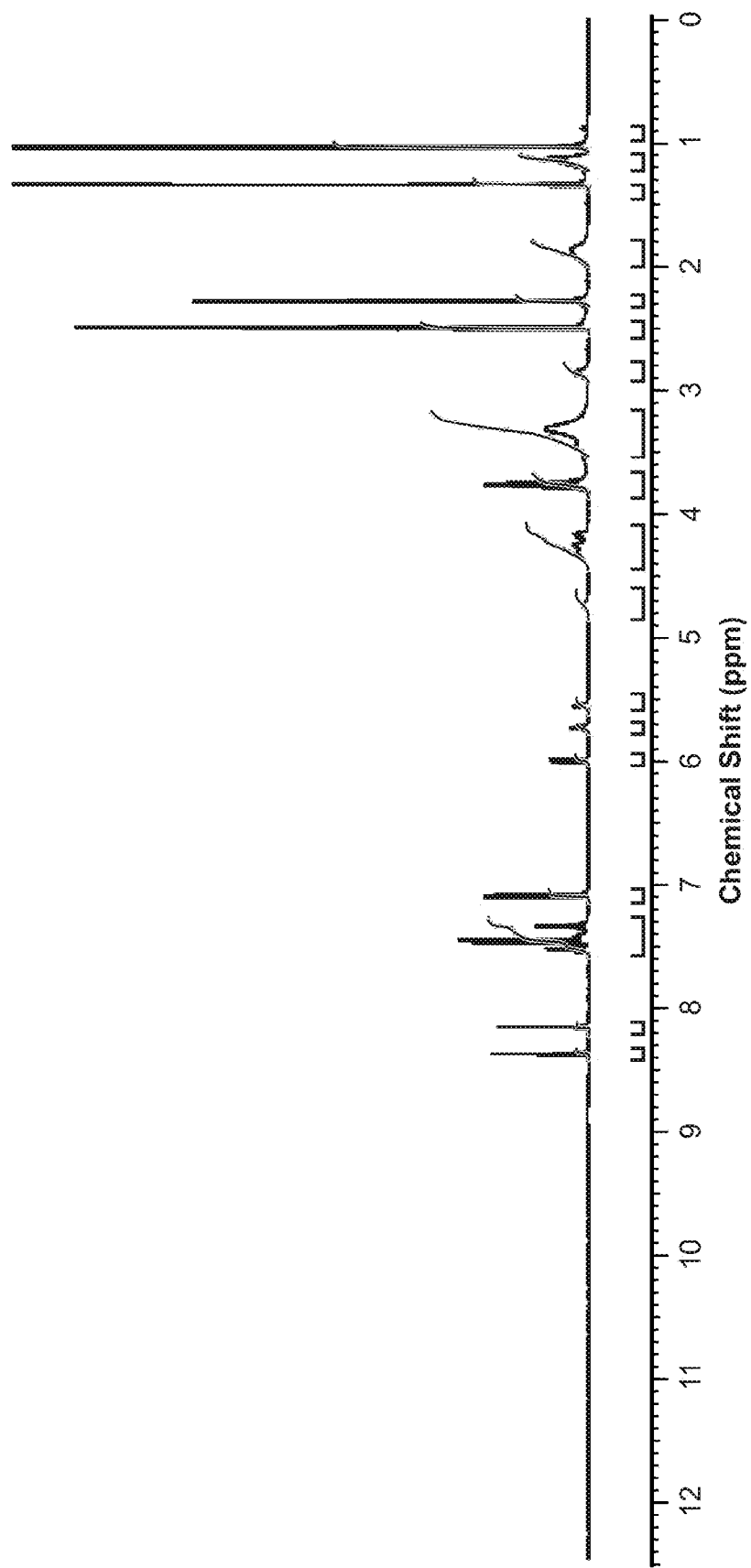
Figure 125:
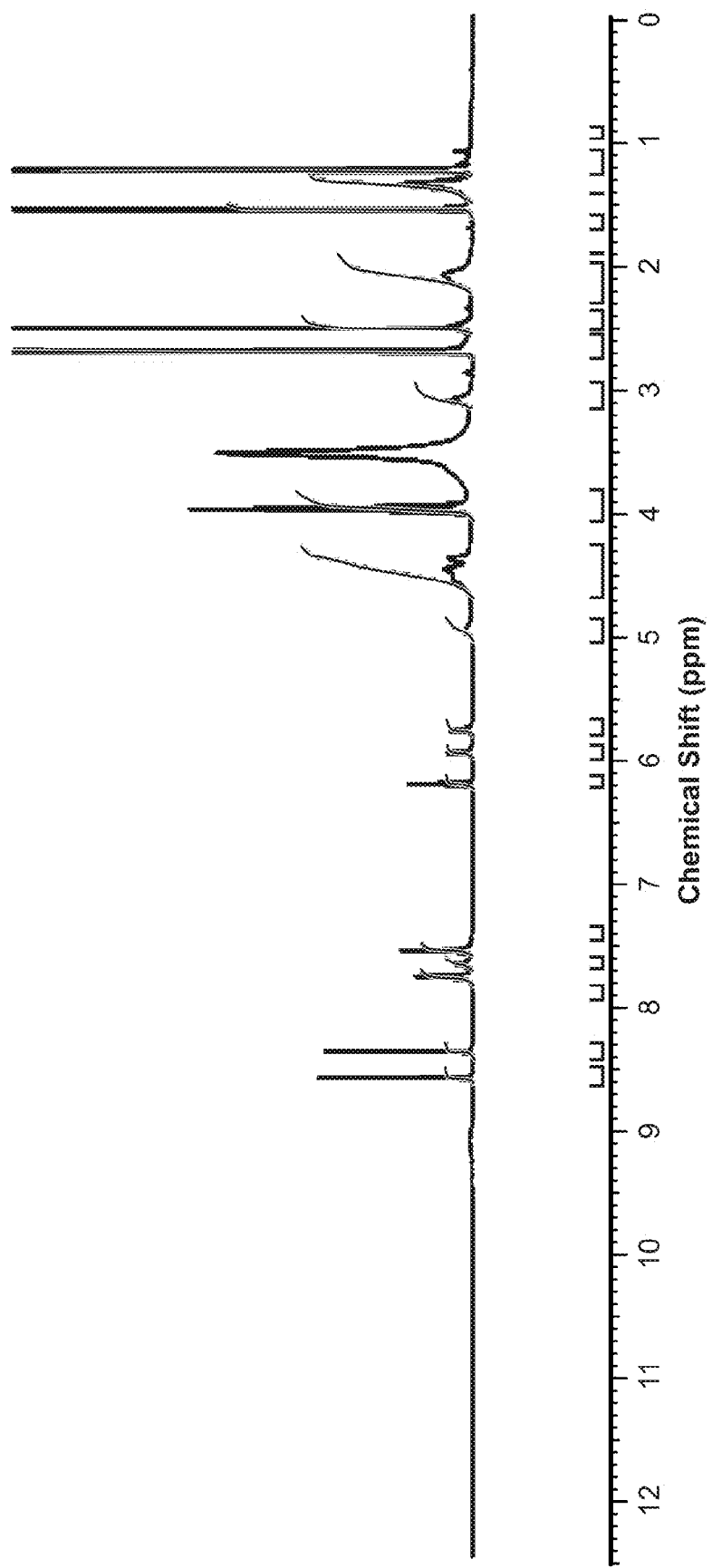
Figure 126:
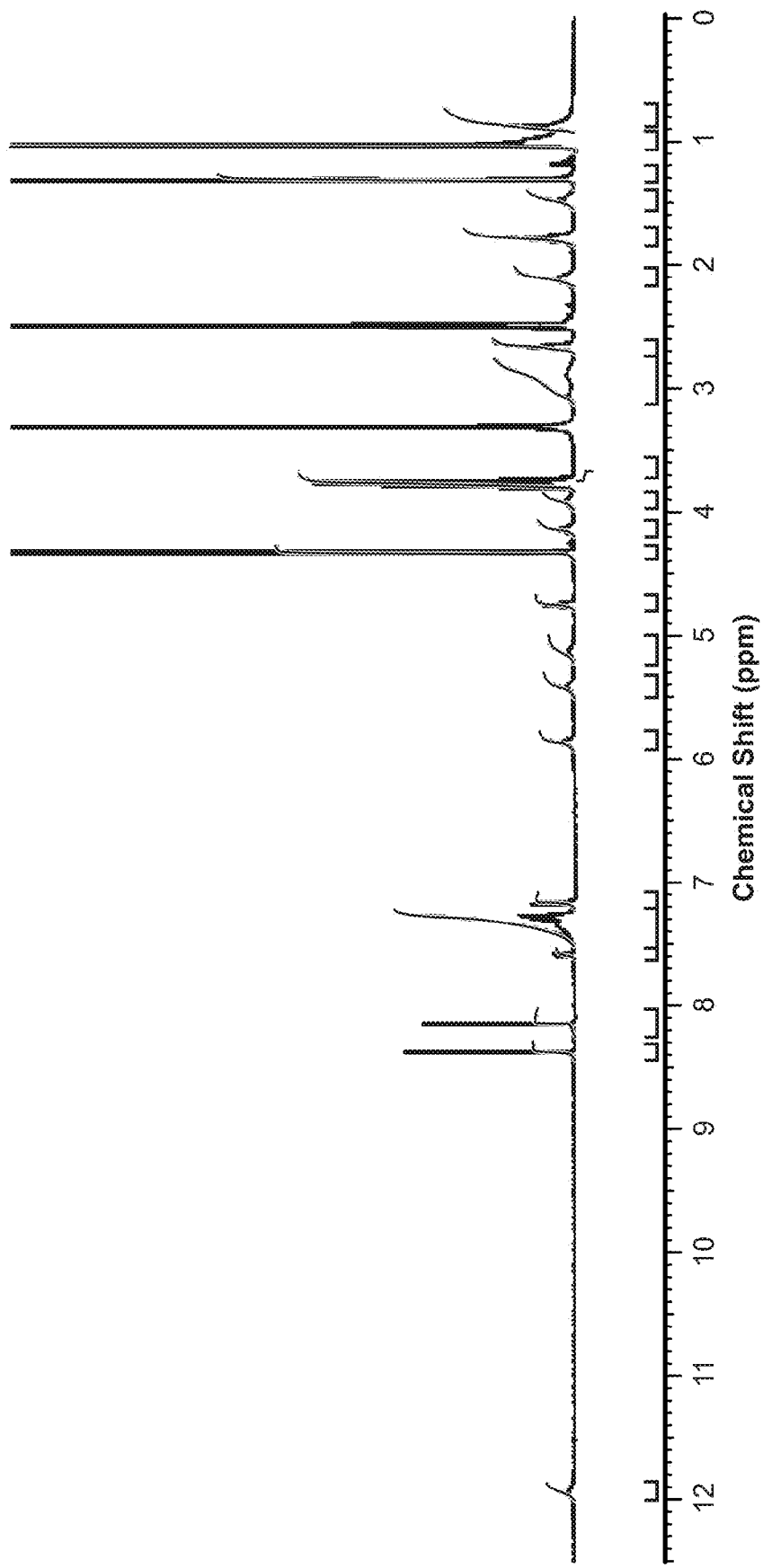
Figure 127:
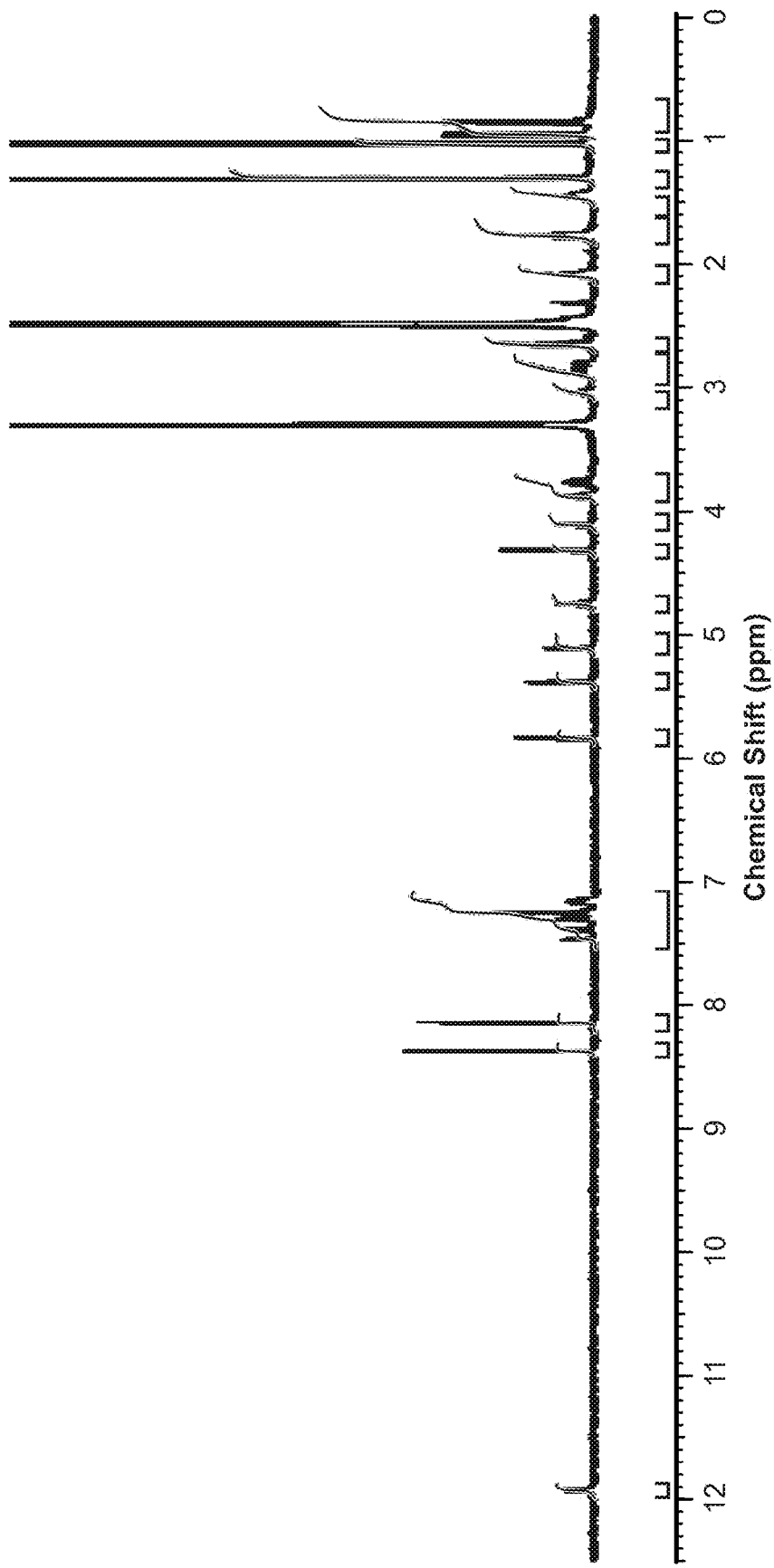

Solution photostability data listed in Table 14 indicated that EP-1 trihydrate (x is 3) (Form B) in water and 0.01N HCl solution is stable upon exposure to UV/Vis. Precipitation was observed for all solutions in 0.01N NaOH. The precipitate was thus re-dissolved using methanol and checked with HPLC. No degradation product was observed from HPLC data (FIG. 25) which suggested the precipitate was EP-1 trihydrate (x is 3) instead of degradates.

TABLE 14

Solution Photostability of EP-1 trihydrate (x is 3) - Form B

| Sample | Vis Stability (1.2 Mil lux-hours) | | | Vis-UV Stability (1.2 Mil lux-hours + 200 Watt-hours/m$^2$) | | |
|---|---|---|---|---|---|---|
| | % area* | % claim$^\&$ | Final pH | % area | % claim | Final pH |
| H$_2$O Light | 99.6 | 98.5 | 7.3 | 99.3 | 94.7 | 7.3 |
| H$_2$O Dark | 100.0 | 100.0 | 7.7 | 100.0 | 100.0 | 8.1 |
| 0.01N HCl Light | 98.5 | 98.8 | 2.1 | 99.9 | 99.9 | 2.1 |
| 0.01N HCl Dark | 99.4 | 100.0 | 2.1 | 99.9 | 100.0 | 2.1 |
| 0.01N NaOH Light | 99.6 | 44.5 | 11.7 | 99.3 | 66.3 | 11.7 |
| 0.01 N NaOH Dark | 99.7 | 100.0 | 11.6 | 100.0 | 100.0 | 11.7 |

*Area % = 100%-TRS %; TRS: Total related substances
$^\&$Claim % = Cs/Ci × 100%; Cs: Concentration in stability sample; Ci: Concentration in initial sample General Methods Starting Material The samples used in the stability study were prepared by recrystallization of EP-1 trihydrate (x is 3) in MeOH/H$_2$O.

Instruments and Methods

X-Ray Powder Diffraction

Analytical Instrument: Panalytical Empyrean. The X-ray powder diffractogram was determined by mounting a sample of the crystalline material on a Si single crystal holder and spreading out the sample into a thin layer with the aid of a microscope slide. The 2θ position was calibrated against Panalytical 640 Si powder standard. The sample irradiated with X-rays generated by a copper long-fine focus tube operated at 45kV and 40 mA with a wavelength of Kα1=1.540598 angstroms and Kα2=1.544426 angstroms (Kα2/Kα1 intensity ratio is 0.50). The collimated X-ray source was passed through an programmed divergence slit set at 10 mm and the reflected radiation directed through a 5.5 mm antiscatter slit. The sample was exposed for 12.7 seconds per 0.0167° 2-theta increment (continuous scan mode) over the range 3 degrees to 40 degrees 2-theta in theta-theta mode. The running time was 3 minutes and 57 seconds. The instrument was equipped with a RTMS detector (X'Celerator). Control and data capture was by means of a Dell Optiplex 780 XP operating with data collector software. Persons skilled in the art of XRPD will realise that the relative intensity of peaks can be affected by, for example, grains above 30 microns in size and non-unitary aspect ratios that may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values. The typical XRPD parameters used are listed in Table 15.

TABLE 15

Typical XRPD Parameters

| | Parameters for Reflection Mode |
|---|---|
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (°2TH) | 2°-40° |
| Step size (°2TH) | 0.0170 |
| Scan speed (°/min) | About 10 |

Differential Scanning Calorimetry (DSC)

Instrument: TA Q200 DSC from TA Instruments

Method: ramp from RT to desired temperature at a heating rate of 10° C./min using N$_2$ as the purge gas, with pan crimped.

Thermogravimetic Analysis (TGA)

Instrument: TA Q500 TGA from TA Instruments

Method: ramp from RT to desired temperature at a heating rate of 10° C./min using N$_2$ as the purge gas.

HPLC Method

Agilent 1100 HPLC was utilized and detailed chromatographic conditions are listed in Table 16 and Table 17.

TABLE 16

Chromatographic Conditions and Parameters

Conditions

| | |
|---|---|
| Column: | Cosmosil 5C18-MS-II 4.6 × 250 mm |
| Flow Rate: | 1.0 ml/min. |
| Injection Volume | 10 µL |
| Detector Wavelength: | 254 nm |
| Run time: | 40 min. |
| Column Temperature: | 40.0° C. |
| Post Time | 5 min. |

TABLE 17

Gradient of Mobile Phase

| Time (min) | Mobile Phase A (100% Acetonitrile) (%) | Mobile Phase B (0.1% NH$_4$OH in H$_2$O): (%) |
|---|---|---|
| 0 | 10.0 | 90.0 |
| 40.0 | 70.0 | 30.0 |
| 40.1 | 10.0 | 90.0 |

Solution Preparation

Simulated Gastric Fluid (Sgf) Preparation:

Weigh appropriate amount of hydrochloride (HCl) and sodium chloride (NaCl) into a 1-L flask followed by addition of 1-L deionized water. The mixture was stirred until all solids are dissolved. Check pH value with a pH-meter and adjust the pH to 1.8 with HCl (1N) or NaOH (1N).

Preparation of pH Buffers pH 2: 0.01N HCl solution. Dilute 1 ml of 1 N HCl with H$_2$O up to a total volume of 100 ml. Measure the pH and precisely adjust to pH=2.00 using a few microliters of 1N HCl or 1N NaOH.

pH 4: 50 mM Na citrate buffer. Prepare a 50 mM citric acid solution by diluting 10 ml of 1N citric acid with H$_2$O up to a total volume of 200 ml. Slowly add solid NaOH under stirring to increase the pH to 3.8-4.0 and use a few microliters of 1N NaOH for final adjustment to pH 4.00.

pH 6: 50 mM Na citrate buffer. Use the same procedure as the pH 4 buffer and adjust to pH=6.00 pH 8: 50 mM Na phosphate buffer. Prepare a 50 mM NaH$_2$PO$_4$ solution by dissolving 6.00 g NaH$_2$PO$_4$ in 1 L of H$_2$O and a 50 mM Na$_2$HPO$_4$ solution by dissolving 7.10 g in 1 L of H$_2$O. Mix 10 ml of the NaH$_2$PO$_4$ solution with 140 ml of the Na$_2$HPO$_4$ solution in a beaker. Adjust to pH 8.00 by addition of small amounts of 50 mM NaH$_2$PO$_4$ or Na$_2$HPO$_4$ solution.

pH 10: 50 mM Na carbonate buffer. Prepare a 50 mM carbonate solution by dissolving 840 mg of sodium bicarbonate (NaHCO$_3$) in about 180 ml of H$_2$O. Slowly adjust the pH to 10.0±0.1 by addition of 1N NaOH. Add water to reach the total volume of 200 ml and adjust to pH 10.00 with 1N NaOH.

In summary, in Examples 3-5, a polymorph screening and selection has been performed for EP-1. Three crystalline forms Form A, Form B and Form C have been obtained and evaluated. The highly crystalline Form B, which is a trihydrate, was identified to be suitable for pharmaceutical development. Form B is the most thermodynamically stable crystalline phase under ambient conditions. It can be consistently produced directly by crystallization. It displays acceptable hygroscopicity and exhibits good physical, chemical, and photostability both in solid state and in solution. It also shows acceptable solubility in biorelevant media. Based on the present study and evaluation, Form B is suitable for pharmaceutical development.

Example 6

Crystalline Forms

Form A is crystalline but may contain a certain amount of amorphous phase. The DSC curve (FIG. 2) of Form A exhibits a dehydration endotherm at ~80° C. (peak temperature) which is accompanied by 5.9 wt % weight loss up to ~150° C. in the TGA curve (FIG. 3). The water content was found to be 6.4 wt % as determined by a Mettler Toledo DL31 KF Titrator. This data confirms that Form A is a hydrate. Form A is hygroscopic as indicated by water adsorption of ~5.8 wt % at 80% RH measured by dynamic vapor sorption (DVS) (FIG. 4). A solid is considered moderately hygroscopic when water uptake at 25° C./80% RH is between 2-15 wt % based on criteria of European Pharmacopeia. The hysteresis in the DVS plot suggests that Form A partially converts to Form B during the experiment, although it converts back to Form A when RH goes back down to zero, therefore no significant change in XRPD pattern was observed post DVS experiment (FIG. 5).

Form B is a trihydrate as confirmed by single crystal analysis. The experimental XRPD pattern of Form B matches well with the simulated one from single crystal data (FIG. 6). This was also confirmed by DSC and TGA data (FIG. 7 and FIG. 8, respectively). DSC data indicates Form B dehydrates at ~132° C. (peak temperature) and TGA data displays a 8.73% weight loss up to 160° C. which is in good agreement with the theoretical value (8.75%) of a trihydrate. Form B is slightly hygroscopic as evidenced by a weight change of ~0.3% between 0% and 95% RH (FIG. 9), (data collection was programmed from 95% RH-0% RH-95% RH at a step size of 10% RH at 25° C.). XRPD results suggested that no form change was observed for Form B after the DVS experiment (FIG. 10).

Form C was observed upon heating of Form B to 120° C. and cooling down to room temperature (FIG. 11). Its DSC and TGA characterization data are shown in FIG. 12 and FIG. 13, respectively. The results suggest it is a channel hydrate. Anhydrate Form C material was produced by dehydration of Form B at 114° C. using hot stage XRPD.

Example 7

Single Crystal Structure of EP-1 Trihydrate (x is 3)

The atomic structure of EP-1 trihydrate (x is 3) is defined by a set of atomic coordinates set forth in Table 18. The terms "structure coordinates" or "atomic coordinates" refer to Cartesian coordinates derived from mathematical equations related to the patterns obtained on diffraction of a monochromatic beam of X-rays by the atoms (scattering centers) of a molecule in crystal form. The diffraction data are used to calculate an electron density map of the repeating unit of the crystal. The electron density maps are then used to establish the positions of the individual atoms of the molecule.

TABLE 18

Atomic coordinates and equivalent isotropic atomic displacement parameters (Å²) for EP-1 trihydrate (x is 3). U(eq) is defined as one third of the trace of the orthogonalized $U_{ij}$ tensor.

|  | x/a | y/b | z/c | U(eq) |
|---|---|---|---|---|
| C1 | 0.3885(4) | −0.1399(7) | 0.5608(4) | 0.0464(16) |
| C2 | 0.4309(3) | −0.0291(6) | 0.5967(6) | 0.058(2) |
| C3 | 0.3484(3) | −0.2019(6) | 0.5980(4) | 0.0362(14) |
| C4 | 0.4335(5) | 0.0345(7) | 0.6574(4) | 0.0492(18) |
| C5 | 0.3528(4) | −0.1341(7) | 0.6655(4) | 0.0504(18) |
| C6 | 0.3920(4) | −0.0215(7) | 0.6952(5) | 0.0506(18) |
| N7 | 0.4784(3) | 0.0490(6) | 0.5636(4) | 0.0514(16) |
| C8 | 0.5038(4) | 0.1426(7) | 0.6171(4) | 0.0456(17) |
| N9 | 0.4778(3) | 0.1385(7) | 0.6711(4) | 0.0573(17) |
| C10 | 0.2998(4) | −0.3200(7) | 0.5720(6) | 0.058(2) |
| C11 | 0.3391(6) | −0.4275(7) | 0.6342(5) | 0.068(2) |
| C12 | 0.3007(6) | −0.3726(11) | 0.4964(6) | 0.080(3) |
| C13 | 0.2135(4) | −0.2985(8) | 0.5500(5) | 0.058(2) |
| C14 | 0.5551(4) | 0.2499(7) | 0.6176(4) | 0.0435(15) |
| C15 | 0.5205(3) | 0.3815(6) | 0.6146(4) | 0.0361(14) |
| C16 | 0.5765(4) | 0.4863(6) | 0.6140(3) | 0.0356(14) |
| C17 | 0.5592(4) | 0.6261(6) | 0.6285(3) | 0.0353(14) |
| C18 | 0.6597(3) | 0.4954(6) | 0.6853(4) | 0.0385(15) |
| C19 | 0.6511(3) | 0.6435(6) | 0.6811(3) | 0.0332(13) |
| N20 | 0.6775(3) | 0.7117(5) | 0.7560(3) | 0.0280(11) |
| C21 | 0.6458(4) | 0.8463(6) | 0.7416(4) | 0.0417(16) |
| C22 | 0.6768(5) | 0.9315(7) | 0.7001(5) | 0.060(2) |
| C23 | 0.6586(4) | 0.9058(6) | 0.8188(5) | 0.0478(18) |
| C24 | 0.7659(3) | 0.7040(6) | 0.8029(3) | 0.0325(13) |
| C25 | 0.7952(3) | 0.6658(6) | 0.8869(3) | 0.0334(14) |
| O26 | 0.7725(2) | 0.5330(4) | 0.8886(2) | 0.0343(10) |
| C27 | 0.8845(4) | 0.6622(5) | 0.9380(4) | 0.0377(15) |
| C28 | 0.8248(3) | 0.4807(6) | 0.9634(3) | 0.0343(13) |
| C29 | 0.8944(4) | 0.5746(6) | 1.0059(4) | 0.0430(16) |
| O30 | 0.9164(3) | 0.7881(4) | 0.9641(3) | 0.0603(17) |
| O31 | 0.8788(4) | 0.6398(6) | 1.0616(3) | 0.079(2) |
| N32 | 0.8478(3) | 0.3506(5) | 0.9499(3) | 0.0271(11) |
| C33 | 0.8177(3) | 0.2390(7) | 0.9620(4) | 0.0358(14) |
| C34 | 0.8965(3) | 0.3141(5) | 0.9183(3) | 0.0258(12) |
| N35 | 0.8432(3) | 0.1364(5) | 0.9431(3) | 0.0356(12) |
| C36 | 0.8935(3) | 0.1822(6) | 0.9148(3) | 0.0265(12) |
| C37 | 0.9385(4) | 0.1196(6) | 0.8838(4) | 0.0366(15) |
| N38 | 0.9815(3) | 0.1936(5) | 0.8596(3) | 0.0339(11) |
| C39 | 0.9793(3) | 0.3228(6) | 0.8671(3) | 0.0320(14) |
| N40 | 0.9389(3) | 0.3914(4) | 0.8949(3) | 0.0271(11) |
| N41 | 0.9387(4) | −0.0074(5) | 0.8747(4) | 0.0539(16) |
| O1W | 0.5218(4) | 0.3015(6) | 0.8066(4) | 0.0682(16) |
| O2W | 0.6617(3) | 0.4231(4) | 0.9663(3) | 0.0411(10) |
| O3W | 0.5882(2) | 0.5561(4) | 0.8214(2) | 0.0371(10) |

What is claimed is:

1. A crystalline form of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl) (isopropyl)amino)methyl)tetrahydrofuran-3,4-diol:

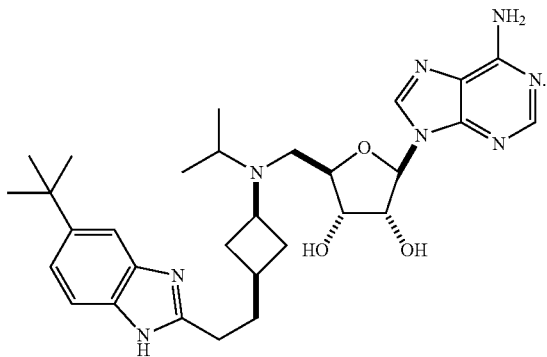

2. The crystalline form of claim 1, characterized by an X-ray powder diffraction (XRPD) pattern comprising peaks at about 16.5, 20.5, and 5.2° 2θ using Cu Kα radiation.

3. The crystalline form of claim 2, characterized by an XRPD pattern comprising peaks at about 16.5, 20.5, 5.2, and 14.2° 2θ using Cu Kα radiation.

4. The crystalline form of claim 3, characterized by an XRPD pattern comprising peaks at about 16.5, 20.5, 5.2, 14.2, 18.0, and 10.4° 2θ using Cu Kα radiation.

5. The crystalline form of claim 1, characterized by an XRPD pattern comprising at least three peaks selected from the group consisting of about 16.5, 20.5, 5.2, 14.2, 18.0, 10.4, 12.3, 10.0, 22.7, and 20.9° 2θ using Cu Kα radiation.

6. The crystalline form of claim 1, characterized by an XRPD pattern comprising peaks at about 5.5, 16.9, and 16.6° 2θ using Cu Kα radiation.

7. The crystalline form of claim 6, characterized by an XRPD pattern comprising peaks at about 5.5, 16.9, 16.6, and 18.8° 2θ using Cu Kα radiation.

8. The crystalline form of claim 7, characterized by an XRPD pattern comprising peaks at about 5.5, 16.9, 16.6, 18.8, 14.3, and 12.7° 2θ using Cu Kα radiation.

9. The crystalline form of claim 1, characterized by an XRPD pattern comprising at least three peaks selected from the group consisting of about 5.5, 16.9, 16.6, 18.8, 14.3, 12.7, 21.8, 20.0, 10.0, and 11.0° 2θ using Cu Kα radiation.

10. The crystalline form of claim 1, characterized by an XRPD pattern comprising peaks at about 16.9, 5.7, and 14.5° 2θ using Cu Kα radiation.

11. The crystalline form of claim 10, characterized by an XRPD pattern comprising peaks at about 16.9, 5.7, 14.5, and 22.2° 2θ using Cu Kα radiation.

12. The crystalline form of claim 11, characterized by an XRPD pattern comprising peaks at about 16.9, 5.7, 14.5, 22.2, 19.1, and 20.0° 2θ using Cu Kα radiation.

13. The crystalline form of claim 1, characterized by an XRPD pattern comprising at least three peaks selected from the group consisting of about 16.9, 5.7, 14.5, 22.2, 19.1, 20.0, 11.3, 12.9, 10.0, and 23.7° 2θ using Cu Kα radiation.

14. A compound of formula I:

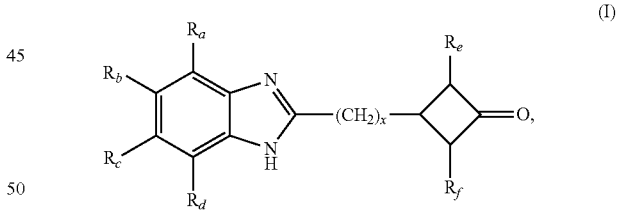

or a salt or solvate thereof, wherein:
$R_a$, $R_b$, $R_c$, and $R_d$ are each independently $-M_2-T_2$;
$M_2$ is a bond, $S(O)_2$, $S(O)$, $S$, $C(O)$, $C(O)O$, $O$, $O—C_1-C_4$ alkyl linker, $C_1-C_4$ alkyl linker, NH, or $NR_t$;
$R_t$ is $C_1-C_6$ alkyl;
$T_2$ is H, halogen, or $R_{S4}$;
$R_{S4}$ is $C_1-C_6$ alkyl, $C_2-C_6$ alkenyl, $C_2-C_6$ alkynyl, $C_3-C_8$ cycloalkyl, $C_6-C_{10}$ aryl, 4 to 8-membered heterocycloalkyl, or 5 to 10-membered heteroaryl;
$R_e$ and $R_f$ are each independently H or $C_1-C_6$ alkyl; and
x is 1, 2, 3, 4, 5, or 6,
wherein each of $O—C_1-C_4$ alkyl linker, $C_1-C_4$ alkyl linker, $R_t$, and $R_{S4}$ is optionally substituted with one or more substituents selected from the group consisting of halogen, hydroxyl, carboxyl, cyano, $C_1-C_6$ alkyl, $C_2-C_6$ alkenyl, $C_2-C_6$ alkynyl, C$_1$-C$_6$ alkoxyl, amino, mono-C$_1$-C$_6$alkylamino, di-C$_1$-C$_6$ alkylamino, C$_3$-C$_8$ cycloalkyl, C$_6$-C$_{10}$ aryl, 4 to 6-membered heterocycloalkyl, and 5 to 6-membered heteroaryl.

15. The compound of claim 14, wherein the compound is:

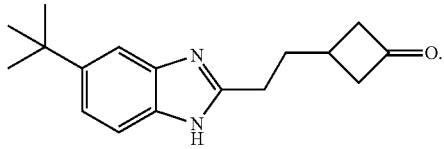 [SMILES: CC(C)(C)c1ccc2[nH]c(CCC3CC(=O)C3)nc2c1]

16. A process for preparing (2R,3R,4S,5R)-2-(6-amino-9H-purin-9-yl)-5-(((1r,3S)-3-(2-(5-(tert-butyl)-1H-benzo[d]imidazol-2-yl)ethyl)cyclobutyl)(isopropyl)amino)methyl) tetrahydrofuran-3,4-diol:

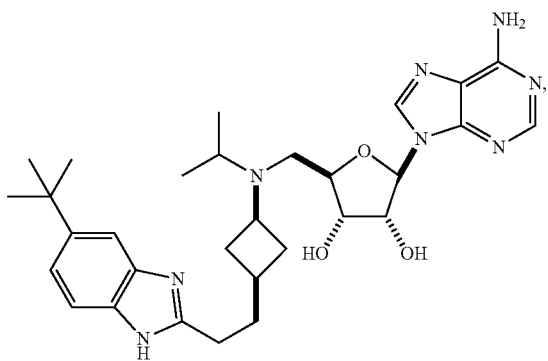

or a salt or hydrate thereof, comprising at least one step selected from the group consisting of:
(1) reacting 9-((3aR,4R,6R,6aR)-6-(aminomethyl)-2,2-dimethyltetrahydrofuro[3,4-d][1,3]dioxol-4-yl)-9H-purin-6-amine with acetone to yield 9-((3aR,4R,6R,6aR)-6-((isopropylamino)methyl)-2,2-dimethyltetrahydrofuro[3,4-d][1,3]dioxol-4-yl)-9H-purin-6-amine;
(2) reacting 9-((3aR,4R,6R,6aR)-6-((isopropylamino)methyl)-2,2 dimethyltetrahydrofuro[3,4-d][1,3]dioxol-4-yl)-9H-purin-6-amine with 3-(2-(5-(tert-butyl)-1H-benzo[d]imidazol-2-yl)ethyl)cyclobutanone to yield 9-((3aR,4R,6R,6aR)-6-(((3-(2-(5-(tert-butyl)-1H-benzo[d]imidazol-2-yl)ethyl)cyclobutyl)(isopropyl) amino) methyl)-2,2-dimethyltetrahydrofuro[3,4-d][1,3]dioxol-4-yl)-9H-purin-6-amine; and
(3) converting 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine to (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino) methyl)tetrahydrofuran-3,4-diol.

17. A process for preparing (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl) tetrahydrofuran-3,4-diol:

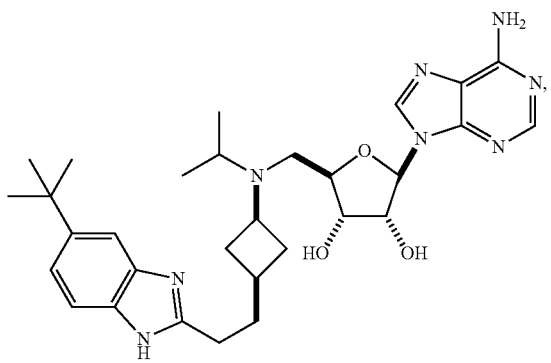

or a salt or hydrate thereof, comprising at least two steps selected from the group consisting of:
(1) reacting 9-((3aR,4R,6R,6aR)-6-(aminomethyl)-2,2-dimethyltetrahydrofuro[3,4-d][1,3]dioxol-4-yl)-9H-purin-6-amine with acetone to yield 9-((3aR,4R,6R,6aR)-6-((isopropylamino)methyl)-2,2-dimethyltetrahydrofuro[3,4-d][1,3]dioxol-4-yl)-9H-purin-6-amine;
(2) reacting 9-((3aR,4R,6R,6aR)-6-((isopropylamino)methyl)-2,2 dimethyltetrahydrofuro[3,4-d][1,3]dioxol-4-yl)-9H-purin-6-amine with 3-(2-(5-(tert-butyl)-1H-benzo[d]imidazol-2-yl)ethyl)cyclobutanone to yield 9-((3aR,4R,6R,6aR)-6-(((3-(2-(5-(tert-butyl)-1H-benzo[d]imidazol-2-yl)ethyl)cyclobutyl)(isopropyl) amino) methyl)-2,2-dimethyltetrahydrofuro[3,4-d][1,3]dioxol-4-yl)-9H-purin-6-amine; and
(3) converting 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine to (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino) methyl)tetrahydrofuran-3,4-diol.

18. A process for preparing (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl) tetrahydrofuran-3,4-diol:

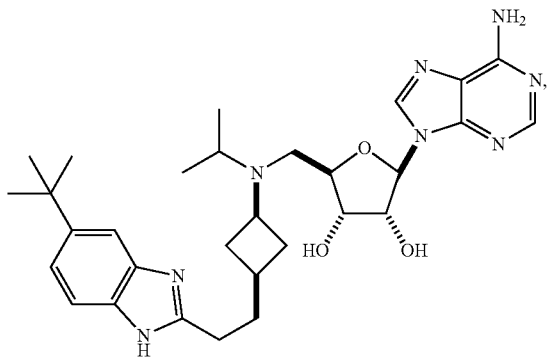

or a salt or hydrate thereof, comprising the steps of:
(1) reacting 9-((3aR,4R,6R,6aR)-6-(aminomethyl)-2,2-dimethyltetrahydrofuro[3,4-d][1,3]dioxol-4-yl)-9H-purin-6-amine with acetone to yield 9-((3aR,4R,6R,6aR)-6-((isopropylamino)methyl)-2,2-dimethyltetrahydrofuro[3,4-d][1,3]dioxol-4-yl)-9H-purin-6-amine;

(2) reacting 9-((3aR,4R,6R,6aR)-6-((isopropylamino)methyl)-2,2 dimethyltetrahydrofuro[3,4-d][1,3]dioxol-4-yl)-9H-purin-6-amine with 3-(2-(5-(tert-butyl)-1H-benzo[d]imidazol-2-yl)ethyl)cyclobutanone to yield 9-((3aR,4R,6R,6aR)-6-(((3-(2-(5-(tert-butyl)-1H-benzo[d]imidazol-2-yl)ethyl)cyclobutyl)(isopropyl) amino) methyl)-2,2-dimethyltetrahydrofuro[3,4-d][1,3] dioxol-4-yl)-9H-purin-6-amine; and (3) converting 9-((3aR,4R,6R,6aR)-6-(((3-(2-(5-(tert-butyl)-1H-benzo[d]imidazol-2-yl)ethyl)cyclobutyl)(isopropyl)amino)methyl)-2,2-dimethyltetrahydrofuro[3,4-d][1,3]dioxol-4-yl)-9H-purin-6-amine to (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino) methyl)tetrahydrofuran-3,4-diol.

19. The process of claim 16, further comprising step (4): recrystallizing (2R,3R,4S,5R)-2-(6-amino-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol to yield (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol or a salt of hydrate thereof.

20. A pharmaceutical composition comprising the crystalline form of claim 1, and a pharmaceutically acceptable carrier.

* * * * *